US012503485B2

(12) United States Patent
Barbut et al.

(10) Patent No.: US 12,503,485 B2
(45) Date of Patent: Dec. 23, 2025

(54) HUMAN AMINOSTEROL ENT-03 COMPOUNDS, RELATED COMPOSITIONS COMPRISING THE SAME, AND METHODS OF USING THE SAME

(71) Applicant: Enterin, Inc., Philadelphia, PA (US)

(72) Inventors: Denise Barbut, Philadelphia, PA (US); Michael Zasloff, Philadelphia, PA (US)

(73) Assignee: Enterin, Inc., Philadelphia, PA (US)

( * ) Notice: Subject to any disclaimer, the term of this patent is extended or adjusted under 35 U.S.C. 154(b) by 997 days.

(21) Appl. No.: 17/631,882

(22) PCT Filed: Jul. 31, 2020

(86) PCT No.: PCT/US2020/044390

§ 371 (c)(1),
(2) Date: Jan. 31, 2022

(87) PCT Pub. No.: WO2021/025973

PCT Pub. Date: Feb. 11, 2021

(65) Prior Publication Data

US 2023/0123701 A1 Apr. 20, 2023

Related U.S. Application Data

(60) Provisional application No. 63/041,031, filed on Jun. 18, 2020, provisional application No. 62/882,358, filed on Aug. 2, 2019.

(51) Int. Cl.

| | |
|---|---|
| ***A61P 25/00*** | (2006.01) |
| ***A61K 31/575*** | (2006.01) |
| ***C07J 9/00*** | (2006.01) |
| ***C07J 41/00*** | (2006.01) |

(52) U.S. Cl.
CPC ......... *C07J 41/0005* (2013.01); *A61K 31/575* (2013.01); *A61P 25/00* (2018.01); *C07J 9/005* (2013.01)

(58) Field of Classification Search
CPC .................................................... C07J 41/0005
See application file for complete search history.

(56) References Cited

U.S. PATENT DOCUMENTS

| | | | |
|---|---|---|---|
| 5,721,226 | A | 2/1998 | Frye et al. |
| 6,962,909 | B2 | 11/2005 | Zasloff |
| 2014/0179658 | A1 | 6/2014 | Zasloff et al. |
| 2016/0222052 | A1 | 8/2016 | Griffiths et al. |

FOREIGN PATENT DOCUMENTS

| | | | |
|---|---|---|---|
| WO | WO-96/008270 | A1 | 3/1996 |
| WO | WO-96/40151 | A1 | 12/1996 |
| WO | WO-96/40728 | A2 | 12/1996 |
| WO | WO-98/27106 | A1 | 6/1998 |
| WO | WO 2009/032321 | A2 | 3/2009 |
| WO | WO-2013/158970 | A2 | 10/2013 |
| WO | WO-2014/132052 | A2 | 9/2014 |
| WO | WO-2015/036726 | A1 | 3/2015 |
| WO | WO 2015/095339 | A1 | 6/2015 |
| WO | WO 2018/050814 | A1 | 3/2018 |
| WO | WO-2018/050815 | A1 | 3/2018 |
| WO | WO-2021/025974 | A1 | 2/2021 |
| WO | WO-2021/025988 | A1 | 2/2021 |

OTHER PUBLICATIONS

Supplementary European Search Report issue in co-pending European Patent Application No. 20849084.7 dated Jul. 7, 2023.
International Preliminary Report on Patentability issued in International Patent Application No. PCT/US2020/044390, dated Feb. 17, 2022.
International Search Report and Written Opinion issued in International Patent Application No. PCT/US2020/044390, dated Nov. 9, 2020.
Aarsland et al., "Neuropsychiatric symptoms in patients with Parkinson's disease and dementia: frequency, profile and associated care giver stress," J. Neurol. Neurosurg. Psychiatry, vol. 78, pp. 36-42 (2007).
Acsadi et al., "Alpha-synuclein loss in spinal muscular atrophy," J. Mol. Neurosci., 43(3), pp. 275-283 (2011).
Ahima et al., "Appetite suppression and weight reduction by a centrally active aminosterol," Diabetes, 51: 2099-2104 (2002).
Ahima RS, Flier JS. "Leptin," Annu Rev Physiol. 62, 413-437 (2000).
Akhter et al., "Squalamine, a novel cationic steroid, specifically inhibits the brush-border Na+/H+ exchanger isoform NHE3." Am. J. Physiol., 276(1 Pt 1): C136-44 (1999).
Andresen et al., "Effect of 5 days linaclotide on transit and bowel function in females with constipation-predominant irritable bowel syndrome," Gastroenterology, 133:761-768 (2007).
Antonelou et al., "Decreased levels of alpha-synuclein in cerebrospinal fluid of patients with clinically isolated syndrome and multiple sclerosis," J. Neurochem., 134(4):748-55 (2015).
Antonio-Rubio, et al., "Abnormal thermography in Parkinson's disease," Parkinsonism Relat Disord., Aug. 2015;21(8):852-7.
Auyeung et al., "Ten year survival and outcomes in a prospective cohort of new onset Chinese Parkinson's disease patients," J. Neurol. Neurosurg. Psychiatry, 83:607-11 (2012).
Beach et al., A Review of Biomarkers for Neurodegenerative Disease: Will They Swing US Across the Valley?, Neurol Ther., Jul; 6(Suppl 1): 5-13 (2017).
Berg et al., MDS Research Criteria for Prodromal Parkinson's Disease, Mov. Disord. 30: pp. 1600-1611 (2015).
Bhargava et al., "A phase I and pharmacokinetic study of squalamine, a novel antiangiogenic agent, in patients with advanced cancers," Clin. Cancer Res., 7(12): 3912-9 (2001).
Bjorkhem, "Five decades with oxysterols," *Biochimie* 95, 448-454 (2013).
Boeve et al., "Synucleinopathy pathology and REM sleep behavior disorder plus dementia or parkinsonism," Neurology 61(1), pp. 40-45 (Jul. 2003).

(Continued)

*Primary Examiner* — Yong S. Chong
(74) *Attorney, Agent, or Firm* — Foley & Lardner LLP

(57) ABSTRACT

The present application relates generally to novel aminosterol compounds, compositions comprising the same, and methods of making and using the novel aminosterol compounds and compositions.

10 Claims, 43 Drawing Sheets

(56) References Cited

OTHER PUBLICATIONS

Boniakowski et al., Murine macrophage chemokine receptor CCR2 plays a crucial role in macrophage recruitment and regulated inflammation in wound healing. *Eur J Immunol* 48, 1445-1455 (2018).
Braak et al., "Idiopathic Parkinson's disease: possible routes by which vulnerable neuronal types may be subject to neuroinvasion by an unknown pathogen," J Neural Transm (Vienna), vol. 110, pp. 517-536 (2003).
Braak et al., "Staging of Brain Pathology Related to Sporadic Parkinson's Disease," Neurobiological Aging, Mar.-Apr. 2003, vol. 24, No. 2 (pp. 197-211).
Breen et al., "Sleep and circadian rhythm regulation in early Parkinson disease," JAMA Neurol. 71:589-595 (2014).
Brundin et al., "Therapeutic approaches to target alpha-synuclein pathology," Exp. Neurology, 298(B):225-235 (2017).
Brunel et al., "Squalamine: A Polyvalent Drug of the Future?" Current Cancer Drug Targets, 5(4):267-272(6) (2005).
Celotti, et al., "The 5 alpha-reductase in the brain: molecular aspects and relation to brain function," *Front Neuroendocrinol* 13, 163-215 (1992).
Chen, et al., "Allosteric inhibition of SHP2 phosphatase inhibits cancers driven by receptor tyrosine kinases," *Nature* 535, 148-152 (2016).
Claassen et al., "REM sleep behavior disorder preceding other aspects of synucleinopathies by up to half a century," Neurology, 75(6):494-499 (Aug. 2010).
Combs AP, "Recent advances in the discovery of competitive protein tyrosine phosphatase 1B inhibitors for the treatment of diabetes, obesity, and cancer" J. Med. Chem., 53(6):2333-2344 (2010).
Connolly, et al., "Squalamine Lactate for Exudative Age-Related Macular Degeneration," Ophthalmology Clinics of North America, 19, 381-391 (2006).
Corrochano et al., "a-synuclein levels modulate Huntington's disease in mice," Hum. Mol. Genet., 21(3):485-94 (Feb. 2012).
Courtney, et al., "CD45 functions as a signaling gatekeeper in T cells," Sci Signal 12, (2019).
Crick et al., "The oxysterol and cholestenoic acid profile of mouse cerebrospinal fluid," Steroids, 99, 172-177 (2015).
Demirel et al., "Decreased Expression of a-Synuclein, Nogo-A and UCH-L1 in Patients with Schizophrenia: A Preliminary Serum Study," Psychiatry Invest., 14(3), pp. 344-349, (2017).
Diao, et al., "Human Kidney is a Target for Novel Severe Acute Respiratory Syndrome Coronavirus 2 (SARS-CoV-2) Infection" 2020 medRxiv Preprint. Posted Apr. 10, 2020, 17 pages.
Diederich et al., "Hallucinations in Parkinson disease," Nat. Rev. Neurol., 5(6):331-42 (2009).
Edlmann, et al., "Pathophysiology of chronic subdural haematoma: inflammation, angiogenesis and implications for pharmacotherapy," J Neuroinflammation 14, 108 (2017).
Eswaran et al., "Crystal structures and inhibitor identification for PTPN5, PTPRR and PTPN7: a family of human MAPK-specific protein tyrosine phosphatases," Biochem J, 395, 483-491 (2006).
Elchebly et al., "Increased insulin sensitivity and obesity resistance in mice lacking the protein tyrosine phosphatase-1B gene" Science. Mar. 5, 1999;283(5407):1544-1548.
Frank, et al., "Psychometric validation of a constipation symptom assessment questionnaire," Scand J Gastroenterol., Sep. 1999;34(9):870-877.
Frisina et al., "The neuropathological basis for depression in Parkinson's disease," Parkinsonism Relat. Disord., 15(2):144-148 (2009).
Genaidy, et al., "Effect of Squalamine on Iris Neovascularization in Monkeys," Retina, vol. 22, No. 6, pp. 772-778 (2002).
Gjerstad et al., "Excessive daytime sleepiness in Parkinson disease: is it the drugs or the disease?" Neurology, 67:853-8 (2006).
Goetz CG, Stebbins GT., "Risk factors for nursing home placement in advanced Parkinson's disease," Neurology, 43:2227-9 (1993).
Gressens et al., "Vasoactive intestinal peptide prevents excitotoxic cell death in the murine developing brain," J. Clin. Invest., 100(2): 390-7 (1997).
Hao et al., "A Phase I and pharmacokinetic study of squalamine, an aminosterol angiogenesis inhibitor," Clin. Cancer Res., 9(7): 2465-2471 (2003).
Heaton et al., Defecation frequency and timing, and stool form in the general population: a prospective study. Gut, 33:818-824 (1992).
Herbst, et al., "A Phase I/IIA Trial of Continuous Five-Day Infusion of Squalamine Lactate (MSI-1256F) Plus Carboplatin and Paclitaxel in Patients with Advanced Non-Small Cell Lung Cancer1," Clinical Cancer Research, vol. 9, pp. 4108-4115 (Sep. 2003).
Hicklin, "Brain Cells that Influence Aging," 2 pages (Aug. 2017).
Higgins, et al., "Regression of Retinopathy by Squalamine in a Mouse Model," Pediatric Research, vol. 56, No. 1, pp. 144-149 (2004).
Higgins, et al., "Squalamine Improves Retinal Neovacsularization," Investigative Ophthalmology & Visual Science, vol. 41, No. 6, pp. 1507-1512 (May 2000).
Holmqvist et al., "Direct evidence of Parkinson pathology spread from the gastrointestinal tract to the brain in rats," Acta Neuropathol., 128:805-20 (2014).
Hosokawa et al., "Accumulation of multiple neurodegenerative disease-related proteins in familial frontotemporal lobar degeneration associated with granulin mutation," Scientific Reports, 7:1513 (11 pages, (2017).
Hughes et al., "Accuracy of clinical diagnosis of idiopathic Parkinson's disease: a clinico-pathological study of 100 cases," J. Neurol. Neurosurg. Psychiatry, 55:181-4 (1992).
ICAAC Conference, AIDS Research Highlights from the 35th Interscience Conference on Antimicrobial Agents & Chemotherapy, Sep. 17-20, 1995, 45 pages.
Kim et al., "Poststroke Induction of a-Synuclein Mediates Ischemic Brain Damage," J. Neurosci., 36(26):7055-7065 (Jun. 2016).
Kokubo et al., "a-Synuclein Pathology in the Amyotrophic Lateral Sclerosis/Parkinsonism Dementia Complex in the Kii Peninsula, Japan," J. of Neuropathology & Exp., Neurology, 71(7):625-630 (2012).
Kunze, et al., "Squalamine Reverses Age and Loperamide Associated Dysmotility in a Mouse Biomarker Model of Constipation,".
Lewis et al., "Stool form scale as a useful guide to intestinal transit time," Scand. J. Gastroenterol, 32:920-4 (1997).
Madrid-Navarro et al., "Multidimensional Circadian Monitoring by Wearable Biosensors in Parkinson's Disease," Front. Neurol., 9:157 (2018), 14 pages.
McDowell et al., "Sleep dysfunction and EEG alterations in mice overexpressing alpha-synuclein," J. Parkinsons Dis., 4(3):531-539 (2014).
McKhann et al., "The Diagnosis of Dementia Due to Alzheimer's Disease: Recommendations from the National Institute on Aging-Alzheimer's Association Workgroups on Diagnostic Guidelines for Alzheimer's Disease," Alzheimer's & Dementia, May 2011, vol. 7, No. 3 (pp. 263-269).
Mearin et al., "Bowel Disorders," Gastroenterology, 150(6):1393-1407 (2016).
Miller, et al., "Big mice die young: early life body weight predicts longevity in genetically heterogeneous mice," Aging Cell, vol. 1, pp. 22-29 (2002).
Moore, et al., "Squalamine: An aminosterol antibiotic from the shark," Proc. Natl. Acad. Sci., vol. 90, pp. 1354-1358 (1993).
Moussaud et al., "Alpha-synuclein and tau: teammates in neurodegeneration?" Mol. Neurodeg., 9:43 (2014), 14 pages.
Notice of Reasons for Rejection issued in co-pending Japanese Patent Application No. 2022-506659, dated Sep. 10, 2024.
Ondo et al., "Daytime sleepiness and other sleep disorders in Parkinson's disease," Neurology, 57:1392-6 (2001).
Ortiz-Tudela et al., "Ambulatory circadian monitoring (ACM) based on thermometry, motor activity and body position (TAP): a comparison with polysomnography," Physiol. Behav., 126:30-8 (2014).
Palma, et al., "Treatment of autonomic dysfunction in Parkinson disease and other synucleinopathies," Mov. Disord., vol. 33(3), pp. 372-390 (Mar. 2018).

(56) References Cited

OTHER PUBLICATIONS

Palsetia et al., "The Clock Drawing Test versus Mini-mental Status Examination as a Screening Tool for Dementia: A Clinical Comparison," Indian J. Psychol. Med., 40:1-10 (2018).
Papapetropoulos et al., "A questionnaire-based (UM-PDHQ) study of hallucinations in Parkinson's disease," BMC Neurol., 8:21 (2008), 8 pages.
Perni et al., "A natural product inhibits the initiation of alpha-synuclein aggregation and suppresses its toxicity," PNAS, USA, 114:E1009-E17 (2017).
Phukan et al., "Cognitive impairment in amyotrophic lateral sclerosis," Lancet Neurol., 6(11):994-1003 (2007).
Poyiadji et al., COVID-19-associated "Acute Hemorrhagic Necrotizing Encephalopathy: CT and MRI Features" Radiology, Mar. 31, 2020, 5 pages.
Rahn et al., "Cognitive Impairment in Multiple Sclerosis: A Forgotten Disability Remembered," Cerebrum., 201214 (Nov.-Dec. 2012), 19 pages.
Rocca, et al., "The Role of T1-Weighted Derived Measures of Neurodegeneration for Assessing Disability Progression in Multiple Sclerosis," Frontiers in Neurology, 25 pages (Sep. 2017).
Salmi, et al., Squalamine: An Appropriate Stretegy Against the Emergence of Multidrug Resistant Gram-negative Bacteria? PLos One, vol. 3, No. 7, 8 pages (Jul. 2008).
Sarabia et al., "Circadian rhythm of wrist temperature in normal-living subjects A candidate of new index of the circadian system," Physiol. Behav., 95:570-80 (2008).
Schiller, et al., "Potentiation of Platinum Antitumor Effects in Human Lung Tumor Xenografts by the Angiogenesis Inhibitor Squalamine: Effects on Tumor Neovascularization," Clinical Cancer Search, vol. 5, pp. 4287-4294 (Dec. 1999).
Shehata, et al., "Neuronal Stimulation Induces Autophagy in Hippocampal Neurons That Is Involved in AMPA Receptor Degradation after Chemical Long-Term Depression," J. Neurosci., vol. 32, pp. 10413-10422 (2012).
Sokoloff, et al., "Adjunctive therapy for men with high risk localized and locally advanced prostate cancer: targeting disseminated tumor cells," J Urol., 172(6 Pt 2):, pp. 2539-2544 (Dec. 2004).
Sriwimol, et al., "Significant Changes in Plasma Alpha-Synuclein and Beta-Synuclein Levels in Male Children with Autism Spectrum Disorder," BioMed Res. Int., vol. 2018, Article ID 4503871 (Apr. 8, 2018), 7 pages.
Steer et al., "Use of the Beck Depression Inventory-II with depressed geriatric inpatients," Behav. Res. Ther., 38:311-8 (2000).
Stoessl, Jon, "Neuroimaging in the early diagnosis of neurodegenerative disease," Transl. Neurodegener., 1:5 (2012).
Sumioka et al., "TARP phosphorylation regulates synaptic AMPA receptors through lipid bilayers," Neuron,66(5): 755-67 (2009).
Tang et al., "Loss of mTOR-Dependent Macroautophagy Causes Autistic-like Synaptic Pruning Deficits," Neuron, 83(5):1131-1143 (2014).
The US Burden of Disease Collaborators, "The State of US Health, 1990-2016: Burden of Diseases, Injuries, and Risk Factors Among US States," JAMA, 319(14):1444-1472 (2018).
Members of the UPDRS Development Committee. Unified Parkinson's Disease Rating Scale. Florham Park, NJ: Macmillan Health Care Information, vol. 18, No. 7, pp. 738-750 (2003).
Vanhooren, et al., "The mouse as a model organism in aging research: Usefulness, pitfalls and possibilities," Ageing Res. Rev., vol. 12, pp. 8-21 (2013). [Abstract].
Videnovic, et al., "Circadian Dysregulation in Parkinson's Disease, Neurobiology of Sleep and Circadian Rhythms," vol. 2, pp. 52-58 (2017).
West, et al., "A293 Squalamine increases vagal afferent firing frequency in aging mice," J. of the Canadian Association of Gastroenterology, 1 (2018), Abstract.
Williams, et al., "Squalamine Treatment of Human Tumors in nu/nu Mice Enhances Platinum-based Chemotherapies1," American Associate ion for Cancer Research, vol. 7, pp. 724-733 (Mar. 2001).
Wimo, et al., "The Worldwide Economic Impact of Dementia 2010," Alzheimer's & Dementia, vol. 9, pp. 1-11 (2013).
Wu P, Duan F, Luo C, et al. Characteristics of Ocular Findings of Patients With Coronavirus Disease 2019 (COVID-19) in Hubei Province, China. JAMA Ophthalmol., pp. 575-578 (Mar. 2020).
Yancopoulou et al., "Tau and alpha-synuclein inclusions in a case of familial frontotemporal dementia and progressive aphasia," J. Neuropathol. Exp. Neurol., 64(3):245-53 (2005).
Zahodne et al., "Mood and motor trajectories in Parkinson's disease: multivariate latent growth curve modeling," Neuropsychology, 26:71-80 (2012).
Zasloff et al., "Squalamine as a broad-spectrum systemic antiviral agent with therapeutic potential," Proc. Natl. Acad. Sci. USA, 108(38): 15978-15983 (2011).
Zasloff, et al., "A spermine-coupled cholesterol metabolite from the shark with potent appetite suppressant and antidiabetic properties," International Journ. of Obseity, vol. 25, pp. 689-697 (2001).
Zhang et al., "Hypothalamic programming of systemic ageing involving IKK-ß, NF-? B and GnRH," Nature, 497: pp. 211-216 (2013).
Zhang et al., "Hypothalamic stem cells control ageing speed partly through exosomal miRNAs," Nature, 548(7665): pp. 52-57 (2017).
Zhao et al., "A comparative study of the amount of a-synuclein in ischemic stroke and Parkinson's disease," Neurol. Sci., 37(5):749-54 (May 2016).
Zinsmeister et al., "Pharmacodynamic and clinical endpoints for functional colonic disorders: statistical considerations," Dig. Dis. Sci., 58:509-18 (2013).
Fortanet et al., Allosteric Inhibition of SHP2: Identification of a Potent, Selective, and Orally Efficacious Phosphatase Inhibitor. J Med Chem 59, 7773-7782 (2016).
Fukunaga, et al., "Role of MAP kinase in neurons," *Mol Neurobiol* 16, 79-95 (1998).
Hofmann, et al., "Bile salts of vertebrates: structural variation and possible evolutionary significance," J Lipid Res 51, 226-246 (2010).
S. Huber et al., IL-22BP is regulated by the inflammasome and modulates tumorigenesis in the intestine. Nature 491, 259-263 (2012).
Javitt, "25R,26-Hydroxycholesterol revisited: synthesis, metabolism, and biologic roles," J Lipid Res 43, 665-670 (2002).
Kimura, et al., "Profile of urinary bile acids in infants and children: developmental pattern of excretion of unsaturated ketonic bile acids and 7beta-hydroxylated bile acids," Pediatr. Res 45, 603-609 (1999).
Krishnan, et al., "Targeting the disordered C terminus of PTP1B with an allosteric inhibitor," Nat Chem Biol 10, 558-566 (2014).
Kuo, et al., "Tyrosine phosphatases Shp1 and Shp2 have unique and opposing roles in oligodendrocyte development," J Neurochem 113, 200-212 (2010).
Lantz, et al., "Inhibition of PTP1B by trodusquemine (MSI-1436) causes fat-specific weight loss in diet-induced obese mice," Obesity (Silver Spring) 18, 1516-1523 (2010).
Lee, et al., "Protein tyrosine phosphatase-PEST and beta8 integrin regulate spatiotemporal patterns of RhoGDI1 activation in migrating cells," *Mol Cell Biol* 35, 1401-1413 (2015).

B

Figures 10A-C
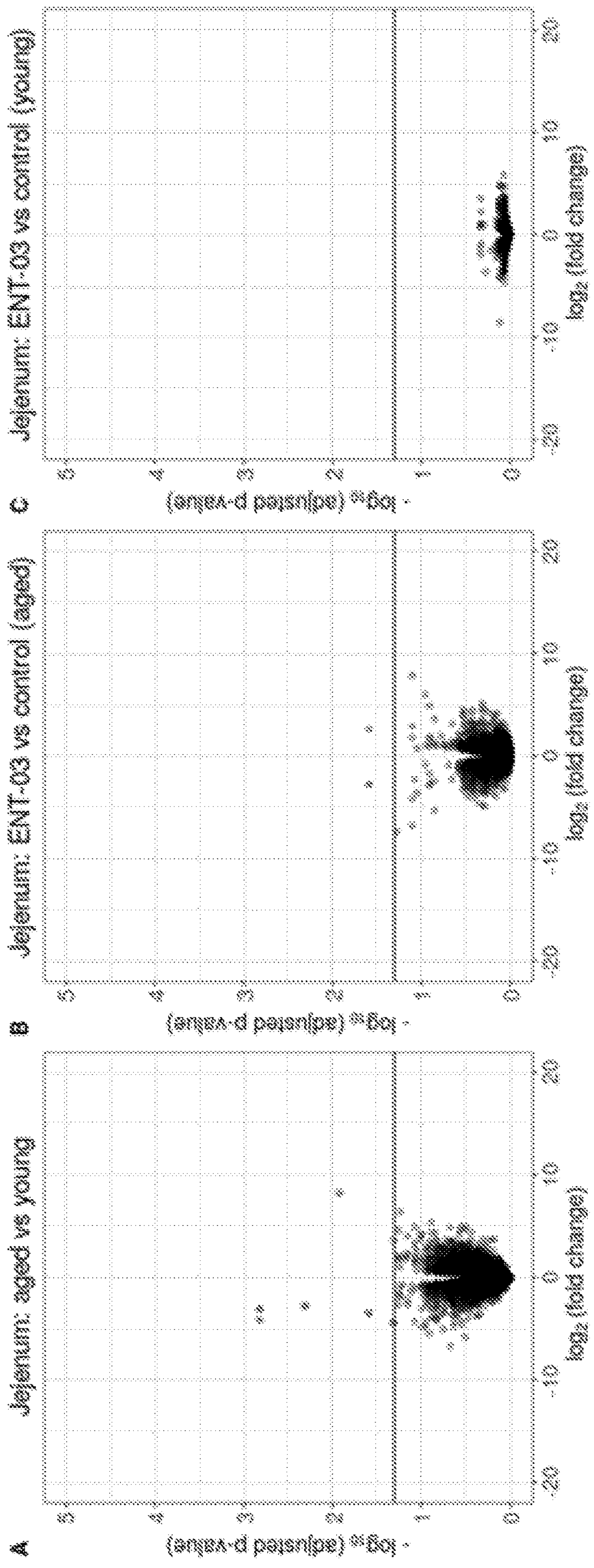

Figures 10D-F
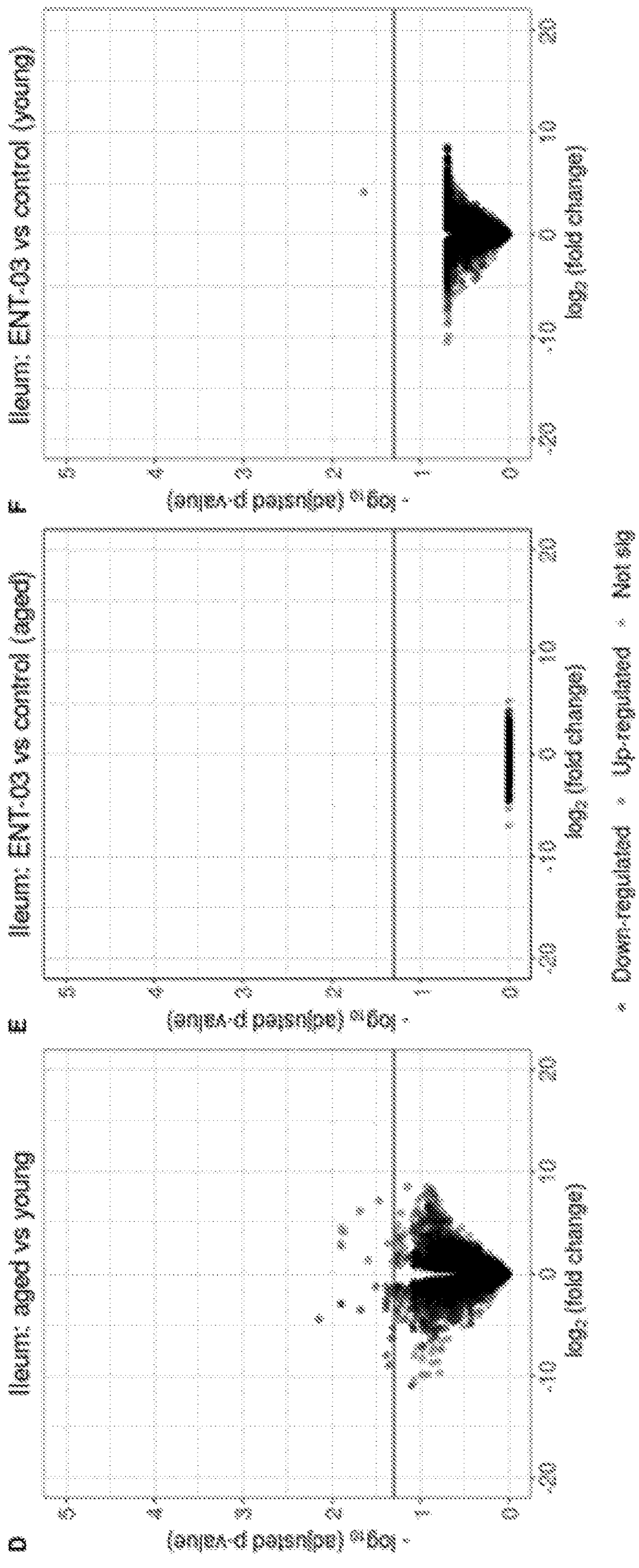

Transcripts down-regulated in ageing and up-regulated in treatment.

HUMAN AMINOSTEROL ENT-03 COMPOUNDS, RELATED COMPOSITIONS COMPRISING THE SAME, AND METHODS OF USING THE SAME

CROSS-REFERENCE TO RELATED APPLICATIONS

This application is the U.S. National Stage of International Patent Application No. PCT/US2020/044390, filed Jul. 31, 2020, which claims priority to U.S. Provisional Patent Application Nos. 62/882,358, filed Aug. 2, 2019, and Application No. 63/041,031, filed Jun. 18, 2020. The contents of these applications are incorporated herein by reference in their entirety.

FIELD

The present application relates generally to aminosterol compounds for the treatment of human disease.

BACKGROUND

Aminosterols are amino derivatives of a sterol. Squalamine is the most abundant member of a larger aminosterol family comprising at least 12 related compounds (Rao et al., 2000).

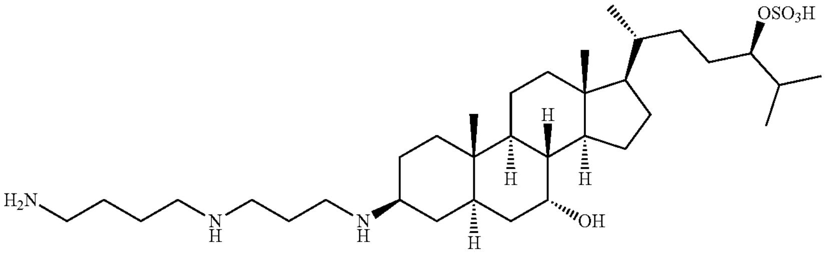

squalamine

The discovery of squalamine, the structure of which is shown above, was reported by Michael Zasloff in 1993 (U.S. Pat. No. 5,192,756).

Exemplary aminosterols also include ENT-02, also known as aminosterol 1436, trodusquemine, and MSI-1436. These aminosterols (U.S. Pat. No. 5,192,756) exhibit diverse pharmacological activity in mammalian systems. Aminosterol 1436 causes weight loss and adipose tissue mobilization in vertebrates (Zasloff et al., 2001).

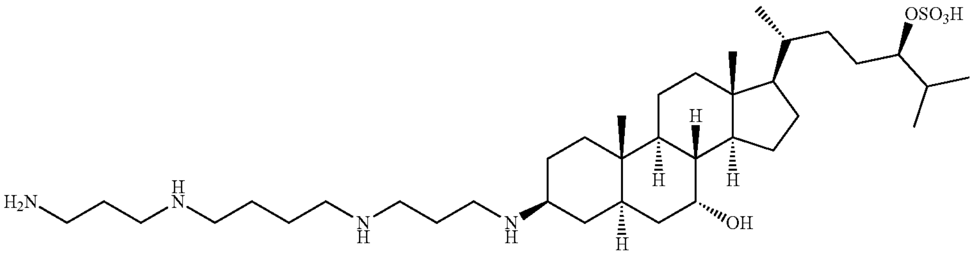

aminosterol 1436

Aminosterol 1436 was shown to act within the nuclei of the hypothalamus involved in appetite and energy balance, and to reverse insulin resistance in both diet-induced and genetic models in mice and rats. The compound was shown to inhibit PTP1B, the phosphatase that turns off the activated insulin receptor, with evidence of its activity in vivo, on the hypothalamic insulin receptors. Phase 1 human clinical trials of intravenously administered Aminosterol 1436 in obese subjects demonstrated improvement in insulin sensitivity.

With the recognition that Aminosterol 1436 exhibited PTP1B inhibition in vivo, numerous studies were conducted. These included: amelioration of the metabolic syndrome in a mouse model of hypothalamic insulin resistance; the reversal of atherosclerosis in LDL receptor knockout mice; the inhibition of the growth of malignancy; stimulation of the regeneration of tail and heart muscle in zebrafish; regenerative repair of myocardial infarction and traumatic limb muscle injury by mobilizing stem cells in adult mice; relief of stress-induced anxiety in mice by targeting the mGluR5 receptors of the limbic system; reversal of memory impairment and normalization of behavior and reduction in neuronal loss in beta amyloid and tau mouse models of Alzheimer's disease via a neuronal PTP1B dependent mechanism; reduction in the toxicity of beta amyloid aggregates in vitro and in a *C. elegans* model of Alzheimer's disease (Limbocker et al., 2019); and reduction in toxic alpha synuclein aggregate formation and an increase in lifespan in a *C. elegans* Parkinson's model (Perni et al., 2018).

Several clinical trials have been conducted relating to the use of Aminosterol 1436, including: (1) ClinicalTrials.gov Identifier NCT00509132 for "A Phase I, Double-Blind, Randomized, Placebo-Controlled Ascending IV Single-Dose Tolerance and Pharmacokinetic Study of Trodusquemine in Healthy Volunteers," by Genaera Corp.; (2) ClinicalTrials.gov Identifier NCT00606112 for "A Single Dose, Tolerance and Pharmacokinetic Study in Obese or Overweight Type 2 Diabetic Volunteer," by Genaera Corp.; (3) ClinicalTrials.gov Identifier NCT00806338 for "An Ascending Multi-Dose, Tolerance and Pharmacokinetic Study in Obese or Overweight Type 2 Diabetic Volunteers," by Genaera Corp.; and (4) ClinicalTrials.gov Identifier: NCT02524951 for "Safety and Tolerability of MSI-1436C in Metastatic Breast Cancer," by DepyMed Inc.

There is a need in the art for novel aminosterol compounds and methods of using the same. The present disclosure satisfies these needs.

SUMMARY

In one aspect, an aminosterol compound is provided having the formula:

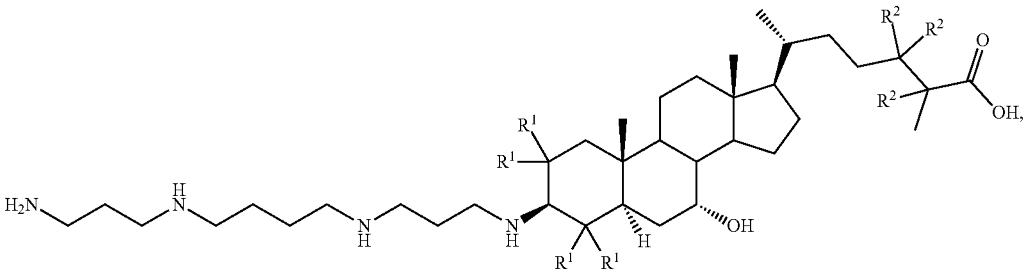

wherein: $R^1$ is H or D; and $R^2$ is H or D; provided that all of $R^1$ are H, all of $R^2$ are H, or all of $R^1$ and $R^2$ are H, or a pharmaceutically acceptable salt, solvate, prodrug, or derivative thereof.

In one embodiment, the aminosterol compound has the formula:

ENT-03 (Compound III)

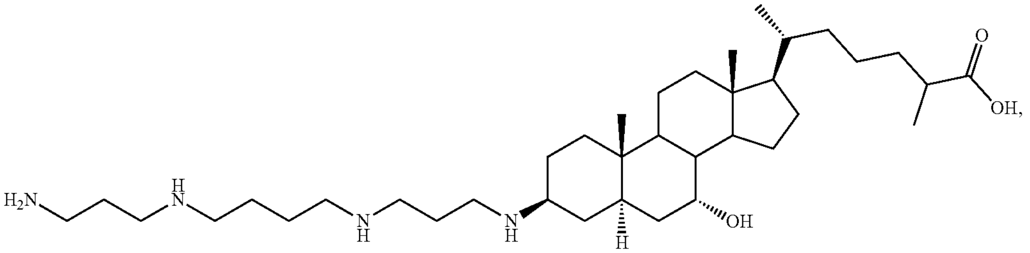

or a pharmaceutically acceptable salt, solvate, prodrug, or derivative thereof.

In one embodiment, the aminosterol has the formula:

$C_{25}$ (*R*) ENT-03 ($C_{25}$ (*R*) Compound III)

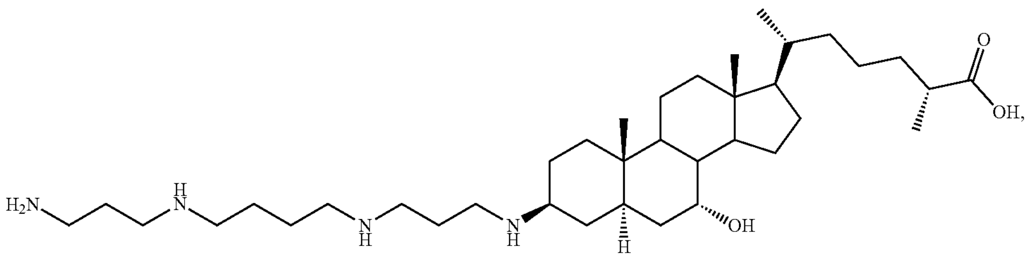

or a pharmaceutically acceptable salt, solvate, prodrug, or derivative thereof.

In one embodiment, the aminosterol has the formula:

ENT-03-d4 (Compound III-d4)

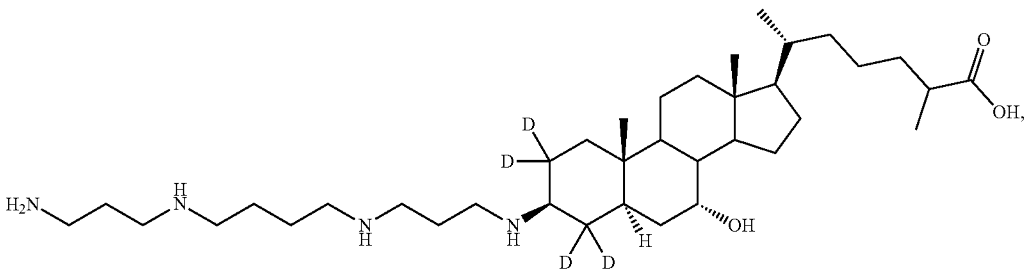

or a pharmaceutically acceptable salt, solvate, prodrug, or derivative thereof.

In one embodiment, the aminosterol has the formula:

ENT-03-d3 (Compound III-d3)

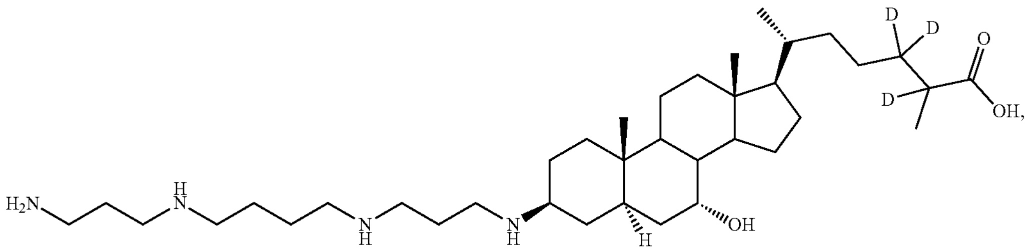

or a pharmaceutically acceptable salt, solvate, prodrug, or derivative thereof.

In another aspect, an aminosterol compound having the formula:

Compound IV (Δ5 ENT-03)

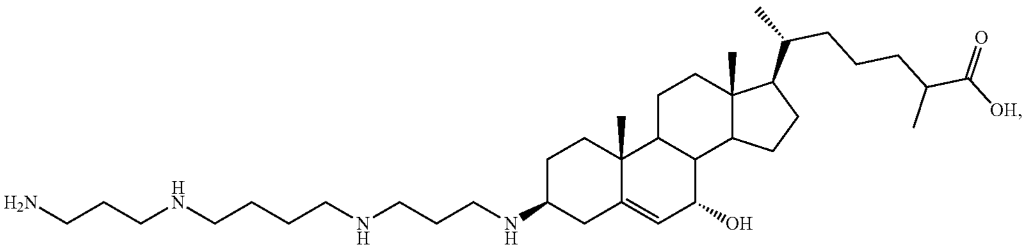

is provided, or a pharmaceutically acceptable salt, solvate, prodrug, or derivative thereof.

In one embodiment, the aminosterol compound has the formula:

$C_{25}$ (*R*) Compound IV (Δ5 ENT-03)

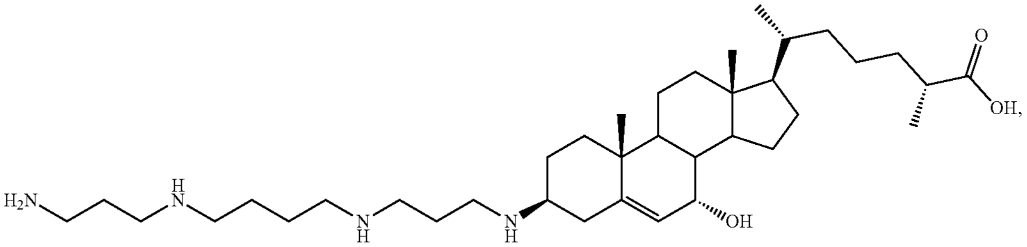

or a pharmaceutically acceptable salt, solvate, prodrug, or derivative thereof.

In one aspect, an aminosterol compound having the formula:

Compound V (Δ4 ENT-03)

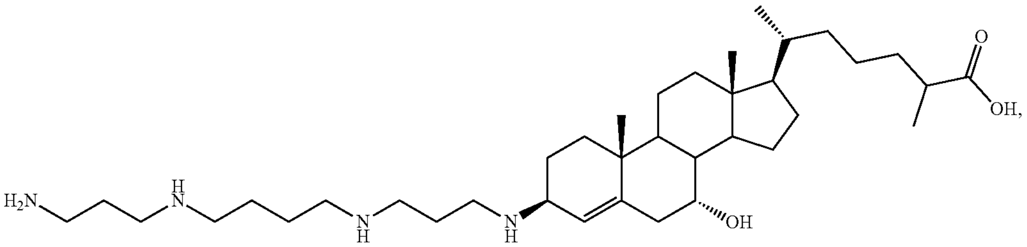

is provided, or a pharmaceutically acceptable salt, solvate, prodrug, or derivative thereof.

In one embodiment, the aminosterol compound has the formula:

$C_{25}$ (*R*) Compound V (Δ4 ENT-03)

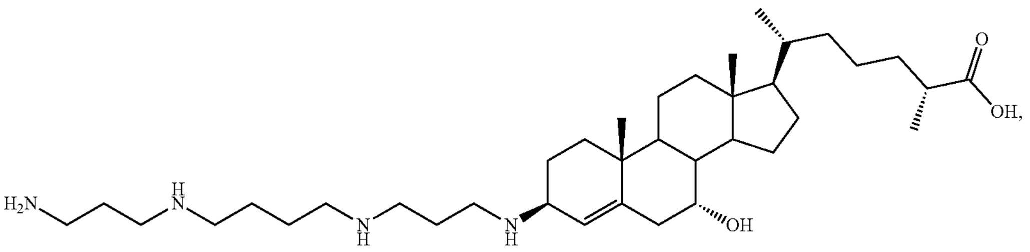

or a pharmaceutically acceptable salt, solvate, prodrug, or derivative thereof.

In another aspect, an aminosterol compound having the formula:

Compound IV-P

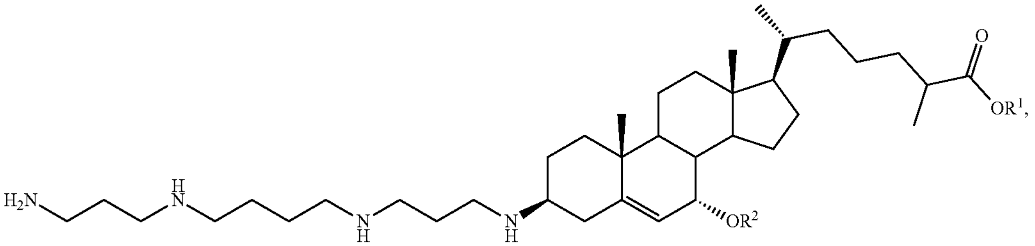

is provided wherein: $R^1$ is H, an optionally substituted aryl, optionally substituted heteroaryl, optionally substituted $C_1$-$C_6$ alkyl, optionally substituted $C_1$-$C_6$ alkynyl, optionally substituted heterocyclyl, optionally substituted $C_3$-$C_8$ cycloalkyl, and optionally substituted $C_1$-$C_6$ alkenyl; and $R^2$ is H or —C(O)$R^3$, wherein $R^3$ is an optionally substituted aryl, optionally substituted heteroaryl, optionally substituted $C_1$-$C_6$ alkyl, optionally substituted $C_1$-$C_6$ alkynyl, optionally substituted heterocyclyl, optionally substituted $C_3$-$C_8$ cycloalkyl, or optionally substituted $C_1$-$C_6$ alkenyl; provided that at least one of $R^1$ and $R^2$ is not H, or a pharmaceutically acceptable salt, solvate, prodrug, or derivative thereof.

In one embodiment, the aminosterol compound has the formula:

$C_{25}$ (*R*) Compound IV-P

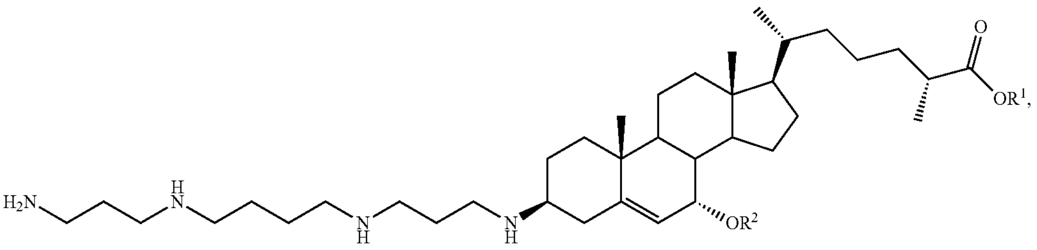

or a pharmaceutically acceptable salt, solvate, prodrug, or derivative thereof.

In another aspect, an aminosterol compound having the formula:

ENT-03-P (Compound III-P)

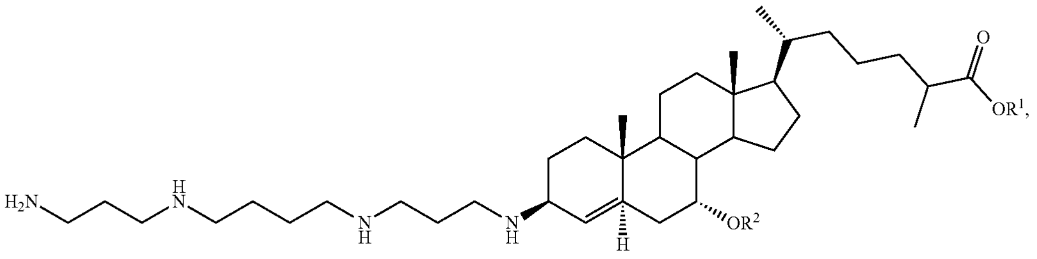

is provided, wherein: $R^1$ is H, optionally substituted aryl, optionally substituted heteroaryl, optionally substituted $C_1$-$C_6$ alkyl, optionally substituted $C_1$-$C_6$ alkynyl, optionally substituted heterocyclyl, optionally substituted $C_3$-$C_8$ cycloalkyl, or optionally substituted $C_1$-$C_6$ alkenyl; and $R^2$ is H or —C(O)$R^3$, wherein $R^3$ is an optionally substituted aryl, optionally substituted heteroaryl, optionally substituted $C_1$-$C_6$ alkyl, optionally substituted $C_1$-$C_6$ alkynyl, optionally substituted heterocyclyl, optionally substituted $C_3$-$C_8$ cycloalkyl, or optionally substituted $C_1$-$C_6$ alkenyl; provided that at least one of $R^1$ and $R^2$ is not H, or a pharmaceutically acceptable salt, solvate, prodrug, or derivative thereof.

In some embodiments, the aminosterol has the formula:

$C_{25}$ (R) ENT-03-P ($C_{25}$ (R) Compound III-P)

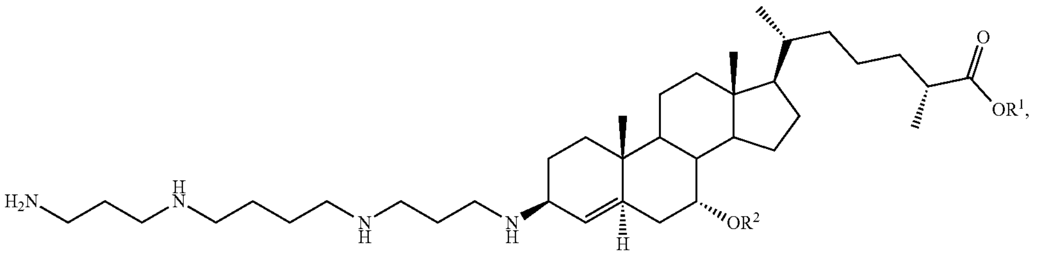

or a pharmaceutically acceptable salt, solvate, prodrug, or derivative thereof.

In another aspect, an aminosterol compound having the formula:

Compound V-P

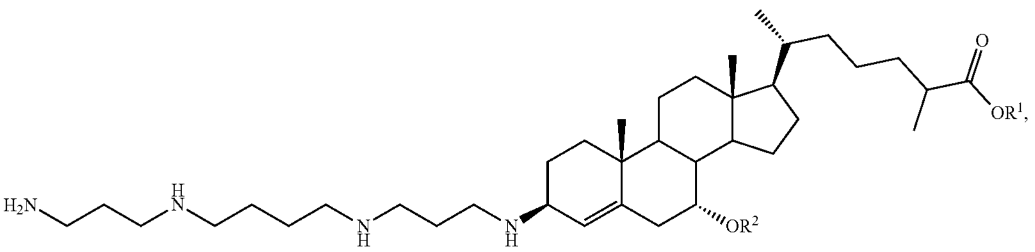

is provided wherein: $R^1$ is H, an optionally substituted aryl, optionally substituted heteroaryl, optionally substituted $C_1$-$C_6$ alkyl, optionally substituted $C_1$-$C_6$ alkynyl, optionally substituted heterocyclyl, optionally substituted $C_3$-$C_8$ cycloalkyl, and optionally substituted $C_1$-$C_6$ alkenyl; and $R^2$ is H or —C(O)$R^3$, wherein $R^3$ is an optionally substituted aryl, optionally substituted heteroaryl, optionally substituted $C_1$-$C_6$ alkyl, optionally substituted $C_1$-$C_6$ alkynyl, optionally substituted heterocyclyl, optionally substituted $C_3$-$C_8$ cycloalkyl, or optionally substituted $C_1$-$C_6$ alkenyl; provided that at least one of $R^1$ and $R^2$ is not H, or a pharmaceutically acceptable salt, solvate, prodrug, or derivative thereof.

In one embodiment, the aminosterol compound has the formula:

$C_{25}$ (R) Compound V-P

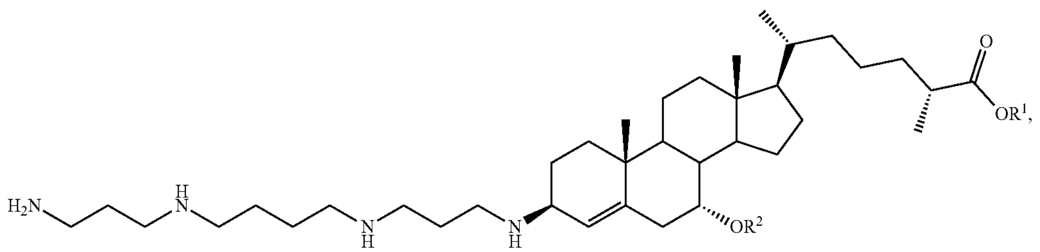

or a pharmaceutically acceptable salt, solvate, prodrug, or derivative thereof.

In some embodiments, the aminosterol is formulated as a pharmaceutically acceptable salt. In some embodiments, the pharmaceutically acceptable salt is a phosphate salt.

In one aspect, a composition comprising an aminosterol compound according to any embodiment herein is provided, the composition comprising at least one pharmaceutically acceptable carrier or excipient. In some embodiments, the composition comprises one or more of the following: (a) an aqueous carrier; (b) a buffer; (c) a sugar; and/or (d) a polyol compound. In some embodiments, the composition comprises at least one additional active agent.

In some embodiments, the composition is formulated (a) for administration selected from the group consisting of oral, pulmonary, rectal, colonic, parenteral, intracisternal, intravaginal, intraperitoneal, intravenous, subcutaneous, intramuscular, nebulization, inhalation, ocular, otic, local, buccal, nasal, and topical administration; (b) into a dosage form selected from the group consisting of liquid dispersions, gels, aerosols, ointments, creams, lyophilized formulations, tablets, capsules; (c) into a dosage form selected from the group consisting of controlled release formulations, fast melt formulations, delayed release formulations, extended release formulations, pulsatile release formulations, and mixed immediate release and controlled release formulations; or (d) any combination of (a), (b), and (c).

In some embodiments, the composition is formulated for oral administration. In some embodiments, the composition is formulated as an oral tablet or capsule. In some embodiments, the composition is formulated for intranasal administration.

In one aspect a method of treating a subject in need is provided, the subject having a condition susceptible to treatment with an aminosterol, the method comprising administering to the subject the composition according to any embodiment herein. In some embodiments, the condition is correlated with abnormal alpha-synuclein pathology and/or dopaminergic dysfunction.

In another aspect, a method of treating, preventing, and/or slowing the onset or progression of a condition or disorder, or a related symptom, correlated with abnormal alpha-synuclein pathology and/or dopaminergic dysfunction, in a subject in need, is provided, the method comprising administering a therapeutically effective amount of a composition according to any embodiment herein.

In some embodiments, (a) the symptom is selected from the group consisting of constipation, hallucinations, cognitive impairment, and inflammation; (b) the symptom is correlated with a synucleopathy, a neurodegenerative disease, a neurological disease or disorder, a psychological and/or behavior disorder, or a cerebral or general ischemic disorder or condition; (c) the condition or disorder is a synucleopathy, neurodegenerative disease, or neurological disease or disorder; (d) the condition or disorder is a psychological and/or behavior disorder; or (e) the condition or disorder is a cerebral or general ischemic disorder or condition.

In some embodiments, (a) the synucleopathy, neurodegenerative disease, or neurological disease or disorder is selected from the group consisting of Parkinson's disease, Alzheimer's disease, schizophrenia, multiple system atrophy, Lewy body dementia, dementia with Lewy bodies, Huntington's Disease, Multiple Sclerosis, Amyotorphic Lateral Sclerosis, Friedreich's ataxia, vascular dementia, spinal muscular atrophy, supranuclear palsy, progressive nuclear palsy, frontotemporal dementia, progressive nuclear palsy, Guadeloupian Parkinsonism, spinocerebellar ataxia, parkinsonism, traumatic brain injury, degenerative processes associated with aging, and dementia of aging; (b) the psychological or behavior disorder is selected from the group consisting of depression, autism, autism spectrum disorder, down syndrome, Gaucher's disease, Krabbe's disease, lysosomal conditions affecting glycosphingolipid metabolism, ADHD, agitation, anxiety, delirium, irritability, illusion and delusions, amnesia, apathy, bipolar disorder, disinhibition, aberrant motor and obsessive-compulsive behaviors, addiction, cerebral palsy, epilepsy, major depressive disorder, and sleep disorders such as REM sleep behavior disorder (RBD), sleep fragmentation, REM behavior disorder, circadian rhythm dysfunction, sleep apnea, and cognitive impairment; or (c) the cerebral or general ischemic disorder or condition is selected from the group consisting of microangiopathy, intrapartum, cerebral ischemia, cerebral ischemia during/after cardiac arrest or resuscitation, cerebral ischemia due to intraoperative problems, cerebral ischemia during carotid surgery, chronic cerebral ischemia due to stenosis of blood-supplying arteries to the brain, sinus thrombosis or thrombosis of cerebral veins, cerebral vessel malformations, diabetic retinopathy, high cholesterol, myocardial infarction, cardiac insufficiency, cardiac failure, congestive heart failure, myocarditis, pericarditis, perimyocarditis, coronary heart disease, angina pectoris, congenital heart disease, shock, ischemia of extremities, stenosis of renal arteries, diabetic retinopathy, thrombosis associated with malaria, artificial heart valves, anemias, hypersplenic syndrome, emphysema, lung fibrosis, erectile dysfunction, cardiac conduction defects, high blood pressure, low blood pressure, and pulmonary edema.

In another aspect, a method of treating, preventing, and/or slowing the onset or progression a cerebral or general ischemic disorder and/or a related symptom, correlated with abnormal alpha-synuclein pathology and/or dopaminergic dysfunction, in a subject in need, is provided, the method comprising administering a therapeutically effective amount of a composition according to any embodiment herein.

In one embodiment, the cerebral or general ischemic disorder and/or a related symptom is selected from the group consisting of microangiopathy, intrapartum cerebral ischemia, cerebral ischemia during/after cardiac arrest or resuscitation, cerebral ischemia due to intraoperative problems, cerebral ischemia during carotid surgery, chronic cerebral ischemia due to stenosis of blood-supplying arteries to the brain, sinus thrombosis or thrombosis of cerebral veins, cerebral vessel malformations, diabetic retinopathy, high blood pressure, low blood pressure, high cholesterol, myocardial infarction, cardiac insufficiency, cardiac failure, congestive heart failure, myocarditis, pericarditis, perimyocarditis, coronary heart disease, angina pectoris, congenital heart disease, shock, ischemia of extremities, stenosis of renal arteries, diabetic retinopathy, thrombosis associated with malaria, artificial heart valves, anemias, hypersplenic syndrome, emphysema, lung fibrosis, erectile dysfunction, cardiac conduction defects (CCDs) and/or a related symptom, and pulmonary edema.

In one aspect, a method of inhibiting a regulatory phosphatase, such as protein tyrosine phosphatase 1B (PTP1B), in a subject is provided, the method comprising administering to the subject a therapeutically effective amount of a composition according to any embodiment herein. Other regulatory phosphatases inhibited by the aminosterols described herein are also detailed herein. In some embodiments, the inhibition in one or more regulatory phosphatases is selected from about 1% to about 10%, about 10% to about 20%, about 20% to about 30%, about 30% to about 40%, about 40% to about 50%, about 50% to about 60%, about 60% to about 70%, about 70% to about 80%, about 80% to about 90%, and about 90% to about 100%.

In another aspect, a method of suppressing, preventing and/or slowing the onset or progression of appetite or weight gain, and/or one or more related symptoms, in a subject in need thereof is provided, the method comprising administering to the subject a therapeutically effective amount of a composition according to any embodiment herein.

In another aspect, a method of increasing gene transcription in the gut of a subject is provided, the method comprising administering to the subject a therapeutically effective amount of an aminosterol compound of any embodiment herein, or a pharmaceutically acceptable salt, solvate, prodrug, or derivative thereof.

In some embodiments, the increase in gene transcription is for one or more genes selected from caspase 14, collagen type XVII alpha 1, corneodesmosin, cornifelin, cystatin E/M, dermokine, desmocollin 1, desmoglein 1 beta, filaggrin, gap junction protein beta 4, gap junction protein beta 6, H19 imprinted maternally expressed transcript, hornerin, kallikrein related-peptidase 7 chymotryptic stratum, keratin 1, keratin 10, keratinocyte differentiation associated protein, keratinocyte expressed proline-rich, late cornified envelope 1A1, late cornified envelope 1A2, late cornified envelope 1B, late cornified envelope 1C, late cornified envelope 1E, late cornified envelope 1F, late cornified envelope 1G, late cornified envelope 1H, late cornified envelope 11, late cornified envelope 1J, late cornified envelope 1L, late cornified envelope 1M, late cornified envelope 3C, late cornified envelope 3E, late cornified envelope 3F, lectin galactose binding soluble 7, loricrin, sciellin, myoglobin, myosin binding protein C slow-type, myosin heavy polypeptide 1 skeletal muscle, myosin heavy polypeptide 8 skeletal muscle, myosin light chain phosphorylatable fast ske, myosin light polypeptide 3, myozenin 1, myozenin 2, and titin-cap.

In some embodiments, the method further comprises administering to the subject one or more non-aminosterol compounds that upregulate or down regulate one or more genes selected from caspase 14, collagen type XVII alpha 1, corneodesmosin, cornifelin, cystatin E/M, dermokine, desmocollin 1, desmoglein 1 beta, filaggrin, gap junction protein beta 4, gap junction protein beta 6, H19 imprinted maternally expressed transcript, hornerin, kallikrein related-peptidase 7 chymotryptic stratum, keratin 1, keratin 10, keratinocyte differentiation associated protein, keratinocyte expressed proline-rich, late cornified envelope 1A1, late cornified envelope 1A2, late cornified envelope 1B, late cornified envelope 1C, late cornified envelope 1E, late cornified envelope 1F, late cornified envelope 1G, late cornified envelope 1H, late cornified envelope 11, late cornified envelope 1J, late cornified envelope 1L, late cornified envelope 1M, late cornified envelope 3C, late cornified envelope 3E, late cornified envelope 3F, lectin galactose binding soluble 7, loricrin, sciellin, myoglobin, myosin binding protein C slow-type, myosin heavy polypeptide 1 skeletal muscle, myosin heavy polypeptide 8 skeletal muscle, myosin light chain phosphorylatable fast ske, myosin light polypeptide 3, myozenin 1, myozenin 2, and titin-cap. The non-aminosterol compound may be any compound known in the art to regulate any of the aforementioned genes.

In some embodiments, the increase in gene transcription is selected from about 1% to about 10%, about 10% to about 20%, about 20% to about 30%, about 30% to about 40%, about 40% to about 50%, about 50% to about 60%, about 60% to about 70%, about 70% to about 80%, about 80% to about 90%, about 90% to about 100%, about 100% to about 125%, about 125% to about 150%, about 150% to about 175%, about 175% to about 200%, about 200% to about 250%, about 250% to about 300%, about 300% to about 350%, about 350% to about 400%, about 400% to about 450%, about 500% to about 600%, about 600% to about 700%, about 700% to about 800%, about 800% to about 900%, about 900% to about 1000%, or about 1000% to about 1500%. The increase in gene transcription can be measured, for example, by qualitatively or quantitatively measuring an increase in expression of a protein correlated with transcription of the relevant gene, or using a clinically recognized scale or tool.

In one aspect, encompassed is method of inhibiting one or more regulatory phosphatases to achieve a therapeutic or prophylactic benefit comprising administering a therapeutically effective amount of aminosterol compound or a composition comprising the same, as described herein.

In some embodiments, the method of administration comprises oral, nasal, pulmonary, sublingual, buccal, rectal, vaginal, intravenous, intra-arterial, intradermal, intraperitoneal, intrathecal, intramuscular, epidural, intracerebral, intracerebroventricular, transdermal, or any combination thereof. In some embodiments, the method of administration is nasal administration, oral administration, or a combination thereof.

In some embodiments, the therapeutically effective amount of the aminosterol compound or a pharmaceutically acceptable salt, solvate, prodrug, or derivative thereof comprises: (a) about 0.1 to about 20 mg/kg body weight of the subject; (b) about 0.1 to about 15 mg/kg body weight of the subject; (c) about 0.1 to about 10 mg/kg body weight of the subject; (d) about 0.1 to about 5 mg/kg body weight of the subject; or (e) about 0.1 to about 2.5 mg/kg body weight of the subject.

In some embodiments, the therapeutically effective amount of the aminosterol compound or a pharmaceutically acceptable salt, solvate, prodrug, or derivative thereof comprises: (a) about 0.001 to about 500 mg/day; (b) about 0.001 to about 250 mg/day; (c) about 0.001 to about 125 mg/day; (d) about 0.001 to about 50 mg/day; (e) about 0.001 to about 25 mg/day; (f) about 0.001 to about 10 mg/day; (g) about 0.001 to about 6 mg/day; (h) about 0.001 to about 4 mg/day; or (i) about 0.001 to about 2 mg/day.

In some embodiments, the method of administration comprises oral administration and the therapeutically effective amount of the aminosterol compound or a pharmaceutically acceptable salt, solvate, prodrug, or derivative thereof comprises: (a) about 1 to about 300 mg/day; or (b) about 25 to about 500 mg/day.

In some embodiments, the aminosterol compound or a pharmaceutically acceptable salt, solvate, prodrug, or derivative thereof is administered in combination with at least one additional active agent to achieve either an additive or synergistic effect. In some embodiments, the additional active agent is administered via a method selected from the group consisting of (a) concomitantly; (b) as an admixture; (c) separately and simultaneously or concurrently; and (d) separately and sequentially. In some embodiments, the additional active agent is a second aminosterol having a different structure from the aminosterol administered in any embodiment herein.

In some embodiments, administration of the composition comprises administration on an empty stomach, optionally within two hours of the subject waking. In some embodiments, no food is consumed by the subject after about 60 to about 90 minutes from administration of the composition.

In some embodiments, the aminosterol, or a pharmaceutically acceptable salt, solvate, prodrug, or derivative thereof, is of pharmaceutically acceptable grade. In some embodiments, a phosphate salt of the aminosterol is administered. In some embodiments, the subject is a human.

In some embodiments, the method further comprises (a) determining a dosage of the aminosterol or a pharmaceutically acceptable salt, solvate, prodrug, or derivative for the subject, wherein the aminosterol dosage is determined based on the effectiveness of the aminosterol dosage in improving or resolving a symptom being evaluated, (b) followed by administering a composition comprising the dosage of the aminosterol to the subject for a period of time, wherein the method comprises: (i) identifying a symptom to be evaluated, wherein the symptom is susceptible to treatment with an aminosterol; (ii) identifying a starting dosage of an aminosterol thereof for the subject; (iii) administering an escalating dosage of the aminosterol to the subject over a period of time until an effective dosage for the symptom being evaluated is identified, wherein the effective dosage is the aminosterol dosage where improvement or resolution of the symptom is observed, and fixing the aminosterol dosage at that level for that particular symptom in that particular subject. In some embodiments, improvement or resolution of the symptom is measured using a clinically recognized scale or tool.

In some embodiments, the composition is administered orally and: (a) the starting aminosterol dosage ranges from about 10 mg up to about 150 mg/day; (b) the dosage of the aminosterol for the subject following escalation is fixed at a range of from about 25 mg up to about 500 mg/day; and/or (c) the dosage of the aminosterol or a salt or derivative thereof is escalated in about 25 mg increments.

In some embodiments, the composition is administered intranasally and: (a) the starting aminosterol dosage ranges from about 0.001 mg to about 3 mg/day; (b) the dosage of the aminosterol for the subject following escalation is fixed at a range of from about 0.001 mg up to about 6 mg/day; (c) the dosage of the aminosterol for the subject following escalation is a dosage which is subtherapeutic when given orally or by injection; and/or (c) the dosage of the aminosterol is escalated in increments of about 0.1, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, about 1, about 1.1, about 1.2, about 1.3, about 1.4, about 1.5, about 1.6, about 1.7, about 1.8, about 1.9, or about 2 mg.

In some embodiments, the dosage of the aminosterol is escalated every about 3 to about 5 days. In some embodiments, the starting aminosterol dosage is higher if the symptom being evaluated is severe.

In some embodiments, the symptom is correlated with abnormal alpha-synuclein pathology and/or dopaminergic dysfunction. In some embodiments, the symptom to be evaluated is selected from the group consisting of: (a) at least one non-motor aspect of experiences of daily living as defined by Part I of the Unified Parkinson's Disease Rating Scale selected from the group consisting of cognitive impairment, hallucinations and psychosis, depressed mood, anxious mood, apathy, features of dopamine dysregulation syndrome, sleep problems, daytime sleepiness, pain, urinary problems, constipation problems, lightheadedness on standing, and fatigue; (b) at least one motor aspect of experiences of daily living as defined by Part II of the Unified Parkinson's Disease Rating Scale selected from the group consisting of speech, saliva and drooling, chewing and swallowing, eating tasks, dressing, hygiene, handwriting, turning in bed, tremors, getting out of a bed, a car, or a deep chair, walking and balance, and freezing; (c) at least one motor symptom identified in Part III of the Unified Parkinson's Disease Rating Scale selected from the group consisting of speech, facial expression, rigidity, finger tapping, hand movements, pronation-supination movements of hands, toe tapping, leg agility, arising from chair, gait, freezing of gait, postural stability, posture, body bradykinesia, postural tremor of the hands, kinetic tremor of the hands, rest tremor amplitude, and constancy of rest tremor; (d) at least one motor complication identified in Part IV of the Unified Parkinson's Disease Rating Scale selected from the group consisting of time spent with dyskinesias, functional impact of dyskinesias, time spent in the off state, functional impact of fluctuations, complexity of motor fluctuations, and painful off-state dystonia; (e) constipation; (f) depression; (g) cognitive impairment; (h) sleep problems or sleep disturbances; (i) circadian rhythm dysfunction; (j) hallucinations; (k) fatigue; (l) REM disturbed sleep; (m) REM behavior disorder; (n) erectile dysfunction; (o) apnea; (p) postural hypotension; (q) correction of blood pressure or orthostatic hypotension; (r) nocturnal hypertension; (s) regulation of temperature; (t) improvement in breathing or apnea; (u) correction of cardiac conduction defect; (v) amelioration of pain; (w) restoration of bladder sensation and urination; (x) urinary incontinence; and/or (y) control of nocturia.

In some embodiments, the symptom to be evaluated is constipation, and wherein: (a) the fixed escalated aminosterol dosage for constipation is defined as the aminosterol dosage that results in a complete spontaneous bowel movement (CSBM) within 24 hours of dosing on at least 2 of 3 days at a given dosage; (b) if average complete spontaneous bowel movement (CSBM) or average spontaneous bowel movement (SBM) is greater than or equal to 1 per week, then the starting aminosterol dosage prior to escalation is 75 mg/day; and/or (c) if average CSBM or SBM is less than 1 per week, then the starting aminosterol dosage prior to escalation is 150 mg/day.

In one aspect, a method of making an aminosterol of formula:

ENT-03 (Compound III)

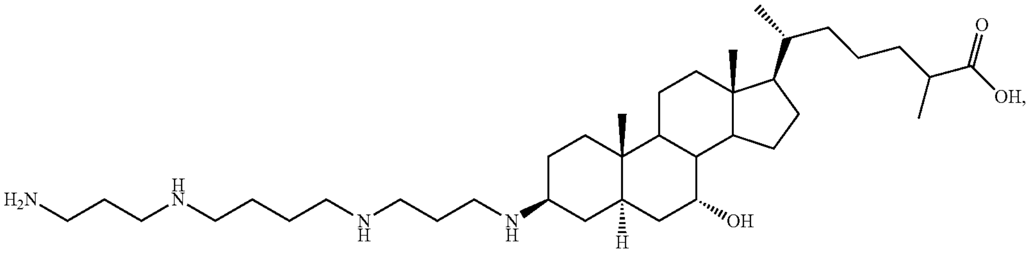

is provided, the method comprising stimulating the addition of spermine to Compound Ia:

Compound Ia

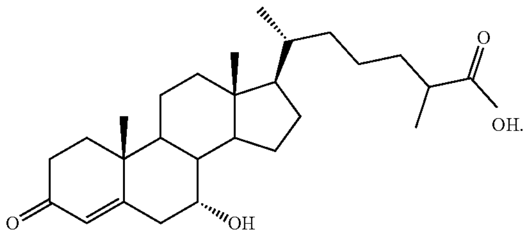

In some embodiments, (a) the aminosterol is produced in vivo in a subject; or (b) the aminosterol is produced in vitro.

In another aspect, a method of suppressing the formation of an aminosterol of formula:

ENT-03 (Compound III)

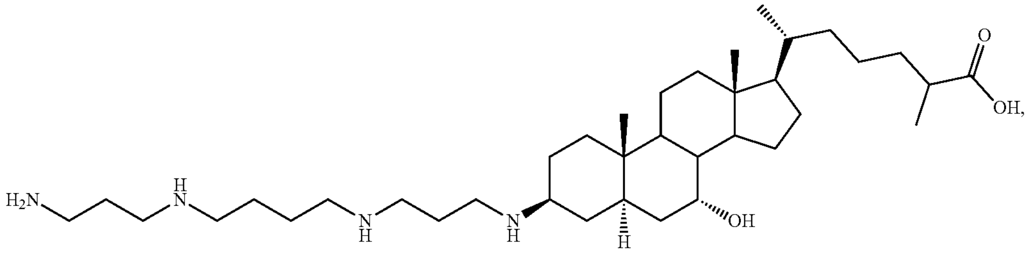

is provided, the method comprising suppressing the addition of spermine to Compound Ia:

Compound Ia

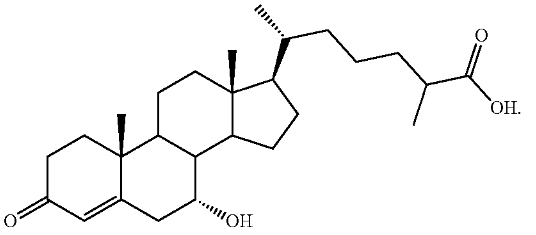

In some embodiments, (a) the addition of spermine to Compound Ia is suppressed in vivo in a subject; or (b) the addition of spermine to Compound Ia is suppressed in vitro.

In some embodiments, Compound Ia has the formula:

ENT-01 (Compound I)

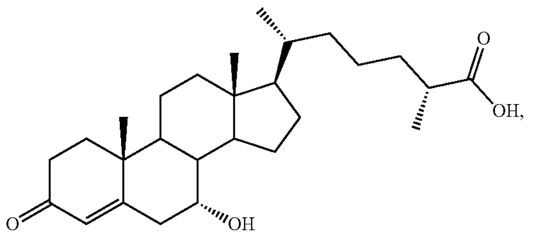

and ENT-03 (Compound III) has the formula:

$C_{25}$ (R) ENT-03 ($C_{25}$ (R) Compound III)

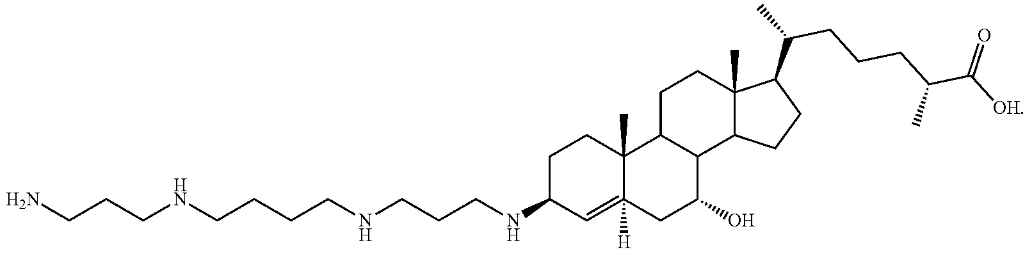

In another aspect, a method of making an aminosterol of formula:

Compound IV

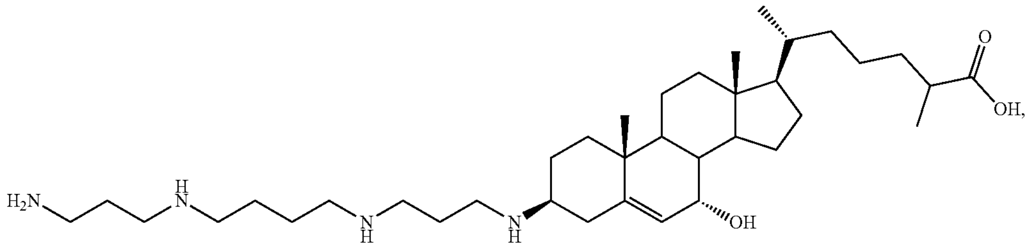

is provided, the method comprising stimulating the addition of spermine to Compound Ia:

Compound Ia

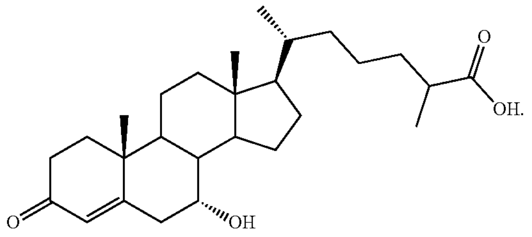

In some embodiments, (a) the aminosterol is produced in vivo in a subject; or (b) the aminosterol is produced in vitro.

In another aspect, a method of suppressing the formation of an aminosterol of formula:

Compound IV

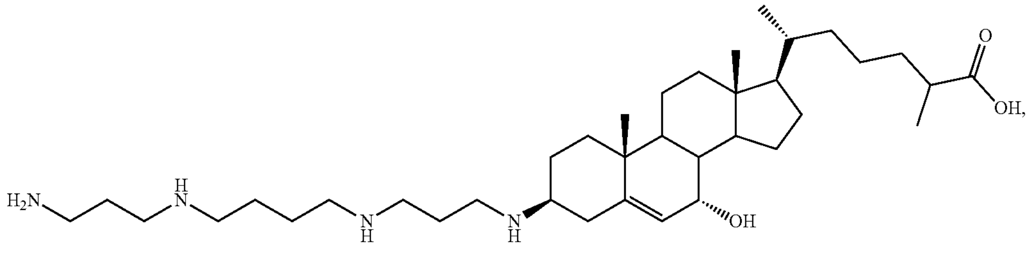

is provided, the method comprising suppressing the addition of spermine to Compound Ia:

Compound Ia

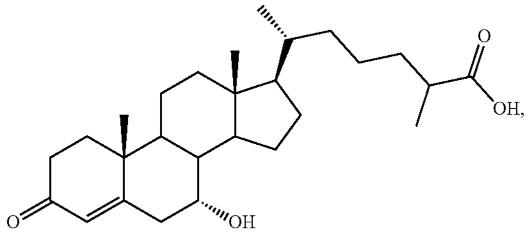

In some embodiments, (a) the addition of spermine to Compound Ia is suppressed in vivo in a subject; or (b) the addition of spermine to Compound Ia is suppressed in vitro.

In some embodiments, Compound Ia has the formula:

(Compound I; ENT-01)

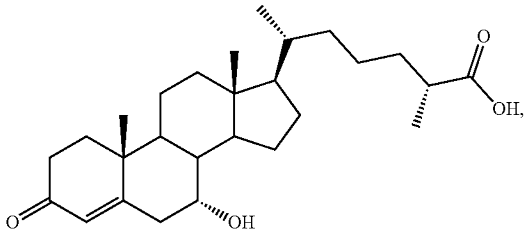

and Compound IV has the formula:

($C_{25}$ (R) Compound IV)

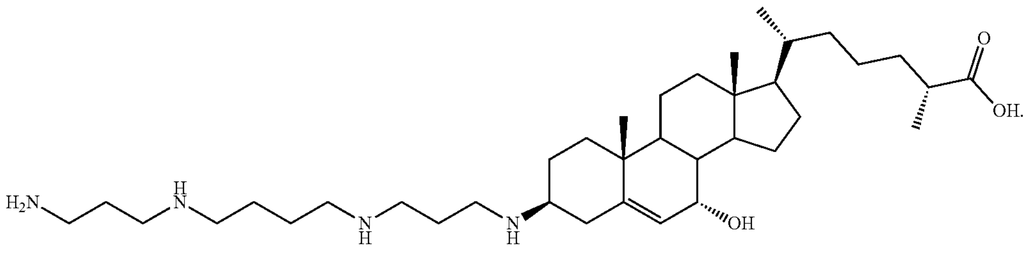

In another aspect, a method of producing an aminosterol of formula:

Compound V

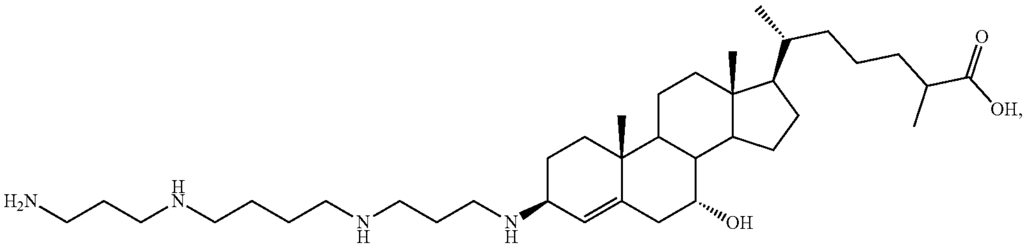

is provided, the method comprising stimulating the addition of spermine to Compound Ia:

Compound Ia

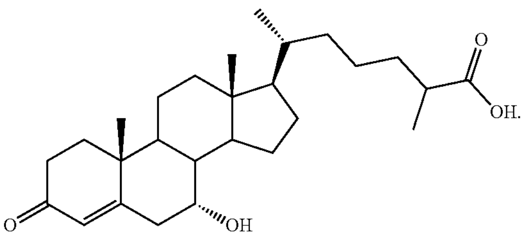

In some embodiments, (a) the aminosterol is produced in vivo in a subject; or (b) the aminosterol is produced in vitro.

In another aspect, a method of suppressing the formation of an aminosterol of formula:

Compound V

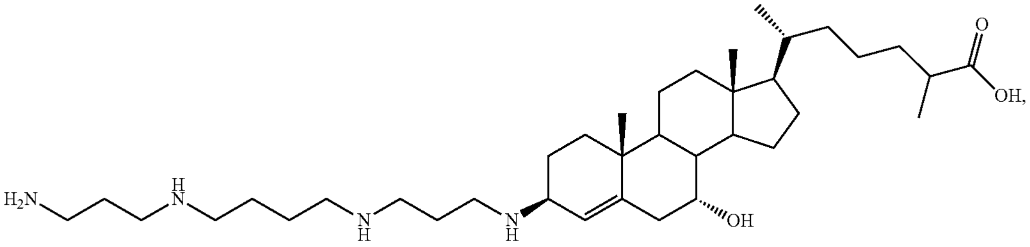

is provided, the method comprising suppressing the addition of spermine to Compound Ia:

Compound Ia

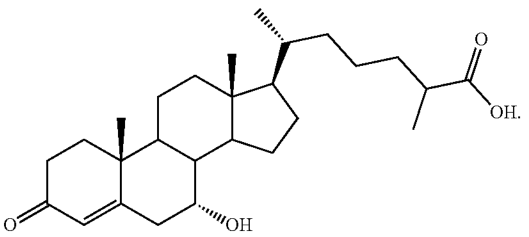

In some embodiments, (a) the addition of spermine to Compound Ia is suppressed in vivo in a subject; or (b) the addition of spermine to Compound Ia is suppressed in vitro.

In some embodiments, Compound Ia has the formula:

Compound I

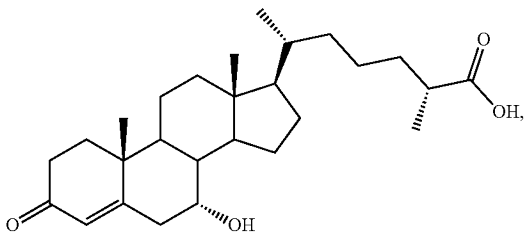

ENT-01 and Compound V has the formula:

C25 (R) Compound V

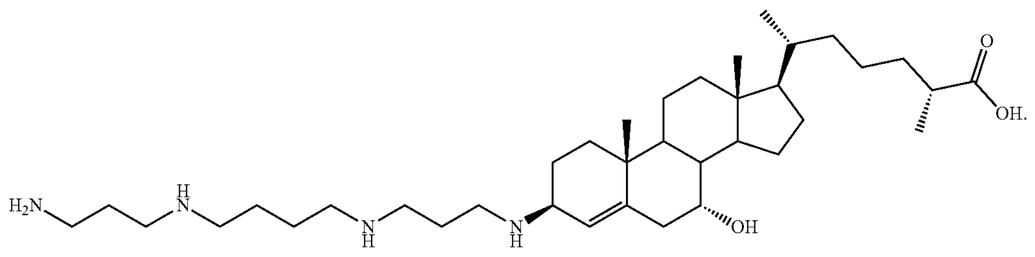

Both the foregoing summary and the following description of the drawings and detailed description are exemplary and explanatory. They are intended to provide further details of the disclosure, but are not to be construed as limiting. Other objects, advantages, and novel features will be readily apparent to those skilled in the art from the following detailed description of the disclosure.

BRIEF DESCRIPTION OF THE DRAWINGS

(FIG. 6A) aged mice compared to young mice, (FIG. 6C) ENT-03-treated aged mice compared to vehicle-treated aged mice, (FIG. 6B) ENT-03-treated young mice compared to vehicle-treated young mice. Genes identified as having different levels between groups are represented as red (up-regulated) or blue (down-regulated) dots, and non-significant genes are represented as black dots. The horizontal red lines represent the applied p-value threshold.

FIG. 7A is the chromatogram for the brain extract and FIG. 7B is a quality control sample of synthetic ENT-03.

FIG. 10 shows gene expression profiles of the jejunum (FIGS. 10A-10D) or ileum (FIGS. 10D-10F) of young and aged mice treated with ENT-03 or control.

(FIG. 11A) differentially expressed genes in both directions, (FIG. 11B) up-regulated genes, (FIG. 11C) down-regulated genes, and (FIG. 11D) genes up-regulated in one contrast and down-regulated in the other contrast. Note that the numbers in grey squares represent the total number of selected differentially expressed genes of a specific contrast.

FIG. 13A: MRM 619.6/545.5, upper tracing: endogenous ENT-03 in extract; MRM 623.6/549.5 lower tracing: extract +2.2 ng ENT-03-d4/gram brain tissue; FIG. 13B: MRM 619.6/474.5, upper tracing: endogenous ENT-03 in extract; MRM 623.6/478.5 lower tracing: extract +2.2 ng ENT-03-d4/gram brain tissue.

FIG. 18A: A Venn diagram of overlapping genes in MSI-1436 (aminosterol 1436) vs control (young) against ENT-03 vs untreated (young)—all vs all. FIG. 18B shows a Venn diagram of overlapping genes in MSI-1436 vs control (young) against ENT-03 vs untreated (young)—up vs up. FIG. 18C shows a Venn diagram of overlapping genes in MSI-1436 vs control (young) against ENT-03 vs untreated (young)—down vs down. FIG. 18D shows a Venn diagram of overlapping genes in MSI-1436 vs control (young) against ENT-03 vs untreated (young)—up vs down. FIG. 18E shows a Venn diagram of overlapping genes in MSI-1436 vs control (young) against ENT-03 vs untreated (young)—down vs up.

FIG. 21A shows a Venn diagram of overlapping genes in ENT-02 (MSI-1436) vs control (old) against ENT-03 vs untreated (old)—all vs all. FIG. 21B shows a Venn diagram of overlapping genes in ENT-02 (MSI-1436) vs control (old) against ENT-03 vs untreated (old)—up vs up. FIG. 21C shows a Venn diagram of overlapping genes in ENT-02 (MSI-1436) vs control (old) against ENT-03 vs untreated (old)—down vs down. FIG. 21D shows a Venn diagram of overlapping genes in ENT-02 (MSI-1436) vs control (old) against ENT-03 vs untreated (old)—up vs down. FIG. 21E shows a Venn diagram of overlapping genes in ENT-02 (MSI-1436) vs control (old) against ENT-03 vs untreated (old)—down vs up.

FIG. 24A shows a Venn diagram of overlapping genes in Old vs young (control) against Old vs young (untreated)—all vs all. FIG. 24B shows a Venn diagram of overlapping genes in Old vs young (control) against Old vs young (untreated)—up vs up. FIG. 24C shows a Venn diagram of overlapping genes in Old vs young (control) against Old vs young (untreated)—down vs down. FIG. 24D shows a Venn diagram of overlapping genes in Old vs young (control) against Old vs young (untreated)—up vs down. FIG. 24E shows a Venn diagram of overlapping genes in Old vs young (control) against Old vs young (untreated) down vs up.

FIG. 27A shows a Venn diagram of overlapping genes in Old vs young (MSI-1436) against Old vs young (ENT-03)—all vs all. FIG. 27B shows a Venn diagram of overlapping genes in Old vs young (MSI-1436) against Old vs young (ENT-03)—up vs up. FIG. 27C shows a Venn diagram of overlapping genes in Old vs young (MSI-1436) against Old vs young (ENT-03)—down vs down. FIG. 27D shows a Venn diagram of overlapping genes in Old vs young (MSI-1436) against Old vs young (ENT-03)—up vs down. FIG. 27E shows a Venn diagram of overlapping genes in Old vs young (MSI-1436) against Old vs young (ENT-03)—down vs up.

FIG. 28: Heatmaps of overlaps between contrasts: A plot showing the number of overlapping selected genes between the contrasts performed. Note that the numbers on the diagonal represent the total number of selected genes found for each contrast. The colours of the squares represent the Jaccard index (the intersection over the union) for the contrasts on the x-axis with those on the y-axis.

DETAILED DESCRIPTION

I. Overview

Figure 1A:
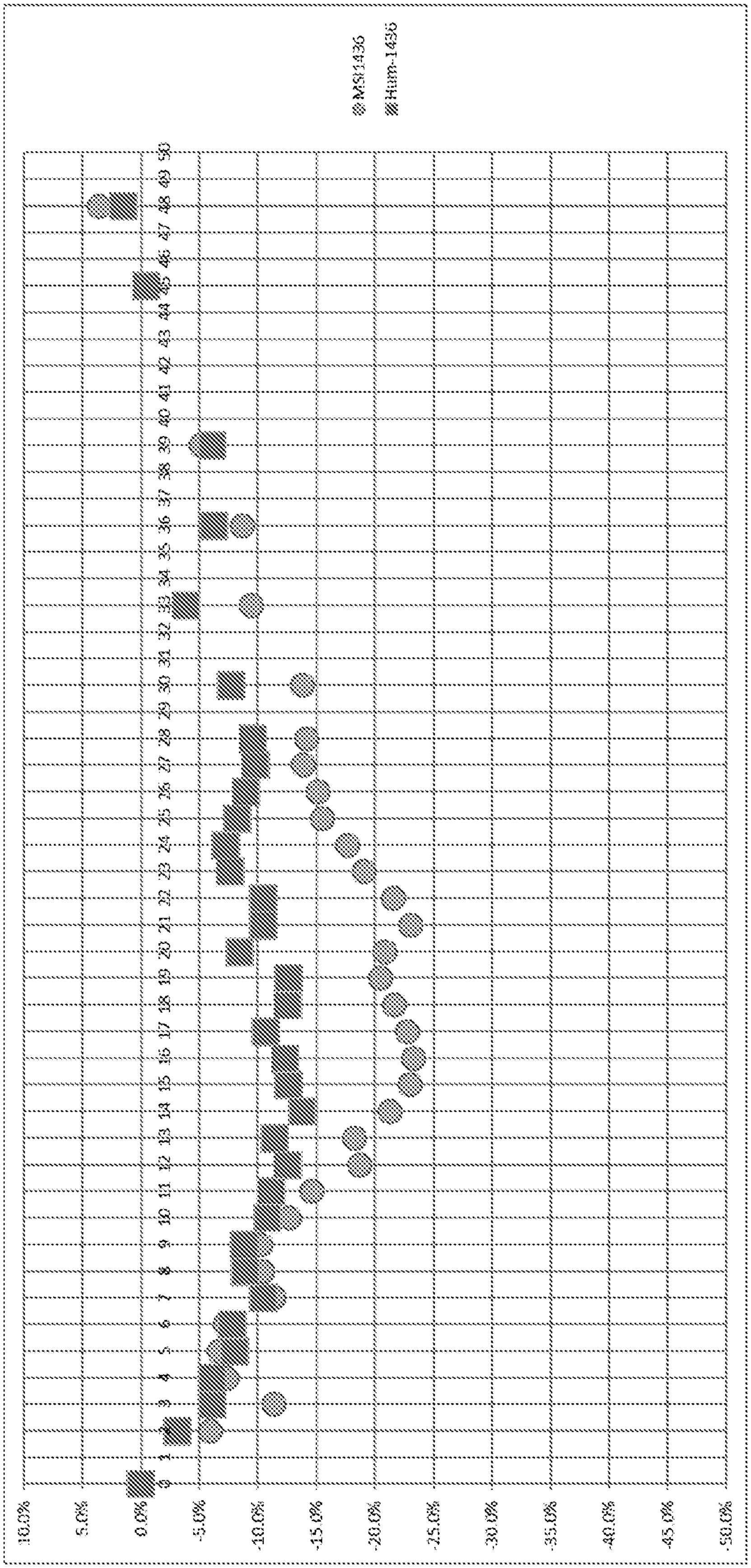
FIGS. 1A and 1B show percent weight loss over time in mice administered ENT-02 (MSI-1436) (circles) or ENT-03 (Compound III; squares).

The pharmacological activities of aminosterols require a highly specific chemical structure, suggesting that the shark molecules are utilized by physiological circuits that exist to accommodate analogous compounds made by mammals. To date, no such compounds have been discovered nor even hypothesized to exist. This disclosure provides such compounds, modified versions thereof, and methods for their use. Thus, in some embodiments, the present technology relates to Compound III, or a pharmaceutically acceptable salt, solvate, prodrug, or derivative thereof, methods of preparing such compounds, compositions comprising one or more of Compound III or derivatives thereof, and methods of using the same.

A. Overview of the Chemistry of the Disclosure

It has been known since the 1980's that 3-oxocholenic acids with specific chemical structures can be isolated from humans under specific circumstances. In particular, fluid withdrawn from a chronic subdural hematoma was shown to contain high concentrations of the bile acid Compound I, the function of which is unknown.

Compound I

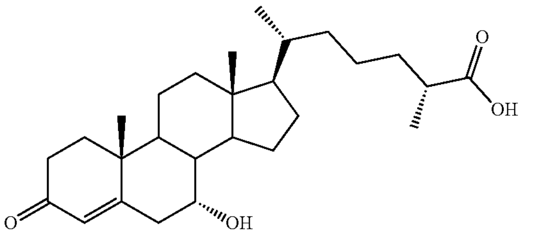

(detected in humans)

Later, this same compound was found to be present, also at high concentrations, in the cerebrospinal fluid (CSF) following subarachnoid hemorrhage, and at low concentrations in the CSF of healthy adults. Compound I, bearing a hydroxyl at the $C_{12}$ position, was also discovered in both the amniotic fluid and urine of newborn, healthy humans. The function of Compound I and its related metabolic variants has remained a mystery. It appears to be produced by a minor bile acid pathway that converts cholesterol initially to 27-hydroxycholesterol and then to Compound I. The role of this minor pathway remains unknown and is responsible for about 5% of bile acids produced in humans. It is believed that the products of this "acidic" pathway do not play a significant role in the emulsification of fats, the major function of bile acids in human physiology.

Although not the same, the structure of Compound I is reminiscent of the *Squalus* aminosterols, including those shown and discussed herein. Both steroid scaffolds are substantially flat, due to steric constraints imposed between the A and B rings. In the case of Compound I, the 4-ene double bond imparts flatness. In the shark molecules, flatness is imposed by the 5-alpha hydrogen. The carboxyl moiety of Compound I is spatially positioned similar to the sulfate on $C_{24}$ of the shark molecules, with both structures presenting a negative charge in the same general position in space relative to the steroid scaffold. Based on this spatial positioning, ENT-03 (Compound III) was synthesized by coupling the polyamine, spermine with Compound I, as shown below.

As detailed in the Examples, Applicant discovered that ENT-03 (Compound III) is found in subdural hematoma fluid in humans and in mouse pup brains. Compound III may synthesized in the brain through the condensation of spermine and Compound I. Compound I is believed to arise from the metabolism of 27-hydroxycholesterol (also called (25R) 26-dihydroxycholesterol), a biologically active oxysterol released into the circulation from many tissues, including vascular endothelium and macrophages (Griffiths et al., 2019; Bjorkhem et al., 2002; Javitt et al., 2002). Within the brain, 27-hydroxycholesterol undergoes successive metabolism by CYP27A1, CYP7B1, and HSD-3B7, possibly in that sequence (Meaney et al., 2007). The synthesis of Ent-03 (Compound III) would require three additional biosynthetic steps: the reduction of the double bond in the cholesterol A ring to create the 5 alpha hydrogen; the condensation of spermine with the 3-oxo group to form the imine; and the subsequent reduction of the imine. The first step is likely catalyzed by a brain steroid 5 alpha-reductase (Celotti et al., 1992). The missing biosynthetic link is the enzyme that couples the spermine to the bile acid.

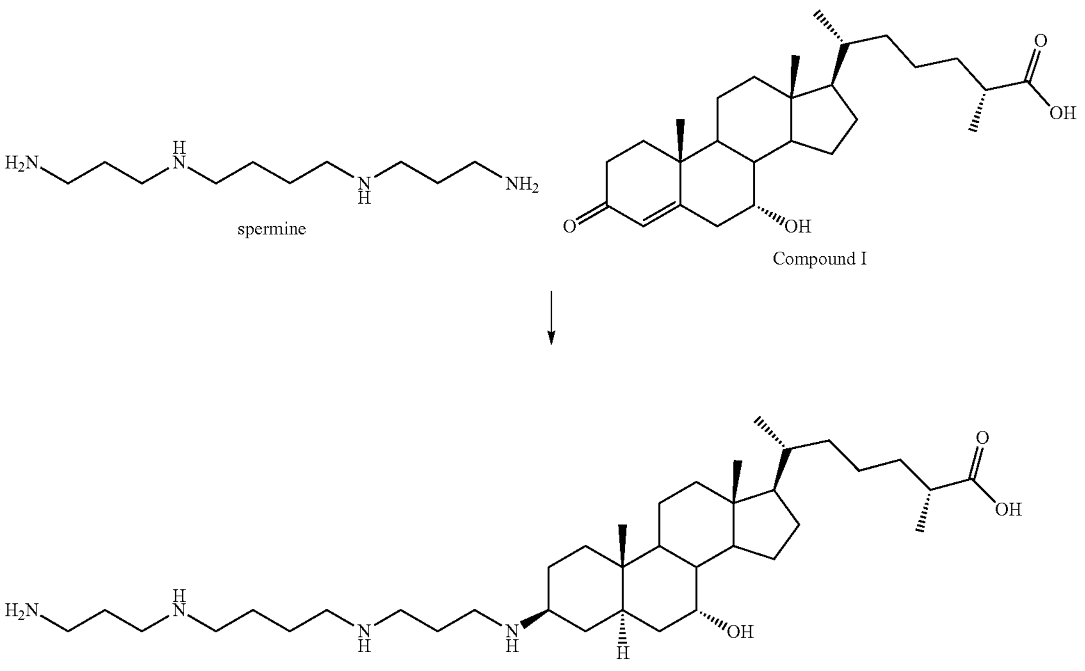

spermine

Compound I

Compound III

ENT-03 (Compound III) contains a 5-α hydrogen, offering greater chemical stability versus a 4-ene such as that of Compound I. ENT-03 (Compound III), like the shark derived ENT-02, reduces food intake and promotes weight loss in animal models, as discussed below and evidenced by the Examples below. By confirming that ENT-03 (Compound III; 3-β-Spermino-7α-hydroxy-5α-cholestanoic acid) has the same pharmacological activity known to be associated with shark derived ENT-02 (MSI-1436), the usefulness of ENT-03 (Compound III) in other applications where ENT-02 as well as other aminosterols are known to be useful can be validated.

ENT-03 contains a 5 alpha hydrogen rather than the 4-ene because of the greater chemical stability of the former versus the latter. Because of the replacement of the C24 sulfated hydroxyl on ENT-02 with the C27 carboxylic acid in ENT-03, ENT-03 will be subject to metabolism in a fashion common to all bile acids, namely via progressive cleavage of the cholesterol side chain. Differences in pharmacology are likely in part due to differences in metabolic handling of the two compounds.

ENT-03 (Compound III) is also shown in Example 1 to be a protein tyrosine phosphatase 1B (PTP1B) inhibitor. PTP1B is an effective target for the treatment of both type 2 diabetes and obesity; however, targeting PTP1B for drug discovery is challenging because of the highly conserved and positively charged active-site pocket. PTP1B is a negative regulator of insulin and leptin signaling and is a highly validated therapeutic target for diabetes and obesity. Conventional approaches to drug development have produced potent and specific PTP1B inhibitors, but prior publications have reported that these inhibitors lack oral bioavailability, "which limits their potential for drug development," as it was believed that drugs must be absorbed into the blood stream to produce a pharmacological effect (Krishnan et al., 2018).

As further described in the Examples, it has been shown that ENT-03 and trodusquemine have similar pharmacological activities, therapeutic effects in conditions such as Alzheimer's disease, and reverses the ageing phenotype of the gastrointestinal tract.

B. ENT-03 (Compound III) Suppresses Appetite

Example 2 of the present disclosure demonstrates that ENT-03 (Compound III) shares appetite-suppressing and weight loss promoting properties with the shark derived ENT-02 (MSI-1436). While appetite suppression itself is a utility of aminosterols, it is believed that ENT-03 (Compound III) may also possess the same efficacy against brain-gut disorders that the shark-derived aminosterols have recently been shown to have (data not shown; see e.g., ClinicalTrials.gov Identifier NCT03047629 for "Evaluation of Safety and Tolerability of ENT-01 for the Treatment of Parkinson's Disease Related Constipation (RASMET)"; and ClinicalTrials.gov Identifier NCT03781791 for "Orally Administered ENT-01 for Parkinson's Disease-Related Constipation (KARMET)"). ENT-01 is a squalamine phosphate. Also, the activity of ENT-03 (Compound III) and derivatives thereof may extend to a variety of conditions marked by αS pathology and/or dopaminergic dysfunction, as detailed herein.

Obesity is defined as having a body mass index (BMI) of 30.0 or higher, while 25.0 to <30 is defined as being in the overweight range. BMI is calculated by dividing a person's mass (in kg) by the square of their height in meters. Factors contributing to obesity include poor diet (high in calories), sedentary lifestyle, lack of sleep, genetics, aging, and pregnancy. Less than 5% of adults participate in 30 minutes of physical activity each day and only one in three children are physically active every day. A variety of medical conditions also may lead to obesity by causing weight gain and excessive hunger or food consumption. Lastly, more than 5% of the population may suffer from food addiction.

Mortality associated with weight gain or obesity is often the result of secondary conditions caused by excessive weight. These conditions include fatty liver disease, type 2 diabetes, heart disease, stroke, hypertension, gallbladder disease, gout, sleep apnea, osteoarthritis, High LDL cholesterol, low HDL cholesterol, high levels of triglycerides (dyslipidemia), endometrial cancer, breast cancer, colon cancer, kidney cancer, gallbladder cancer, and liver cancer. Obesity also results in damage to the joints and osteoarthritis. Increased fat content is also believed to promote inflammation and further damage joints.

The shark-derived ENT-02 (MSI-1436) is known to have pharmacological activity resulting in appetite suppression and weight loss. The Examples below show that ENT-03 (Compound III) also displays this same activity (Example 2). The examples also show that ENT-03 (Compound III), like the shark-derived ENT-02 (MSI-1436), is an inhibitor of regulatory phosphatases such as protein tyrosine phosphatase 1B (PTP1B) (Example 1). Since ENT-03 (Compound III) and the shark-derived ENT-02 share the same appetite suppression and weight loss promoting properties, and have similar chemical structures that may share pharmacophores, it is believed that ENT-03 (Compound III) and deuterated derivatives thereof may be useful in treating indications where other aminosterols are known to be useful.

C. ENT-02 (MSI-1436 or Aminosterol 1436) and Disease

Not to be bound by theory, it is believed that aminosterols work by targeting neurotoxic aggregates of alpha-synuclein (αS) in the gastrointestinal tract to restore function of the enteric nerve cells, thereby treating and/or preventing brain-gut disorders described herein. Several clinical trials are in process or completed using squalamine to treat Parkinson's disease based upon this theory. See e.g., (1) ClinicalTrials.gov Identifier: NCT03047629 for "A Multi-Center, Single-Dose, Multiple-Dose, Double-Blind, Placebo-Controlled Study to Evaluate Safety, Tolerability, Pharmacokinetics and Pharmacodynamics of Orally Administered ENT-01 for the Treatment of Parkinson's Disease Related Constipation," with 50 participants (study completed Jun. 14, 2018); (2) ClinicalTrials.gov Identifier: NCT03781791 for "A Multicenter, Randomized, Double-Blind, Placebo-Controlled, Multiple Dose Study to Evaluate Safety, Tolerability and Efficacy of Orally Administered ENT-01 for the Treatment of Parkinson's Disease-Related Constipation (KARMET)," with 72 participants (estimated study completion date of June 2019); and (3) ClinicalTrials.gov Identifier: NCT03938922 for "A Multicenter, Randomized, Double Blind Study to Evaluate Tolerability and Efficacy of Orally Administered ENT-01 for the Treatment of Parkinson's Disease Dementia," with a target of 40 participants (estimated study start date of Jun. 3, 2019, and estimated study completion date of February 2020).

This effect of aminosterols is highly unexpected given that aminosterols have a very low bioavailability; e.g., ENT-02 and ENT-03 appear to work locally rather than via absorption into the blood stream. The now-functional enteric nerve cells prevent retrograde trafficking of proteins, such as αS, to the brain. In addition to restoring GI function, this effect is believed to slow and possibly reverse disease progression of brain-gut disorders such as Parkinson's disease (PD), as well as other related brain-gut diseases and conditions as described herein.

A strategy that targets neurotoxic aggregates of αS in the gastrointestinal tract represents a novel approach to the treatment of brain-gut disorders such as PD and other neurodiseases and conditions described herein, and that may restore the function of enteric nerve cells and prevent retrograde trafficking to the brain. Such actions may potentially slow progression of the brain-gut disease in addition to restoring gastrointestinal function. Accordingly, but not to be bound by theory, the methods described herein using the novel ENT-03 (Compound III) or a pharmaceutically acceptable salt, solvate, prodrug, or derivative thereof, as well as compositions comprising the same, are expected to apply to the treatment and/or prevention of any of the described brain-gut diseases and symptoms described herein.

PD correlates with the formation of toxic alpha-synuclein (αS) aggregates within the enteric nervous system (ENS) (Braak et al. 2003 (a); Braak et al. 2003 (b)). αS is a member of the synuclein family of soluble proteins (αS, β-synuclein and γ-synuclein) that are commonly present in the central nervous system (CNS) of vertebrates. αS is expressed in the neocortex, hippocampus, substantia niagra, thalamus and cerebellum, with the main location within the presynaptic terminals of neurons in both membrane-bound and cytosolic free forms. Presynaptic terminals release chemical messengers, called neurotransmitters, from compartments known as synaptic vesicles. The release of neurotransmitters relays signals between neurons and is critical for normal brain function. αS can be seen in neuroglial cells and melanocytic cells and is highly expressed in the neuronal mitochondria of the olfactory bulb, hippocampus, striatum and thalamus.

αS aggregates to form insoluble fibrils in pathological conditions characterized by Lewy bodies, such as PD, dementia with Lewy bodies (DLB), and multiple system atrophy (MSA). These disorders are known as synucleinopathies. αS pathology is also found in both sporadic and familial cases with AD. Thus, one indicator of αS pathology is the formation of αS aggregates.

At the molecular level, protein misfolding, accumulation, aggregation and subsequently the formation of amyloid deposits are common features in many neurological disorders including Alzheimer's disease (AD) and PD. Thus, neurodegenerative diseases are sometimes referred to as proteinopathies. The existence of a common mechanism suggests that neurodegenerative disorders likely share a common trigger and that the nature of the pathology is determined by the type of the aggregated protein and the localization of the cell affected.

Starting two decades ago with the discoveries of genetic links between αS and PD risk and the identification of aggregated αS as the main protein constituent of Lewy pathology, αS has emerged as the major therapeutic target in PD and related synucleinopathies (Brundin et al., 2017). The α-synuclein abnormalities typically found in PD are believed to be responsible for apparent catecholamine-deficits (dopamine is a catecholamine sharing metabolic pathways with other catecholamines) (Frisina et al., 2009).

Examples of conditions associated with abnormal αS pathology, and/or dopaminergic dysfunction, also referred to as "brain-gut" disorders, include but are not limited to, synucleinopathies, neurodiseases, psychological and/or behavior disorders, cerebral and general ischemic disorders, and/or disorders or conditions. Examples of synucleinopathies, neurodegenerative disease and/or neurological diseases include, for example, AD, PD, Lewy body dementia (LBD) or dementia with Lewy bodies (DLB), multiple system atrophy (MSA), Huntington's Disease, Multiple Sclerosis (MS), Amyotorphic Lateral Sclerosis (ALS), schizophrenia, Friedreich's ataxia, vascular dementia, spinal muscular atrophy (SMA), progressive nuclear palsy, supranuclear palsy, frontotemporal dementia (FTD), progressive supranuclear palsy, Guadeloupian Parkinsonism, parkinsonism, spinocerebellar ataxia, stroke, traumatic brain injury, degenerative processes associated with aging, and dementia of aging. Examples of psychological or behavior disorders include for example depression, autism, down syndrome, Gaucher's disease (GD), Krabbe's disease (KD), lysosomal conditions affecting glycosphingolipid metabolism, ADHD, agitation, anxiety, delirium, irritability, illusion and delusions, amnesia, apathy, bipolar disorder, disinhibition, aberrant motor and obsessive-compulsive behaviors, addiction, cerebral palsy, epilepsy, major depressive disorder, and sleep disorders such as REM sleep behavior disorder (RBD), sleep fragmentation, REM behavior disorder, circadian rhythm dysfunction, sleep apnea, and cognitive impairment. Examples of general ischemic or cerebral ischemic disorders include for example microangiopathy, intrapartum, cerebral ischemia, cerebral ischemia during/after cardiac arrest or resuscitation, cerebral ischemia due to intraoperative problems, cerebral ischemia during carotid surgery, chronic cerebral ischemia due to stenosis of blood-supplying arteries to the brain, sinus thrombosis or thrombosis of cerebral veins, cerebral vessel malformations, diabetic retinopathy, high blood pressure, high cholesterol, myocardial infarction, cardiac insufficiency, cardiac failure, congestive heart failure, myocarditis, pericarditis, perimyocarditis, coronary heart disease, angina pectoris, congenital heart disease, shock, ischemia of extremities, stenosis of renal arteries, diabetic retinopathy, thrombosis associated with malaria, artificial heart valves, anemias, hypersplenic syndrome, emphysema, lung fibrosis, erectile dysfunction, cardiac conduction defects, high blood pressure, low blood pressure and pulmonary edema.

Constipation serves as an early indicator of many neurodiseases such as PD to the extent that it is suspected to correlate with the formation of toxic αS aggregates within the enteric nervous system (ENS) (Braak et al. 2003 (b)). As a result of the normal trafficking of αS aggregates from the ENS to the central nervous system (CNS) via afferent nerves such as the vagus (Holmqvist et al. 2014; Svensson et al. 2015), neurotoxic aggregates accumulate progressively within the brainstem and more rostral structures. Inhibiting αS aggregation in the ENS may therefore reduce the continuing neuro disease process in both the ENS and CNS (Phillips et al. 2008). This relationship between the ENS and CNS is sometimes described herein as "brain-gut" in relation to a class of disorders or the axis of aminosterol activity.

Not to be bound by theory, it is believed that aminosterols improve bowel function by acting locally on the gastrointestinal tract (as supported by the low oral bioavailability, e.g., less than about 0.3%). An orally administered aminosterol such as ENT-02 stimulates gastrointestinal motility in mice with constipation due to overexpression of human αS (West et al, manuscript in preparation). Perfusion of an aminosterol through the lumen of an isolated segment of bowel from the PD mouse model results in excitation of IPANs (intrinsic primary afferent neuron), the major sensory neurons of the ENS that communicate with the myenteric plexus, increasing the frequency of propulsive peristaltic contractions and augmenting neural signals projecting to the afferent arm of the vagus.

It is theorized that nerve impulses initiated from the ENS following administration of an aminosterol such as Compound III augment afferent neural signaling to the CNS. This may stimulate the clearance of αS aggregates within the afferent neurons themselves as well as the secondary and tertiary neurons projecting rostrally within the CNS, since it is known that neural stimulation is accompanied by increased neuronal autophagic activity (Shehata et al. 2012). It is believed that after cessation of aminosterol administration, the neurons of the CNS gradually re-accumulate an αS burden either locally or via trafficking from αS re-aggregation within the gut.

Disturbance of the circadian rhythm has been described in neurodiseases such as PD both clinically and in animal models and might play a role in the abnormal sleep architecture, dementia, mood and autonomic dysfunction associated with neurodiseases such as PD (Breen et al. 2014; Videnovic et al. 2017; Antonio-Rubio et al. 2015; Madrid-Navarro et al. 2018). Circadian cycles of wrist skin temperature have been shown to correlate with sleep wake cycles, reflecting the impact of nocturnal heat dissipation from the skin on the decrease in core temperature and the onset of sleep (Sarabia et al. 2008; Ortiz-Tudela et al. 2014). It is believed that administration of ENT-03 (Compound III) will have a significant positive impact on the circadian rhythm of patients. Not to be bound by theory, it is believed that Compound III can affect neuronal circuits involving the master clock (the suprachiasmatic nucleus) and its autonomic projections and opens the possibility of therapeutic correction of circadian dysfunction.

In one aspect aminosterol dosing can be patient specific, as a therapeutically effective dose of ENT-03 (Compound III) may be related to the extent of neuronal damage, with greater neuronal damage correlating with the need for a higher ENT-03 (Compound III) dose to obtain a desired therapeutic result. As described in greater detail herein, ENT-03 (Compound III) dosing can range from about 0.01 to about 500 mg/day, with dosage determination described in more detail below. However, the present disclosure is not limited to a method of determining a patient-specific ENT-03 (Compound III) dose, as therapeutic ENT-03 (Compound III) doses which are not patient specific are also described herein.

D. Experimental Results (1) Detection of ENT-03 in Humans and Mouse Pup Brain

In 1992 Nagata et al identified high concentrations of the bile acid, 7-alpha hydroxy-3-oxo-4-cholestenoic acid (7-HOCA), in human chronic subdural hematoma fluid, (FIG. 1C) (Nagata et al., 1992) and later in acute subarachnoid hemorrhage (Nagata et al., 1995). In 1997, Zhang et al reported that rat brain cells could metabolize 27-hydroxycholesterol to 7-HOCA (Zhang et al., 1997). Subsequently, Björkhem, Sjövall, Griffiths and their collaborators identified 7-HOCA as the most abundant bile acid in human cerebrospinal fluid (Ogundare et al., 2010; Meaney et al., 2007; Saeed et al., 2014; Saeed et al., 2014). 7-HOCA did not appear to a be a biologically active bile acid, in that it did not activate either the FXR, LXR, or RXR/NURR1 receptors, for which bile acids and oxysterols are known ligands (Ogundare et al., 2010). Björkhem proposed that the brain metabolizes 27-hydroxycholesterol that enters from the periphery into 7-HOCA to facilitate the efflux of the oxysterol back into the circulation (Meaney et al., 2007).

The present disclosure suggests that the presence of ENT-03 in subdural hematoma fluid reflects its possible role in the development of this structure. Following head injury, generally in older people and rarely in infants, a highly vascularized sac-like "organ" develops, with one side deriving from the dura ("outer membrane"), the other from the subarachnoid ("inner membrane") (Yamashima et al., 2000). High concentrations of numerous growth factors, including VEGF accumulate within the fluid (Edlmann et al., 2017). The present disclosure suggests that ENT-03 appears within the subdural hematoma in an attempt to repair the intracranial injury. In this context, one might wish to speculate why healthy newborns who (rather commonly) experience intracranial trauma following passage through the birth canal, resulting in subdural and parenchymal hemorrhage, generally recover asymptomatically (Looney et al., 2007).

Figure 7A:
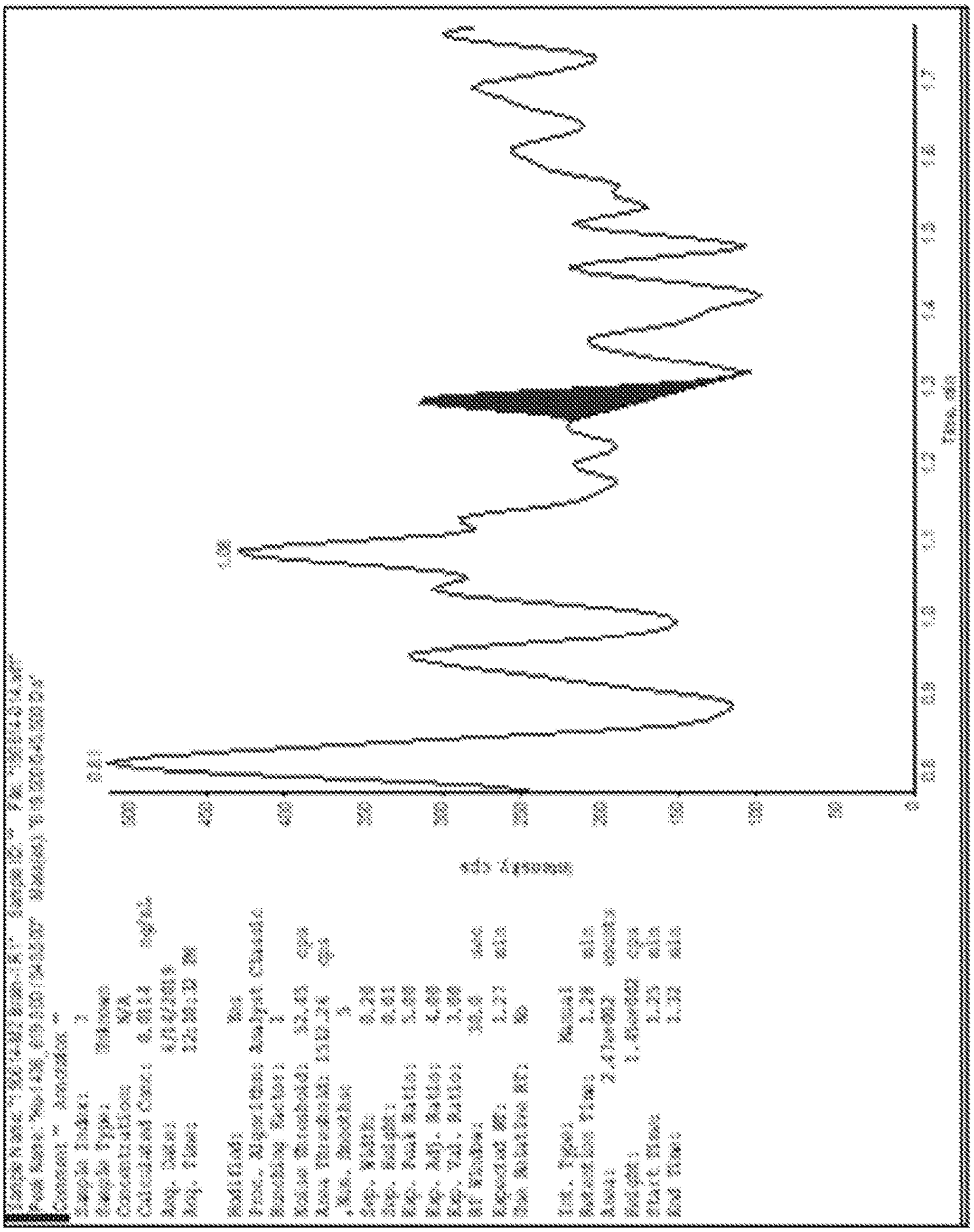
FIGS. 7A and 7B show chromatograms for the LC/MS/MS analysis of brain extract from elderly humans for ENT-03.
Figure 7B:
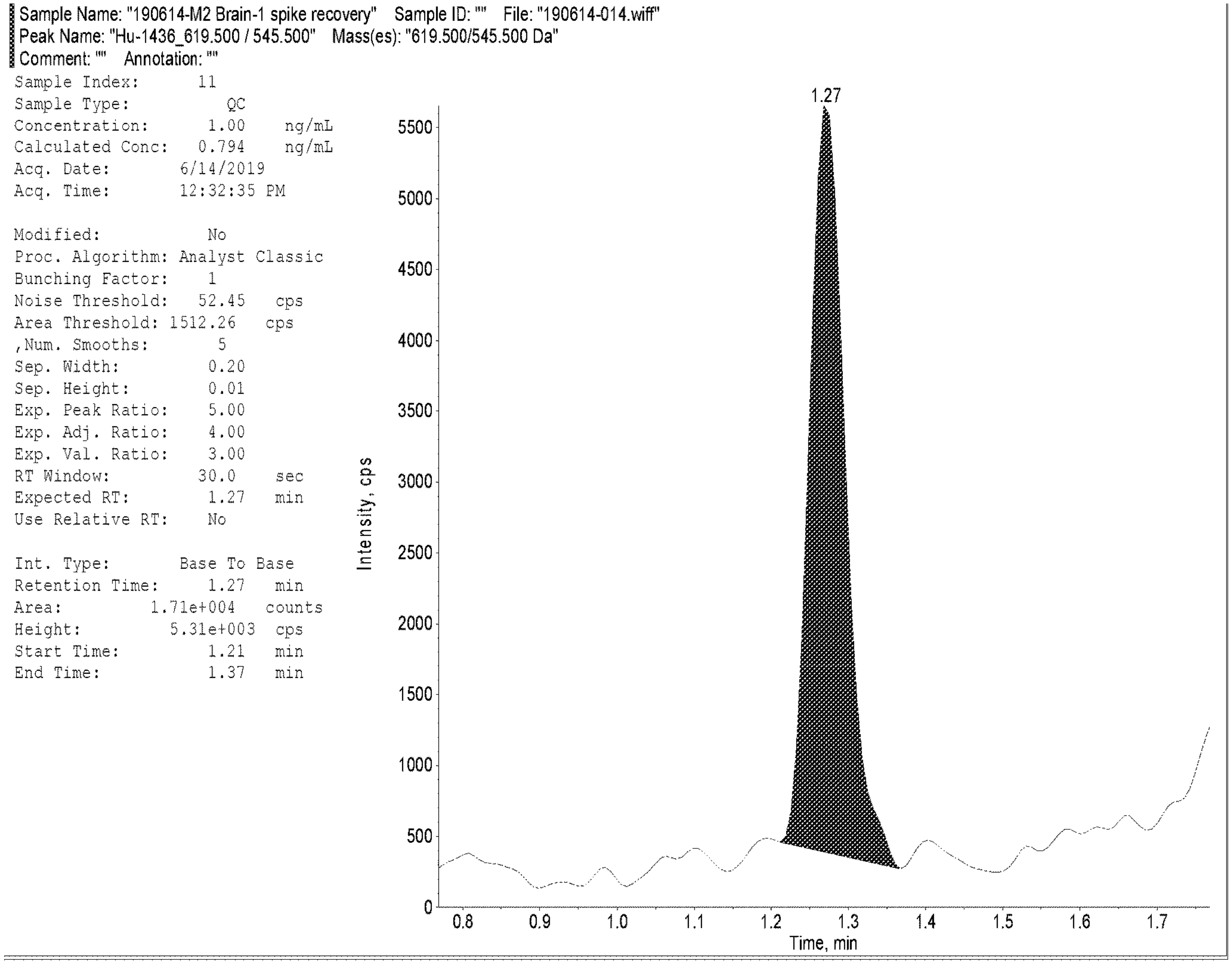

Because of the known high concentrations of Compound Ia (7-HOCA) in the chronic subdural hematoma fluid, the fluid evacuated from 3 elderly patients with chronic subdurals via LC/MS/MS was analyzed for the presence of ENT-03. Brain extracts were analyzed via LC/MS/MS for ENT-03. FIG. 7A shows the presence of ENT-03 in brain extract. FIG. 7B shows a reference sample of synthetic ENT-03.

Based on these data, extracts of brain, liver, and kidneys from newborn mice over the first two postnatal weeks were analyzed for the presence of ENT-03. 3-oxo-bile acids comprise between 18-40% of the unconjugated bile acids within amniotic fluid during the last trimester of human fetal development (Nakagawa et al. 1990) and are present as a significant percentage of the bile acids in healthy newborn urine, gradually diminishing during the first postnatal month (Wahlen et al., 1989 and Kimura et al., 1999). Since 3-oxo-bile acids are abundant during the newborn period, the search for the putative polyamine-bile acid molecule was focused in neonatal mice. Brain and liver extracts were prepared from mice between day 1 through day 24 of age using a protocol designed to capture ENT-03 based on its physical properties (see Example 7).

Figure 8A:
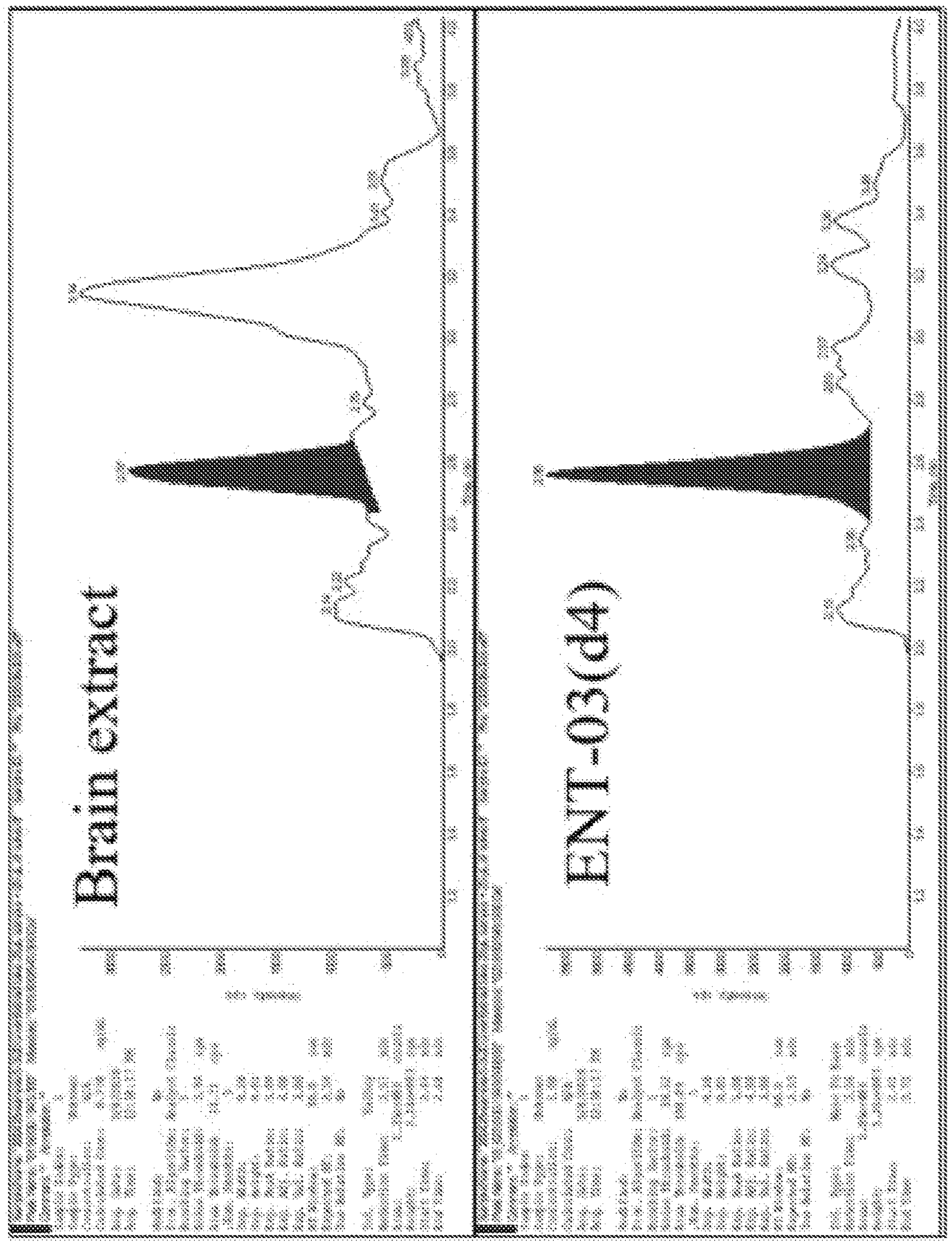
FIGS. 8A and 8B show chromatograms for the LC/MS/MS analysis of mouse pup brain extract (FIG. 8A) and liver extract (FIG. 8B).
Figure 8B:
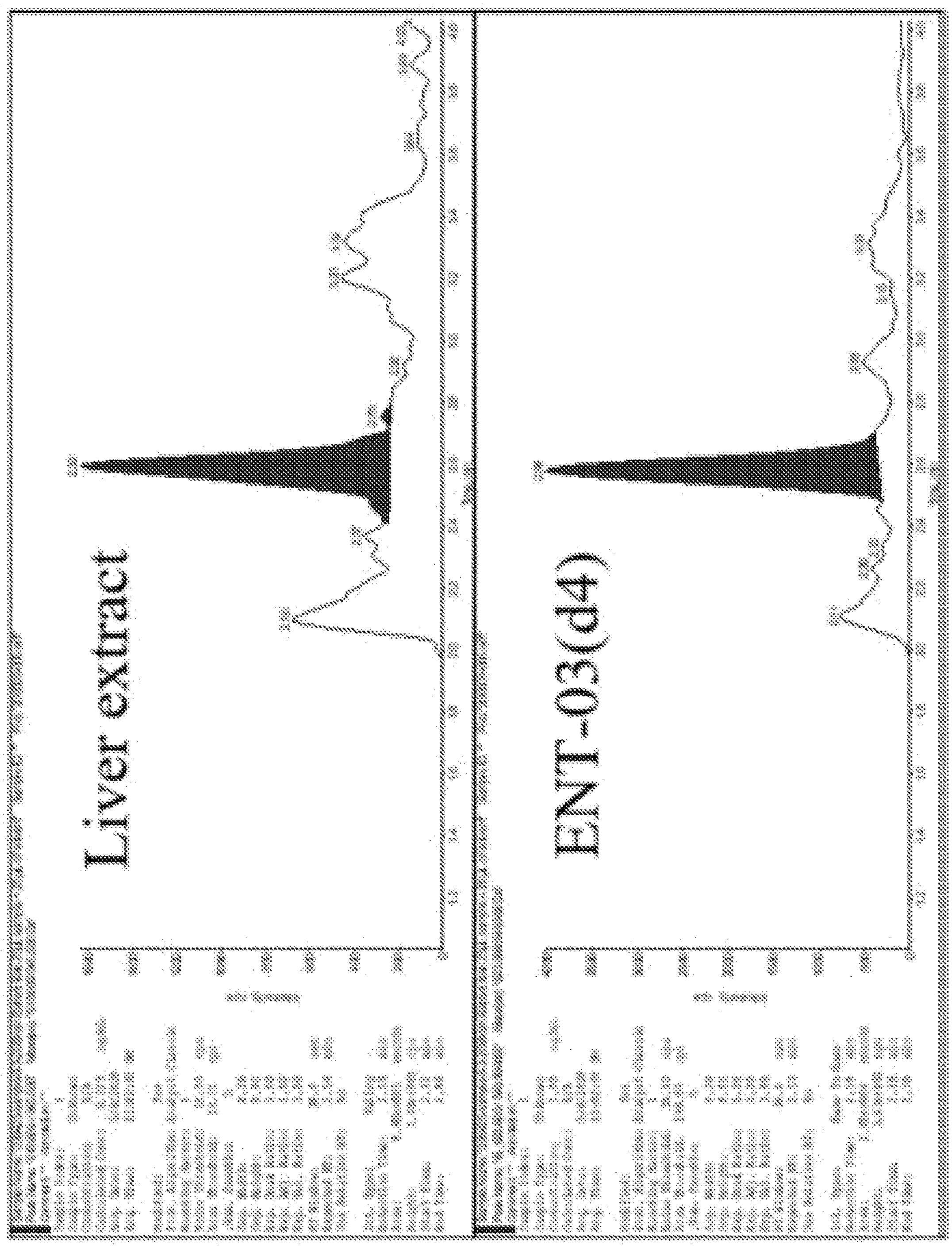
Figure 9:
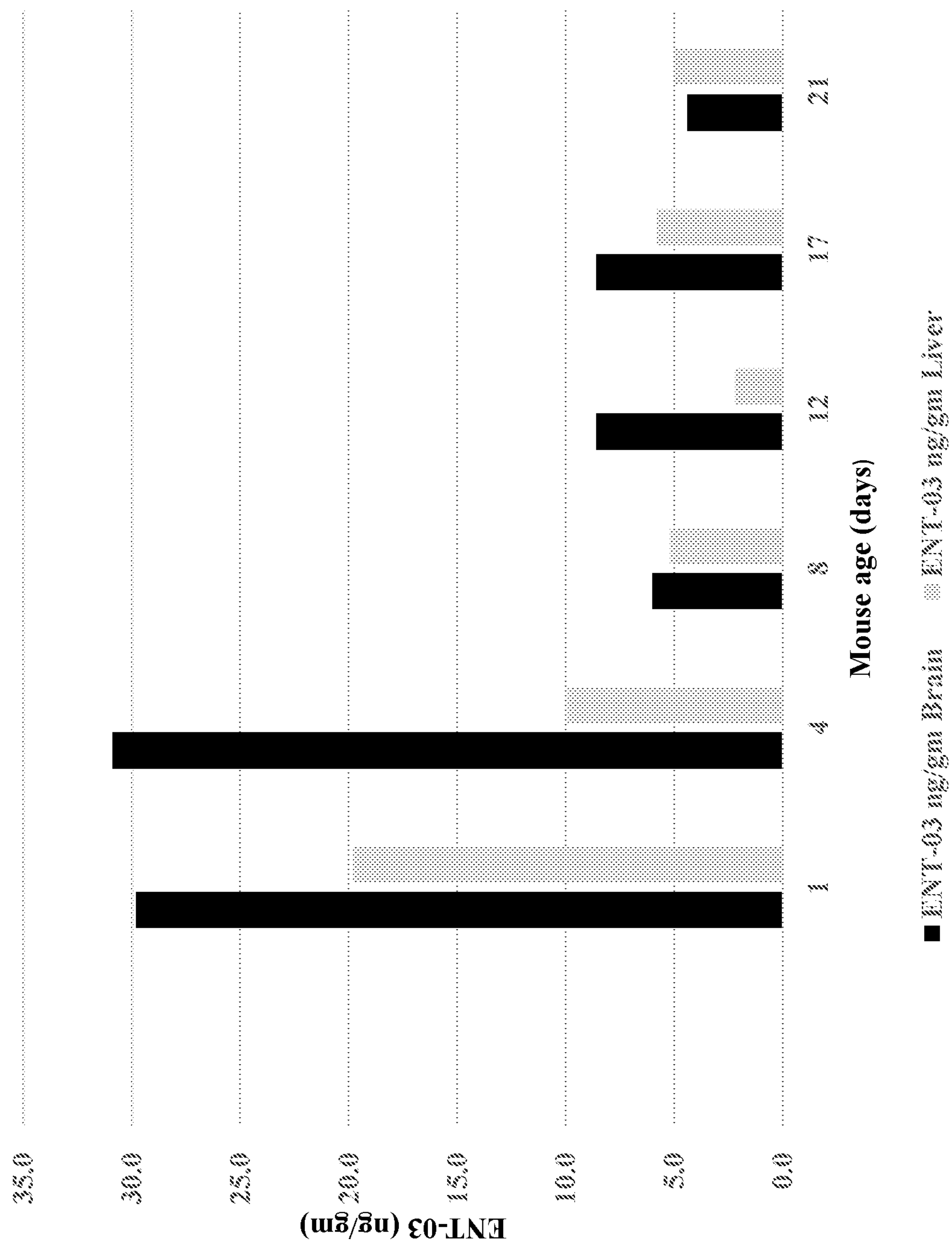
FIG. 9 shows approximate concentrations of ENT-03 measured in the brain and liver of neonatal mice over the first 3 weeks of life.
Figure 13A:
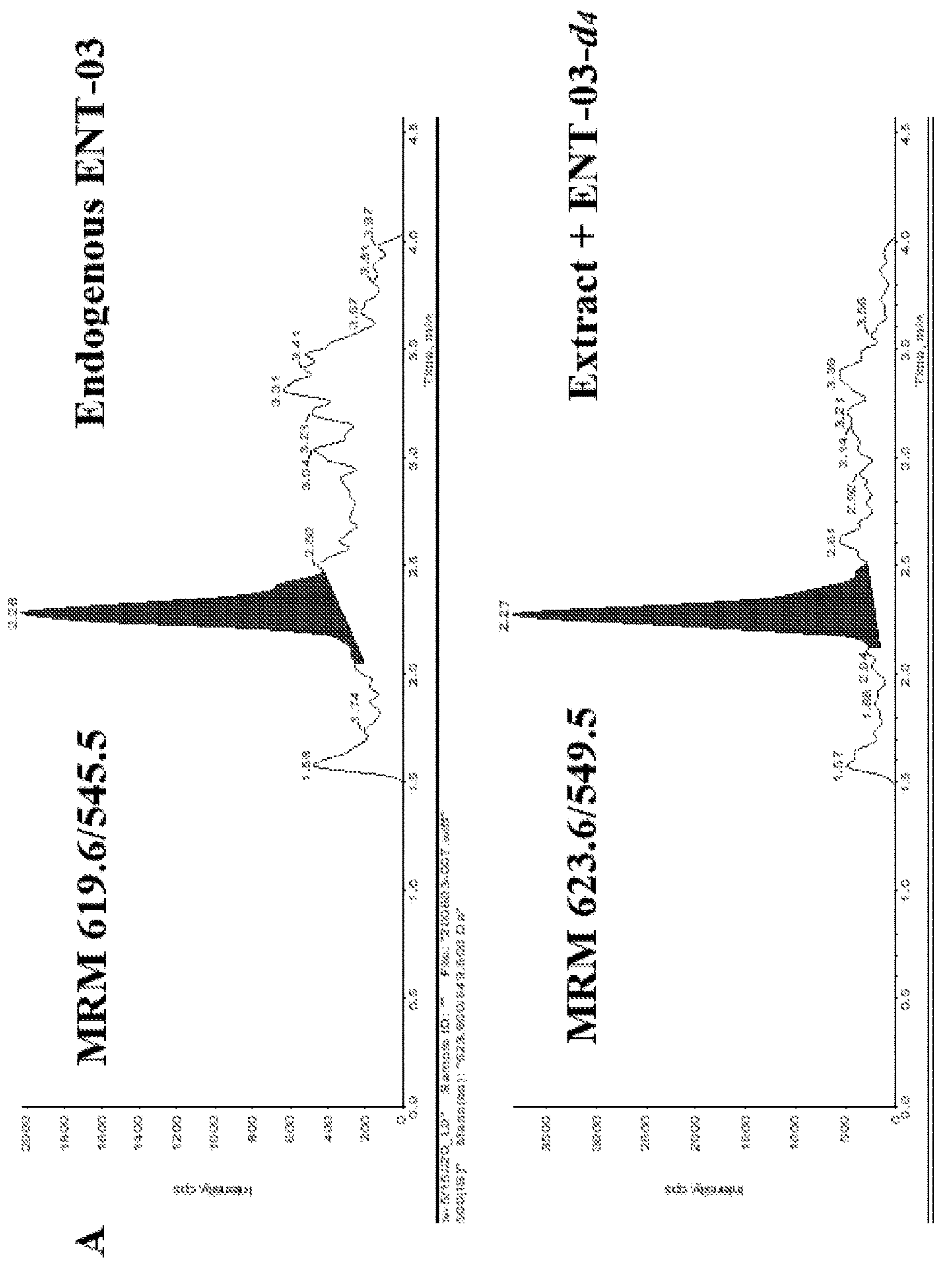
FIGS. 13A and 13B show representative chromatograms of ENT-03 in 4 day old mouse brain extracts.
Figure 13B:
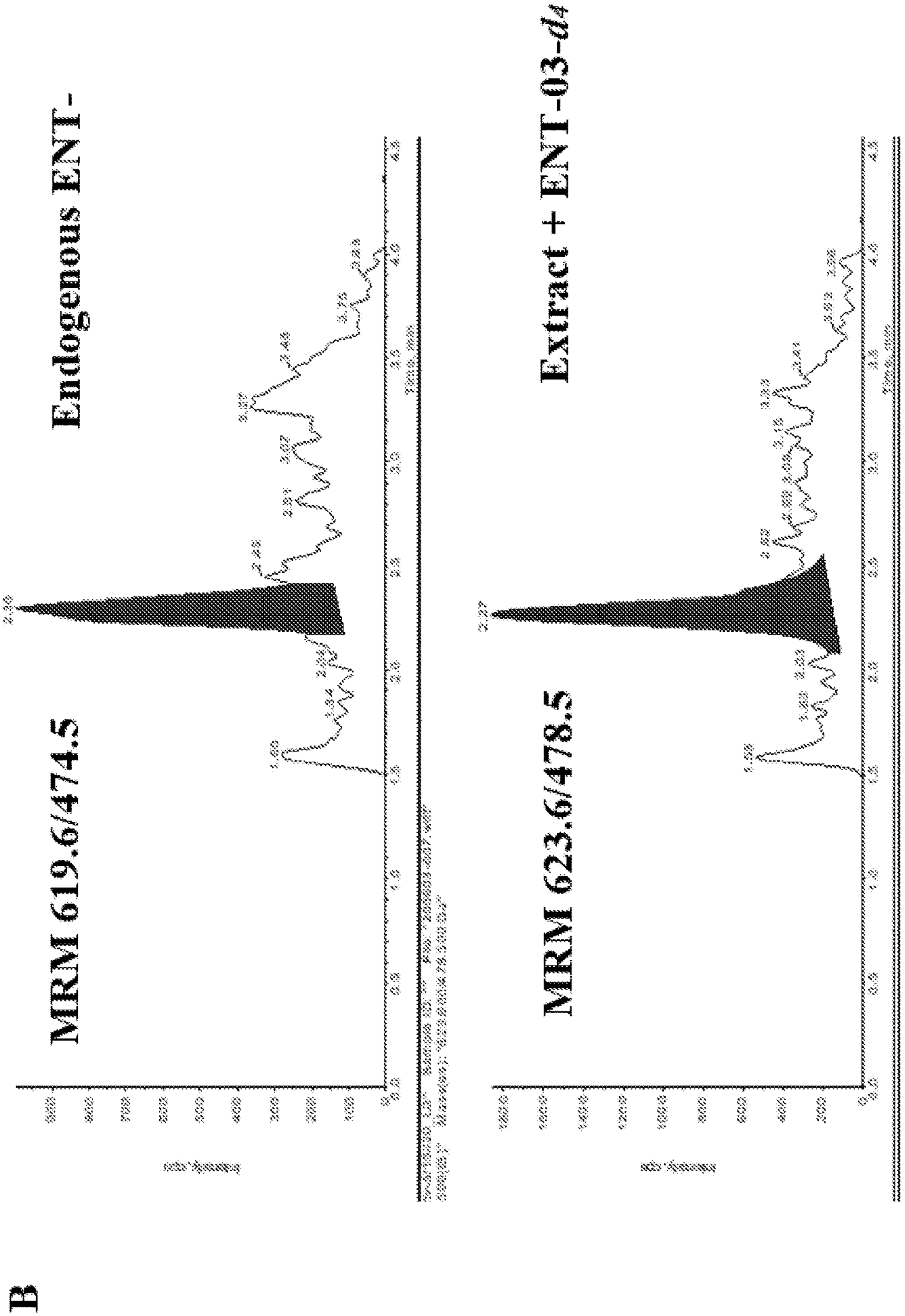

The results of the experiment showed that ENT-03 could be detected in brain and liver of neonatal mice (FIGS. 8A and 8B, respectively). The identity of the endogenous ENT-03 was established by its retention time, mass ($[M+H^+]$ m/z=619.6), and MS/MS MRM of the characteristic fragments of mass 545.57 (FIG. 13A) and 474.39 (FIG. 13B). Approximate concentrations of ENT-03 measured in the brain and liver of neonatal mice over the first 3 weeks of life are presented in FIG. 9. In both brain and liver the highest concentrations appear at birth with a gradual reduction over the following 3 weeks. Synthetic deuterated ENT-03-$d_4$ ($-C2D_2$, $-C4D_2$) was used as an internal standard to determine the concentration of endogenous ENT-03 present in the chromatographed sample. The identical retention times (FIGS. 13A and 13B) of the endogenous and synthetic molecules supports the tentative assignment of a 5-alpha configuration, based on significant differences in retention time that characterize the "flat" (5a) and "twisted" (5β) conformers of the synthetic steroid precursor of ENT-03.

(2) Inhibition of Regulatory Phosphatases

In one aspect, encompassed is method of inhibiting one or more regulatory phosphatases to achieve a therapeutic or prophylactic benefit comprising administering a therapeutically effective amount of aminosterol compound or a composition comprising the same, as described herein.

Many cellular processes involved in health and disease are regulated by phosphorylation. The protein kinases are involved in the phosphorylation of cellular targets. Phosphatases reverse the action of the kinases. There are two broad classes of regulatory phosphatases. The first group is the tyrosine specific PTPs that dephosphorylate protein substrates on tyrosine. Tyrosine-specific PTPs comprise receptor-like PTPs and non-transmembrane PTPs. The second group is the DSPs (dual-specificity phosphatases) that dephosphorylate protein substrates on tyrosine, serine, and threonine residues, as well as lipid substrates. The focus of the current invention is on the first group of phosphatases.

While significant effort has been directed at the development of therapeutics that inhibit protein kinases comparable success with respect to the development of inhibitors has lagged. The active site of most phosphatases is configured as a deep well at the bottom of which is a positively charged residue. The corresponding inhibitor must carry a negative charge or other hydrogen bond accepting functionalities to dock within the base of the well and must be sufficiently elongated to extend into the well. Since large strongly charged molecules generally have limited cellular permeability few compounds that exhibit activity in in vitro enzyme assays also exhibit activity when assayed in cell culture or in vivo.

The phosphatases that the current invention targets include several that regulate vital cellular and physiological functions. They include: PTP1B, which downregulates many receptor tyrosine kinases, such as the insulin and IGF receptors; growth factor receptors such as VEGF, PDGF, EGF, FGF; stat proteins within the leptin pathway. PTPN11 (E76K) which is recognized as an oncogene driving numerous human malignancies. PTPRC/CD45 has been extensively studied in lymphocytes and shown to act as a signaling gatekeeper in T cells following antigen stimulation. PTPN7/LC-PTP inactivates MAPKs, dampening such processes as neuronal signaling and growth factor stimulation. PTPN12/PTP-PEST has a primary role in cytoskeletal rearrangement that impacts on processes such as cell migration, cell spreading and cell division.

ENT-03 is an inhibitor of regulatory phosphatases with highest specificity against PTP1B. In addition, it exhibits the expected pharmacological activity in mice, that being reduction in food intake and weight loss. The aminosterols described herein are various derivatives of ENT-03 that exhibit inhibitory activity in vitro and in vivo against regulatory phosphatases.

Example 1 shows that ENT-03 (Compound III) is an inhibitor of regulatory phosphatases such as protein tyrosine phosphatase 1B (PTP1B). PTP1B is a negative regulator of the insulin signaling pathway and is considered a promising potential therapeutic target, in particular for treatment of type 2 diabetes (Combs, et al. 2010). Gene knockout studies conducted in murine models have provided substantial evidence for the role PTP1B plays in the regulation of insulin signaling and the development of obesity (Elchebly et al., 1999).

ENT-03 (Compound III) and ENT-02 (MSI-1436) were tested in a 10-dose $IC_{50}$ mode with 3-fold serial dilution, in singlet, starting at 100 μM. Fluorescence was measured to monitor enzyme activity. As seen in Table 2, ENT-02 (MSI-1436, aminosterol 1436), already known to inhibit PTP1B, exhibited an $IC_{50}$ of 2.89 μM; ENT-03 (Compound III) exhibited an $IC_{50}$ of 1.03 μM. Half maximal inhibitory concentration, or $IC_{50}$, is a measure of the potency of a substance in inhibiting a specific biological or biochemical function. This quantitative measure indicates how much of a particular drug or other substance is needed to inhibit a given biological process by half. Thus, ENT-03 (Compound III) is significantly more potent than aminosterol 1436 as the $IC_{50}$ of ENT-03 (Compound III) is less than half that of ENT-02 (MSI-1436).

As detailed in Example 1, although ENT-02 (MSI-1436) is described as a PTP1B inhibitor, both it as well as ENT-03 (Compound III) exhibit comparable inhibitory activity against other phosphatases involved in cellular signaling. In particular, both are active against full length PTPN11/SHP2. SHP2 (SH2 domain-containing phosphatase 2) is a protein tyrosine phosphatase implicated in multiple cell signaling processes and directly associated with both human genetic disorders and cancer (Zheng et al., 2018; Chen et al., 2016). Furthermore, both compounds potently inhibit the gain of function PTPN11 (E76K) variant recognized as an oncogene driving numerous human malignancies. Neither compound inhibits the closely related phosphatase PTPN6/SHP1, which plays a functionally distinct role in biological pathways. Both also target PTPRC/CD45, PTPN7/LC-PTP, and PTPN12/PTP-PEST. PTPRC/CD45 has been extensively studied in lymphocytes and shown to act as a signaling gatekeeper in T cells following antigen stimulation. PTPN7/LC-PTP inactivates MAPKs, dampening such processes as neuronal signaling and growth factor stimulation (Fukunaga et al., 1998; Eswaran et al., 2006). PTPN12/PTP-PEST has a primary role in cytoskeletal rearrangement that impact on processes such as cell migration, cell spreading and cell division.

Figure 2:
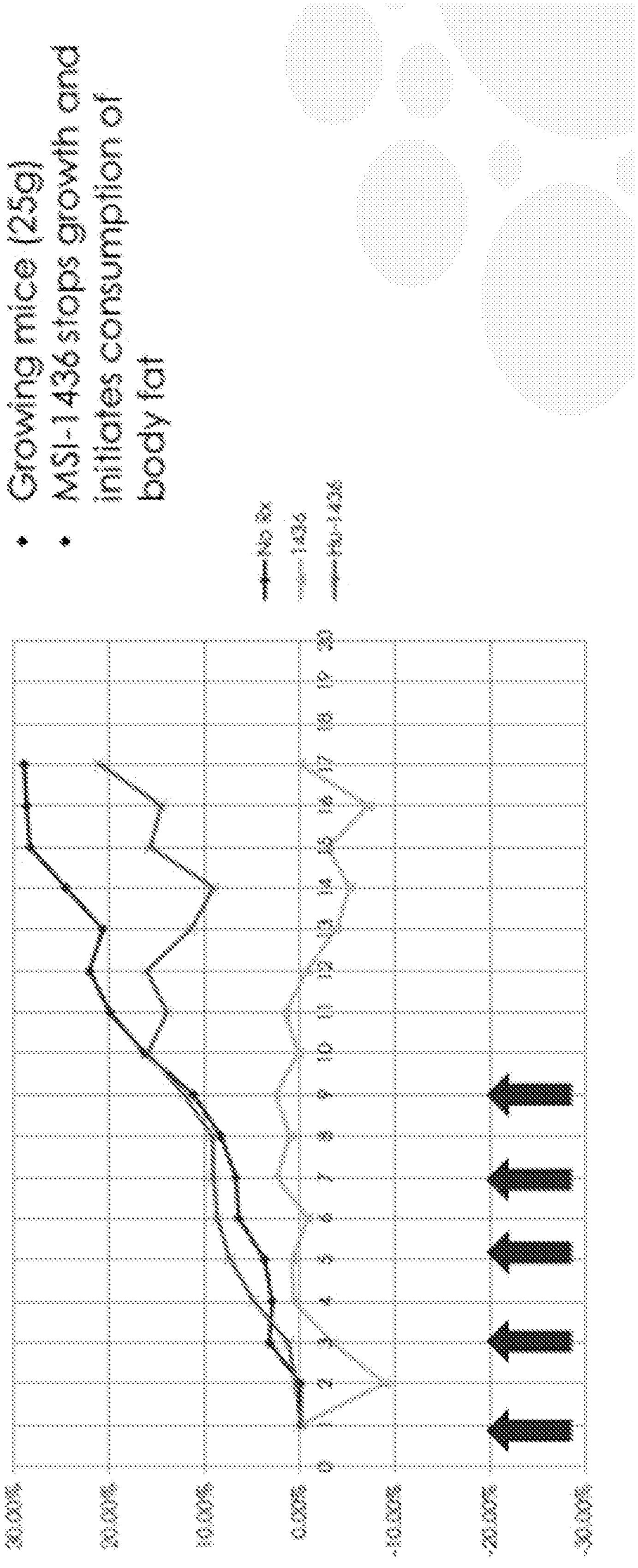
FIG. 2 shows the results of administration of ENT-03 (Compound III) and ENT-02 (MSI-1436) on growing mice. While both compounds affected weight gain, ENT-02 had a more profound effect, having suppressed growth as well as having induced consumption of body fat. In contrast, the animals treated with ENT-03 continued normal growth, although they "slimmed down", suggesting that ENT-03 re-established a new optimal body weight "set point."

Example 2 describes the activity of ENT-03 (Compound III) as a weight-loss agent in mice. Mice were treated with either ENT-03 (Compound III) or ENT-02 (MSI-1436) on days 0, 2, 4, 6, 8 and 10, while food was provided ad lib. As seen in FIG. 2, administration of both compounds resulted in a decrease in weight.

These data demonstrate that ENT-03 (Compound III) exhibits a pharmacological response with respect to appetite and weight similar to ENT-02 (MSI-1436) and suggests that ENT-03 (Compound III) can have utility in all therapeutic applications known to be associated with shark-derived aminosterol 1436, including neurodegenerative diseases or neurological diseases (such as PD), psychological or behavior disorders, and general ischemic or cerebral ischemic disorders.

Although ENT-03 (Compound III) inhibits PTP1B, it has also shown that along with ENT-02, ENT-03 (Compound III) also inhibits several other phosphatases with comparable $K_i$'s. Of particular interest is the proto-oncogene PTPN11, also called SHP2, a ubiquitously expressed non-receptor protein tyrosine phosphatase that regulates, along with PTP1B, the PI3K/Akt, Ras/Raf/Erk, and JAK/STAT signaling pathways, utilized by hormones such as insulin, leptin, and numerous growth factors (Pulido et al., 2013). In the mouse forebrain, neuronal SHP2 appears to enhance leptin signaling in the hypothalamus, in contrast to PTP1B, which acts primarily as a negative regulator of hypothalamic leptin signaling (Zhang et al., 2004). Thus, by targeting the two phosphatases that modulate, in opposing directions, the two main intracellular pathways downstream of leptin, ENT-03 (Compound III) can control the gain on the leptin circuit.

Finally, Example 9 details evaluation of the activity of ENT-05 in vivo. The example demonstrates that modification of ENT-03 (Compound III) to create ENT-05 yielded a compound with specificity towards PTPN11 (E76K) and likely other as yet undescribed phosphatases. The in vivo pharmacological effect on the tadpole is that of inhibition of sodium reabsorption, most likely in the kidney. The likely target is the sodium-potassium chloride cotransporter type 2 (NKCC2). Very little is currently known about the phosphatases that regulate the activity the NKCC2 of the renal tubule.

The example teaches that ENT-05 has identified a phosphatase that activates the NKCC2 transporter of the channel that can be inhibited by ENT-05. ENT-05 clearly has a potential utility in the treatment of hypertension, similar to the drug furosemide which inhibits renal NKCC2 by a mechanism not involving inhibition of phosphatase activity as well as intracranial hypertension (raised intracranial pressure) and intraocular hypertension (glaucoma).

(3) Gut Rejuvenation

Example 3 shows that squalamine is effective at increasing the transcriptome in old mice. As discussed in section I.A, ENT-03 (Compound III) and the shark-derived aminosterols such as squalamine share similar structures and spatial positioning of functional groups. Thus, the activity of squalamine is believed to extend to ENT-03 (Compound III).

Figure 6A:
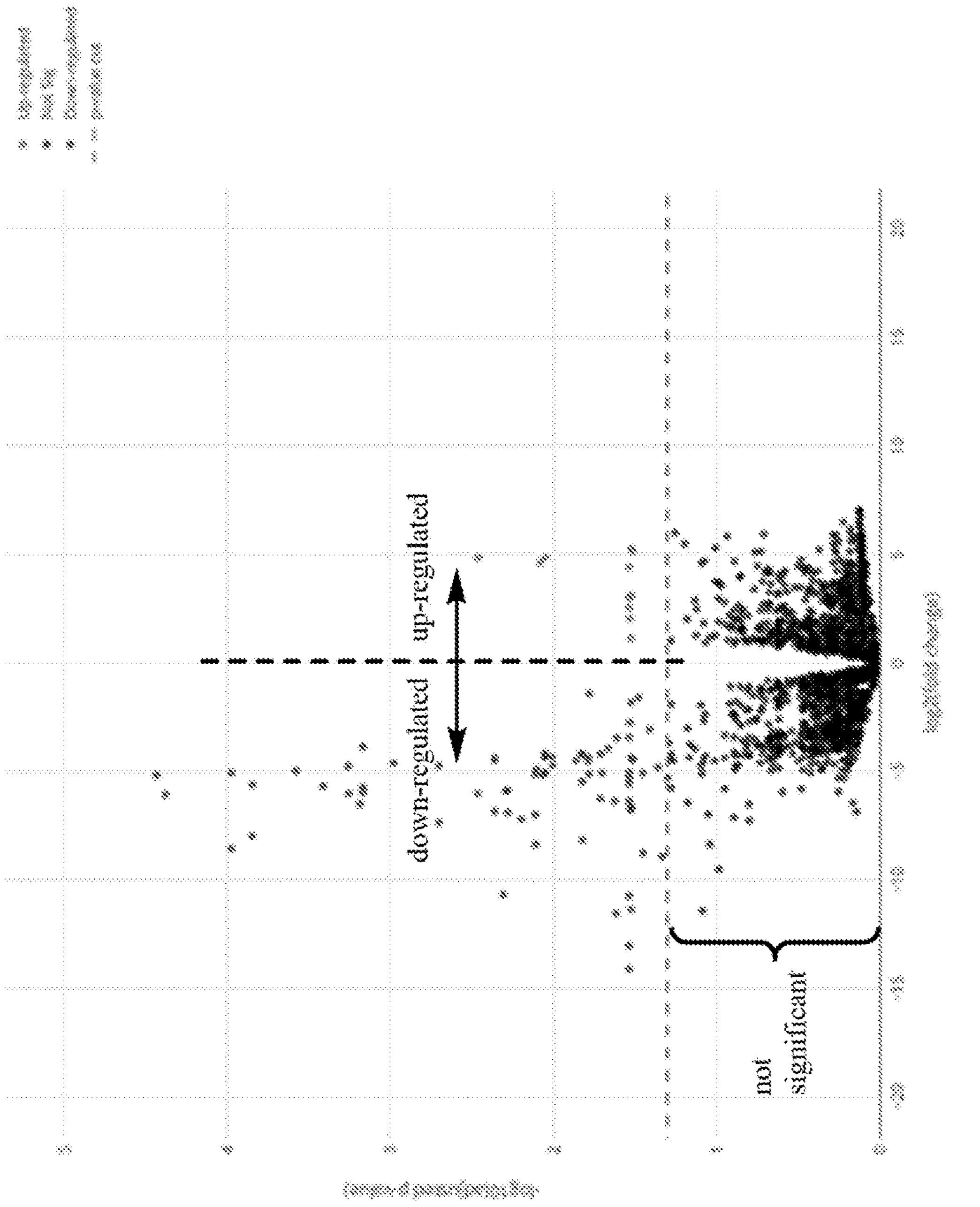
FIGS. 6A-6C show volcano plots showing significance (as negative $\log_{10}$-transformed FDR-adjusted p-values) against the magnitude ($\log_2$-transformed fold change) of differentially expressed genes in the following three contrasts.
Figure 6B:
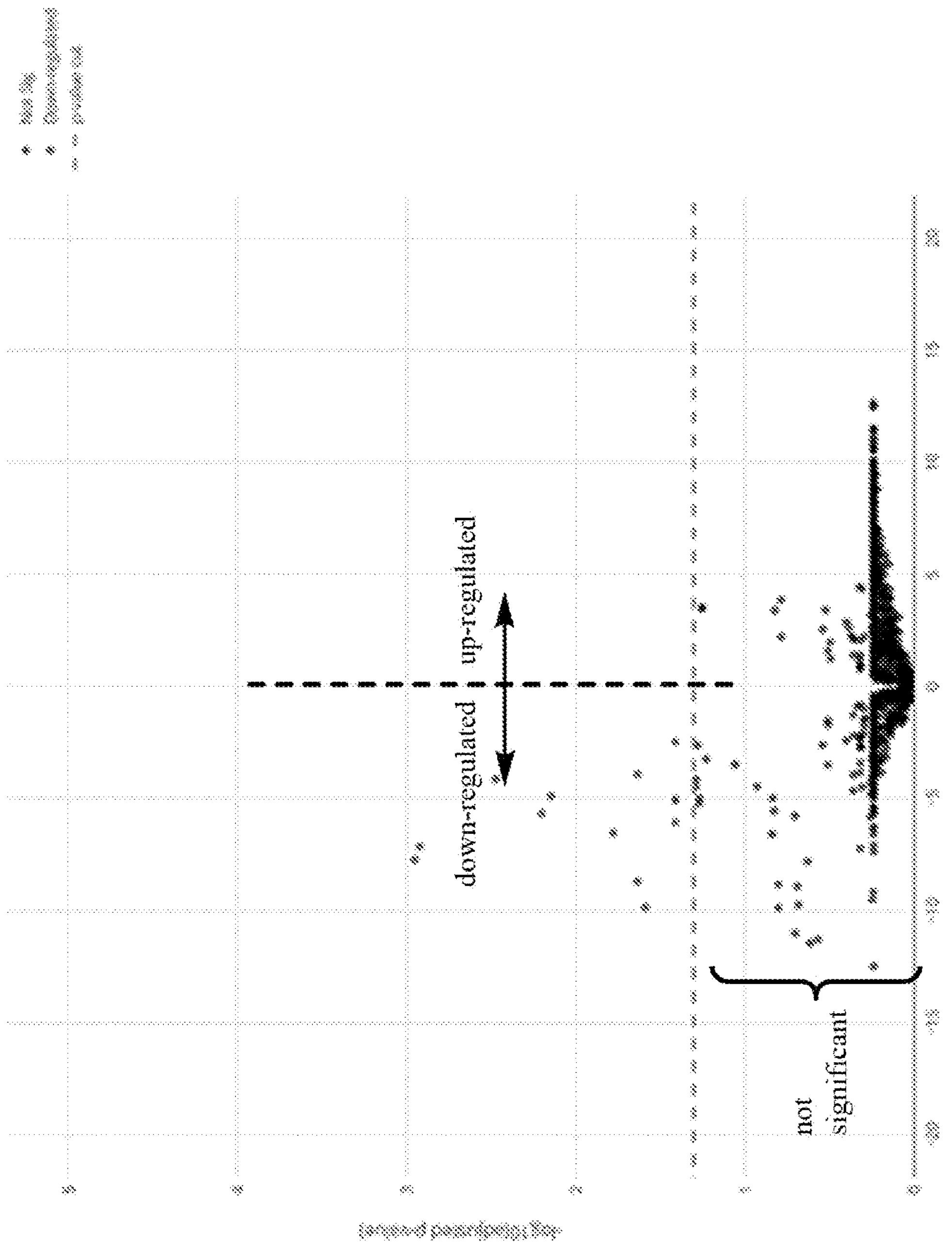
Figure 6C:
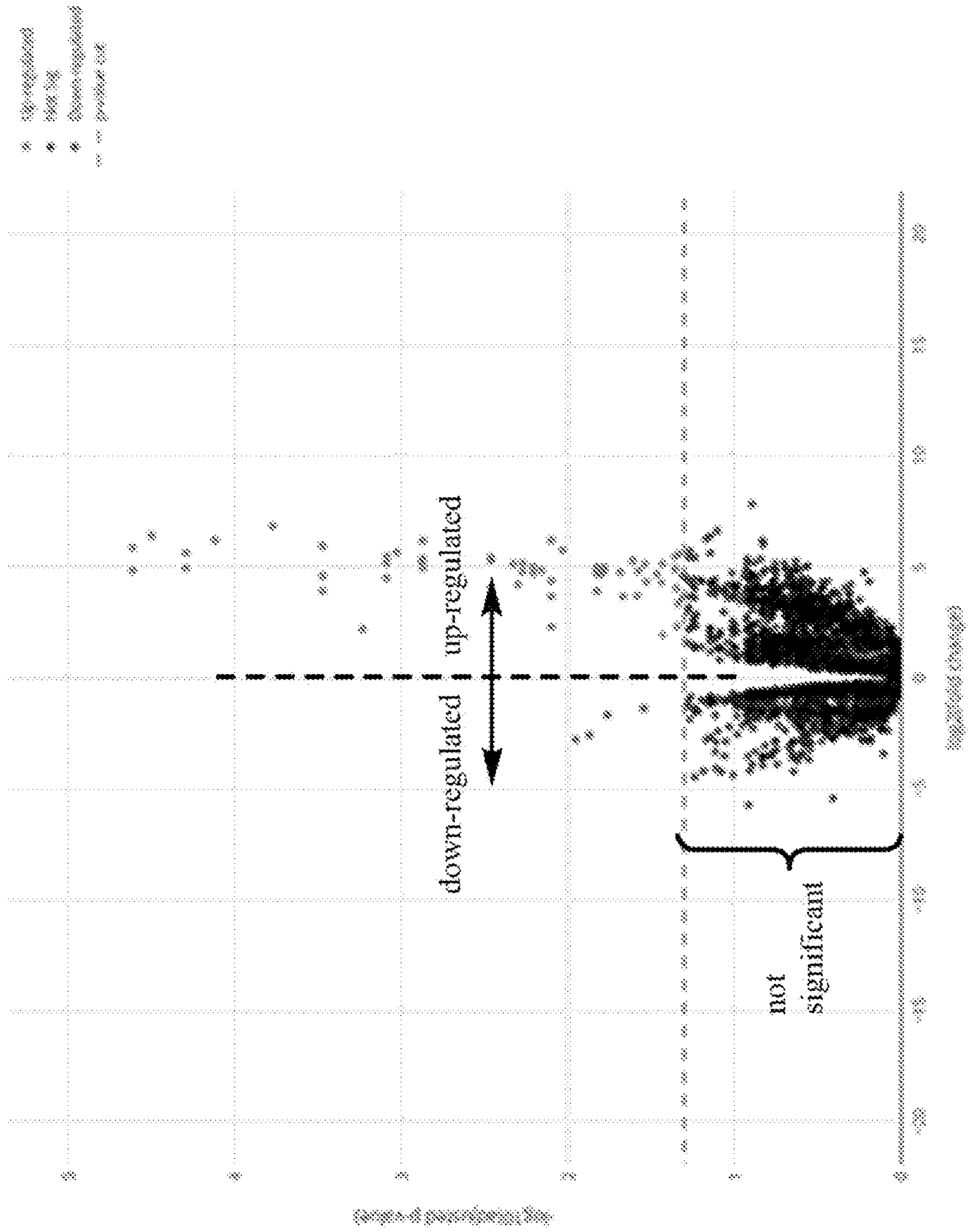

Aging involves a depletion of gene expression in the gut, evidenced by reduced RNA transcriptome in the gut in aged mice vs. young mice Example 3 evaluated the impact of oral dosing of ENT-01 (squalamine phosphate) on old mice. After 2 weeks of dosing, the animals were euthanized, and the GI tracts sectioned into stomach, duodenum, jejunum, ileum, caecum, colon, and rectum. The stomach tissues were then sent for histology, and the transcriptomes analyzed by RNAseq.

mRNA levels for all of the genes of Table 4 in the Examples showed a significant increase after treatment with ENT-01 (squalamine phosphate) (see e.g., Table 5A). This suggests that squalamine has a rejuvenating effect in the aged gut and this activity would be believed to extend to ENT-03 (Compound III) and salts, solvates, derivatives, and prodrugs thereof. Further, when the effect of oral administration of ENT-03 (Compound III) on the transcriptome of the tissues was examined, in each case it was observed that the transcriptional response in the young was blunted in comparison to that occurring in the aged animals (FIGS. 6A-6C). For example, in the stomach of treated young animals, 13 genes were differentially expressed, while 63 were in the aged group. Similarly, for the jejunum 42 genes were differentially expressed in the young, and 382 genes on treatment in the aged group. In the ileum, 80 genes were differentially expressed in the young, and 1162 genes in the aged animals treated with ENT-03 (Compound III).

The sets of genes that were differentially expressed (DEGs) with ageing were compared with those that were differentially expressed in the treated aged animals or in the treated young animals. Analysis of the overlapping DEGs between contrasts revealed, for example, in the stomach 37 genes down-regulated in ageing (old versus young) significantly overlapped with genes up-regulated by treatment with ENT-03 in old mice. In contrast the only significant overlap between the stomach ageing genes and those in the young ENT-03 treated stomach were 12 genes that were further down regulated in the ageing direction.

The "ageing" genes that ENT-03 (Compound III) appears to complement most significantly within the stomach are listed in Table 5B. Notably, in the stomach, the "restored" ageing genes include those involved in tissue renewal (fibroblast growth factor 2; zinc finger protein 383; forkhead box C2); neuronal differentiation (neural cell adhesion molecule 2); immunity (toll-like receptors 9 and 12; interleukin 2 receptor, beta chain), neurotransmitter synthesis and uptake (choline and serotonin transporters), and mitochondrial respiration (cytochrome c oxidase subunit 6B2).

Genes that significantly changed in expression between young and aged mice were identified (FIG. 6A). With ageing, the expression of 75 genes in the stomach was significantly decreased, and the expression of 11 genes was significantly increased (FIG. 6A). Meanwhile, fewer differences were observed between the gene expression profiles of the jejunum (FIGS. 10A-10D) or ileum (FIGS. 10D-10F) of young and aged mice. In the jejunum, 5 genes decreased in expression and 2 genes increased in expression with ageing. Whereas in the ileum, 19 genes decreased and 9 genes increased in expression. These results are consistent with the recognized reduced regenerative capacity of the ageing rodent stomach (Fukunaga et al., 1998), and the resilience with ageing of the small intestine (Eswaran et al., 2006).

Following oral administration of ENT-03 (Compound III) to young mice (20 weeks), 13 stomach genes responded and all were transcriptionally repressed by ENT-03 treatment (FIG. 6B). The expression of no more than 2 genes changed significantly in response to ENT-03 exposure in the jejunum and ileum for both young and aged mice.

In contrast, a more robust effect on gene expression in the stomach was observed in the older animals (78 weeks) treated with ENT-03 (Compound III). 63 genes were transcriptionally induced (FIG. 6C). Interestingly, 36 of the genes that increased in expression upon ENT-03 (Compound III) treatment of aged mice were the same that decreased in expression with ageing. These genes include those involved in tissue renewal (fibroblast growth factor 2 (Fgf2), zinc finger protein 382 (Zfp382) and forkhead box C2 (Foxc2)); in neuronal differentiation (neural cell adhesion molecule 2 (Ncam2)); in immunity (toll-like receptors 9 and 12 (Tlr9, Tlr12), interleukin 2 receptor, beta chain (Il2rb) and CD300 (Cd300ld)); in neurotransmitter synthesis and uptake (choline and serotonin transporters (Slc5a7, Slc6a4)); and in mitochondrial respiration (cytochrome c oxidase subunit 6B2 (Cox6b2)). These data support the hypothesis that oral administration of ENT-03 (Compound III) to old mice can reverse some of the changes in gene expression associated with ageing within the GI tract.

(4) Compound III and Alzheimer's Treatment

Example 6 details data supporting the use of ENT-03 (Compound III) in treating neurological diseases such as Alzheimer's disease. PTP1B dependent mechanisms have been utilized for reversal of memory impairment and normalization of behavior and reduction in neuronal loss in beta amyloid and tau mouse models of Alzheimer's disease (Ricke, Cruz et al. 2020). Other studies have shown reduction in the toxicity of beta amyloid aggregates by ENT-02 in vitro and in a *C. elegans* model of Alzheimer's disease (Limbocker, Chia et al. 2019).

ENT-02 (MSI-1436) reverses several conditions (in mice) that are associated with ageing, such as metabolic syndrome, Alzheimer's disease, atherosclerosis, cancer and a reduced capacity for regenerative repair. The data in Example 6 demonstrates that ENT-03 can treat Alzheimer's disease in murine models, which are acceptable animal models for human Alzheimer's disease.

The Morris water maze was used to test the effect of ENT-03 (Compound III) on spatial learning and memory deficits in 2 mouse models of familial Alzheimer's disease, hAPP-J20 mice that express a double mutant of the human amyloid precursor protein (Mucke et al., 2000), and PS19 mice that express the P301S mutant of the human microtubule associated protein tau (Yoshiyama et al., 2007). In both disease models, one with amyloidopathy and the other with a tauopathy, learning during the training phase (FIGS. 5A and 5E) and memory on the probe day (FIGS. 5B, 5C, 5F and 5G) were improved with ENT-03 treatment as compared to vehicle treated hAPP-J20 or PS19 littermate control mice (FIG. 5). The effect on preventing cognitive decline is similar to what has been observed with the related compound ENT-02 and hAPP-J20 and PS19 mice (Ricke et al., 2020).

(5) Synthetic Methods of Preparing ENT-03 (Compound III)

Synthetic methods of preparing aminosterols described herein, including ENT-03 (Compound III), are described in the example. In particular, the synthetic method comprises first comprises preparing BDG-5 from BDG-4:

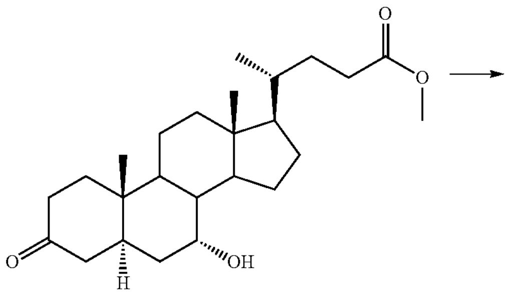
BDG-4
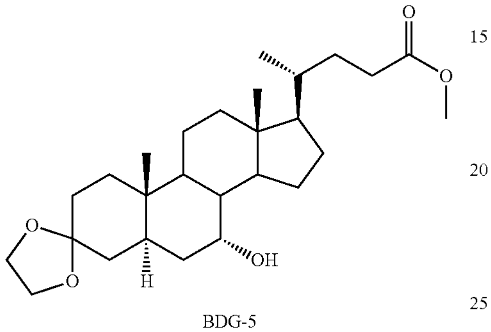
BDG-5
BDG-5: $^{1}$H NMR (500 MHz, $CDCl_3$) δ 3.93 (m, 4H), 3.82 (br s, 1H), 3.66 (s, 3H), 2.4-2.2 (m, 2H), 1.9-1.2 (m, 24H), 0.92 (d, 3H, J=7 Hz), 0.81 (s, 3H), 0.66 (s, 3H); $^{13}$C NMR ($CDCl_3$) δ 177, 109, 67.9, 64.2, 64.1, 55.8, 51.4, 50.5, 45.6, 42.6, 39.5, 39.4, 37.5, 36.3, 36.1, 35.7, 35.5, 35.4, 31.2, 31.0, 30.9, 28.0, 23.6, 20.9, 18.3, 11.8, 10.4.
Next, BDG-6 is prepared from BDG-5:
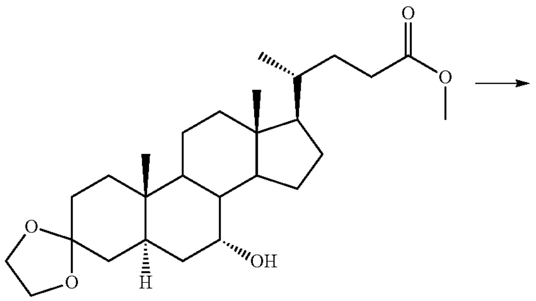
BDG-5
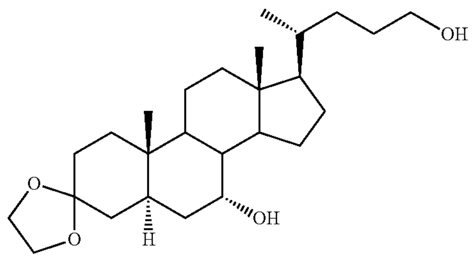
BDG-6
BDG-6: $^{1}$H NMR (500 MHz, $CDCl_3$) δ 3.93 (m, 4H), 3.82 (br s, 1H), 3.61 (m, 2H), 1.97-1.84 (m, 4H), 1.7-1.0 (m, 22H), 0.93 (d, 3H, J=7 Hz), 0.81 (s, 3H), 0.66 (s, 3H); $^{13}$C NMR ($CDCl_3$) δ 109.3, 67.9, 64.15, 64.13, 63.5, 56.0, 50.6, 45.6, 42.6, 39.51, 39.48, 37.5, 36.3, 36.1, 35.7, 35.6, 35.5, 31.8, 31.2, 29.4, 28.2, 23.6, 20.9, 18.6, 11.8, 10.4.
Next, BDG-7 is prepared from BDG-6:
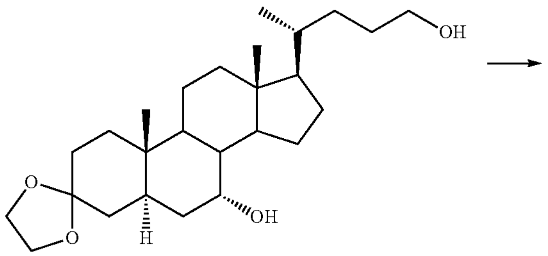
BDG-6
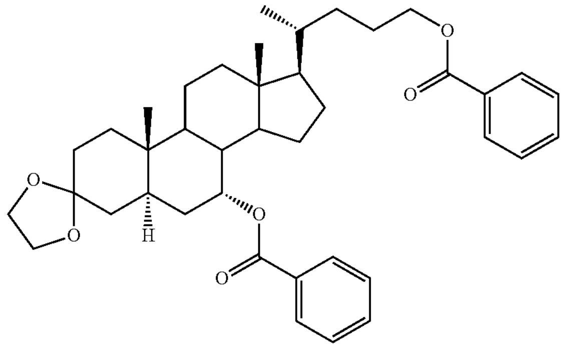
BDG-7
BDG-7: $^{1}$H NMR (500 MHz, $CDCl_3$) δ 8.07 (d, 2H, J=8 Hz), 8.00 (d, 2H, J=8 Hz), 7.57 (t, 1H, J=8 Hz), 7.53 (t, 1H, J=8 Hz), 7.47 (t, 2H, J=8 Hz), 7.41 (t, 2H, J=8 Hz), 5.16 (br s, 1H), 4.25 (m, 2H), 3.87 (m, 4H), 2.02-1.85 (m, 2H), 1.8-1.1 (m, 22H), 0.95 (d, 3H, J=7 Hz), 0.88 (s, 3H), 0.68 (s, 3H); $^{13}$C NMR ($CDCl_3$) δ 166.7, 166.0, 132.8, 131.1, 130.5, 129.7, 129.5, 128.4, 128.3, 109.0, 71.9, 65.5, 64.2, 64.1, 55.8, 50.7, 47.2, 42.8, 39.5, 38.6, 37.4, 37.2, 35.7, 35.5, 35.3, 33.3, 32.0, 31.2, 28.0, 25.2, 23.6, 21.1, 18.6, 11.8, 10.5.
Next, BDG-8 is prepared from BDG-7:
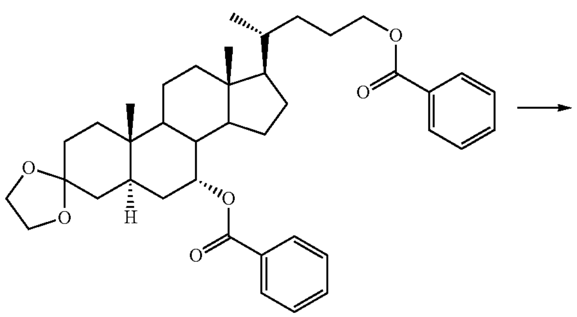
BDG-7

-continued

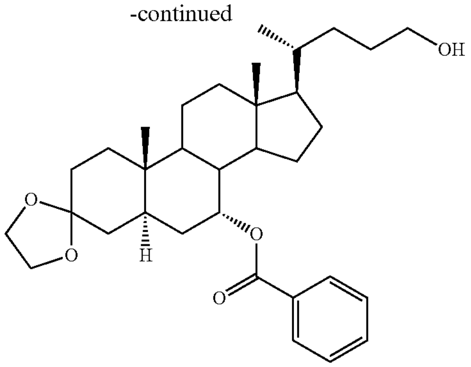

BDG-8

BDG-8: 17.24 kg, 93.3%). $^1$H NMR (500 MHz, $CDCl_3$) δ 8.07 (d, 2H, J=8 Hz), 7.57 (t, 1H, J=7 Hz), 7.48 (t, 2H, J=7 Hz), 5.15 (br s, 1H), 3.88 (m, 4H), 3.56 (br s, 2H), 2.02-1.84 (m, 2H), 1.75-0.98 (m, 24H), 0.92 (d, 3H, J=6.5 Hz), 0.88 (s, 3H), 0.67 (s, 3H). $^{13}$C NMR ($CDCl_3$) δ 166.0, 132.7, 131.0, 129.7, 128.4, 109.0, 71.9, 64.2, 64.1, 63.5, 55.8, 50.7, 47.2, 42.7, 39.5, 38.6, 37.3, 37.2 35.7, 35.5, 33.3, 31.7, 31.3, 29.3, 28.0, 23.6, 21.1, 18.6, 11.8, 10.5.

Next, Compound 1 is prepared from BDG-8:

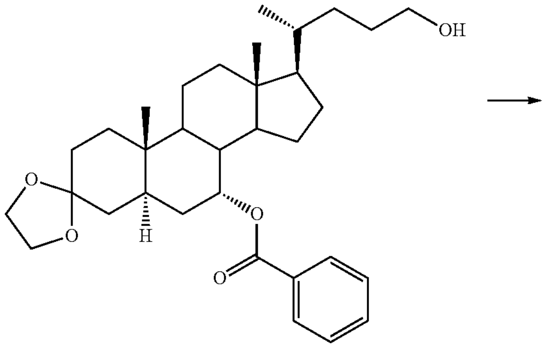

BDG-8

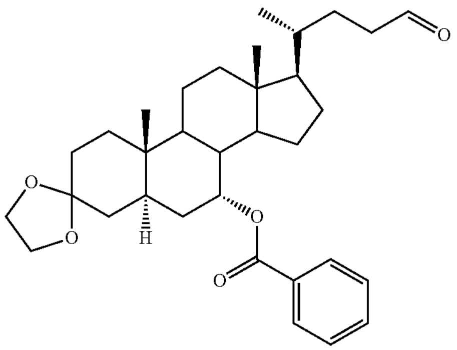

1

Compound 1: $^1$H NMR (500 MHz, $CDCl_3$) δ 9.72 (s, 1H), 8.07 (d, 2H, J=7 Hz), 7.59 (t, 1H, J=7 Hz), 7.49 (t, 2H, J=7 Hz), 5.16 (br s, 1H), 3.88 (m, 4H), 2.45-2.27 (m, 2H), 2.00-1.85 (m, 2H), 1.78-1.17 (m, 22H), 0.913 (d, 3H, J=Hz), 0.88 (s, 3H), 0.68 (s, 3H). $^{13}$C NMR ($CDCl_3$) δ 203, 166, 132.8, 131.0, 129.8, 128.4, 109, 72.0, 64.17, 64.11, 55.7, 50.7, 47.2, 42.8, 40.8, 39.5, 38.6, 37.3, 37.2, 35.7, 35.5, 35.4, 33.3, 31.2, 27.9, 27.8, 23.7, 21.1, 18.3, 11.7, 10.5.

Next, Compound 2 is prepared from Compound 1:

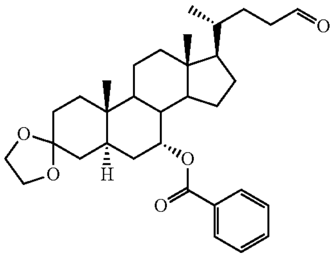

1
Molecular Weight: 522.73

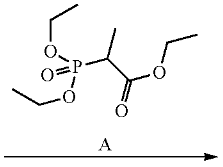

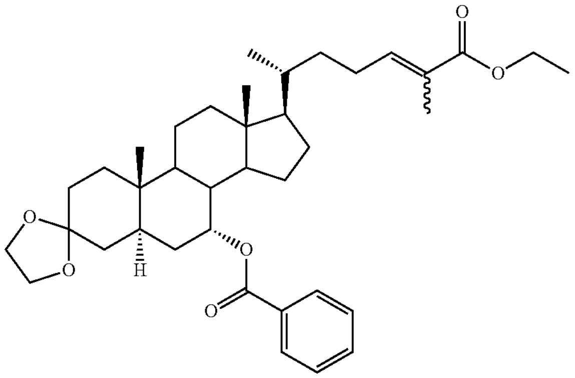

2
Molecular Weight: 606.84

Compound 2: $^1$H NMR ($CDCl_3$, 300 MHz) δ 8.10-8.07 (m, 2H), 7.60-7.57 (m, 1H), 7.52-7.47 (m, 2H), 6.7, 5.9 (t, 1H), 5.17 (m, 1H), 4.21-4.12 (m, 2H), 3.92-3.88 (m, 4H), 2.06 (s, 3H), 2.2-1.0 (m, 29H), 0.95 (d, 3H, J=7 Hz), 0.90 (s, 3H), 0.69 (s, 3H); MS (ES+) 485.45 ($M-C_7H_7O_2+H$).

Next, Compound 3 is prepared from Compound 2:

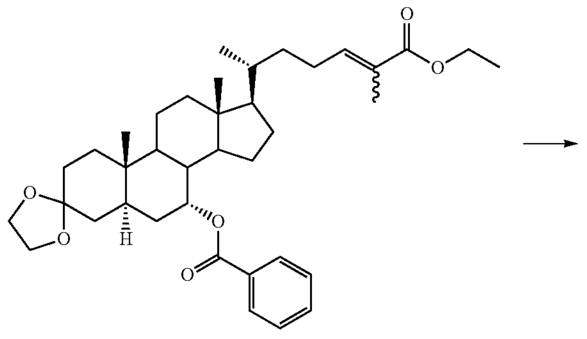

2
Molecular Weight: 606.84

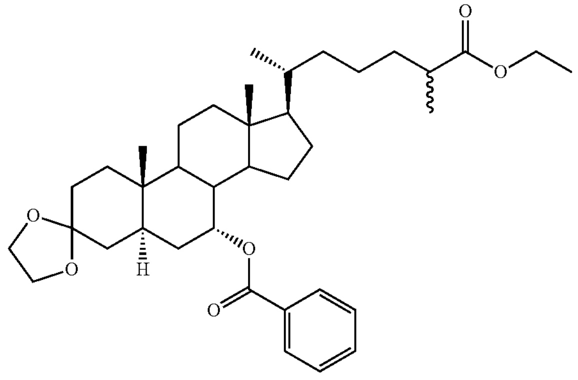

3
Molecular Weight: 608.86

Compound 3: $^{1}H$ NMR ($CDCl_3$, 300 MHz) δ 8.09-8.06 (m, 2H), 7.58-7.56 (m, 1H), 7.55-7.45 (m, 2H), 5.16 (m, 1H), 4.12-4.05 (m, 2H), 3.90-3.85 (m, 4H), 2.39-2.36 (m, 1H), 2.0-1.0 (m, 35H), 1.11 (d, 3H, J=7 Hz), 0.88 (s, 3H), 0.67 (s, 3H); MS (ES+) 487.46 ($M-C_7H_7O_2+H$).

Next, Compound 4 is prepared from Compound 3:

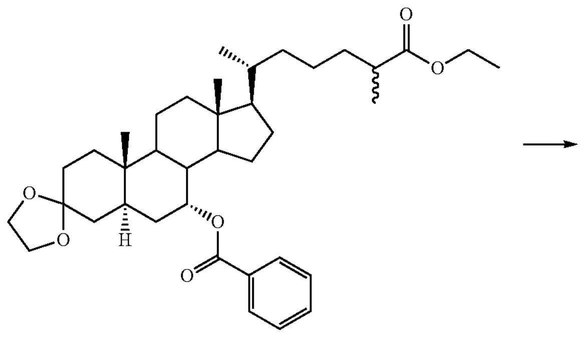

3
Molecular Weight: 608.86

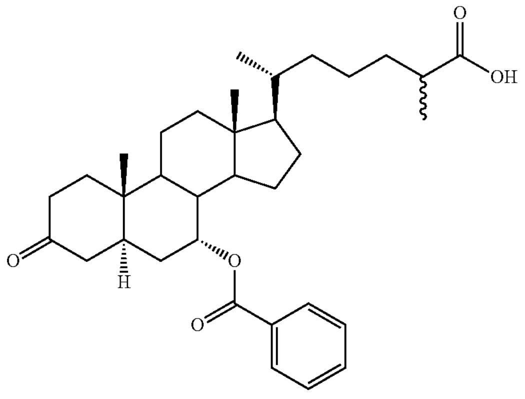

4
Molecular Weight: 536.75

Compound 4: $^{1}H$ NMR ($CDCl_3$, 300 MHz) δ 8.05-8.02 (m, 2H), 7.60-7.57 (m, 1H), 7.51-7.45 (m, 2H), 5.21 (m, 1H), 2.4-1.0 (m, 32H), 1.15 (d, 3H, J=7 Hz), 1.09 (s, 3H), 0.91 (d, 3H, J=7 Hz), 0.67 (s, 3H); MS (ES+) 415.52 ($M-C_7H_7O_2+H$).

Next, Compound 5 is prepared from Compound 4:

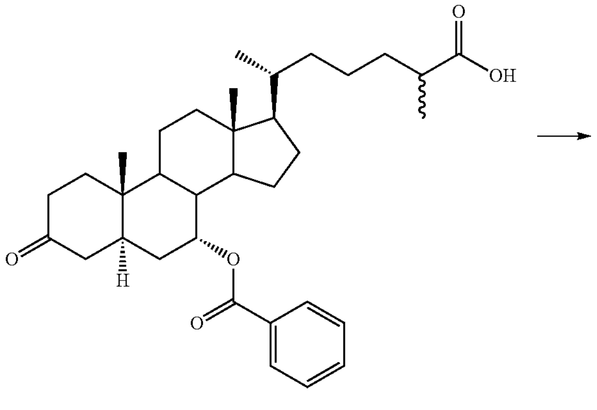

4
Molecular Weight: 536.75

-continued
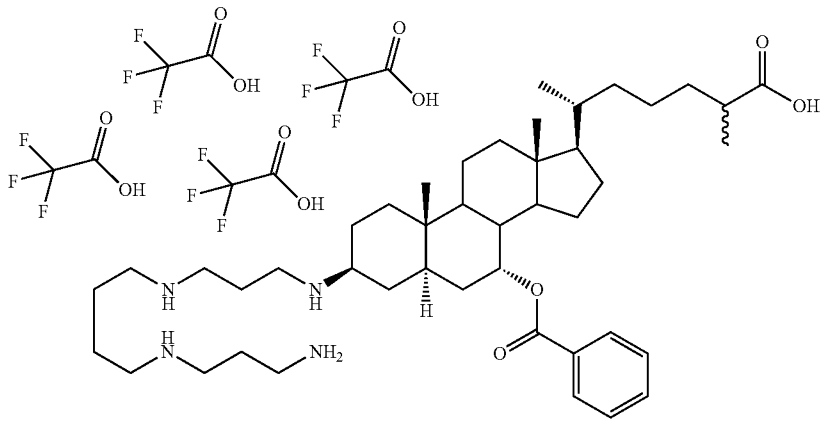
5
Exact Mass: 722.57
Molecular Weight: 723.10
Compound 5: $^1H$ NMR ($CD_3OD$, 300 MHz) δ 8.05-8.02 (m, 2H), 7.66-7.60 (m, 1H), 7.54-7.49 (m, 2H), 5.17 (m, 1H), 3.36-3.04 (m, 13H), 2.37 (m, 1H), 2.1-1.0 (m, 39H), 1.10 (d, 3H, J=7 Hz), 0.95 (m, 6H), 0.74 (s, 3H); MS (ES+) 723.78 (M+H).
Next, ENT-03 (Compound III) is prepared from Compound 5:
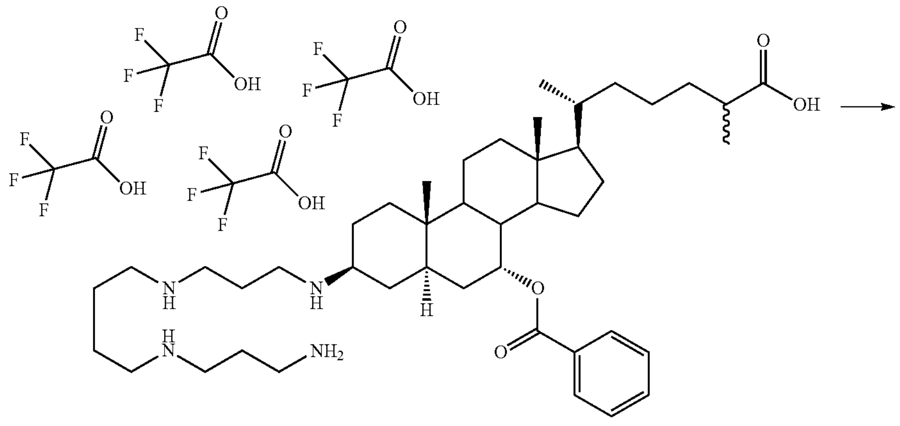
5
Exact Mass: 722.57
Molecular Weight: 723.10
Molecular Weight: 1179.19

-continued

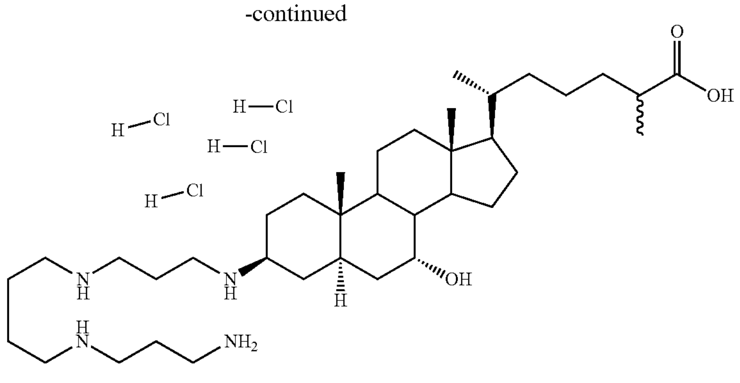

ENT-03
Exact Mass: 618.54
Molecular Weight: 618.99
Molecular Weight: 764.82

Compound III (ENT-03) as the tetra-HCl salt: $^{1}H$ NMR ($CD_3OD$, 300 MHz) δ 3.80 (br s, 1H), 3.20-3.05 (m, 13H), 2.37 (m, 1H), 2.2-1.0 (m, 36H), 1.13 (d, 3H, J=7 Hz), 0.93 (d, 3H, J=7 Hz), 0.87 (s, 3H), 0.69 (s, 3H); MS (ES+) 619.31 (M+H).

Exemplary synthetic methods of preparing deuterated ENT-03 (ENT-03-d3 and ENT-03-d4) are also described in the examples below.

II. Compounds

In one aspect, an aminosterol compound is provided having the formula:

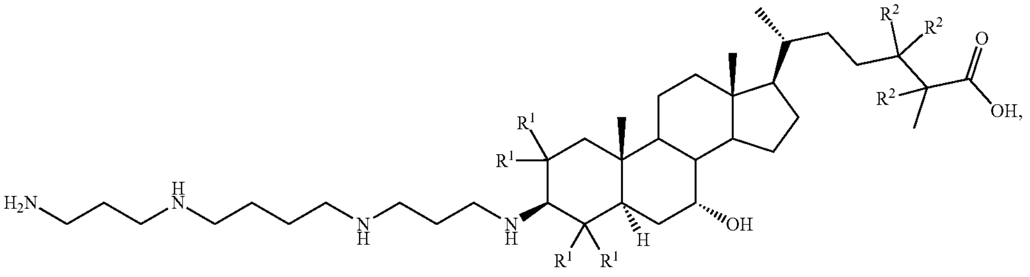

wherein: $R^1$ is H or D; and $R^2$ is H or D; provided that all of $R^1$ are H, all of $R^2$ are H, or all of $R^1$ and $R^2$ are H, or a pharmaceutically acceptable salt, solvate, prodrug, or derivative thereof.

In one embodiment, the aminosterol compound h the formula:

Compound III

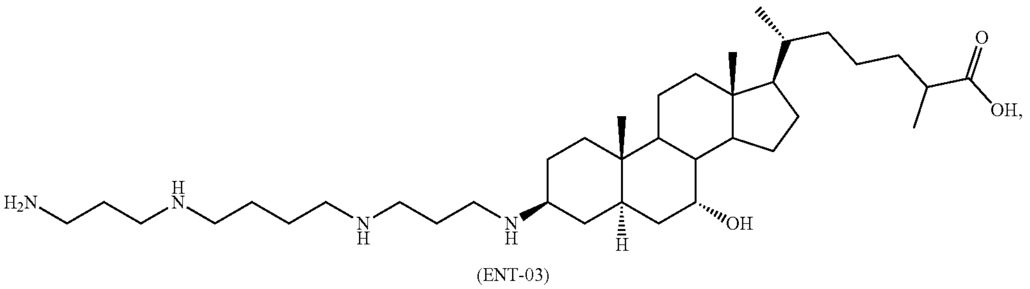

(ENT-03)

is provided, or a pharmaceutically acceptable salt, solvate, prodrug, or derivative thereof.

In one embodiment, the aminosterol has the formula:

C25 (R) Compound III (ENT-03)

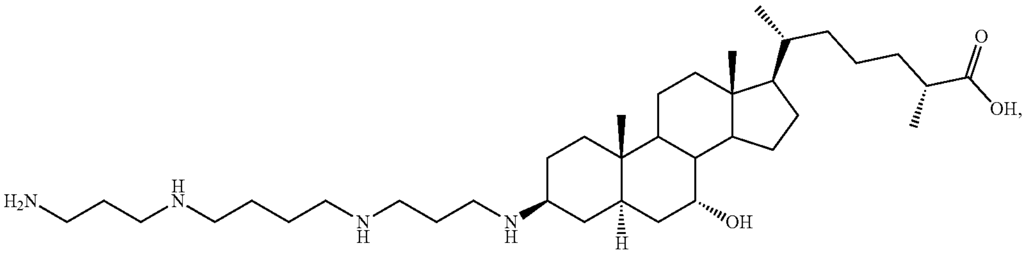

or a pharmaceutically acceptable salt, solvate, prodrug, or derivative thereof.

In one embodiment, the aminosterol has the formula:

Compound III

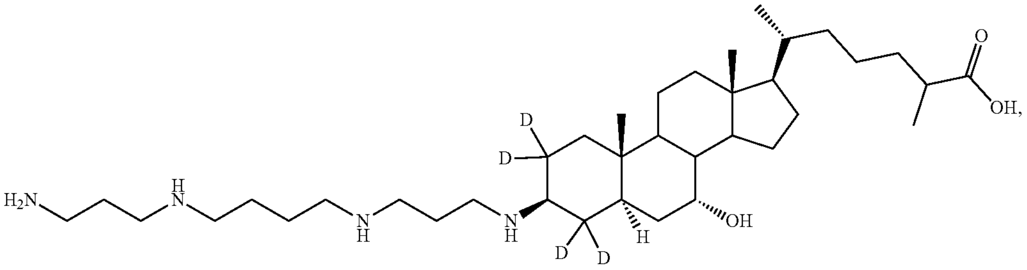

(ENT-03-d4)

or a pharmaceutically acceptable salt, solvate, prodrug, or derivative thereof.

In one embodiment, the aminosterol has the formula:

Compound III

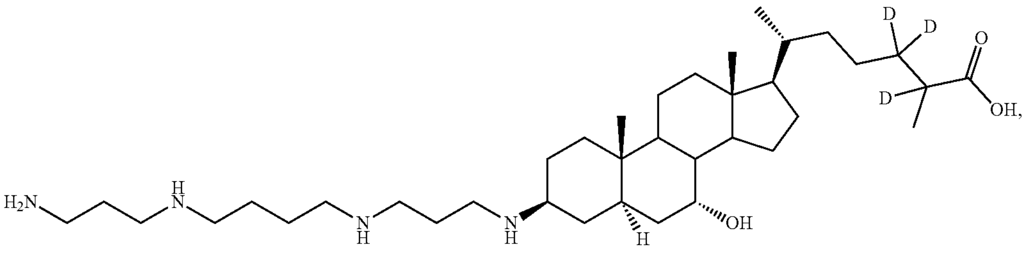

(ENT-03-d4)

or a pharmaceutically acceptable salt, solvate, prodrug, or derivative thereof.

In one aspect an aminosterol is provided having the formula:

(Compound IV)

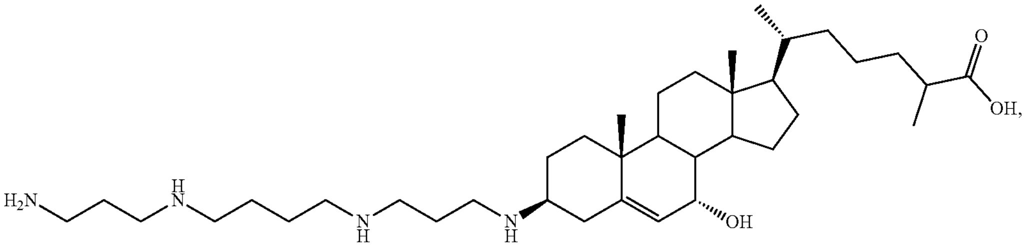

or a pharmaceutically acceptable salt, solvate, prodrug, or derivative thereof.

In one embodiment, the aminosterol has the formula:

(C25 (R) Compound IV) (D5 ENT-03)

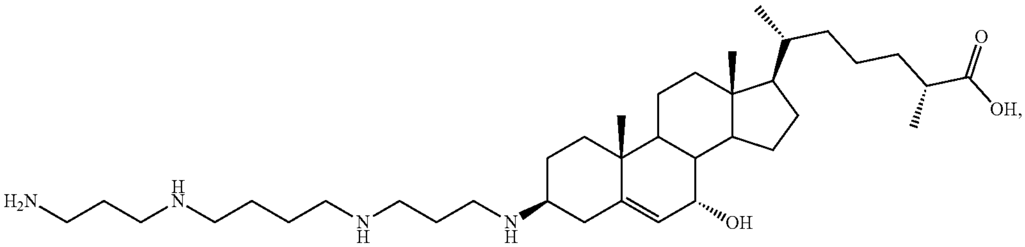

or a pharmaceutically acceptable salt, solvate, prodrug, or derivative thereof.

In another aspect, an aminosterol compound having the formula:

Compound V

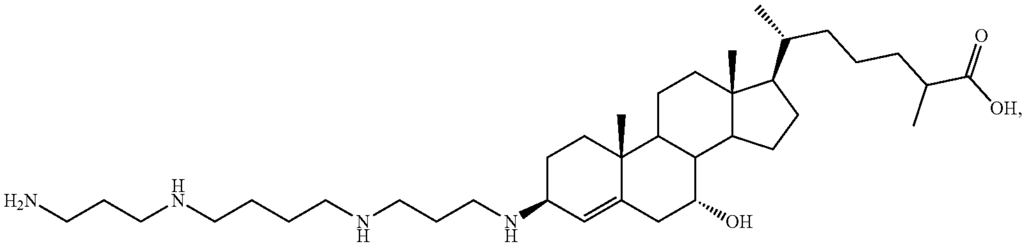

(Δ4 ENT-03)

is provided, or a pharmaceutically acceptable salt, solvate, prodrug, or derivative thereof.

In some embodiments, the aminosterol compound has the formula:

C25 (R) Compound V (D4 ENT-03)

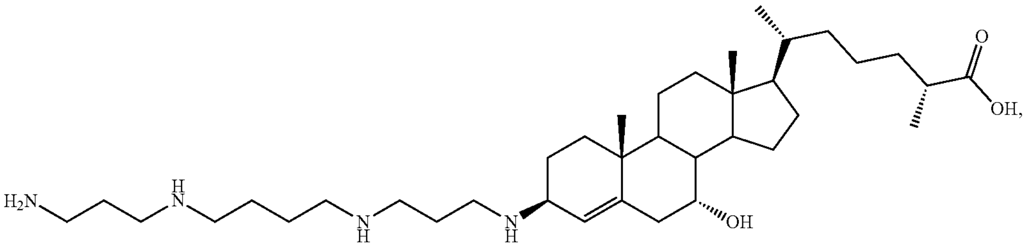

or a pharmaceutically acceptable salt, solvate, prodrug, or derivative thereof.

In one embodiment, the prodrug comprises a compound of formula:

(Compound III-P)

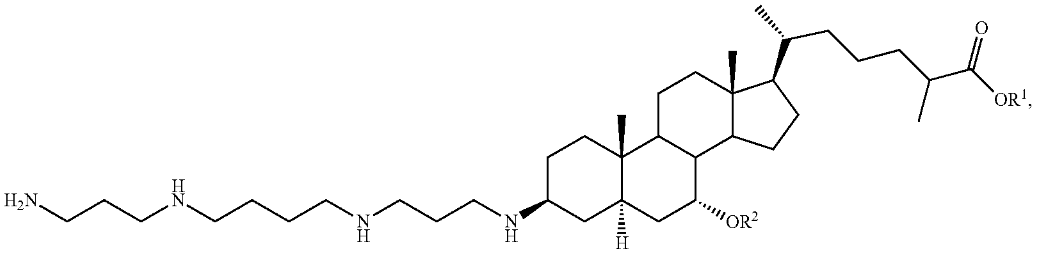

wherein:

$R^1$ is H, an optionally substituted aryl, optionally substituted heteroaryl, optionally substituted $C_1$-$C_6$ alkyl, optionally substituted $C_1$-$C_6$ alkynyl, optionally substituted heterocyclyl, optionally substituted $C_3$-$C_8$ cycloalkyl, or optionally substituted $C_1$-$C_6$ alkenyl; and $R^2$ is H or —C(O)$R^3$, wherein $R^3$ is an optionally substituted aryl, optionally substituted heteroaryl, optionally substituted $C_1$-$C_6$ alkyl, optionally substituted $C_1$-$C_6$ alkynyl, optionally substituted heterocyclyl, optionally substituted $C_3$-$C_8$ cycloalkyl, or optionally substituted $C_1$-$C_6$ alkenyl; provided that at least one of $R^1$ and $R^2$ is not H, or a pharmaceutically acceptable salt, solvate, prodrug, or derivative thereof.

In one embodiment, the prodrug comprises a compound of formula:

(C25 (R) Compound III-P)

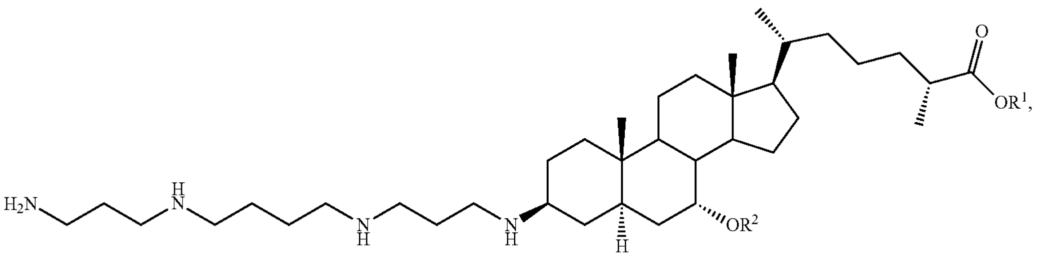

or a pharmaceutically acceptable salt, solvate, prodrug, or derivative thereof.

In one aspect, the prodrug comprises a compound having the formula:

(Compound Iv-P)

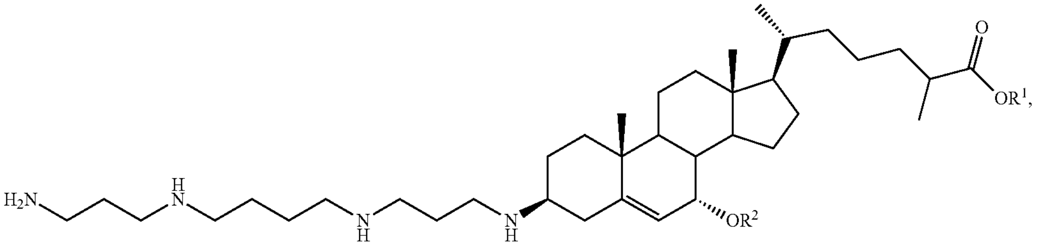

wherein:

$R^1$ is H, an optionally substituted aryl, optionally substituted heteroaryl, optionally substituted $C_1$-$C_6$ alkyl, optionally substituted $C_1$-$C_6$ alkynyl, optionally substituted heterocyclyl, optionally substituted $C_3$-$C_8$ cycloalkyl, and optionally substituted $C_1$-$C_6$ alkenyl; and $R^2$ is H or —C(O)$R^3$, wherein $R^3$ is an optionally substituted aryl, optionally substituted heteroaryl, optionally substituted $C_1$-$C_6$ alkyl, optionally substituted $C_1$-$C_6$ alkynyl, optionally substituted heterocyclyl, optionally substituted $C_3$-$C_8$ cycloalkyl, or optionally substituted $C_1$-$C_6$ alkenyl; provided that at least one of $R^1$ and $R^2$ is not H, or a pharmaceutically acceptable salt, solvate, prodrug, or derivative thereof.

In one embodiment, the prodrug comprises a compound of formula:

(C25 (R) Compound Iv-P)

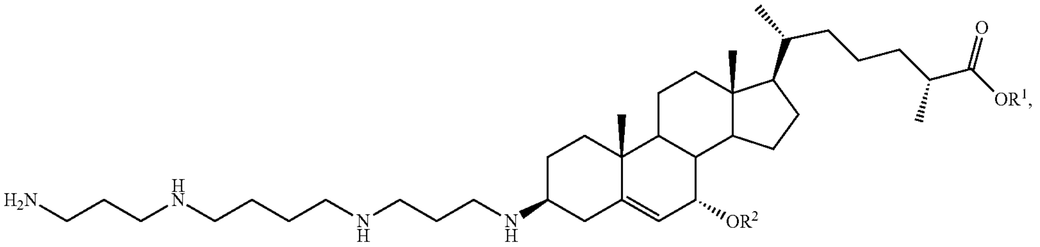

or a pharmaceutically acceptable salt, solvate, prodrug, or derivative thereof.

In another aspect, an aminosterol compound having the formula:

Compound V-P

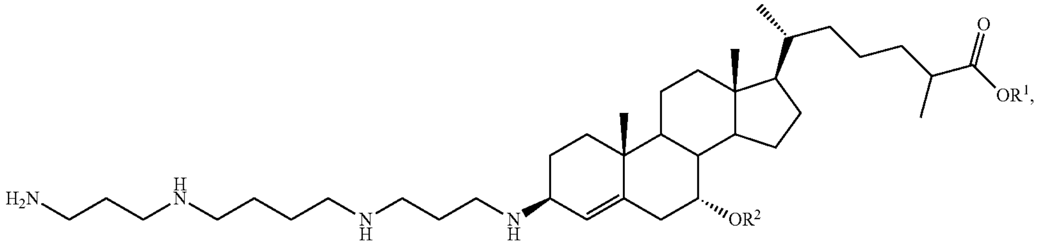

is provided wherein: $R^1$ is H, an optionally substituted aryl, optionally substituted heteroaryl, optionally substituted $C_1$-$C_6$ alkyl, optionally substituted $C_1$-$C_6$ alkynyl, optionally substituted heterocyclyl, optionally substituted $C_3$-$C_8$ cycloalkyl, and optionally substituted $C_1$-$C_6$ alkenyl; and $R^2$ is H or —C(O)$R^3$, wherein $R^3$ is an optionally substituted aryl, optionally substituted heteroaryl, optionally substituted $C_1$-$C_6$ alkyl, optionally substituted $C_1$-$C_6$ alkynyl, optionally substituted heterocyclyl, optionally substituted $C_3$-$C_8$ cycloalkyl, or optionally substituted $C_1$-$C_6$ alkenyl; provided that at least one of $R^1$ and $R^2$ is not H, or a pharmaceutically acceptable salt, solvate, prodrug, or derivative thereof.

In one embodiment, the aminosterol compound has the formula:

(C25 (R) Compound V-P)

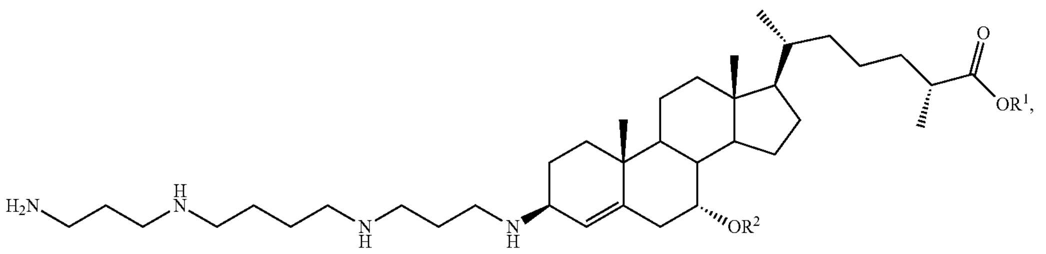

or a pharmaceutically acceptable salt, solvate, prodrug, or derivative thereof.

Exemplary structures proposed herein include:

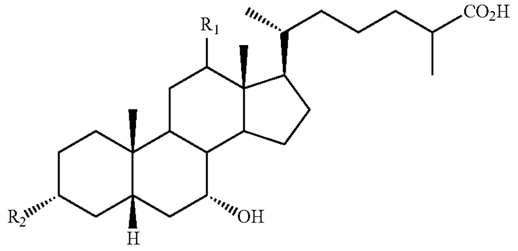

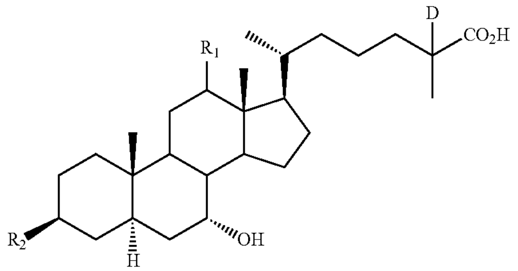

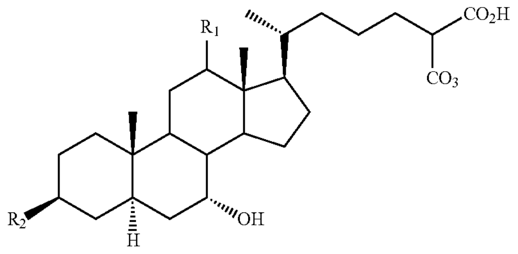

-continued

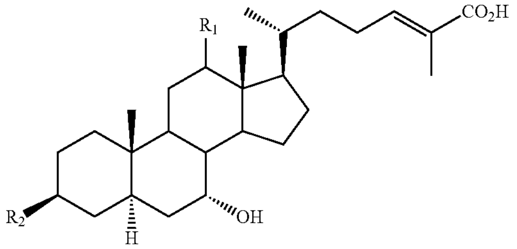

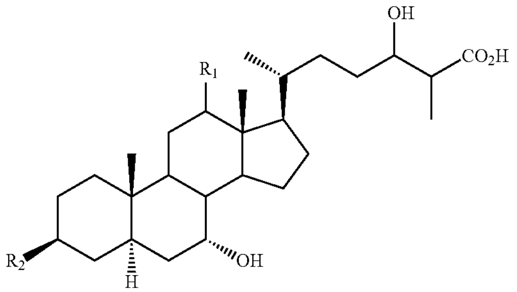

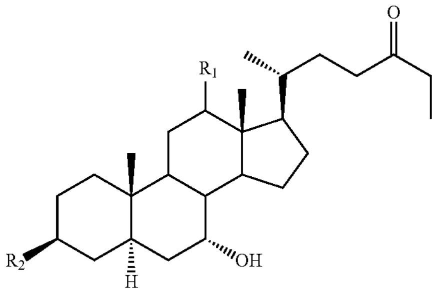

-continued

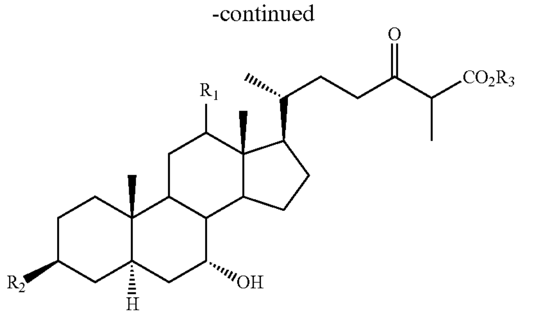

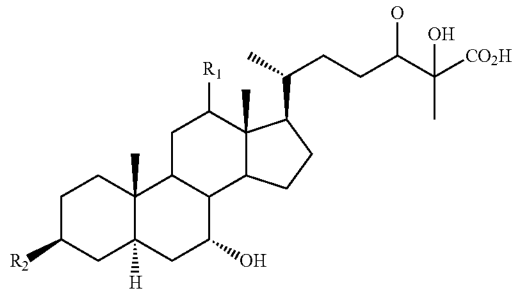

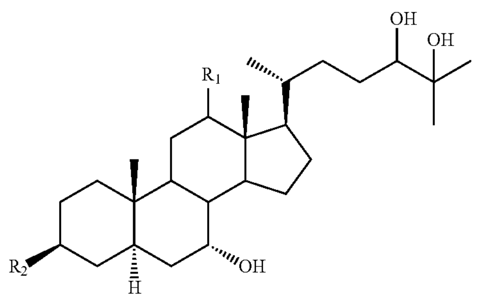

$R_1$ H or OH $R_2$

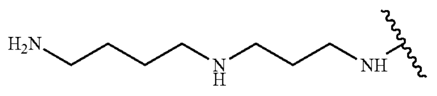

or

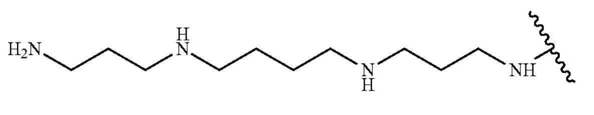

$R_3$ —$CH_3$, iso-propyl, H

The aminosterols of the present disclosure may comprise an asymmetric carbon atom. As such, aminosterols of this disclosure can exist as either individual enantiomers, or mixtures of entdepicted above. The present disclosure encompasses both the mixture at C25 and the natural R-orientation of the compound. Accordingly, an aminosterol of the present disclosure can include both racemic mixtures, and also individual respective stereoisomers that are substantially free from another possible stereoisomer. The term "substantially free of other stereoisomers" as used herein means less than about 25%, less than about 20%, less than about 15%, less than about 10%, less than about 5%, less than about 4%, less than about 3%, less than about 2%, or less than about 1% of other stereoisomers, or less than "about X"% of other stereoisomers (wherein X is a number between 0 and 100, inclusive) are present.

In some embodiments, the aminosterol is a derivative of any of the aminosterols disclosed herein, or a derivative of Compound III (ENT-03), modified through medical chemistry to improve biodistribution, ease of administration, metabolic stability, or any combination thereof. In some embodiments, Compound III or the derivative aminosterol is modified to include one or more of the following: (1) substitutions of the carboxylate by a sulfonate, phosphate, or other anionic moiety chosen to circumvent metabolic removal of the sulfate moiety and oxidation of the cholesterol side chain; (2) replacement of a hydroxyl group by a non-metabolizable polar substituent, such as a fluorine atom, to prevent its metabolic oxidation or conjugation; and/or (3) substitution of various ring hydrogen atoms to prevent oxidative or reductive metabolism of the steroid ring system.

The present technology also provides salts, solvates and hydrates of the aminosterols disclosed herein. A salt of an aminosterol of this technology is formed between an acid and a basic group of the aminosterol, such as an amino functional group, or a base and an acidic group of the aminosterol, such as a carboxyl functional group. According to another embodiment, the aminosterol is a pharmaceutically acceptable acid addition salt. Examples of pharmaceutically acceptable salts include, but are not limited to, hydrochloride, sodium, sulfate, acetate, phosphate or diphosphate, chloride, potassium, maleate, calcium, citrate, mesylate, nitrate, tartrate, aluminum, and gluconate.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosutfate, bisulfate, sulfite, bisulfate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-I,6-dioate, benzoate, chlorobenzoate, methylbenzoate, dinitrobenzoate, hydroxybenzoate, methoxybenzoate, phthalate, terephathalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In some embodiments, pharmaceutically acceptable acid addition salts include those formed with mineral acids such as hydrochloric acid, hydrobromic acid, and phosphoric acid.

III. Methods of Making Aminosterol Compounds of the Disclosure
In one aspect, a method of producing an aminosterol of formula:
ENT-03 (Compound III)
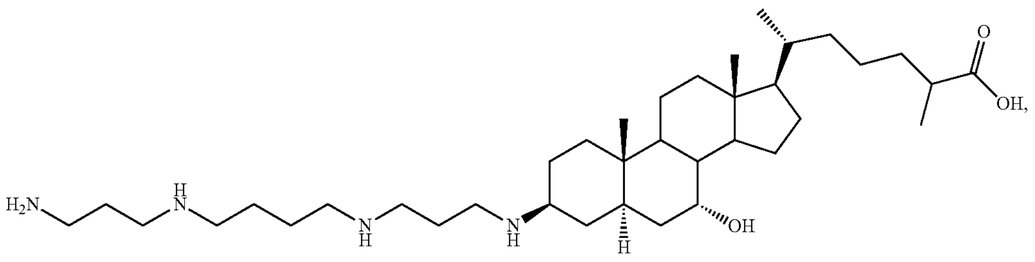
is provided, comprising stimulating the addition of spermine to ENT Ia (Compound Ia):
ENT-01a (Compound Ia)
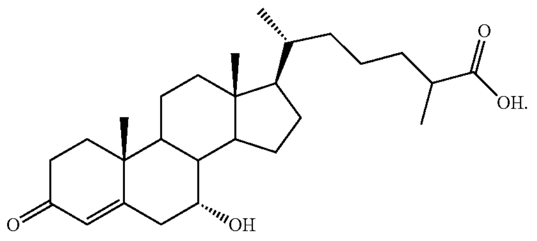
In one aspect, a method of suppressing the formation of an aminosterol of formula:
ENT-03 (Compound III)
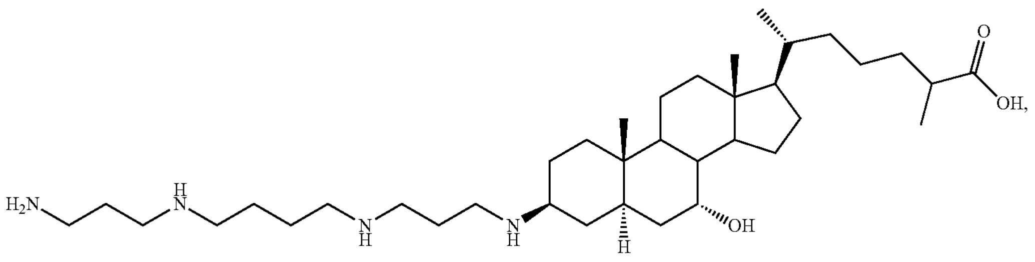

is provided, comprising suppressing the addition of spermine to ENT-Ola (Compound Ia):
ENT-01a (Compound Ia)
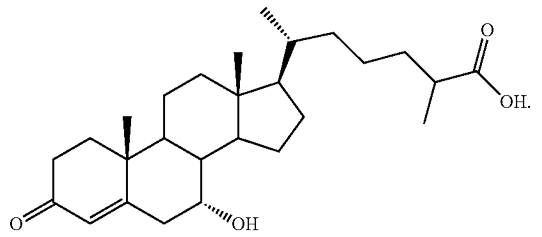
In some embodiments, ENT-Ola (Compound Ia) has the formula:
ENT-01 (Compound I)
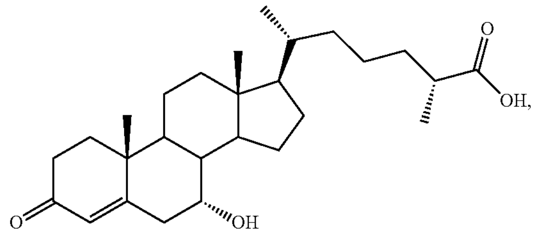
and ENT-03 (Compound III) has the formula:
C25 (R) ENT-03 (C25 (R) Compound III)
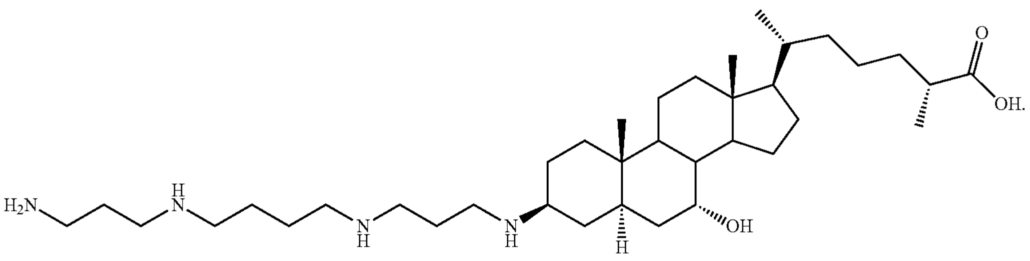
In one aspect, a method of producing an aminosterol of formula:
(Compound IV)
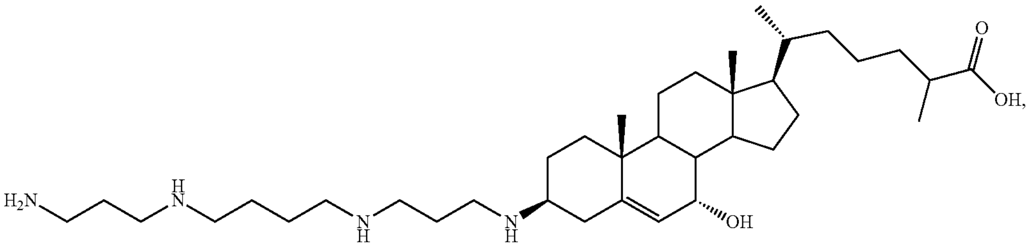

is provided, the method comprising stimulating the addition of spermine to Compound Ia (ENT-01a):

(Compound Ia)

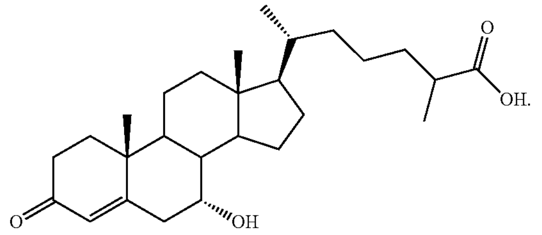

In one aspect, a method of suppressing the formation of an aminosterol of formula:

(Compound IV)

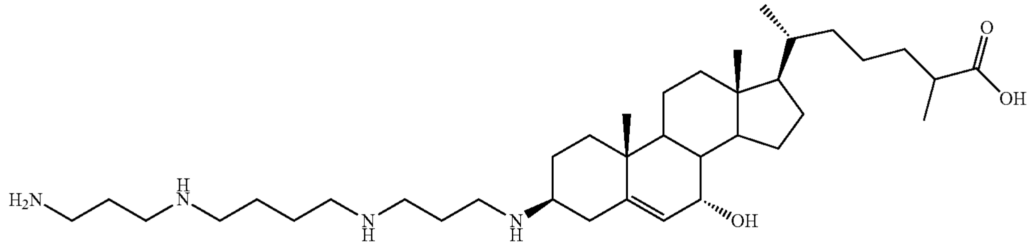

is provided, the method comprising suppressing the addition of spermine to Compound Ia:

(Compound Ia)

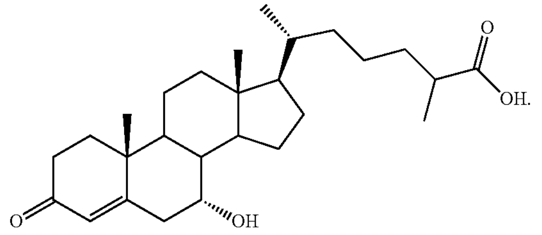

In some embodiments, Compound Ia has the formula:

(Compound I; ENT-01)

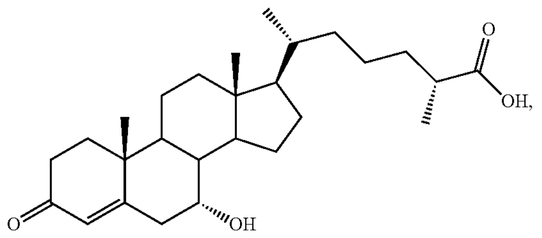

and Compound IV has the formula:

($C_{25}$ (R) Compound IV)

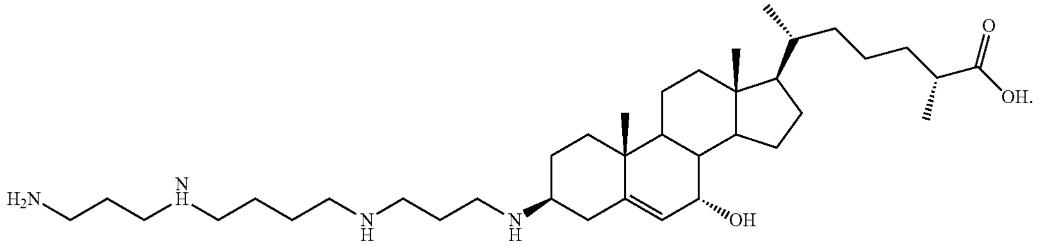

In another aspect, a method of producing an aminosterol of formula:

(Compound V)

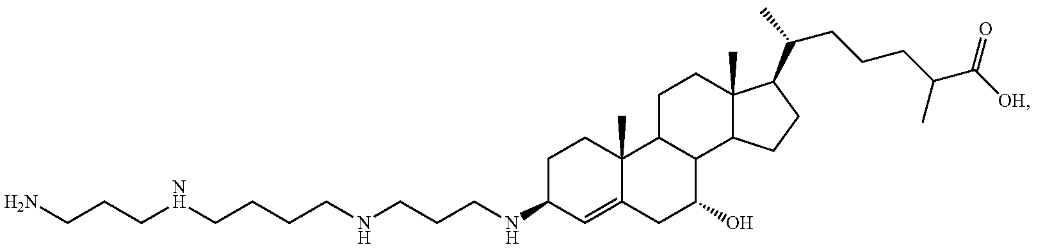

is provided, the method comprising stimulating the addition of spermine to Compound Ia:

ENT-01a (Compound Ia)

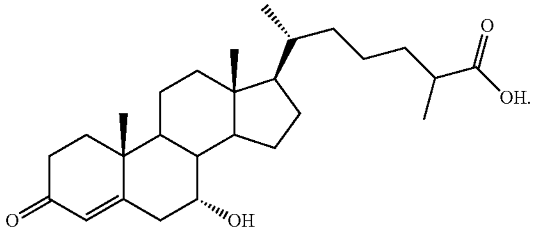

In another aspect, a method of suppressing the formation of an aminosterol of formula:

(Compound V)

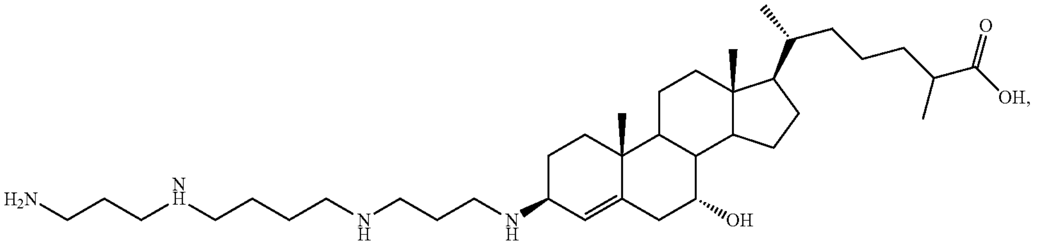

is provided, the method comprising suppressing the addition of spermine to Compound Ia:

ENT-01a (Compound Ia)

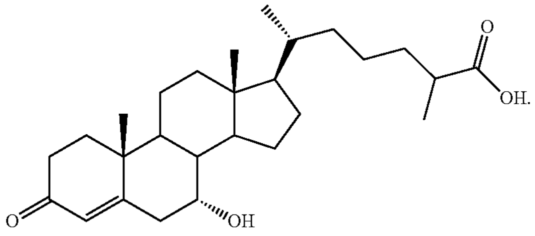

In some embodiments, Compound Ia has the formula:

ENT-01 (Compound I

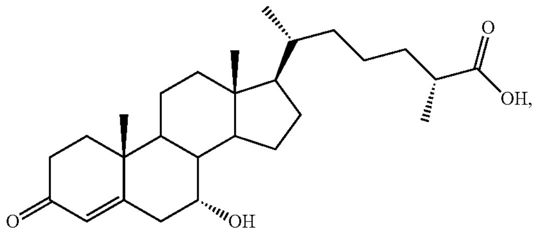

and Compound V has the formula:

($C_{25}$ (R) Compound V)

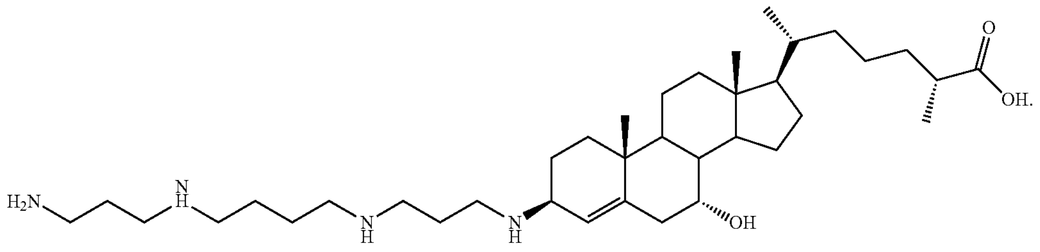

In some embodiments, the aminosterol is produced in vivo in a subject. In some embodiments, the aminosterol is produced in vitro.

In some embodiments, the addition of spermine to Compound I is suppressed in vivo in a subject. In some embodiments, the addition of spermine to Compound I is suppressed in vitro. In some embodiments, the addition of spermine to Compound Ia is suppressed in vivo in a subject. In some embodiments, the addition of spermine to Compound Ia is suppressed in vitro.

In some embodiments, stimulating the addition of spermine to Compound Ia comprises contacting a matrix comprising spermine and Compound Ia with an agent that facilitates the addition of spermine to Compound Ia. In some embodiments, stimulating the addition of spermine to Compound Ia comprises contacting a cell comprising spermine and Compound Ia with an agent that facilitates the addition of spermine to Compound Ia. In some embodiments, the aminosterol is produced in vivo in a subject, and stimulating the addition of spermine to Compound Ia comprises administering to the subject an effective amount of an agent that facilitates the addition of spermine to Compound Ia. Administration of the agent may comprise administration by any of the same routes discussed herein for administering aminosterols.

In some embodiments, an agent that facilitates the addition of spermine to Compound Ia comprises a promoter or effector. The effector may comprise an enzyme activator, enzyme inducer, a protein, a small molecule, or a nucleic acid. In some embodiments, the agent may comprise any agent that activates or catalyzes the addition of spermine to Compound Ia. In some embodiments, the agent comprises one or more enzymes that catalyze the addition of spermine to Compound Ia. In some embodiments, the agent comprises one or more polynucleotides encoding enzymes that catalyze the addition of spermine to Compound Ia, or one or more polynucleotides encoding peptide effectors. The one or more polynucleotides may comprise recombinant DNA and/or RNA. In some embodiments, the agent may comprise a vector comprising the one or more polynucleotides.

In some embodiments, the spermine addition is an enzymatic reductive amination. In some embodiments, the spermine addition is a synthetic reductive amination. In some embodiments, the subject is human. In some embodiments, the subject includes human and non-human animals, including mammals, as well as immature and mature animals, including human children and adults. The human subject can be an infant, toddler, school-aged child, teenager, young adult, adult, or elderly patient.

IV. Compositions

In another aspect, provided herein are compositions comprising an aminosterol compound disclosed herein, or a pharmaceutically acceptable salt, solvate, prodrug, or derivative thereof, and one or more pharmaceutically acceptable carriers and/or excipients. Administration of an aminosterol disclosed herein, or a pharmaceutically acceptable salt, solvate, or prodrug thereof may comprise administration of the composition.

A. Pharmaceutical Carriers

While it is possible for an aminosterol, or a pharmaceutically acceptable salt, solvate or prodrug thereof, to be administered alone, it is preferable to administer it as a pharmaceutical formulation, together with one or more pharmaceutically acceptable carriers. The carrier(s) must be "acceptable" in the sense of being compatible with the aminosterol, or a pharmaceutically acceptable salt, solvate or prodrug thereof, and not deleterious to the recipients thereof.

Generally, the formulations are prepared by contacting an aminosterol described herein, or a pharmaceutically acceptable salt, solvate, prodrug, or derivative thereof, uniformly and intimately with liquid carriers or finely divided solid carriers or both. Then, if necessary, the product is shaped into the desired formulation. Non-aqueous vehicles such as fixed oils and ethyl oleate are also useful herein, as well as liposomes.

The carrier suitably comprises minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as gelatin, serum albumin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

In instances where aerosol administration is appropriate, an aminosterol described herein, or a pharmaceutically acceptable salt, solvate or prodrug thereof, can be formulated as an aerosol using standard procedures. The term "aerosol" includes any gas-borne suspended phase of a compound described herein which is capable of being inhaled into the bronchioles or nasal passages, and includes dry powder and aqueous aerosol, and pulmonary and nasal aerosols. Specifically, aerosol includes a gas-born suspension of droplets of a compound described herein, as may be produced in a metered dose inhaler or nebulizer, or in a mist sprayer. Aerosol also includes a dry powder composition of a composition of the present technology suspended in air or other carrier gas, which may be delivered by insufflation from an inhaler device, for example. See Ganderton & Jones, *Drug Delivery to the Respiratory Tract* (Ellis Horwood, 1987); Gonda, *Critical Reviews in therapeutic Drug Carrier Systems,* 6:273-313 (1990); and Raeburn et al., *Pharmacol. Toxicol. Methods,* 27:143-159 (1992).

B. Dosage Forms

The aminosterol compositions may conveniently be presented in unit dosage form and may be prepared by any of the methods well known in the art of pharmacy. Exemplary aminosterol dosage forms include, but are not limited to, oral, intranasal, and injectable (IP, IV, or IM). Preferably, the aminosterol formulation is administered orally, intranasally, or a combination thereof. In yet another embodiment, administration comprises non-oral administration.

Formulations or compositions of the present technology may be packaged together with, or included in a kit with, instructions or a package insert. "Pharmaceutically acceptable carrier" refers to a non-toxic solid, semisolid or liquid filler, diluent, encapsulating material or formulation auxiliary of any type.

Pharmaceutical compositions according to the present technology may also comprise one or more binding agents, filling agents, lubricating agents, suspending agents, sweeteners, flavoring agents, preservatives, buffers, wetting agents, disintegrants, effervescent agents, and other excipients. Such excipients are known in the art.

Examples of filling agents include lactose monohydrate, lactose anhydrous, and various starches; examples of binding agents include various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™).

Suitable lubricants, including agents that act on the flowability of the powder to be compressed, may include colloidal silicon dioxide, such as Aerosil® 200, talc, stearic acid, magnesium stearate, calcium stearate, and silica gel.

Examples of sweeteners may include any natural or artificial sweetener, such as sucrose, xylitol, sodium saccharin, cyclamate, aspartame, and acesulfame. Examples of flavoring agents are Magnasweet® (trademark of MAFCO), bubble gum flavor, and fruit flavors, and the like.

Examples of preservatives include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

C. Dosages & Dosing Period

Dosage of an aminosterol described herein can range from about 1 to about 500 mg/day, or any amount in-between these two values. In some embodiments, a subject is administered a therapeutically effective dose of an aminosterol described herein. The therapeutically effect amount of the at least one aminosterol or a salt or derivative thereof in the methods of the disclosure can be, for example, about 0.1 to about 20 mg/kg, about 0.1 to about 15 mg/kg, about 0.1 to about 10 mg/kg, about 0.1 to about 5 mg/kg, or about 0.1 to about 2.5 mg/kg body weight of the subject. In another aspect, the therapeutically effect amount of the at least one aminosterol or a salt or derivative thereof in the methods of the disclosure can be, for example, about 0.001 to about 500 mg/day, about 0.001 to about 250 mg/day, about 0.001 to about 125 mg/day, about 0.001 to about 50 mg/day, about 0.001 to about 25 mg/day, or about 0.001 to about 10 mg/day.

Oral dosage of an aminosterol described herein can range from about 1 to about 500 mg/day, or any amount in-between these two values. In one embodiment, the method of administration comprises oral administration and the therapeutically effective amount of the aminosterol comprises (i) about 1 to about 300 mg/day; (ii) about 25 to about 300 mg/day; (iii) about 50 to about 300 mg/day; or (iv) about 75 to about 300 mg/day. Other exemplary dosages of orally administered aminosterols include, but are not limited to, about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, about 250, about 255, about 260, about 265, about 270, about 275, about 280, about 285, about 290, about 295, about 300, about 305, about 310, about 315, about 320, about 325, about 330, about 335, about 340, about 345, about 350, about 355, about 360, about 365, about 370, about 375, about 380, about 385, about 390, about 395, about 400, about 405, about 410, about 415, about 420, about 425, about 430, about 435, about 440, about 445, about 450, about 455, about 460, about 465, about 470, about 475, about 480, about 485, about 490, about 495, or about 500 mg/day.

Intranasal dosages of an aminosterol are much lower than oral dosages of the aminosterol. Examples of such intranasal aminosterol low dosages include, but are not limited to, about 0.001 to about 6 mg/day, or any amount in-between these two values. In some embodiments, the method of administration comprises nasal administration and the therapeutically effective amount of the aminosterol comprises (i) about 0.001 to about 6 mg/day; (ii) about 0.001 to about 4 mg/day; or (iii) about 0.001 to about 2 mg/day. For example, the low dosage of an intranasally administered aminosterol can be about 0.001, about 0.005, about 0.01, about 0.02, about 0.03, about 0.04, about 0.05, about 0.06, about 0.07, about 0.08, about 0.09, about 0.1, about 0.2, about 0.3, about 0.4, about 0.5, about 0.6, about 0.7, about 0.8, about 0.9, about 1, about 1.1, about 1.2, about 1.3, about 1.4, about 1.5, about 1.6, about 1.7, about 1.8, about 1.9, about 2, about 2.1, about 2.2, about 2.3, about 2.4, about 2.5, about 2.6, about 2.7, about 2.8, about 2.9, about 3, about 3.1, about 3.2, about 3.3, about 3.4, about 3.5, about 3.6, about 3.7, about 3.8, about 3.9, about 4, about 4.1, about 4.2, about 4.3, about 4.4, about 4.5, about 4.6, about 4.7, about 4.8, about 4.9, about 5, about 5.1, about 5.2, about 5.3, about 5.4, about 5.5, about 5.6, about 5.7, about 5.8, about 5.9, or about 6 mg/day.

For intranasal (IN) administration, it is contemplated that the aminosterol dosage may be selected such that the same dosage would not provide any pharmacological effect if administered by any other route—e.g., a "subtherapeutic" dosage, and, in addition, does not result in negative effects. For example, as described herein, Compound III (ENT-03) has the pharmacological effects of a reduction in food intake and weight loss. Therefore, in certain embodiments of the IN methods of the disclosure, if the aminosterol may be Compound III (ENT-03) or a salt, solvate, prodrug, or derivative thereof, then if the same IN Compound III dosage is administered via another route, such as oral, IP, or IV, then the Compound III dosage will not result in a noticeable reduction in food intake or noticeable weight loss. Similarly, some aminosterols are known to produce the pharmacological effects of nausea, vomiting and/or reduced blood pressure. Thus, in certain embodiments of the IN methods of the disclosure, if the aminosterol has this effect when given IN, then if the same IN aminosterol dosage is administered via another route, such as oral, IP, or IV, then the aminosterol dosage will not result in noticeable nausea, vomiting, and/or a reduction in blood pressure. In some embodiments, intranasal administration comprises delivery of the aminosterol to the brain. Suitable exemplary aminosterol dosages are described above.

Aminosterol doses can be de-escalated (reduced) if any given aminosterol dose induces a persistent undesirable side effect, such as diarrhea, vomiting, or nausea. In another embodiment, a dose of an aminosterol can be varied plus or minus a defined amount to enable a modest reduction in a dose to eliminate adverse events, or a modest increase in a dose if clinical results suggest this is desirable—e.g., no or minimal adverse events and potential increased efficacy with a modest increase in dose. For example, in one embodiment an aminosterol dose can be increased or decreased by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20%.

The pharmaceutical composition comprising an aminosterol or a derivative, salt, solvate, or prodrug thereof can be administered for any suitable period of time, including as a maintenance dose for a prolonged period of time. Dosing can be done on an as needed basis using any pharmaceutically acceptable dosing regimen. Aminosterol dosing can be no more than 1× per day, once every other day, once every three days, once every four days, once every five days, once every six days, once a week, or divided over multiple time periods during a given day (e.g., twice daily). In an exemplary embodiment, dosing is 1×/day.

In other embodiments, the composition can be administered: (1) as a single dose, or as multiple doses over a period of time; (2) at a maintenance dose for an indefinite period of time; (3) once, twice or multiple times; (4) daily, every other day, every 3 days, weekly, or monthly; (5) for a period of time such as about 1, about 2, about 3, or about 4 weeks, about 1, about 2, about 3, about 4, about 5, about 6, about 7, about 8, about 9, about 10, about 11, or about 12 months, about 1 year, about 1.5 years, about 2, about 2.5, about 3, about 3.5, about 4, about 4.5, about 5, about 5.5, about 6, about 6.5, about 7, about 7.5, about 8, about 8.5, about 9, about 9.5, about 10, about 10.5, about 11, about 11.5, about 12, about 12.5, about 13, about 13.5, about 14, about 14.5, about 15, about 15.5, about 16, about 16.5, about 17, about 17.5, about 18, about 18.5, about 19, about 19.5, about 20, about 20.5, about 21, about 21.5, about 22, about 22.5, about 23, about 23.5, about 24, about 24.5, or about 25 years, or (6) any combination of these parameters, such as daily administration for 6 months, weekly administration for 1 or more years, etc.

Yet another exemplary dosing regimen includes periodic dosing, where an effective dose can be delivered once every about 1, about 2, about 3, about 4, about 5, about 6 days, or once weekly.

In a preferred embodiment, the aminosterol dose is taken in the morning, i.e. on an empty stomach preferably within about two hours of waking up and may be followed by a period without food, such as for example about 60 to about 90 minutes. In other embodiments, the aminosterol dose is taken within about 15 min, about 30 min, about 45 min, about 1 hr, about 1.25 hrs, about 1.5 hrs, about 1.75 hrs, about 2 hrs, about 2.25 hrs, about 2.5 hrs, about 2.75 hrs, about 3 hrs, about 3.25 hrs, about 3.5 hrs, about 3.75 hrs, or about 4 hrs within waking up. In yet further embodiments, the aminosterol dose is followed by about period without food, wherein the period is at least about 30 min, about 45 min, about 60 min, about 1.25 hrs, about 1.5 hrs, about 1.75 hrs, or about 2 hrs.

Not to be bound by theory, it is believed that since aminosterols have an impact on circadian rhythms, likely due to ENS signaling thereof, taking the aminosterol dose in the morning enables the synchronization of all the autonomic physiological functions occurring during the day. In other embodiments of the disclosure, the aminosterol dosage is taken within about 15 min, about 30 min, about 45 min, about 1 hour, about 1.25 hrs, about 1.5 hrs, about 1.75 hrs, about 2 hrs, about 2.25 hrs, about 2.5 hrs, about 2.75 hrs, about 3 hrs, about 3.25 hrs, about 3.5 hrs, about 3.75 hrs, or about 4 hrs of waking up. In addition, in other embodiments of the disclosure, following the aminosterol dosage the subject has a period of about 15 min, about 30 min, about 45 min, about 1 hours, about 1.25 hrs, about 1.5 hrs, about 1.75 hrs, about 2 hrs, about 2.25 hrs, about 2.5 hrs, about 2.75 hrs, or about 3 hours without food.

D. "Fixed Aminosterol Dose"

In one aspect, the present application relates to the discovery of a method to determine a "fixed dose" of an aminosterol described herein, that is not age, size, or weight dependent but rather is individually calibrated. The "fixed dose" obtained through this method yields highly effective results in treating the symptom(s) based on which the "fixed dose" was determined, related symptoms along the "brain-gut" axis, and the underlying disorder. Further, contemplated herein are methods of leveraging this same "fixed dose" method for methods of prevention of the underlying disorder. The present disclosure is not limited to methods whereby a fixed aminosterol dosage is determined for a specific patient.

A "fixed aminosterol dose," also referred to herein as a "fixed escalated aminosterol dose," which will be therapeutically effective is determined for each patient by establishing a starting dose of an aminosterol composition and a threshold for improvement of a particular symptom which is used as a tool or marker for evaluating the effectiveness of the aminosterol dosage. Following determining a starting aminosterol dosage for a particular patient, the aminosterol dose is then progressively escalated by a consistent amount over consistent time intervals until the desired improvement is achieved; this aminosterol dosage is the "fixed escalated aminosterol dosage" for that particular patient for that particular symptom. In exemplary embodiments, an orally administered aminosterol dose is escalated every about 3 to about 5 days by about 25 mg until the desired improvement is reached. Symptoms evaluated, along with tools for measuring symptom improvement, may be specifically described below, including but not limited to constipation, hallucinations, sleep disturbances (e.g. REM disturbed sleep or circadian rhythm dysfunction), cognitive impairment, depression, or alpha-synuclein aggregation.

This therapeutically effective "fixed dose" is then maintained throughout treatment and/or prevention. Thus, even if the patient goes "off drug" and ceases taking the aminosterol composition, the same "fixed dose" is taken with no ramp up period following re-initiation of aminosterol treatment. Not to be bound by theory, it is believed that the aminosterol dose is dependent on the severity of nerve damage relating to the symptom establishing the "fixed dose" threshold—e.g. for constipation, the dose may be related to the extent of nervous system damage in the patient's gut.

Dose escalation: When determining a "fixed aminosterol dosage" for a particular patient, a patient is started at a lower dose and then the dose is escalated until a positive result is observed for the symptom being evaluated. An exemplary symptom to be evaluated can be constipation, but any symptom associated with the disease or disorder to be treated can be used as a marker for evaluating aminosterol dosage. Aminosterol doses can also be de-escalated (reduced) if any given aminosterol dose induces a persistent undesirable side effect, such as diarrhea, vomiting, or nausea.

The starting aminosterol dose is dependent on the severity of the symptom—e.g. for a patient experiencing severe constipation, defined as less than one spontaneous bowel movement (SBM) a week, the starting oral aminosterol dose can be about 150 mg/day or greater. In contrast, for a patient having moderate constipation, e.g., defined as having more than one SBM a week, the starting oral aminosterol dose can be about 75 mg/day. Thus, as an example, a patient experiencing moderate constipation can be started at an oral aminosterol dosage of about 75 mg/day, whereas a patient experiencing severe constipation can be started at an oral aminosterol dosage of about 150 mg/day.

In other embodiments, a patient experiencing moderate symptoms (for the symptom being used to calculate a fixed escalated aminosterol dose) can be started at an oral aminosterol dosage of from about 10 mg/day to about 75 mg/day, or any amount in-between these values. For example, the starting oral aminosterol dosage for a moderate symptom can be about 10, about 15, about 20, about 25, about 30, about 35, about 40, about 45, about 60, about 65, about 70, or about 75 mg/day.

In yet further embodiments, when the patient is experiencing severe symptoms (for the symptom being used to calculate the fixed escalated aminosterol dose), the patient can be started at an oral aminosterol dosage ranging from about 75 to about 175 mg/day, or any amount in-between these two values. For example, the starting oral aminosterol dosage for a severe symptom can be about 75, about 80, about 85, about 90, about 95, about 100, about 105, about 110, about 115, about 120, about 125, about 130, about 135, about 140, about 145, about 150 about 155, about 160, about 165, about 170, or about 175 mg/day.

In some embodiments, the starting oral aminosterol dose may be about 125 mg or about 175 mg/day; again dependent on the severity of the symptom, such as constipation.

Starting intranasal (IN) aminosterol dosages prior to dose escalation can be, for example, about 0.001 mg to about 3 mg/day, or any amount in-between these two values. For example, the starting aminosterol dosage for IN administration, prior to dose escalation, can be, for example, about 0.001, about 0.005, about 0.01, about 0.02, about 0.03, about 0.05, about 0.06, about 0.07, about 0.08, about 0.09, about 0.1, about 0.15, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 1.0, about 1.1, about 1.25, about 1.3, about 1.4, about 1.5, about 1.6, about 1.7, about 1.75, about 1.8, about 1.9, about 2.0, about 2.1, about 2.25, about 2.3, about 2.4, about 2.5, about 2.6, about 2.7, about 2.75, about 2.8, about 2.9, or about 3 mg/day.

In exemplary embodiments, the aminosterol dose is given periodically as needed. For example, the aminosterol dose can be given once per day. The aminosterol dose can also be given every other day, 2, 3, 4, or 5× per week, once/week, or 2×/week. In another embodiment, the aminosterol dose can be given every other week, or it can be given for a few weeks, followed by skipping a few weeks (as the effects persist following treatment), followed by restarting aminosterol treatment.

When calculating a fixed escalated aminosterol dose, the dose can be escalated following any suitable time period. In one embodiment, the aminosterol dose is escalated every about 3 to about 7 days by about a defined amount until a desired improvement is reached. For example, when the symptom being treated/measured is constipation, threshold improvement can be an increase of one SBM per week or at least a total of three bowel movements per week. In other embodiments, the aminosterol dose can be escalated every about 1, about 2, about 3, about 4, about 5, about 6, about 7, about 8, about 9, about 10, about 11, about 12, about 13, or about 14 days. In other embodiments, the aminosterol dose can be escalated about 1×/week, about 2×/week, about every other week, or about 1×/month.

During dose escalation, the aminosterol dosage can be increased by a defined amount. For example, when the aminosterol is administered orally, the dose can be escalated in increments of about 5, about 10, about 15, about 20, about 25, about 30, about 35, about 40, about 45, or by about 50 mg. When the aminosterol is administered intranasally, then the dosage can be increased in increments of about, for example, about 0.1, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, about 1, about 1.1, about 1.2, about 1.3, about 1.4, about 1.5, about 1.6, about 1.7, about 1.8, about 1.9, or about 2 mg.

Other symptoms that can be used as an endpoint to determine aminosterol dosage for a patient's fixed escalated aminosterol dosage are any symptom known to be associated with the disease, disorder, or condition intended to be treated. For example, neurodisease symptoms described herein and include, but are not limited to, (a) at least one non-motor aspect of experiences of daily living as defined by Part I of the Unified Parkinson's Disease Rating Scale (UPDRS), such as for example cognitive impairment, hallucinations and psychosis, depressed mood, anxious mood, apathy, features of dopamine dysregulation syndrome, sleep problems, daytime sleepiness, pain, urinary problems, constipation problems, lightheadedness on standing, and fatigue; (b) at least one motor aspect of experiences of daily living as defined by Part II of the UPDRS, such as for example, speech, saliva and drooling, chewing and swallowing, eating tasks, dressing, hygiene, handwriting, turning in bed, tremors, getting out of a bed, a car, or a deep chair, walking and balance, and freezing; (c) at least one motor symptom identified in Part III of the UPDRS, such as for example, speech, facial expression, rigidity, finger tapping, hand movements, pronation-supination movements of hands, toe tapping, leg agility, arising from chair, gait, freezing of gait, postural stability, posture, body bradykinesia, postural tremor of the hands, kinetic tremor of the hands, rest tremor amplitude, and constancy of rest tremor; (d) at least one motor complication identified in Part IV of the UPDRS, such as for example, dyskinesias, functional impact of dyskinesias, time spent in the off state, functional impact of fluctuations, complexity of motor fluctuations, and painful off-state dystonia; (e) constipation; (f) depression; (g) cognitive impairment; (h) sleep problems or sleep disturbances; (i) circadian rhythm dysfunction; (j) hallucinations; (k) fatigue; (l) REM disturbed sleep; (m) REM behavior disorder; (n) erectile dysfunction; (o) apnea; (p) postural hypotension; (q) correction of blood pressure or orthostatic hypotension; (r) nocturnal hypertension; (s) regulation of temperature; (t) improvement in breathing or apnea; (u) correction of cardiac conduction defect; (v) amelioration of pain; (w) restoration of bladder sensation and urination; (x) urinary incontinence; and/or (y) control of nocturia.

V. Methods of Treatment and/or Prevention

Aspects of this disclosure relate to methods of treating certain symptoms and/or methods of treating and/or preventing diseases or disorders associated with one or more of these symptoms by administration of a therapeutically effective amount of an aminosterol disclosed herein (e.g., ENT-03 (Compound III) or another aminosterol described herein), or a pharmaceutically acceptable salt, solvate, prodrug, or derivative thereof, optionally present in one or more pharmaceutically acceptable carriers. The therapeutically effective amount can be as described herein, which includes but is not limited to a "fixed aminosterol dosage" determined as described herein.

In one embodiment, the symptoms, diseases, and/or disorders are generally correlated with abnormal αS pathology and/or dopaminergic dysfunction, which means they are amenable to treatment with aminosterols described herein. The compositions of the present technology can be administered using any pharmaceutically acceptable method, including but not limited to oral, pulmonary, nasal, and nebularization administration. In yet another embodiment, administration comprises non-oral administration.

In some embodiments, provided herein are methods for treating a subject in need having a condition or symptom susceptible to treatment with an aminosterol, comprising administering to the subject a therapeutically effective amount of an aminosterol described herein, or a pharmaceutically acceptable salt, solvate, or prodrug thereof. In some embodiments, provided herein are methods for treating a subject in need having a condition susceptible to treatment with an aminosterol, comprising administering to the subject a therapeutically effective amount of a composition comprising or consisting essentially of an aminosterol disclosed herein, or a pharmaceutically acceptable salt, solvate, or prodrug thereof, and one or more pharmaceutically acceptable carriers and/or excipients.

Non-limiting examples of symptoms amenable to treatment with aminosterols include but are not limited to constipation, hallucinations, sleep disorders, cognitive impairment, depression, and inflammation.

Examples of diseases amenable to treatment with aminosterols are described herein and include but are not limited to those described herein, such as neurological diseases, e.g., PD, AD, MSA, schizophrenia, Huntington's disease (HD), Progressive supranuclear palsy, Frontotemporal dementia (FTD), vascular dementia, Amyotrophic lateral sclerosis (ALS), multiple sclerosis (MS), spinal muscular atrophy (SMA), Friedreich's ataxia. In another embodiment, the aminosterols described herein and compositions comprising the same can be used in methods of treating, preventing, and/or slowing the onset or progression of psychological or behavior disorder and/or a related symptom in a subject in need is provided. In one embodiment, the psychological or behavior disorder can be, for example, depression, anxiety, delirium, irritability, illusion and delusions, amnesia, autism, apathy, bipolar disorder, disinhibition, aberrant motor and obsessive-compulsive behaviors, sleep disorders, sleep fragmentation, REM behavior disorder, circadian rhythm dysfunction, sleep apnea, and cognitive impairment. In another embodiment, a method of treating, preventing, and/or slowing the onset or progression of a cerebral or general ischemic disorder and/or a related symptom in a subject in need is provided. The cerebral or general ischemic disorder can be, for example, microangiopathy, intrapartum cerebral ischemia, cerebral ischemia during/after cardiac arrest or resuscitation, cerebral ischemia due to intraoperative problems, cerebral ischemia during carotid surgery, chronic cerebral ischemia due to stenosis of blood-supplying arteries to the brain, sinus thrombosis or thrombosis of cerebral veins, cerebral vessel malformations, diabetic retinopathy, high blood pressure, high cholesterol, myocardial infarction, cardiac insufficiency, cardiac failure, congestive heart failure, myocarditis, pericarditis, perimyocarditis, coronary heart disease, angina pectoris, congenital heart disease, shock, ischemia of extremities, stenosis of renal arteries, diabetic retinopathy, thrombosis associated with malaria, artificial heart valves, anemias, hypersplenic syndrome, emphysema, lung fibrosis, erectile dysfunction, and pulmonary edema.

In one embodiment, a method of inhibiting protein tyrosine phosphatase 1B (PTP1B) is provided, comprising contacting PTP1B with at least one aminosterol disclosed herein, or pharmaceutically acceptable salt, solvate, or prodrug thereof.

Applicant has shown in Example 3, that squalamine can increase transcription in the gut of old mice, thus having a rejuvenating effect on the gut. It is believed that this activity extends to ENT-03 (Compound III) and derivatives thereof. Thus, in another aspect, a method of increasing transcription in the gut of a subject is provided, the method comprising administering to the subject a therapeutically effective amount of an aminosterol compound of any embodiment herein, or a pharmaceutically acceptable salt, solvate, prodrug, or derivative thereof.

A. Exemplary Symptoms Correlated with Abnormal αS Pathology and/or Dopaminergic Dysfunction and Amenable to Aminosterol Treatment

(1) Constipation

In one embodiment, a method of treating, preventing, and/or slowing the onset or progression of constipation and/or a related symptom in a subject in need is provided, comprising administering to the subject a therapeutically effective amount of at least one aminosterol disclosed herein, or pharmaceutically acceptable salt, solvate, or prodrug thereof.

Constipation is a common problem worldwide, affecting 2% to 27% of the population, with most estimates varying from 12% to 20%. The prevalence of constipation increases to 30%-40% among people aged >65 years and women are disproportionately affected. In North America, 63M people meet the Rome IV criteria for constipation and in the US alone, constipation is responsible for over 2M physician visits annually. Laxatives are prescribed to 2-3M patients every year and furthermore, in most patients, the condition is chronic requiring lifelong treatment.

Constipation is much more common among patients with PD than in the general population. There are 1M people suffering from PD in the US, of which roughly 60%, or 600,000 suffer from chronic constipation and in most, the condition is chronic, severe and unresponsive to standard therapy. This represents an economic burden to the individual with PD and to the healthcare system. According to the Federal Supply Schedule April 2016, available at fss.gsa.gov, the average 30-day reimbursed price for a basket of orally administered drugs for constipation is approximately $260 or $3120 per year. This represents about $1.8B of prescription laxatives just for patients with PD.

Constipation is defined as a lower than normal frequency of bowel movements in a fixed duration of time (e.g. less than 3 bowel movements per week). While often dismissed as strictly a gastrointestinal symptom, constipation is believed to be an early indicator of neurodegenerative disease to the extent that ENS degeneration can be indicative of later CNS degeneration. Indeed, not to be bound by theory, but constipation is believed to be one of the earliest indicators of PD pathology. Accordingly, method embodiments disclosed herein relate to the treatment of constipation or the treatment and/or prevention of an underlying disorder associated with constipation.

Constipation is common in PD and often becomes symptomatic years before the onset of the motor dysfunction and the subsequent diagnosis of PD. There is substantial evidence that the neurodegenerative process associated with PD, namely the accumulation of toxic aggregates of alpha-synuclein, occurs within the enteric nervous system years before they appear within the brain. It is believed that the enteric nervous system (ENS), with its vast surface area, is subject to continuous insults from infectious agents and toxic substances. Although the function of alpha-synuclein is not known, inflammation within the nervous system leads to an increase in its intracellular levels. In individuals with PD the increase in alpha-synuclein leads to the formation of neurotoxic aggregates, perhaps because of a failure by the neuron (due to genetic factors) to effectively dispose of them. The aggregates of alpha-synuclein then traffic along the vagal nerve to the dorsal motor nucleus within the brainstem, and from there to more rostral structures.

The individual with PD suffers from a form of constipation that is believed to be caused principally by delayed transit through the colon. In addition, defecation is often impaired by dysfunction of the PD subject's anorectal reflex. For many individuals, bowel issues represent a significant detriment to quality of life. Failure to effectively manage this problem can also lead to bowel obstruction, especially as the terminal phase of PD approaches. A limited number of therapies have been subjected to clinical trials and they include agents that increase the fluid content of the stool, either by blocking fluid resorption or increasing the osmolar load within the intestine.

The pathophysiology of the GI dysfunction in PD involves deposition of αS within both the ENS as well as within the brainstem. For reasons that remain unknown αS, which is a protein normally produced in neurons, forms neurotoxic intracellular aggregates in PD. Numerous studies suggest that the αS aggregate formation begins in the ENS of the PD individual many years before the onset of the motor symptoms. As a consequence of the normal retrograde neuronal trafficking that occurs within the vagus nerve, toxic αS aggregates are transported from the neurons of the ENS to the dorsal motor nucleus of the vagus, and then, gradually to sites within the brain that are involved in physical movement and balance. Because the constipation is fundamentally of an acquired neurodegenerative nature, it differs from other forms of this condition.

Examples of tools that can be used to measure and evaluate the effect of aminosterol treatment on constipation include for example: (1) Rome-IV Criteria for Constipation (7 criteria, with constipation diagnosis requiring two or more of the following: (i) straining during at least 25% of defecations, (ii) lumpy or hard stools in at least 25% of defecations, (iii) sensation of incomplete evacuation for at least 25% of defecations, (iv) sensation of anorectal obstruction/blockage for at least 25% of defecations; (v) manual maneuvers to facilitate at least 25% of defecations; (vi) fewer than 3 defecations per week; and (vii) loose stools are rarely present without the use of laxatives); (2) Constipation—Ease of Evacuation Scale (from 1-7, with 7=incontinent, 4=normal, and 1=manual disimpaction); (3) Bristol Stool Chart, which is a patient-friendly means of categorizing stool characteristics (assessment of stool consistency is a validated surrogate of intestinal motility) and stool diary; (4) Unified Parkinson's Disease Scale (UPSRS), section 1.11 (Constipation Problems); (5) Patient Assessment of Constipation Symptoms (PAC-SYM); and (5) Patient Assessment of Constipation Quality of Life (PAC-QOL).

Examples of characteristics of constipation that can be positively affected by aminosterol treatment include, but are not limited to, frequency of constipation, duration of constipation symptoms, bowel movement frequency, stool consistency, abdominal pain, abdominal bloating, incomplete evacuation, unsuccessful attempts at evacuation, pain with evacuation, and straining with evacuation. Potentially all of these characteristics can be positively impacted by the methods of the disclosure. Further, assessments of these characteristics are known in the art, e.g. spontaneous bowel movements (SBMs)/week, stool consistency (Bristol Stool Form Scale) (Lewis and Heaton 1997; Heaton et al. 1992), ease of passage (Ease of Evacuation Scale) (Andresen et al. 2007), rescue medication use and symptoms and quality of life related to bowel function (PAC-SYM (Frank et al. 1999) and PAC-QOL (Marquis et al. 2005)).

The methods of using a therapeutically effective dose of an aminosterol composition according to the disclosure to treat and/or prevent constipation preferably results in an increase in the number of spontaneous bowel movements per week and/or an improvement in other stool conditions. The increase can be, for example, an increase of between about 1 to about 3 spontaneous bowel movements in a week, or, optionally, full restoration of regular bowel function.

In one embodiment of the disclosure, treatment of a subject having constipation with an aminosterol in a method described herein results in an improvement of one or more characteristics of constipation. The improvement can be, for example, about 5, about 10, about 15, about 20, about 25, about 30, about 35, about 40, about 45, about 50, about 55, about 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, about 300, about 325, about 350, about 375 or about 400%. Examples of constipation characteristics that can be improved by the methods of the disclosure include, but are not limited to, frequency of constipation, duration of constipation symptoms, bowel movement frequency, stool consistency, abdominal pain, abdominal bloating, incomplete evacuation, unsuccessful attempts at evacuation, pain with evacuation, and straining with evacuation. Measurement of a constipation characteristic can be done using any clinically recognized scale or tool.

In one embodiment, the dose of aminosterol required to obtain a positive impact on a symptom being evaluated, referred to herein as a "fixed escalated aminosterol dose," is patient specific, as described herein. In another embodiment, the severity of constipation correlates with a higher required "fixed escalated aminosterol dose." It is theorized that the aminosterol dose required to obtain a positive effect in a subject for the symptom being evaluated correlates with the extent of neuronal damage. Thus, it is theorized that greater neuronal damage correlates with a higher required aminosterol dose to obtain a positive effect in a subject for the symptom being evaluated. The observation that the aminosterol dose required to achieve a desired response increases with constipation severity supports the hypothesis that the greater the burden of αS impeding neuronal function, the higher the dose of aminosterol required to restore normal bowel function. It is also hypothesized that gastrointestinal dysmotility in PD results from the progressive accumulation of αS in the ENS, and that aminosterol treatment can restore neuronal function by displacing αS and stimulating enteric neurons. These results demonstrate that the ENS in PD is not irreversibly damaged and can be restored to normal function.

In calibrating the fixed aminosterol dose for a specific patient, the starting dose is varied based upon the severity of the constipation. Thus, for subjects with severe constipation, e.g., subjects with 1 or less CSBM or SMB per week, oral aminosterol dosing is started at about 100 to about 150 mg/day or more (or any amount in-between these values as described herein). For subjects with less severe constipation, e.g., more than 1 CSBM or SBM per week, oral aminosterol dosing is started at about 25 to about 75/day mg (or any amount in-between these values as described herein). Dosing for both patients is then escalated by defined amounts over a defined period of time until the fixed escalated dose for the patient is identified. Aminosterol doses can also be de-escalated (reduced) if any given aminosterol dose induces a persistent undesirable side effect, such as diarrhea, vomiting, or nausea.

For example, for patients with severe constipation, a starting oral aminosterol dosage can be from 75 mg up to about 300 mg/day, or any amount in-between these two values. In other embodiments, the starting oral aminosterol dosage for severely constipated patients can be, for example, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, about 250, about 255, about 260, about 265, about 270, about 275, about 280, about 285, about 290, about 295, or about 300 mg/day. A "fixed escalated" oral aminosterol dose for a severely constipated patient is likely to range from about 75 mg up to about 500 mg/day.

For patients with less severe constipation, oral aminosterol dosing is started at about 10 to about 75 mg/day, or any amount in-between these two values as described herein. For example, starting oral aminosterol dosage for patients with moderate to mild constipation can be about 1, about 5, about 10, about 15, about 20, about 25, about 30, about 35, about 40, about 45, about 50, about 55, about 60, about 65, about 70, up to less than or equal to about 75 mg/day. A fixed escalated oral aminosterol dose for a mild or moderately constipated patient is likely to range from about 5 mg up to about 350 mg/day, or any amount in-between these two values as described herein.

(2) Hallucinations

In one embodiment, a method of treating, preventing, and/or slowing the onset or progression of hallucinations and/or a related symptom in a subject in need is provided, comprising administering to the subject a therapeutically effective amount of at least one aminosterol disclosed herein (e.g., ENT-03 (Compound III)), or pharmaceutically acceptable salt, solvate, prodrug, or derivative thereof.

A hallucination is a sensory impression or perception of an object or event, in any of the 5 senses (sight, touch, sound, smell, or taste) that has no basis in external stimulation. Hallucinations can have debilitating impact on the subject's health and life by causing harm to self or others, by making it difficult for the subject to function normally in everyday situations, and by causing sleep disruption. Examples of hallucinations include "seeing" someone not there (visual hallucination), "hearing" a voice not heard by others (auditory hallucination), "feeling" something crawling up your leg (tactile hallucination), "smelling" (olfactory), and "tasting" (gustatory). Other examples of hallucination types include hypnagogic hallucination (a vivid, dreamlike hallucination occurring at sleep onset), hypnopompic hallucination (a vivid, dreamlike hallucination occurring on awakening), kinesthetic hallucination (a hallucination involving the sense of bodily movement), and somatic hallucination a hallucination involving the perception of a physical experience occurring within the body.

Hallucinations can be a result of psychiatric conditions or correlated with diseases, such as a neurodisease. Hallucinations, especially auditory hallucinations, are characteristic of certain psychiatric conditions such as schizophrenia, occurring in up to 70-80% of subjects. They also occur in 30-50% of individuals with borderline personality disorder. Auditory hallucinations can take control of actions or behavior and elicit violent defensive behavior or alternatively lead to self-harming behavior. They can also occur in post-partum psychosis. Auditory hallucinations can less commonly occur in severely depressed patients or even in mania. Substance abuse can also be associated with visual hallucinations. Alcohol intoxication or withdrawal, post-traumatic stress disorder (PTSD) and bereavement can also be associated with visual hallucinations.

In some cases, hallucination is the result of a psychiatric or neurological disorder. The aminosterol composition can, for example, reverse the dysfunction of the psychiatric or neurological disorder and treat the hallucination. The psychiatric disorder can be, for example, selected from the group consisting of Bipolar disorder, Borderline personality disorder, Depression (mixed), Dissociative identity disorder, Generalized anxiety disorder, Major depression, Obsessive compulsive disorder, Post-traumatic stress disorder, Psychosis (NOS), Schizoaffective disorder, and Schizophrenia. The neurodegenerative disorder can be, for example, PD, supranuclear palsy, multi-system atrophy, Parkinsonism, Alzheimer's disease, frontotemporal dementia, amyotrophic lateral sclerosis (ALS), Huntington's disease, schizophrenia, Friedreich's ataxia, Multiple sclerosis (MS), Lewy Body dementia or disease, spinal muscular atrophy, frontotemporal dementia, progressive nuclear palsy, Guadeloupian Parkinsonism, spinocerebellar ataxia, or vascular dementia. In a preferred embodiment, the aminosterol compositions of the disclosure reverse the dysfunction of the neurodegenerative disorder and treat the hallucination. The neurological disorder can also be, for example, the result of (a) a brain tumor, (b) a sleep disorder such as narcolepsy, or (c) a focal brain lesion, such as occipital lobe lesions or temporal lobe lesions. In an exemplary embodiment, the temporal lobe lesion can be lesions of the uncinate gyms, cerebral peduncles, or substantia nigra. The neurological disorder can be, for example, the result of (d) a diffuse involvement of the cerebral cortex, such as that caused by a viral infectious disease.

The diffuse involvement of the cerebral cortex can be a result of a cerebral vasculitis condition, and the viral infectious disease can be, for example, acute metabolic encephalopathies, encephalitis, or meningitis. The cerebral vasculitis condition can be caused by an autoimmune disorder, a bacterial or viral infection, or a systemic vasculitis. The autoimmune disorder can be, for example, Systemic Lupus Erythematosus (SLE).

Further still, hallucinations may be caused by a sensory loss. The sensory loss can be, for example, visual, auditory, gustatory, tactile, or olfactory. In a preferred embodiment, the aminosterol compositions of the disclosure reverse the dysfunction of the sensory loss and treat the hallucination. In another preferred embodiment, the aminosterol compositions of the disclosure reverse the dysfunction of the enteric nervous system and treats the hallucination.

The methods of using a therapeutically effective amount of an aminosterol composition according to the disclosure to treat and/or prevent hallucinations preferably result in a decrease in hallucinations. The decrease can be, for example, a reduction in occurrences of hallucinations by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. The methods of the disclosure may also result in the subject being hallucination-free. The hallucination can comprise, for example, a visual, auditory, tactile, gustatory or olfactory hallucination. The improvement can be measured using any clinically recognized assessment or tool.

Examples of tools that can be used to measure and evaluate the effect of aminosterol treatment on hallucinations include for example: The University of Miami Parkinson's Disease Hallucinations Questionnaire (UM-PDHQ), Unified Parkinson's disease Scale (UPSRS)—section 1.2 (Hallucinations and Psychosis), direct questioning, Chicago Hallucination Assessment Tool (CHAT), The Psychotic Symptom Rating Scales (PSYRATS), Auditory Hallucinations Rating Scale (AHRS), Hamilton Program for Schizophrenia Voices Questionnaire (HPSVQ), Characteristics of Auditory Hallucinations Questionnaire (CAHQ), Mental Health Research Institute Unusual Perception Schedule (MUPS), positive and negative syndrome scale (PANSS), scale for the assessment of positive symptoms (SAPS), Launay-Slade hallucinations scale (LSHS), the Cardiff anomalous perceptions scale (CAPS), and structured interview for assessing perceptual anomalies (SIAPA).

(3) Inflammation Related to Abnormal αS Pathology and/or Dopaminergic Dysfunction and Amenable to Aminosterol Treatment In one embodiment, provided is a method of treating, preventing, and/or slowing the onset or progression in a subject of inflammation and/or a related symptom related to αS pathology. The method comprises administering to the subject a therapeutically effective amount of at least one aminosterol disclosed herein (e.g., ENT-03 (Compound III)), or pharmaceutically acceptable salt, solvate, or prodrug thereof.

αS is a potent pro-inflammatory hormone. Inflammation can be blocked by either of two strategies. First, inflammation can be blocked by reducing the tissue concentration of αS by decreasing or stopping production of αS. Alternatively, inflammation can be blocked by interrupting the signaling between αS and inflammatory cells that express CD11b. The subject of the methods of the disclosure can be any mammal, including a human.

The inflammatory disease or condition caused by excessive expression of neuronal αS can be a neurodegenerative disorder (NDD), such as an alpha-synucleinopathy. Exemplary alpha-synucleinopathies include, but are not limited to, PD, Lewy body dementia, multiple system atrophy, amyotrophic lateral sclerosis, Huntington's chorea, multiple sclerosis or schizophrenia. In other embodiments, the inflammatory disease or condition caused by excessive expression of neuronal alpha synuclein can be an autoimmune disease, a chronic inflammatory disease, or an autoinflammatory disease. In other embodiments, the inflammatory disease or condition caused by excessive expression of neuronal αS can be selected from the group consisting of asthma, chronic peptic ulcer, tuberculosis, chronic periodontitis, chronic sinusitis, chronic active hepatitis, psoriatic arthritis, gouty arthritis, acne vulgaris, osteoarthritis, rheumatoid arthritis, lupus, systemic lupus erythematosus, multiple sclerosis, ankylosing spondylitis, Crohn's disease, psoriasis, primary sclerosing cholangitis, ulcerative colitis, allergies, inflammatory bowel diseases, Celiac disease, Chronic prostatitis, diverticulitis, dermatomyositis, polymyositis, systemic sclerosis, glomerulonephritis, hidradenitis suppurativa, hypersensitivities, interstitial cystitis, otitis, pelvic inflammatory disease, reperfusion injury, rheumatic fever, sarcoidosis, transplant rejection, and vasculitis.

In some embodiments of the disclosure, patient populations particularly susceptible to excessive production or secretion of αS can benefit from the methods of the disclosure and are targeted for therapy, including for example preventative therapy. For example, a patient population having a mutated form of αS resulting in increased amounts of αS in tissues can be treated using the methods of the disclosure. Another example of a patient population susceptible for high levels of αS are patients having chronic inflammatory conditions or diseases. A still further example is a patient population having elevated levels of αS aggregation in their enteric nerve cells, manifesting as a constipation.

The methods of the disclosure can result in a decrease in intensity of inflammation, blood levels of inflammatory markers, inflammatory markers in tissue, or number of inflammatory cells in tissue, or a combination thereof, as compared to a control or as compared to the qualitative or quantitative amount from the same patient or subject prior to treatment. For example, the decrease can be about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. The improvement can be measured using any clinically recognized tool or assessment.

In some embodiments, the decrease is measured quantitatively or qualitatively by a method selected from the group consisting of high-performance liquid chromatography, liquid chromatography mass spectrometry, enzyme linked immunosorbent assay, protein immunoprecipitation, immunoelectrophoresis, Western blot, and protein immunostaining.

In addition, it follows from the present disclosure that an individual with an inflammatory condition appropriate for treatment or prophylaxis with the methods targeting αS described herein can be identified by determination of the tissue concentrations of αS at sites of inflammation, with high levels of αS, as compared to a control or healthy subject, correlating with patients appropriate for treatment with a method of the disclosure.

It is theorized that administration of an aminosterol reduces the formation of neurotoxic αS aggregates in vivo, and stimulates gastrointestinal motility in patients with neurodiseases such as PD and constipation. It is also hypothesized that the greater the burden of αS impeding neuronal function, the higher the dose of aminosterol required to restore normal bowel function as well as address other symptoms of alpha-synuclein aggregation.

B. Exemplary Diseases or Disorders Correlated with Abnormal αS Pathology and/or Dopaminergic Dysfunction and Amenable to Aminosterol Treatment The aminosterols described herein (e.g., ENT-03 (Compound III)), including a pharmaceutically acceptable salt, solvate, prodrug, or derivative thereof, can be used in methods of treating and/or preventing a variety of diseases and disorders, which are generally correlated with abnormal αS pathology and/or dopaminergic dysfunction, as described herein and as described below.

In one embodiment, provided is a method of treating, preventing, and/or slowing the onset or progression in a subject of diseases or disorder correlated with abnormal αS pathology and/or dopaminergic dysfunction and/or a related symptom related to αS pathology. The method comprises administering to the subject a therapeutically effective amount of at least one aminosterol disclosed herein (e.g., ENT-03 (Compound III)), or pharmaceutically acceptable salt, solvate, prodrug, or derivative thereof (1) Neurological or Neurodegenerative Disorders or Diseases In one embodiment, a method of treating, preventing, and/or slowing the onset or progression of a neurodegenerative disease or neurological disease and/or a related symptom in a subject in need is provided, comprising administering to the subject a therapeutically effective amount of at least one aminosterol disclosed herein, or pharmaceutically acceptable salt, solvate, prodrug, or derivative thereof.

The methods and aminosterol compositions of the disclosure can be used to treat and/or prevent neurological disorders or diseases such as those described herein, examples of which include but are not limited to AD, PD, Huntington's Disease, Multiple Sclerosis, Amyotorphic Lateral Sclerosis (ALS), multiple system atrophy (MSA), schizophrenia, Friedreich's ataxia, vascular dementia, Lewy Body dementia or disease, spinal muscular atrophy, supranuclear palsy, frontotemporal dementia, progressive nuclear palsy, Guadeloupian parkinsonism, spinocerebellar ataxia, and autism.

A variety of neuroimaging techniques may be useful for the early diagnosis and/or measurement of progression of neurodegenerative disorders. Examples of such techniques include but are not limited to neuroimaging, functional MRI, structural MRI, diffusion tensor imaging (DTI) (including for example diffusion tensor measures of anatomical connectivity), [18F]fluorodeoxyglucose (FDG) PET, agents that label amyloid, [18F]F-dopa PET, radiotracer imaging, volumetric analysis of regional tissue loss, specific imaging markers of abnormal protein deposition (e.g., for AD progression), multimodal imaging, and biomarker analysis. Jon Stoessl, "Neuroimaging in the early diagnosis of neurodegenerative disease," *Transl. Neurodegener.,* 1:5 (2012). Combinations of these techniques can also be used to measure disease progression.

Progression of neurodegeneration can be measured using well known techniques. For example, an electroencephalogram (EEG) can be used as a biomarker for the presence and progression of a neurodegenerative disease (Morairty, 2013). Another exemplary technique that can be used to measure progression of neurodegeneration of MRI (Rocca et al., 2017). Alternatively, neurodegeneration can be measured by measuring the levels of one or more biomarkers known in the art to indicate neurodegeneration using analytical techniques selected from the group consisting of, for example, high-performance liquid chromatography, liquid chromatography mass spectrometry, enzyme linked immunosorbent assay, protein immunoprecipitation, immunoelectrophoresis, Western blot, and protein immunostaining. Biomarkers indicating neurodegeneration are known to the skilled artisan and may include, for example, any of those in Beach et al. 2017, the entire disclosure of which is hereby incorporated by reference.

For example, structural MM can be used to measure atrophy of the hippocampus and entorhinal cortex in AD, as well as involvement of the lateral parietal, posterior superior temporal and medial posterior cingulate cortices. In frontotemporal dementias (FTD), structural MRI can show atrophy in frontal or temporal poles. DTI can be used to show abnormal white matter in the parietal lobes of patients with dementia with Lewy bodies (DLB) as compared to AD. Functional MM may reveal reduced frontal but increased cerebellar activation during performance of a working memory task in FTD compared to AD. In another example, [18F]fluorodeoxyglucose (FDG) PET can show reduced glucose metabolism in parietotemporal cortex in AD. Id.

In one embodiment of the disclosure, the progression or onset of a neurodegenerative disorder is slowed or prevented over a defined time period, following administration of a therapeutically effective amount of an aminosterol according to the disclosure to a subject in need, as measured by a medically-recognized technique. For example, the progression or onset of a neurodegenerative disorder can be slowed by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

The period of time over which the progression or onset of a neurodegenerative disorder is measured can be for example, one or more months or one or more years, e.g., about 6 months, about 1 year, about 18 months, about 2 years, about 36 months, about 3, about 4, about 5, about 6, about 7, about 8, about 9, about 10, about 11, about 12, about 13, about 14, about 15, about 16, about 17, about 18, about 19, or about 20 years, or any amount of months or years in between the values of about 6 months to about 20 years or more.

In another embodiment, a neurodegenerative disorder may be positively impacted by administration of a therapeutically effective amount of an aminosterol according to the disclosure. A "positive impact" includes for example slowing advancement of the condition, improving one or more symptoms, etc.

(i) Parkinson's Disease

In one embodiment, a method of treating, preventing, and/or slowing the onset or progression of Parkinson's disease (PD) and/or a related symptom in a subject in need is provided, comprising administering to the subject a therapeutically effective amount of at least one aminosterol disclosed herein (e.g., ENT-03 (Compound III)), or pharmaceutically acceptable salt, solvate, prodrug, or derivative thereof.

PD is a progressive neurodegenerative disorder caused by accumulation of the protein αS within the peripheral and central nervous system (CNS), including the enteric nervous system (ENS), autonomic nerves and brain (Braak et al. 2003 (a) and (b)). While motor symptoms are still required for a diagnosis of PD (Hughes et al. 1992), non-motor symptoms represent a greater therapeutic challenge (Zahodne et al. 2012). These symptoms include constipation (Ondo et al. 2012; Lin et al. 2014), disturbances in sleep architecture (Ondo et al. 2001; Gjerstad et al. 2006), cognitive dysfunction (Auyeung et al. 2012), hallucinations (Friedman et al. 2016; Diederich et al. 2009), REM behavior disorder (RBD) and depression (Aarsland et al. 2007), all of which result from impaired function of neural pathways not restored by replacement of dopamine. In fact, long-term institutionalization, caregiver burden and decrease in life expectancy correlate more significantly with the severity of these symptoms than with motor symptoms (Goetz et al. 1995). In 2003, Braak proposed that PD begins within the GI tract caused when neurotoxic aggregates of αS form within the ENS, evidenced clinically by the appearance of constipation in a majority of people with PD many years before the onset of motor symptoms (Braak et al., 2003 (a) and (b)). A recent study in rats has demonstrated movement of aggregates of αS from the ENS to the CNS via the vagus and other afferent nerves. Neurotoxic aggregates accumulated progressively within the brainstem and then dispersed rostrally to structures within the diencephalon, eventually reaching the cerebral hemispheres.

PD is defined as a synucleinopathy, and synuclein deposition remains the main final arbiter of diagnosis. Additionally, patients with dementia and Lewy bodies are considered as having PD if they meet clinical disease criteria. Imaging (e.g., MRI, single photon emission computed tomography [SPECT], and positron emission tomography [PET]) allows in vivo brain imaging of structural, functional, and molecular changes in PD patients.

There has been research in the last few years identifying particular markers or combinations of markers that are used for probabilistic estimates of prodromal PD. Researchers have identified a timeline of symptoms indicative of prodromal PD and predictive of PD. The presence of each contributes to an estimate of the likelihood of prodromal PD. Some have been adopted for identification of prodromal PD. Other studies use a combination of symptoms and imaging (e.g., hyposmia combined with dopamine receptor imaging has been found to have a high predictive value). In another example, REM sleep behavior disorder (SBD), constipation, and hyposmia were found to be individually common but to rarely co-occur in individuals without PD, leading to a high predictive value for PD.

PD may also be assessed using the UPDRS, which consists of 42 items in four subscales: (1) Part I, Non-Motor Aspects of Experiences of Daily Living (nM-EDL): cognitive impairment (section 1.1), hallucinations and psychosis (section 1.2), depressed mood (section 1.3), anxious mood (section 1.4), apathy (section 1.5), features of dopamine dysregulation syndrome (section 1.6), sleep problems (section 1.7), daytime sleepiness (section 1.8), pain and other sensations (section 1.9), urinary problems (section 1.10), constipation problems (section 1.11), light headedness on standing (section 1.12), and fatigue (section 1.13); (2) Part II, Motor Aspects of Experiences of Daily Living (M-EDL): speech (section 2.1), saliva & drooling (section 2.2), chewing and swallowing (section 2.3), eating tasks (section 2.4), dressing (section 2.5), hygiene (section 2.6), handwriting (section 2.7), doing hobbies and other activities (section 2.8), turning in bed (section 2.9), tremor (section 2.10), getting out of bed, a car, or a deep chair (section 2.11), walking and balance (section 2.12), and freezing (section 2.13); Part III, Motor Examination: speech (section 3.1), facial expression (section 3.2), rigidity (section 3.3), finger tapping (section 3.4), hand movements (section 3.5), pronation-supination movements of hands (section 3.6), toe tapping (section 3.7), leg agility (section 3.8), arising from chair (section 3.9), gait (3.10), freezing of gait (section 3.11), postural stability (section 3.12), posture (section 3.13), global spontaneity of movement (body bradykinesia) (section 3.14), postural tremor of the hands (section 3.15), kinetic tremor of the hands (section 3.16), rest tremor amplitude (section 3.17), and constancy of rest tremor (section 3.18); Part IV, Motor Complications: time spent with dyskinesias (section 4.1), functional impact of dyskinesias (section 4.2), time spent in the off state (section 4.3), functional impact of fluctuations (section 4.4), complexity of motor fluctuations (section 4.5), and painful off-state dystonia (section 4.6).

Further, symptom-based endpoints can be assessed using known scales. For example, (1) depression can be assessed using the Beck Depression Inventory (BDI-II) (Steer et al. 2000), cognition can be assessed using the Mini Mental State Examination (MMSE) (Palsetia et al. 2018), sleep and REM-behavior disorder (RBD) can be assessed using a daily diary and an RBD questionnaire (RBDQ) (Stiasny-Kolster et al. 2007), and hallucinations can be assessed using the PD hallucinations questionnaire (PDHQ) (Papapetropoulos et al. 2008) and direct questioning. Circadian system status can also be assessed by continuously monitoring wrist skin temperature (Thermochron iButton DS1921H; Maxim, Dallas) following published procedures (Sarabia et al. 2008).

In another embodiment, administration of a therapeutically effective amount of an aminosterol composition described herein to a PD patient results in improvement of one or more symptoms of PD or on one or more clinically accepted scoring metrics, by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. The improvement can be measured using any clinically recognized tool or assessment.

PD progression and treatment is particularly difficult in view of patients' development of resistance to dopamine and subsequent dose escalation until no response can be elicited. Not to be bound by theory, it is believed that prior or co-administration of an aminosterol composition according to the disclosure (e.g., ENT-03 (Compound III)) may reduce the dopamine dosage required to elicit a therapeutic effect for Parkinson's symptoms and/or increase the period during which the patient is sensitive to dopamine. It is also theorized that prior or co-administration of an aminosterol composition according to the disclosure may delay the time period when a patient is advised to begin dopamine therapy. This is significant, as currently patients are encouraged to delay initiation of dopamine treatment as long as possible, as after a period of time subjects become resistant to dopamine.

(ii) Alzheimer's Disease

In one embodiment, a method of treating, preventing, and/or slowing the onset or progression of Alzheimer's disease (AD) and/or a related symptom in a subject in need is provided, comprising administering to the subject a therapeutically effective amount of at least one aminosterol disclosed herein (e.g., ENT-03 (Compound III)), or pharmaceutically acceptable salt, solvate, prodrug, or derivative thereof.

Alzheimer's disease (AD) is a chronic neurodegenerative disease that usually starts slowly and worsens over time. It is the cause of 60-70% of cases of dementia. As the disease advances, symptoms can include problems with language, disorientation, mood swings, loss of motivation, not managing self-care, and behavioral issues. As a person's condition declines, they often withdraw from family and society. Gradually, bodily functions are lost, ultimately leading to death. Although the speed of progression can vary, the typical life expectancy following diagnosis is 3 to 9 years. In 2015, there were approximately 29.8 million people worldwide with AD. It most often begins in people over 65 years of age, although 4% to 5% of cases are early-onset Alzheimer's. It affects about 6% of people 65 years and older. In 2015, dementia resulted in about 1.9 million deaths.

The symptoms of Alzheimer's disease are primarily marked by cognitive deficits including memory impairment, language dysfunction, and visuospatial skills; functional impairment that may span occupational and social issues (e.g., activities of daily living); and behavioral symptoms including depression, anxiety, aggression and psychosis may also appear as the disease progresses in severity.

At this time, unambiguous diagnosis of AD requires clinical findings of cognitive deficits consistent with AD and post-mortem identification of brain pathologies consistent with AD. The term AD dementia is used to describe dementia that is due to the pathophysiologies of AD. The term "probable Alzheimer's disease" is used in life when a subject demonstrates clinical characteristics of AD and when other possible biological causes of dementia (e.g. PD or stroke) are excluded. There are currently a variety of art-accepted methods for diagnosing probable AD. Typically, these methods are used in combination and include determining an individual's ability to carry out daily activities and identifying changes in behavior and personality. Dementia of the AD type is also typically characterized by an amnestic presentation (memory deficit) or language, visuospatial or executive function deficits. Cognitive ability/impairment may be determined by art-accepted methods, including, but not limited to, validated instruments that assess global cognition (e.g., the Modified Mini Mental State Examination (3MS-E)), and specific domains such as visual and verbal memory (e.g., the Brief Visuospatial Memory Test (Revised) (BVMT-R) and the Hopkins Verbal Learning Test (Revised) (HVLT-R), respectively), language (e.g., the Generative Verbal Fluency Test (GVFT)) and executive function and attention (e.g., the Digit Span Test (DST)). Dementia due to AD is also defined by insidious onset and a history of worsening cognitive performance.

The criteria for 'probable AD' are described a National Institute of Aging-Alzheimer's Association workgroup (McKhann et al. 2011). According to this workgroup, for people who first exhibit the core clinical characteristics of AD dementia, evidence of biomarkers associated with the disease may enhance the certainty of the diagnosis.

In another embodiment, administration of a therapeutically effective amount of an aminosterol composition to an AD patient results in improvement of one or more symptoms of AD or on one or more clinically accepted scoring metrics, by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

(iii) Multiple System Atrophy

In one embodiment, a method of treating, preventing, and/or slowing the onset or progression of multiple system atrophy (MSA) and/or a related symptom in a subject in need is provided, comprising administering to the subject a therapeutically effective amount of at least one aminosterol disclosed herein (e.g., ENT-03 (Compound III)), or pharmaceutically acceptable salt, solvate, prodrug, or derivative thereof.

Multiple system atrophy (MSA) is a progressive neurodegenerative disorder characterized by a combination of symptoms that affect both the autonomic nervous system (the part of the nervous system that controls involuntary action such as blood pressure or digestion) and movement. MSA, also known as Shy-Drager syndrome, is a neurodegenerative disorder characterized by tremors, slow movement, muscle rigidity, and postural instability (collectively known as parkinsonism) due to dysfunction of the autonomic nervous system, and ataxia. This is caused by progressive degeneration of neurons in several parts of the brain including the substantia nigra, striatum, inferior olivary nucleus, and cerebellum. There is no known cure for MSA and management is primarily supportive.

Progression of neurodegeneration can be measured using well known techniques. For example, an electroencephalogram (EEG) can be used as a biomarker for the presence and progression of a neurodegenerative disease (Morairty, 2013). Another exemplary technique that can be used to measure progression of neurodegeneration of MRI. Rocca et al. 2017.

A variety of neuroimaging techniques may be useful for the early diagnosis and/or measurement of progression of MSA. Examples of such techniques include but are not limited to neuroimaging, functional MM, structural MM, diffusion tensor imaging (DTI) (including for example diffusion tensor measures of anatomical connectivity), [18F] fluorodeoxyglucose (FDG) PET, agents that label amyloid, [18F]F-dopa PET, radiotracer imaging, volumetric analysis of regional tissue loss, specific imaging markers of abnormal protein deposition (e.g., for MSA progression), multimodal imaging, and biomarker analysis (Stoessl, 2012). Combinations of these techniques can also be used to measure disease progression.

For example, structural MM can be used to measure atrophy of the hippocampus and entorhinal cortex in MSA, as well as involvement of the lateral parietal, posterior superior temporal and medial posterior cingulate cortices. In frontotemporal dementias (FTD), structural MRI can show atrophy in frontal or temporal poles.

In another embodiment, administration of a therapeutically effective amount of an aminosterol composition to an MSA patient results in improvement of one or more symptoms of MSA, by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. Improvement can be measured using any clinically recognized tool or assessment.

(iv) Schizophrenia

In one embodiment, a method of treating, preventing, and/or slowing the onset or progression of schizophrenia (SZ) and/or a related symptom in a subject in need is provided, comprising administering to the subject a therapeutically effective amount of at least one aminosterol disclosed herein (e.g., ENT-03 (Compound III)) or pharmaceutically acceptable salt, solvate, prodrug, or derivative thereof.

Schizophrenia is a chronic progressive disorder that has at its origin structural brain changes in both white and gray matter. It is likely that these changes begin prior to the onset of clinical symptoms in cortical regions, particularly those concerned with language processing. Later, they can be detected by progressive ventricular enlargement. Current magnetic resonance imaging (MRI) technology can provide a valuable tool for detecting early changes in cortical atrophy and anomalous language processing, which may be predictive of who will develop schizophrenia.

A 2013 study of schizophrenia patients documented brain changes seen in MM scans from more than 200 patients beginning with their first episode and continuing with scans at regular intervals for up to 15 years. The scans showed that people at their first episode had less brain tissue than healthy individuals. The findings suggest that those who have schizophrenia are being affected by something before they show outward signs of the disease.

The mainstay of treatment is antipsychotic medication, along with counselling, job training and social rehabilitation. However, the 2013 study found that in general, the higher the anti-psychotic medication doses, the greater the loss of brain tissue.

About 0.3-0.7% of people are affected by schizophrenia during their lifetimes. In 2013 there were an estimated 23.6 million cases globally. Males are more often affected, and on average experience more severe symptoms. About 20% of people do well and a few recover completely. About 50% have lifelong impairment. Social problems, such as long-term unemployment, poverty and homelessness are common. The average life expectancy of people with the disorder is ten to twenty-five years less than for the general population. This is the result of increased physical health problems and a higher suicide rate (about 5%). In 2015 an estimated 17,000 people worldwide died from behavior related to, or caused by, schizophrenia.

While not wished to be bound by theory, it is theorized that administration of a therapeutically effective amount of an aminosterol composition to a schizophrenia patient may treat and/or prevent schizophrenia or any one or more symptoms thereof. In some embodiments, the administration may be oral, resulting in absorption in the ENS. In some embodiments, the administration may be intranasal, resulting in stimulation of neurogenesis, which has a positive impact on the loss of brain tissue characteristic of schizophrenia subjects.

In one embodiment of the disclosure, administration of a therapeutically effective amount of an aminosterol composition to a schizophrenia patient results in improvement of one or more symptoms as determined by a clinically recognized psychiatric symptom rating scale. Examples of such rating scales include for example, the Positive and Negative Syndrome Scale (PANSS), the Psychotic Symptom Rating Scales (PSYRATS), the Quality of Life Scale (QLS), the Schizophrenia Cognition Rating Scale (SCoRS), the Drug Attitude Inventory (DAI), and the Abnormal Involuntary Movement Scale (AIMS).

In another embodiment, administration of a therapeutically effective amount of an aminosterol composition to a schizophrenia patient results in improvement of one or more symptoms as determined by a clinically recognized psychiatric symptom rating scale, by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. Improvement can be measured using any clinically recognized tool or assessment.

(v) Other Neurodiseases

The methods and compositions of the disclosure may also be useful in treating and/or preventing a variety of other neurodiseases. In one embodiment, a method of treating, preventing, and/or slowing the onset or progression of a neurodisease described herein, and/or a related symptom, in a subject in need is provided, comprising administering to the subject a therapeutically effective amount of at least one aminosterol disclosed herein (e.g., ENT-03 (Compound III)), or pharmaceutically acceptable salt, solvate, prodrug, or derivative thereof. Examples of exemplary neurodiseases are described below and herein.

Huntington's disease (HD) is a fatal genetic disorder that causes the progressive breakdown of nerve cells in the brain. It deteriorates a person's physical and mental abilities during their prime working years and has no cure. Full-time care is required in the later stages of the disease. Symptoms of Huntington's disease most commonly become noticeable between the ages of 35 and 44 years, but they can begin at any age from infancy to old age. The most characteristic initial physical symptoms are jerky, random, and uncontrollable movements called chorea. Suicide is the cause of death in about 9% of cases. Death typically occurs 15 to 20 years from when the disease was first detected.

Progressive supranuclear palsy, also called Steele-Richardson-Olszewski syndrome, is a brain disorder that causes serious problems with walking, balance and eye movements. The disorder results from deterioration of cells in areas of the brain that control body movement and thinking. There is no known cure for PSP and management is primarily supportive.

Frontotemporal dementia (FTD) is a group of related conditions resulting from the progressive degeneration of the temporal and frontal lobes of the brain. These areas of the brain play a significant role in decision-making, behavioral control, emotion and language. The frontotemporal dementias (FTD) encompass six types of dementia involving the frontal or temporal lobes. They are: behavioral variant of FTD, semantic variant primary progressive aphasia, nonfluent agrammatic variant primary progressive aphasia, corticobasal syndrome, progressive supranuclear palsy, and FTD associated with motor neuron disease. Currently, there is no cure for FTD.

Vascular dementia, also known as multi-infarct dementia (MID) and vascular cognitive impairment (VCI), is dementia caused by problems in the supply of blood to the brain, typically a series of minor strokes, leading to worsening cognitive decline that occurs step by step. Risk factors for vascular dementia include age, hypertension, smoking, hypercholesterolemia, diabetes mellitus, cardiovascular disease, and cerebrovascular disease. Other risk factors include geographic origin, genetic predisposition, and prior strokes.

Amyotrophic lateral sclerosis (ALS), also known as motor neuron disease (MND), or Lou Gehrig's disease, is a specific disease which causes the death of neurons controlling voluntary muscles. ALS is characterized by stiff muscles, muscle twitching, and gradually worsening weakness due to muscles decreasing in size. This results in difficulty speaking, swallowing, and eventually breathing. The cause is not known in 90% to 95% of cases. The remaining 5-10% of cases are genetic. The underlying mechanism involves damage to both upper and lower motor neurons. No cure for ALS is known. The disease can affect people of any age, but usually starts around the age of 60 and in inherited cases around the age of 50. The average survival from onset to death is 2 to 4 years, although about 10% survive longer than 10 years.

Multiple sclerosis (MS) is a demyelinating disease in which the insulating covers of nerve cells in the brain and spinal cord are damaged. This damage disrupts the ability of parts of the nervous system to communicate, resulting in a range of signs and symptoms, including physical, mental, and sometimes psychiatric problems. MS takes several forms, with new symptoms either occurring in isolated attacks (relapsing forms) or building up over time (progressive forms). There is no known cure for MS. Life expectancy is on average 5 to 10 years lower than that of an unaffected population.

Spinal muscular atrophy (SMA) is an inherited neuromuscular disorder characterized by loss of motor neurons and progressive muscle wasting, often leading to early death. The disorder is caused by a genetic defect in the SMN1 gene, which encodes SMN, a protein necessary for survival of motor neurons. Lower levels of the protein results in loss of function of neuronal cells in the anterior horn of the spinal cord and subsequent system-wide atrophy of skeletal muscles. SMA is the most common genetic cause of infant death. In December 2016, nusinersen became the first approved drug to treat SMA while several other compounds remain in clinical trials.

Friedreich's ataxia is an autosomal recessive inherited disease that causes progressive damage to the nervous system. It manifests in initial symptoms of poor coordination such as gait disturbance; it can also lead to scoliosis, heart disease and diabetes, but does not affect cognitive function. The ataxia of Friedreich's ataxia results from the degeneration of nervous tissue in the spinal cord, in particular sensory neurons essential (through connections with the cerebellum) for directing muscle movement of the arms and legs. The spinal cord becomes thinner and nerve cells lose some of their myelin sheath (the insulating covering on some nerve cells that helps conduct nerve impulses).

(2) Psychological or Behavior Disorders and/or a Related Symptom

In one embodiment, a method of treating, preventing, and/or slowing the onset or progression of psychological or behavior disorder and/or a related symptom in a subject in need is provided, comprising administering to the subject a therapeutically effective amount of at least one aminosterol disclosed herein (e.g., ENT-03 (Compound III)), or pharmaceutically acceptable salt, solvate, prodrug, or derivative thereof. In one embodiment, the psychological or behavior disorder is depression, anxiety, delirium, irritability, illusion and delusions, amnesia, autism, apathy, bipolar disorder, disinhibition, aberrant motor and obsessive-compulsive behaviors, sleep disorders, sleep fragmentation, REM behavior disorder, circadian rhythm dysfunction, sleep apnea, or cognitive impairment.

(i) Depression

In one embodiment, a method of treating, preventing, and/or slowing the onset or progression of depression and/or a related symptom in a subject in need is provided, comprising administering to the subject a therapeutically effective amount of at least one aminosterol disclosed herein (e.g., ENT-03 (Compound III)), or pharmaceutically acceptable salt, solvate, prodrug, or derivative thereof.

Clinical depression is characterized by a sad, blue mood that goes above and beyond normal sadness or grief. One in 10 people will have a depression in their lifetime. Doctors clinically diagnose depression; there is no laboratory test or X-ray for depression.

Research shows that the hippocampus is smaller in some depressed people. For example, in one fMRI study published in *The Journal of Neuroscience*, investigators studied 24 women who had a history of depression. On average, the hippocampus was 9% to 13% smaller in depressed women as compared with those who were not depressed. The more bouts of depression a woman had, the smaller the hippocampus. Stress, which plays a role in depression, may be a key factor, since experts believe stress can suppress the production of new neurons (nerve cells) in the hippocampus.

Researchers are exploring possible links between sluggish production of new neurons in the hippocampus and low moods. An interesting fact about antidepressants supports this theory. These medications immediately boost the concentration of chemical messengers in the brain (neurotransmitters). Yet people typically don't begin to feel better for several weeks or longer. Experts have long wondered why, if depression were primarily the result of low levels of neurotransmitters, people don't feel better as soon as levels of neurotransmitters increase. The answer may be that mood only improves as nerves grow and form new connections, a process that takes weeks. In fact, animal studies have shown that antidepressants do spur the growth and enhanced branching of nerve cells in the hippocampus. So, the theory holds, the real value of these medications may be in generating new neurons (a process called neurogenesis), strengthening nerve cell connections, and improving the exchange of information between nerve circuits.

Thus, in one embodiment of the disclosure, encompassed are methods of treating and/or preventing depression comprising administering therapeutically effective amount of an aminosterol composition according to the disclosure. While not wishing to be bound by theory, it is theorized that the aminosterol compositions of the disclosure trigger neurogenesis, which functions to combat depression.

In some embodiments, the methods of the disclosure produce an improvement in a subject's clinical depression. An improvement in a subject's depression can be measured using any clinically-recognized measurement. For example, improvement can be measured using a depression rating scale. In one embodiment of the disclosure, following treatment a subject experiences an about 5, about 10, about 15, about 20, about 25, about 30, about 35, about 40, about 45, about 50, about 55, about 60, about 65, about 70, about 75, about 80, about 85, about 90, about 95 or an about 100% improvement. The improvement can be measured using any clinically recognized tool or assessment.

Examples of tools that can be used to evaluate depression and/or mood and the improvement following aminosterol treatment include for example: (1) Beck Depression Inventory (BDI-II); (2) UPDRS, sections 1.3 (depressed mood), 1.4 (anxious mood), 1.5 (apathy), and 1.13 (fatigue); and (3) Parkinson's Disease Fatigue Scale (PFS-16). In some embodiments, the improvement can be measured from one or more medically-recognized techniques selected from the group consisting of the Patient Health Questionnaire-9 (PHQ-9); Zung Self-Rating Depression Scale; Center for Epidemiologic Studies-Depression Scale (CES-D); and the Hamilton Rating Scale for Depression (HRSD).

(ii) Cognitive Impairment

In one embodiment, a method of treating, preventing, and/or slowing the onset or progression of cognitive impairment and/or a related symptom in a subject in need is provided, comprising administering to the subject a therapeutically effective amount of at least one aminosterol disclosed herein (e.g., ENT-03 (Compound III)), or pharmaceutically acceptable salt, solvate, prodrug, or derivative thereof.

Cognitive impairment, including mild cognitive impairment (MCI), is characterized by increased memory or thinking problems exhibited by a subject as compared to a normal subject of the same age. Approximately 15 to 20% of people age 65 or older have MCI, and MCI is especially linked to neurodegenerative conditions such as AD and synucleinopathies like PD. In 2002, an estimated 5.4 million people (22%) in the United States over age 70 had cognitive impairment without dementia. Plassman et al. 2009.

Cognitive impairment may entail memory problems including a slight but noticeable and measurable decline in cognitive abilities, including memory and thinking skills. When MCI primarily affects memory, it is known as "amnestic MCI." A person with amnestic MCI may forget information that would previously have been easily recalled, such as appointments, conversations, or recent events, for example. When MCI primarily affects thinking skills other than memory, it is known as "nonamnestic MCI." A person with nonamnestic MCI may have a reduced ability to make sound decisions, judge the time or sequence of steps needed to complete a complex task, or with visual perception, for example.

Mild cognitive impairment is a clinical diagnosis. A combination of cognitive testing and information from a person in frequent contact with the subject is used to fully assess cognitive impairment. A medical workup includes one or more of an assessment by a physician of a subject's medical history (including current symptoms, previous illnesses, and family history), assessment of independent function and daily activities, assessment of mental status using brief tests to evaluate memory, planning, judgment, ability to understand visual information, and other key thinking skills, neurological examination to assess nerve and reflex function, movement, coordination, balance, and senses, evaluation of mood, brain imaging, or neuropsychological testing. Diagnostic guidelines for MCI have been developed by various groups, including the Alzheimer's Association partnered with the National Institute on Aging (NIA), an agency of the U.S. National Institutes of Health (NIH). Jack et al. 2011; McKhann et al. 2011; Albert et al. 2011. Recommendations for screening for cognitive impairment have been issued by the U.S. Preventive Services Task Force. Screening for Cognitive Impairment in Older Adults, U.S. Preventive Services Task Force (March 2014), https://www.uspreventiveservicestaskforce.org/Home/GetFileByID/1882. For example, the Mini Mental State Examination (MMSE) may be used. Palsetia et al. (2018); Kirkevold, 0. & Selbaek, G. (2015). With the MMSE, a score of 24 or greater (out of 30) may indicate normal cognition, with lower scores indicating severe (less than or equal to 9 points), moderate (10-18 points), or mild (19-23 points) cognitive impairment. Other screening tools include the Informant Questionnaire on Cognitive Decline in the Elderly (IQCODE), in which an average score of 3 indicates no cognitive decline and a score greater than 3 indicates some decline. Jorm, A. F. 2004. Alternatively, the 7-Minute Screener, Abbreviated Mental Test Score (AMTS), Cambridge Cognitive Examination (CAMCOG), Clock Drawing Test (CDT), General Practitioner Assessment of Cognition (GPCOG), Mini-Cog, Memory Impairment Screen (MIS), Montreal Cognitive Assessment (MoCA), Rowland Universal Dementia Assessment (RUDA), Self-Administered Gerocognitive Examination (SAGE), Short and Sweet Screening Instrument (SAS-SI), Short Blessed Test (SBT), St. Louis Mental Status (SLUMS), Short Portable Mental Status Questionnaire (SPMSQ), Short Test of Mental Status (STMS), or Time and Change Test (T&C), among others, are frequently employed in clinical and research settings. Cordell et al. 2013. Numerous examinations may be used, as no single tool is recognized as the "gold standard," and improvements in score on any standardized examination indicate successful treatment of cognitive impairment, whereas obtaining a score comparable to the non-impaired population indicates total recovery.

In some embodiments, administration of a therapeutically effective amount of an aminosterol composition to a patient in need results in improvement of cognitive impairment as determined by a clinically recognized assessment scale, by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. The improvement can be measured using any clinically recognized tool or assessment.

Examples of tools that can be used to evaluate cognitive impairment and the improvement following aminosterol treatment include for example: (1) Mini Mental State Examination (MMSE); (2) Trail Making Test (TMT) Parts A and B; and (3) UPDRS, sections 1.1 (cognitive impairment).

(iii) Sleep Disturbance/Sleep Problems (e.g., REM Disturbed Sleep or Circadian Rhythm Dysfunction)

In one embodiment, a method of treating, preventing, and/or slowing the onset or progression of a sleep disturbance, sleep problem, sleep disorder, circadian rhythm dysfunction, and/or a related symptom in a subject in need is provided, comprising administering to the subject a therapeutically effective amount of at least one aminosterol disclosed herein (e.g., ENT-03 (Compound III)), or pharmaceutically acceptable salt, solvate, prodrug, or derivative thereof.

The alternating pattern of sleep and wakefulness occurring every 24 hours is known as the circadian rhythm. The rhythm is set by the "zeitgeber" (time setter), an entity known as the suprachiasmatic nucleus (SCN) and located in the hypothalamus. The SCN is normally "entrained" or synchronized by the external light-dark cycle. The circadian sleep-wake cycle can also shift in response to changes in external light-dark cycles, such as the desynchronization that occurs during travel from one time zone to another (jet-lag). Under such circumstances, a progressive adjustment occurs until the SCN is resynchronized with the external light-dark cycle. A similar "phase-shift" and adjustment occurs in night-shift workers.

Certain diseases and conditions may impair the normal functioning of the "zeitgeber" or circadian clock. These conditions may be reversible, such as desynchronization resulting from jet-lag, night-shift work or hunger, conditions easily remedied by adaptation or food intake. In contrast, damage to the nerves carrying light-dark related information from the retina to the SCN (conditions which may lead to blindness), or damage to the enteric nerves and neural structures which relay messages from the intestine to the SCN (conditions which may lead to neurodegenerative disorders) can cause permanent dysfunction of the circadian rhythm and abnormal sleep behavior.

Dysfunction of the circadian rhythm manifests first and foremost by abnormal sleep patterns. Such abnormalities typically are mild at onset and worsen progressively over time. A common symptom of sleep disorder is a delay in the onset of sleep. This delay can be as long as several hours, and the individual may not be able to fall asleep until the early hours of the morning. Another common symptom is sleep fragmentation, meaning that the individual awakens several times during the course of the night. Once awakened, the individual may not be able to get back to sleep, and each awake fragment may last an hour or more, further reducing "total sleep time," which is calculated by subtracting total time of the awake fragments from total time spent in bed. Total sleep time also diminishes with age, from about 14 to about 16 hours a day in newborns, to about 12 hours by one year of age, to about 7 to about 8 hours in young adults, progressively declining to about 5 to about 6 hours in elderly individuals. Total sleep time can be used to calculate an individual's "sleep age" and to compare it to their chronologic age. Significant discrepancies between sleep age and chronologic age are a reflection of the severity of the sleep disorder. "Sleep efficiency," defined as the percentage of the time spent in bed asleep is another index that can be used to determine the severity of the sleep disorder. Sleep efficiency is said to be abnormal when the percentage is below about 70%.

Sleep disorders and/or sleep disturbances include but are not limited to REM-behavior disorders, disturbances in the Circadian rhythm ("circadian rhythm dysfunction"), delayed sleep onset, sleep fragmentation, REM-behavior disorder" (RBD), and hallucinations. Other sleep disorders or disturbances that can be treated and/or prevented according to the disclosed methods include but are not limited to hypersomnia (i.e., daytime sleepiness), parasomnias (such as nightmares, night terrors, sleepwalking, and confusional arousals), periodic limb movement disorders (such as Restless Leg Syndrome), jet lag, narcolepsy, advanced sleep phase disorder, non-24 hour sleep-wake syndrome.

A "normal" or "restful" sleep period is defined as a sleep period uninterrupted by wakefulness. Alternatively, a said period can be defined by the recommended or appropriate amount of sleep for the subject's age category, e.g., (i) infants 0-3 months=about 11 to about 19 hours; (ii) infants about 4 to about 11 months=about 12 to about 18 hours; (iii) toddlers about 1 to about 2 years=about 9 to about 16 hours; (iv) preschoolers about 3 to about 5 years=about 10 to about 14 hours; (v) school-aged children about 6 to about 13 years=about 7 to about 12 hours; (v) teenagers about 14 to about 17 years=about 7 to about 11 hours; (vi) young adults about 18 to about 25 years=about 6 to about 11 hours; (vii) adults about 26 to about 64 years=about 6 to about 10 hours; and (viii) older adults ≥65 years=about 5 to about 9 hours. Thus, for treating sleep disturbance in a subject, the treatment can result in a restful sleep period of at least about 4, about 5, about 6, about 7, about 8, about 9, about 10, about 11, or about 12 hours.

TABLE 1

| Age | Recommended | May be appropriate | Not recommended |
|---|---|---|---|
| Newborns 0-3 months | 14 to 17 hours | 11 to 13 hours<br>18 to 19 hours | Less than 11 hours<br>More than 19 hours |
| Infants 4-11 months | 12 to 15 hours | 10 to 11 hours<br>16 to 18 hours | Less than 10 hours<br>More than 18 hours |
| Toddlers 1-2 years | 11 to 14 hours | 9 to 10 hours<br>15 to 16 hours | Less than 9 hours<br>More than 16 hours |
| Preschoolers 3-5 years | 10 to 13 hours | 8 to 9 hours<br>14 hours | Less than 8 hours<br>More than 14 hours |
| School-aged Children 6-13 years | 9 to 11 hours | 7 to 8 hours<br>12 hours | Less than 7 hours<br>More than 12 hours |

TABLE 1-continued

| Age | Recommended | May be appropriate | Not recommended |
|---|---|---|---|
| Teenagers 14-17 years | 8 to 10 hours | 7 hours<br>11 hours | Less than 7 hours<br>More than 11 hours |
| Young Adults 18-25 years | 7 to 9 hours | 6 hours<br>10 to 11 hours | Less than 6 hours<br>More than 11 hours |
| Adults 26-64 years | 7 to 9 hours | 6 hours<br>10 hours | Less than 6 hours<br>More than 10 hours |
| Older Adults ≥65 years | 7 to 8 hours | 5 to 6 hours<br>9 hours | Less than 5 hours<br>More than 9 hours |

There are several different scientifically acceptable ways to measure a sleep period uninterrupted by wakefulness. First, electrodes attached to the head of a subject can measure electrical activity in the brain by electroencephalography (EEG). This measure is used because the EEG signals associated with being awake are different from those found during sleep. Second, muscle activity can be measured using electromyography (EMG), because muscle tone also differs between wakefulness and sleep. Third, eye movements during sleep can be measured using electrooculography (EOG). This is a very specific measurement that helps to identify Rapid Eye Movement or REM sleep. Any of these methods, or a combination thereof, can be used to determine if a subject obtains a restful sleep period following administration of at least one aminosterol or a salt or derivative thereof to the subject.

Further, circadian rhythm regulation can be monitored in a variety of ways, including but not limited to monitoring wrist skin temperature as described by Sarabia et al. 2008. Similarly, symptoms of RBD can be monitored using a daily diary and RBD questionnaire (Stiasny-Kolster et al. 2007).

In some embodiments, administration of a therapeutically effective amount of an aminosterol composition to a patient with disturbed results in improvement in frequency of normal or restful sleep as determined by a clinically recognized assessment scale for one or more types of sleep dysregulation, by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. The improvement can be measured using any clinically recognized tool or assessment.

Examples of tools that can be used to measure and evaluate the effect of aminosterol treatment on sleep include for example: (1) Sleep Diary (participants completed a sleep diary on a daily basis throughout the study. The diaries included time into bed and estimated time to sleep as well as wake time and duration during the night); (2) I-Button Temperature Assessment. The I-Button is a small, rugged self-sufficient system that measures temperature and records the results in a protected memory section. The Thermochron I-Button DS1921H (Maxim Integrated, Dallas, TX) was used for skin temperature measurement. I-Buttons were programmed to sample every 10 mins., and attached to a double-sided cotton sport wrist band using Velcro, with the sensor face of the I-Button placed over the inside of the wrist, on the radial artery of the dominant hand. Subjects removed and replaced the data logger when necessary (i.e., to have a bath or shower). The value of skin temperature assessment in sleep research is that the endogenous skin warming resulting from increased skin blood flow is functionally linked to sleep propensity. From the collected data, the mesor, amplitude, acrophase (time of peak temperature), Rayleight test (an index of interdaily stability), mean waveforms are calculated); (3) UPDRS, sections 1.7 (sleep problems), 1.8 (daytime sleepiness) and 1.13 (fatigue); (4) Parkinson's Disease Fatigue Scale (PFS-16); (5) REM Sleep Behavior Disorder Screening Questionnaire; and (6) Parkinson's Disease Sleep Scale.

(iv) Autism

In one embodiment, a method of treating, preventing, and/or slowing the onset or progression of autism spectrum disorder (ASD) and/or a related symptom in a subject in need is provided, comprising administering to the subject a therapeutically effective amount of at least one aminosterol disclosed herein (e.g., ENT-03 (Compound III)), or pharmaceutically acceptable salt, solvate, prodrug, or derivative thereof.

Autism, or autism spectrum disorder, refers to a range of conditions characterized by challenges with social skills, repetitive behaviors, speech and nonverbal communication, as well as by unique strengths and differences. There are many types of autism, caused by different combinations of genetic and environmental influences. Autism's most-obvious signs tend to appear between 2 and 3 years of age. In some cases, it can be diagnosed as early as 18 months. Some developmental delays associated with autism can be identified and addressed even earlier.

The Centers for Disease Control and Prevention (CDC) estimates autism's prevalence as 1 in 59 children in the United States. This includes 1 in 37 boys and 1 in 151 girls. Around one third of people with autism remain nonverbal, and about one third of individuals with autism have an intellectual disability. Certain medical and mental health issues frequently accompany autism. They include gastrointestinal (GI) disorders, seizures, sleep disturbances, attention deficit and hyperactivity disorder (ADHD), anxiety and phobias.

Experts are still uncertain regarding the causes of autism. In all likelihood, there are multiple causes. It appears that a number of different circumstances, including environmental, biologic, and genetic factors, set the stage for autism and make a child more likely to have the disorder. It is likely that genetics play a large factor in the development of autism. Identical twins are more likely to both be affected than twins who are fraternal (not genetically identical). In a family with one autistic child, the chance of having another child with autism is about 5%, which is much higher than in the normal population. Research also has found that some emotional disorders (such as manic depression) occur more often in families of a child with autism.

At least one group of researchers has found a link between an abnormal gene and autism. The gene may be just one of 3-5 or more genes that interact in some way to cause the condition. Scientists suspect that a faulty gene or genes might make a person more likely to develop autism when there are also other factors present, such as a chemical imbalance, viruses or chemicals, or a lack of oxygen at birth. Other potential causes of autism are environmental toxins, including pesticides and heavy metals such as mercury. Heavy metals are certainly more commonly encountered in the environment now than they were in the past. It may be that people with autism or those at higher risk for developing it are more sensitive than others to these toxins.

A recent brain-tissue study suggests that children affected by autism have a surplus of synapses, or connections between brain cells. The excess is due to a slowdown in the normal pruning process that occurs during brain development. During normal brain development, a burst of synapse formation occurs in infancy. This is particularly pronounced in the cortex, which is central to thought and processing information from the senses. However, by late adolescence, pruning eliminates about half of these cortical synapses. In addition, many genes linked to autism are known to affect the development or function of brain synapses. The study also found that the brain cells from individuals with autism were filled with damaged parts and deficient in signs of a normal breakdown pathway called "autophagy." Tang et al. 2014.

Thus, one embodiment of the disclosure is directed to methods of treating autism comprising administering a therapeutically effective amount of an aminosterol composition according to the disclosure. In one embodiment, treatment results in improvement in one or more characteristics of autism. Such characteristics can be, for example, communication skills, social interaction, sensory sensitivity, and behavior. Improvement can be measured using any clinically recognized tool or assessment.

For example, the methods of the disclosure may show an improvement in one or more characteristics of autism, such as behavior, communication, mood, etc., as measured by a medically recognized scale. The improvement may be, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

(3) Cerebral or General Ischemic Disorder and/or a Related Symptom

In one embodiment, a method of treating, preventing, and/or slowing the onset or progression of a cerebral or general ischemic disorder and/or a related symptom in a subject in need is provided, comprising administering to the subject a therapeutically effective amount of at least one aminosterol disclosed herein (e.g., ENT-03 (Compound III)), or pharmaceutically acceptable salt, solvate, prodrug, or derivative thereof.

In one embodiment, the cerebral or general ischemic disorder is selected from microangiopathy, intrapartum cerebral ischemia, cerebral ischemia during/after cardiac arrest or resuscitation, cerebral ischemia due to intraoperative problems, cerebral ischemia during carotid surgery, chronic cerebral ischemia due to stenosis of blood-supplying arteries to the brain, sinus thrombosis or thrombosis of cerebral veins, cerebral vessel malformations, diabetic retinopathy, high blood pressure, high cholesterol, myocardial infarction, cardiac insufficiency, cardiac failure, congestive heart failure, myocarditis, pericarditis, perimyocarditis, coronary heart disease, angina pectoris, congenital heart disease, shock, ischemia of extremities, stenosis of renal arteries, diabetic retinopathy, thrombosis associated with malaria, artificial heart valves, anemias, hypersplenic syndrome, emphysema, lung fibrosis, erectile dysfunction, or pulmonary edema.

For example, the methods of the disclosure may show an improvement in one or more characteristics of the cerebral or general ischemic disorder as measured by a medically recognized scale. The improvement may be, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Medically recognized scales or techniques to measure improvement include, for example, cholesterol test, high-sensitivity C-reactive protein test, lipoprotein (a), plasma ceramides, natriuretic peptides, low density lipoprotein cholesterol, high density lipoprotein cholesterol, triglycerides, electrocardiogram (EKG), Holter monitor, stress test, echocardiogram, positron emission tomography (PET), thallium scans, myocardial perfusion scans, implantable loop recorder, tilt table test, electrophysiology study, coronary angiogram, magnetic resonance imaging, magnetic resonance angiography, cardiac CT scan, and event recorder.

(1) Erectile Dysfunction

In one embodiment, a method of treating, preventing, and/or slowing the onset or progression of erectile dysfunction (ED) and/or a related symptom in a subject in need is provided, comprising administering to the subject a therapeutically effective amount of at least one aminosterol disclosed herein (e.g., ENT-03 (Compound III)), or pharmaceutically acceptable salt, solvate, prodrug, or derivative thereof, or pharmaceutically acceptable salt, solvate, or prodrug thereof.

Erectile dysfunction can be a sign of a physical or psychological condition. It can cause stress, relationship strain, and low self-confidence. The main symptom is a man's inability to get or keep an erection firm enough for sexual intercourse. ED can occur manifest through different mechanisms. Based on its mechanism, ED can be classified as psychogenic, neurogenic (failure to initiate erection), artereogenic (failure of the penis to fill with blood), cavernosal (failure of vascular system to retain blood in penis once filled) (Dean et al. 2005).

Many neurodiseases causing ED such as PD are suspected to correlate with the formation of toxic αS aggregates within the enteric nervous system (ENS) (Braak et al. 2003 (a) and (b)). ED has been reported to affect in the range of 60-79% of men having PD, while the prevalence of ED in non-Parkinson men is only about 37.5% (Papatsoris, 2006). As a result of the normal trafficking of αS aggregates from the ENS to the central nervous system (CNS) via afferent nerves such as the vagus (Holmqvist et al. 2014; Svensson et al. 2015), neurotoxic aggregates accumulate progressively within the brainstem and more rostral structures. Inhibiting αS aggregation in the ENS may, thus, reduce the continuing neuro disease process in both the ENS and CNS (Phillips et al. 2008), and thereby positively impact ED associated with abnormal αS pathology.

It is known that central dopamine is a key neurotransmitter in the control of sexual function including erection (Giuliano et al 2001). It is thought that dopamine deficiency may be responsible for erectile dysfunction often observed in PD patients (Palma et al 2014). In patients with PD, αS-related pathology develops in serotonergic and cholinergic neurons in parallel with that seen in the nigral dopamine neurons. Thus, regulation of αS may play a role in ED in PD via dopaminergic dysfunction.

In one embodiment, the method results in a decrease in the number of instances in which the subject cannot attain erection, and the decrease in number of instances in which the subject cannot attain erection comprises a reduction in number of instances in which the subject cannot attain erection over a defined period of time. In another aspect, the method results in a decreased severity of ED over a defined period of time, wherein the decreased severity of ED is measured by a medically recognized technique selected from the group consisting of bone-pressed erect length (BPEL) measurement, girth measurement, Erection Hardness Scale (EHS), and International Index of Erectile Function (IIEF).

(ii) Blood Pressure

In one embodiment, a method of treating, preventing, and/or slowing the onset or progression of high blood pressure (HBP) or low blood pressure (LBP) and/or a related symptom in a subject in need is provided, comprising administering to the subject a therapeutically effective amount of at least one aminosterol disclosed herein (e.g., ENT-03 (Compound III)), or pharmaceutically acceptable salt, solvate, prodrug, or derivative thereof.

High blood pressure (HBP), also referred to as hypertension, is a long-term medical condition in which the blood pressure in the arteries is persistently elevated. Long-term high blood pressure, is a major risk factor for coronary artery disease, stroke, heart failure, atrial fibrillation, peripheral vascular disease, vision loss, chronic kidney disease, and dementia. HBP may be characterized as (a) a systolic blood pressure (BP)≥120 and a diastolic BP<80; or (b) a systolic blood pressure (BP)≥130 or a diastolic BP≥80; while low blood pressure (LBP) may be characterized as (a) a systolic blood pressure ≤80; or (b) a diastolic blood pressure ≤50.

Low blood pressure (LBP), also referred to as hypotension, is generally classified as a systolic blood pressure of less than 90 millimeters of mercury (mm Hg) or diastolic of less than 60 mm Hg. Primary symptoms include lightheadedness, vertigo and fainting. Severely low blood pressure can deprive the brain and other vital organs of oxygen and nutrients, leading to a life-threatening condition called shock. For some people who exercise and are in top physical condition, low blood pressure is a sign of good health and fitness. For many people, excessively low blood pressure can cause dizziness and fainting or indicate serious heart, endocrine or neurological disorders.

Blood Pressure (BP) and αS pathology: Many neurodiseases causing HBP or LBP, such as PD, are suspected to correlate with the formation of toxic αS aggregates within the enteric nervous system (ENS) (Braak et al. 2003 (a) and (b)). In a study of 11.55 million PD patient doctor visits in the US, the most commonly recorded comorbidity was hypertension, in 37.8% of visits (Lingala et al. 2017). Orthostatic hypotension (OH) is one of the commonly occurring nonmotor symptoms in patients with idiopathic Parkinson's disease (IPD) (Fereshtehnejad et al. 2014).

Examples of conditions associated with abnormal αS pathology, and/or dopaminergic dysfunction, correlated with HBP or LBP include, but are not limited to, synucleopathies, neurodiseases, psychological and/or behavior disorders, cerebral and general ischemic disorders, examples of which are described herein.

In one embodiment, in a subject having HBP, the method lowers the systolic and/or diastolic blood pressure by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%, as measured using a clinically recognized scale or tool.

In one embodiment, in a subject having LBP, the method raises the systolic and/or diastolic blood pressure by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%, as measured using a clinically recognized scale or tool.

In one embodiments, the clinically recognized scale or tool is selected from the group consisting of sphygmomanometry, arterial penetration, palpitation, asuculatoration, oscillometry, continuous noninvasive arterial pressure (CNAP), pulse wave velocity, and ambulatory monitoring.

(iii) Cardiac Conduction Defects

In one embodiment, a method of treating, preventing, and/or slowing the onset or progression of cardiac conduction defects (CCDs) and/or a related symptom in a subject in need is provided, comprising administering to the subject a therapeutically effective amount of at least one aminosterol disclosed herein (e.g., ENT-03 (Compound III)), or pharmaceutically acceptable salt, solvate, prodrug, or derivative thereof.

Cardiac conduction defects (CCDs) involve an aberration in how electrical impulses travel to and through the heart. The cardiac conduction system transmits electrical signals generated usually by the sinoatrial node to cause contraction of cardiac muscle. Cardiac conduction defect (CCD) is a serious and potentially life-threatening disorder. It belongs to a group of pathologies with an alteration of cardiac conduction through the atrioventricular (AV) node, the His-Purkinje system with right or left bundle branch block, and widening of QRS complexes in the electrocardiogram (EKG). Originally, CCD was considered a structural disease of the heart with anatomic changes in the conduction system underlying abnormal impulse propagation. In a substantial number of cases, however, conduction disturbances are found to occur in the absence of anatomical abnormalities. In these cases functional rather than structural alterations appear to underlie conduction disturbances. These functional defects are called "primary electrical disease of the heart." The pathophysiological mechanisms underlying CCD are diverse, but the most frequent form of CCD is a degenerative form also called Lenegre-Lev disease (idiopathic bilateral bundle branch fibrosis). Today Lenègre-Lev disease represents a major cause of pacemaker implantation in the world.

In one embodiment, the CCD includes or results in (a) QT interval (QTc)≥440 ms; (b) syncope; (c) presence of delta wave in electrocardiogram (EKG); (d) pseudo-right bundle branch block in EKG; (e) ST elevations in V1-V3 in EKG; (f) a QRS complex>100 ms in EKG; (g) PR interval <120 ms in EKG; (h) heart rate above 100 beats per minute (BPM); (i) heart rate below 60 BPM; (j) PR interval >200 ms in EKG; (k) QRS not following a P wave in EKG; (1) no repeating relation between P wave and QRS complex in EKG; (m) differing atrial and ventricular rates; (n) QS or rS complex in lead V1 in EKG; (o) notched ('M'-shaped) R wave in lead V6; (p) T wave discordance in EKG; (q) left axis deviation between −45° and −60° in EKG; (r) qR pattern (small q, tall R) in the lateral limb leads I and aVL in EKG; (s) rS pattern (small r, deep S) in the inferior leads II, III, and aVF in EKG; (t) delayed intrinsicoid deflection in lead aVL (>0.045 s) in EKG; (u) frontal plane axis between 90° and 180° in EKG; (v) rS pattern in leads I and aVL in EKG; (w) qR pattern in leads III and aVF in EKG; (x) chest pain; (y) palpitations; (z) difficulty breathing; (aa) rapid breathing; (bb) nausea; (cc) fatigue; (dd) sleep problem, sleep disorder, or sleep disturbance; (ee) constipation; and (ff) cognitive impairment.

In one embodiment, progression or onset of CCD is slowed, halted, or reversed over a defined period of time following administration of the fixed escalated dose of the aminosterol or a salt or derivative thereof, as measured by a medically-recognized technique. In addition, the CCD can be positively impacted by the fixed escalated dose of the aminosterol or a salt or derivative thereof, as measured by a medically-recognized technique. The positive impact and/or progression of CCD can be measured quantitatively or qualitatively by one or more techniques selected from the group consisting of echocardiography, electrocardiography (ECG or EKG), magnetic resonance imaging (MRI), positron-emission tomography (PET); coronary catheterization, intravascular ultrasound, Holter monitoring, stress test, computed tomography angiography (CTA), and coronary CT calcium scan. In addition, the progression or onset of CCD can be slowed, halted, or reversed by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, as measured by a medically-recognized technique.

In another embodiment, the aminosterol or a salt or derivative thereof reverses dysfunction caused by the CCD and treats, prevents, improves, and/or resolves the symptom being evaluated. The improvement or resolution of the CCD symptom is measured using a clinically recognized scale or tool. In addition, the improvement in the CCD symptom can be at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%, as measured using, for example, the techniques described above.

C. Appetite Suppression/Obesity Treatment

In one embodiment, a method of suppressing, preventing and/or slowing the onset or progression of appetite and/or one or more related symptoms in a subject in need is provided, comprising administering to the subject a therapeutically effective amount of at least one aminosterol disclosed herein (e.g., ENT-03 (Compound III)), or pharmaceutically acceptable salt, solvate, prodrug, or derivative thereof.

In one embodiment, the subject suffers from an appetite-increasing condition, and the increase in appetite is relative to the subject's appetite prior to suffering from the appetite-increasing condition. The increase in appetite can be measured using a clinical scale or tool.

In one embodiment, the method results in a decrease in the subject's appetite over a defined time period, wherein the decrease in appetite is relative to the subject's appetite prior to administration of the aminosterol (e.g., v) or a pharmaceutically acceptable salt, solvate, prodrug, or derivative thereof. The decrease in the subject's appetite can be about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 100%, as measured by a clinical appetite scale or tool. In one embodiment, the clinical appetite scale or tool is selected from the group consisting of self-assessment of appetite, subjective assessment of appetite, visual analogue scale (VAS), Functional Assessment of Anorexia/Cachexia Therapy (FAACT) score, and the Anorexia Questionnaire (AQ).

In one embodiment, the appetite-increasing condition is selected from the group consisting of stress, anxiety, depression, premenstrual syndrome, pregnancy, bulimia, hyperthyroidism, leptin resistance, Grave's disease, hypoglycemia, diabetes, Prader-Willi syndrome (PWS), binge-eating disorder, (BED), obesity, drug withdrawal, and drug consumption.

In one embodiment, the one or more related appetite symptoms is selected from the group consisting of borborygmi (stomach growling); faintness, dizziness, or lightheadedness; headache; irritability; cognitive impairment; and nausea. Performing the method may result in reduction or elimination of one or more of the related symptoms.

In one embodiment, (a) the method results in a decreased severity of faintness, dizziness, or lightheadedness of the subject over a defined period of time, as measured by a clinically-recognized faintness, dizziness, or lightheadedness scale or tool; (b) the method results in a decreased severity of faintness, dizziness, or lightheadedness over a defined period of time, wherein the decrease in severity is selected from the group consisting of by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%, as measured by a clinically-recognized faintness, dizziness, or lightheadedness scale or tool; and/or (c) the method results in the subject being free of faintness, dizziness, or lightheadedness.

In one embodiment, the clinically-recognized faintness, dizziness, or lightheadedness scale or tool is selected from the group consisting of The Amer Dizziness Diagnostic Scale (ADDS), The Vertigo Symptom Scale, Dizziness Handicap Inventory, Vestibular Disorders of Daily Living Scale, Activities-specific Balance Confidence, Vertigo Handicap Questionnaire, Vertigo, Dizziness, Imbalance Questionnaire, UCLA Dizziness Questionnaire, Dizzy Factor Inventory, European Evaluation of Vertigo, and Meniere's Disease Patients-Oriented Severity Index.

In one embodiment, (a) the method results in reduction of the subject's headache over a defined period of time, as measured by one or more clinically-recognized headache rating scales; (b) the method results in reduction of the subject's headache over a defined period of time, as measured by one or more clinically-recognized headache rating scales and the reduction is in one or more headache types selected from the group consisting of tension, cluster, migraine, hypertension headache and hypotension headache; and/or (c) the method results in reduction of the subject's headache over a defined period of time, as measured by one or more clinically-recognized headache rating scales, and the reduction of the subject's headache is about 5, about 10, about 15, about 20, about 25, about 30, about 35, about 40, about 45, about 50, about 55, about 60, about 65, about 70, about 75, about 80, about 85, about 90, about 95, or about 100%.

In one embodiment, the one or more clinically-recognized headache rating scales is selected from the group consisting of ID-Migraine, Visual Aura Rating Scale (VARS), Migraine Disability Assessment Questionnaire (MIDAS), Migraine-Specific Quality of Life Survey (MSQ 2.1), and Headache Under-Response to Treatment (HURT) Questionnaire.

In one embodiment, (a) the method results in improvement in a subject's cognitive impairment over a defined period of time, as measured by one or more clinically-recognized cognition rating scales; (b) the method results in improvement in a subject's cognitive impairment over a defined period of time, as measured by one or more clinically-recognized cognition rating scales, and the improvement is about 5, about 10, about 15, about 20, about 25, about 30, about 35, about 40, about 45, about 50, about 55, about 60, about 65, about 70, about 75, about 80, about 85, about 90, about 95, or about 100%.

In one embodiment, the one or more clinically-recognized cognition rating scales is selected from the group consisting of ADASCog, Woodcock-Johnson Tests of Cognitive Abilities, Leiter International Performance Scale, Miller Analogies Test, Raven's Progressive Matrices, Wonderlic Personnel Test, IQ tests, Uniformed Parkinson's Disease Scale (UPDRS), Mini Mental State Examination (MMSE), Mini Mental Parkinson (MMP), Informant Questionnaire on Cognitive Decline in the Elderly (IQCODE), The 7-Minute Screen, Abbreviated Mental Test Score (AMTS), Cambridge Cognitive Examination (CAMCOG), Clock Drawing Test (CDT), General Practitioner Assessment of Cognition (GPCOG), Mini-Cog, Memory Impairment Screen (MIS), Montreal Cognitive Assessment (MoCA), Rowland Universal Dementia Assessment (RUDA), Self-Administered Gerocognitive Examination (SAGE), Short and Sweet Screening Instrument (SAS-SI), Short Blessed Test (SBT), St. Louis Mental Status (SLUMS), Short Portable Mental Status Questionnaire (SPMSQ), Short Test of Mental Status (STMS), Time and Change Test (T&C), Test Your Memory (TYM) test, Addenbrooke's Cognitive Examination-Revised (ACER); and a computerized tested selected from Cantab Mobile, Cognigram, Cognivue, Cognision, and Automated Neuropsychological Assessment Metrics Cognitive Performance Test (CPT).

In one embodiment, a method of reversing, preventing, and/or slowing the onset or progression of weight gain and/or a related symptom in a subject in need is provided, comprising administering to the subject a therapeutically effective amount of at least one aminosterol disclosed herein (e.g., ENT-03 (Compound III)), or pharmaceutically acceptable salt, solvate, prodrug, or derivative thereof.

In one embodiment, a method of reducing weight in a subject in need thereof is provided, comprising administering to the subject a therapeutically effective amount of an aminosterol disclosed herein (e.g., ENT-03 (Compound III)), or pharmaceutically acceptable salt, solvate, prodrug, or derivative thereof.

In some embodiments, the method results in weight reduction in the subject over a defined period time of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the method results in a decrease in consumption of calories by the subject over a defined period of time, wherein the decrease is relative to calories consumed by the subject during a span of time before the administration of the aminosterol (e.g., ENT-03 (Compound III)) or a pharmaceutically acceptable salt, solvate, prodrug, or derivative thereof. The defined period of time and the span of time can be the same length of time. In addition, the decrease in consumption of calories can be about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the method results in a decrease in food mass consumption by the subject over a defined period of time relative to food mass consumed by the subject during a span of time before the administration of the aminosterol or a pharmaceutically acceptable salt, solvate, or prodrug thereof; wherein the defined period of time and the span of time are the same length of time, and wherein the decrease in food mass consumption is by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the method results in a decrease in weight in the subject over a defined period of time, wherein the decrease in weight is by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% of the subject's weight prior to administration of the aminosterol or a pharmaceutically acceptable salt, solvate, prodrug, or derivative thereof.

In some embodiments, each defined period of time is independently selected from the group consisting of about 1 day to about 10 days, about 10 days to about 30 days, about 30 days to about 3 months, about 3 months to about 6 months, about 6 months to about 12 months, and about greater than 12 months.

In some embodiments, the subject is suffering from and/or at risk of suffering from one or more conditions selected from the group consisting of obesity, fatty liver disease, type 2 diabetes, heart disease, stroke, hypertension, gallbladder disease, gout, sleep apnea, osteoarthritis, High LDL cholesterol, low HDL cholesterol, high levels of triglycerides (dyslipidemia), endometrial cancer, breast cancer, colon cancer, kidney cancer, gallbladder cancer, and liver cancer.

D. Antimicrobial Treatment (1) Microbial Infection

In one aspect, the aminosterols described herein can be administered to a subject in need to treat a microbial infection. In some embodiments, the subject in need has a condition selected from the group consisting of viral infections, microbial infections, bacterial infections, e.g., Gram-negative and/or Gram-positive bacterial infections, Mycobacteria infections, fungal infections, and/or protozoan infections.

In some embodiments, the viral infection is caused by a virus selected from the group consisting of Yellow Fever, Cytomegalovirus, Eastern Equine Encephalitis virus, Hepatitis B virus, Hepatitis Delta virus, Dengue virus, and Human Immunodeficiency virus. In some embodiments, the condition to be treated is a viral infection caused by a virus selected from the group consisting of "African Swine Fever Viruses," Arbovirus, Adenoviridae, Arenaviridae, Arterivirus, Astroviridae, Baculoviridae, Bimaviridae, Birnaviridae, Bunyaviridae, Caliciviridae, Caulimoviridae, Circoviridae, Coronaviridae, Cystoviridae, Dengue, EBV, HIV, Deltaviridae, Filviridae, Filoviridae, Flaviviridae, Hepadnaviridae (Hepatitis), Herpesviridae (such as, Cytomegalovirus, Herpes Simplex, Herpes Zoster), Iridoviridae, Mononegavirus (e.g., Paramyxoviridae, Morbillivirus, Rhabdoviridae), Myoviridae, Orthomyxoviridae (e.g., Influenza A, Influenza B, and parainfluenza), Papiloma virus, Papovaviridae, Paramyxoviridae, Prions, Parvoviridae, Phycodnaviridae, Picomaviridae (e.g., Rhinovirus, Poliovirus), Poxviridae (such as Smallpox or Vaccinia), Potyviridae, Reoviridae (e.g., Rotavirus), Retroviridae (HTLV-I, HTLV-II, Lentivirus), Rhabdoviridae, Tectiviridae, Togaviridae (e.g., Rubivirus), herpes, pox, papilloma, corona, influenza, hepatitis, sendai, sindbis, vaccinia viruses, west nile, hanta, viruses which cause the common cold, and any combination thereof. In some embodiments, the condition to be treated is selected from the group consisting of AIDS, viral meningitis, Dengue, EBV, hepatitis, a chronic disease suspected to be of viral origin, multiple sclerosis, Type I diabetes, Type II diabetes, atherosclerosis, cardiomyopathies, Kawaski disease, aplastic anemia, and any combination thereof.

In some embodiments, the method further comprises administering one or more antiviral drugs.

(2) Coronavirus Infection

In one aspect, a method of treating or preventing an infection by a coronavirus in a subject is provided, comprising administering to the subject a therapeutically effective amount of the aminosterol compound of any embodiment herein or the composition of any embodiment herein.

In some embodiments, the coronavirus comprises a virus selected from the group consisting of an Alphacoronavirus; a Colacovirus such as Bat coronavirus CDPHE15; a Decacovirus such as Bat coronavirus HKU10 or Rhinolophus ferrumequinum alphacoronavirus HuB-2013; a Duvinacovirus such as Human coronavirus 229E; a Luchacovirus such as Lucheng Rn rat coronavirus; a Minacovirus such as a Ferret coronavirus or Mink coronavirus 1; a Minunacovirus such as Miniopterus bat coronavirus 1 or Miniopterus bat coronavirus HKU8; a Myotacovirus such as Myotis ricketti alphacoronavirus Sax-2011; a nyctacovirus such as Nyctalus velutinus alphacoronavirus SC-2013; a Pedacovirus such as Porcine epidemic diarrhea virus or Scotophilus bat coronavirus 512; a Rhinacovirus such as Rhinolophus bat coronavirus HKU2; a Setracovirus such as Human coronavirus NL63 or NL63-related bat coronavirus strain BtKYNL63-9b; a Tegacovirus such as Alphacoronavirus 1; a Betacoronavirus; a Embecovirus such as Betacoronavirus 1, Human coronavirus OC43, China Rattus coronavirus HKU24, Human coronavirus HKU1 or Murine coronavirus; a Hibecovirus such as Bat Hp-betacoronavirus Zhejiang2013; a Merbecovirus such as Hedgehog coronavirus 1, Middle East respiratory syndrome-related coronavirus (MERS-CoV), Pipistrellus bat coronavirus HKU5 or *Tylonycteris* bat coronavirus HKU4; a Nobecovirus such as Rousettus bat coronavirus GCCDC1 or Rousettus bat coronavirus HKU9, a Sarbecovirus such as a Severe acute respiratory syndrome-related coronavirus, Severe acute respiratory syndrome coronavirus (SARS-CoV) or Severe acute respiratory syndrome coronavirus 2 (SARS-CoV-2, COVID-19); a Deltacoronavirus; an Andecovirus such as Wigeon coronavirus HKU20; a Buldecovirus such as Bulbul coronavirus HKU11, Porcine coronavirus HKU15, Munia coronavirus HKU13 or White-eye coronavirus HKU16; a Herdecovirus such as Night heron coronavirus HKU19; a Moordecovirus such as Common moorhen coronavirus HKU21; a Gammacoronavirus; a Cegacovirus such as Beluga whale coronavirus SW1; and an Igacovirus such as Avian coronavirus.

In some embodiments, the coronavirus is encoded by a polynucleotide comprising the sequence of SARS-CoV-2, or a polynucleotide having at least 80% sequence identity to the polynucleotide comprising the sequence of SARS-CoV-2. In some embodiments, the coronavirus comprises or is characteristic of human coronavirus 229E, human coronavirus OC43, SARS-CoV, HCoV NL63, HKU1, MERS-CoV, or SARS-CoV-2. In some embodiments, the coronavirus comprises or is characteristic of SARS-CoV-2.

In some embodiments, the subject is deemed at risk for severe illness and/or serious complications from the coronavirus infection. In some embodiments, the subject is about age 50 or older, about age 55 or older, about age 60 or older, or about age 65 or older. In some embodiments, the subject suffers from one or more pre-existing conditions selected from the group consisting of diabetes, asthma, a respiratory disorder, high blood pressure, and heart disease. In some embodiments, the subject is immunocompromised. In some embodiments, the subject is immunocompromised due to AIDS, cancer, a cancer treatment, hepatitis, an autoimmune disease, steroid receiving, immunosenescence, or any combination thereof.

In some embodiments, administration increases the chance of survival for the subject following exposure to a coronavirus. In some embodiments, the chance of survival is increased by about 10%, about 20%, about 30%, about 40%, about 50%, about 60%, about 70%, about 80%, about 90%, or about 100%, as measured using any clinically recognized technique.

In some embodiments, the subject is exposed to or is anticipated to be exposed to an individual who is contagious for a coronavirus. In some embodiments, the individual who is contagious for a coronavirus has one or more symptoms selected from the group consisting of fever, cough, shortness of breath, diarrhea, sneezing, runny nose, and sore throat. In some embodiments, the subject is a healthcare worker, aged 60 years or older, frequent traveler, military personnel, caregiver, or a subject with a preexisting condition that results in increased risk of mortality with infection.

In some embodiments, the method further comprises administering one or more antiviral drugs. In some embodiments, the one or more antiviral drugs are selected from the group consisting of chloroquine, hydroxychloroquine, darunavir, galidesivir, interferon beta, lopinavir, ritonavir, remdesivir, and/or triazavirin.

In some embodiments, administration reduces the risk of transmission of coronavirus. In some embodiments, the reduction in risk of transmission is by about 10%, about 20%, about 30%, about 40%, about 50%, about 60%, about 70%, about 80%, about 90%, or about 100%, as measured using any clinically recognized technique. In some embodiments, the medically recognized technique comprises PCR (polymerase chain reaction) or immunoassay.

VI. Patient Populations

The disclosed aminosterols and compositions comprising the same can be used to treat a range of subjects, including human and non-human animals, including mammals, as well as immature and mature animals, including human children and adults. The human subject to be treated can be an infant, toddler, school-aged child, teenager, young adult, adult, or elderly patient.

In embodiments disclosed herein relating to prevention, particular patient populations may be selected based on being "at risk for" the development of any of the conditions disclosed herein. For example, genetic markers of the condition or family history may be used as signs to identify subjects likely to develop the particular condition. Thus, in some embodiments, prevention may involve first identifying a patient population at risk of developing the condition. Alternatively, certain symptoms are considered early signs of particular disorders. Thus, in some embodiments, a patient population may be selected for being "at risk" for developing the condition based on age and experiencing symptoms associated with the condition. Further genetic or hereditary signs may be used to refine the patient population.

VII. Kits

Aminosterol formulations or compositions of the disclosure may be packaged together with or included in a kit along with instructions or a package insert. Such instructions or package inserts may address recommended storage conditions, such as time, temperature and light, taking into account the shelf-life of the aminosterol or derivatives or salts thereof. Such instructions or package inserts may also address the particular advantages of the aminosterol or derivatives or salts thereof, such as the ease of storage for formulations that may require use in the field, outside of controlled hospital, clinic or office conditions.

The disclosure also provides a pharmaceutical pack or kit comprising one or more containers filled with one or more aminosterol pharmaceutical compositions disclosed herein. The kits may include, for instance, containers filled with an appropriate amount of an aminosterol pharmaceutical composition, either as a powder, a tablet, to be dissolved, or as a sterile solution. Associated with such container(s) can be a notice in the form prescribed by a governmental agency regulating the manufacture, use or sale of pharmaceuticals or biological products, which notice reflects approval by the agency of manufacture, use or sale for human administration. In addition, the aminosterol or a derivative or salt thereof may be employed in conjunction with other therapeutic compounds.

In other aspects, a kit comprising a nasal spray device as described herein is disclosed. In one aspect, the kit may comprise one or more devices as disclosed herein, comprising a disclosed low dose aminosterol composition, wherein the device is sealed within a container sufficient to protect the device from atmospheric influences. The container may be, for example, a foil, or plastic pouch, particularly a foil pouch, or heat-sealed foil pouch. Suitable containers sufficient to adequately protect the device will be readily appreciated by one of skill in the art.

In one aspect, the kit may comprise one or more devices as disclosed herein, wherein the device may be sealed within a first protective packaging, or a second protective packaging, or a third protective packaging, that protects the physical integrity of the product. One or more of the first, second, or third protective packaging may comprise a foil pouch. The kit may further comprise instructions for use of the device. In one aspect, the kit contains two or more devices.

In one aspect, the kit may comprise a device as disclosed herein, and may further comprise instructions for use. In one aspect, the instructions may comprise visual aid/pictorial and/or written directions to an administrator of the device.

VIII. Combination Therapy

In the methods of the disclosure, the aminosterol compositions may be administered alone or in combination with one or more other therapeutic agents. An example of an additional therapeutic agent is one known to treat the condition the aminosterol is being administered to treat.

For example, in methods of treating, preventing, and/or slowing the onset or progression of PD and/or a related symptom, the aminosterol composition can be co-administered or combined with drugs commonly prescribed to treat PD or related symptoms, such as levodopa (usually combined with a dopa decarboxylase inhibitor or COMT inhibitor), dopamine agonists and MAO-B inhibitors. Exemplary dopa decarboxylase inhibitors are carbidopa and benserazide. Exemplary COMT inhibitors are tolcapone and entacapone. Dopamine agonists include, for example, bromocriptine, pergolide, pramipexole, ropinirole, piribedil, cabergoline, apomorphine, lisuride, and rotigotine. MAO-B inhibitors include, for example, selegiline and rasagiline. Other drugs commonly used to treat PD include, for example, amantadine, anticholinergics, clozapine for psychosis, cholinesterase inhibitors for dementia, and modafinil for daytime sleepiness.

In methods of treating, preventing, and/or slowing the onset or progression of AD or related symptoms associated with AD, the aminosterol composition can be co-administered or combined with drugs commonly prescribed to treat AD or related symptoms, such as glutamate, antipsychotic drugs, huperzine A, acetylcholinesterase inhibitors and NMDA receptor antagonists such as memantine (Akatinol®, Axura®, Ebixa®/Abixa®, Memox® and Namenda). Examples of acetylcholinesterase inhibitors are donepezil (Aricept®), galantamine (Razadyne®), and rivastigmine (Exelon®).

In methods of treating, preventing, and/or slowing the onset or progression of diabetes or related symptoms associated with diabetes and/or diabetes mellitus, including both Type 1 and Type 2 diabetes, or neuropathy of diabetes, the aminosterol composition can be co-administered or combined with drugs commonly prescribed to treat diabetes mellitus or related symptoms, such as insulin (NPH insulin or synthetic insulin analogs) (e.g., Humulin®, Novolin®) and oral antihyperglycemic drugs. Oral antihyperglycemic drugs include but are not limited to (1) biguanides such as metformin (Glucophage®); (2) Sulfonylureas such as acetohexamide, chlorpropamide (Diabinese®), glimepiride (Amaryl®), glipizide (Glucotrol®), tolazamide, Tolbutamide, and glyburide (Diabeta®, Micronase®); (3) Meglitinides such as repaglinide (Prandin®) and nateglinide (Starlix®); (4) Thiazolidinediones such as rosiglitazone (Avandia) and pioglitazone (Actos®); (5) Alpha-glucosidase inhibitors such as acarbose (Precose®) and miglitol (Glyset®); (6) Dipeptidyl peptidase-4 inhibitors such as Sitagliptin (Januvia®); (7) Glucagon-like peptide agonists such as exenatide (Byette); and (8) Amylin analogs such as pramlintide (Symlin).

In methods of treating, preventing, and/or slowing the onset or progression of HD or related symptoms associated with Huntington's chorea or disease, the aminosterol composition can be co-administered or combined with drugs commonly prescribed to treat Huntington's chorea or related symptoms, such as medications prescribed to help control emotional and movement problems associated with Huntington's chorea. Such medications include, but are not limited to, (1) antipsychotic drugs, such as haloperidol and clonazepam; (2) drugs used to treat dystonia, such as acetylcholine regulating drugs (trihexyphenidyl, benztropine (Cogentin®), and procyclidine HCl); GABA-regulating drugs (diazepam (Valium®), lorazepam (Ativan®), clonazepam (Klonopin®), and baclofen (Lioresal®); dopamine-regulators (levodopa/carbidopa) (Sinemet®), bromocriptine (parlodel), reserpine, tetrabenazine); anticonvulsants (carbamazepine (Tegretol®) and botulinum toxin (Botox®); and (3) drugs used to treat depression (fluoxetine, sertraline, and nortriptyline). Other drugs commonly used to treat HD include amantadine, tetrabenazine, dopamine blockers, and co-enzyme $Q_{10}$.

In methods of treating, preventing, and/or slowing the onset or progression of peripheral sensory neuropathy or related symptoms associated with peripheral sensory neuropathy, the aminosterol composition can be co-administered or combined with drugs commonly prescribed to treat peripheral sensory neuropathy or related symptoms. Peripheral sensory neuropathy refers to damage to nerves of the peripheral nervous system, which may be caused either by diseases of or trauma to the nerve or the side-effects of systemic illness. Drugs commonly used to treat this condition include, but are not limited to, neurotrophin-3, tricyclic antidepressants (e.g., amitriptyline), antiepileptic therapies (e.g., gabapentin or sodium valproate), synthetic cannabinoids (Nabilone) and inhaled cannabis, opiate derivatives, and pregabalin (Lyrica®).

In methods of treating, preventing, and/or slowing the onset or progression of traumatic head and/or spine injury or related symptoms associated with traumatic head and/or spine injury, the aminosterol composition can be co-administered or combined with drugs commonly prescribed to treat traumatic head and/or spine injury or related symptoms, such as analgesics (acetaminophen, NSAIDs, salicylates, and opioid drugs such as morphine and opium) and paralytics.

In methods of treating, preventing, and/or slowing the onset or progression of stroke or related symptoms associated with stroke, the aminosterol composition can be co-administered or combined with drugs commonly prescribed to treat stroke or related symptoms, such as aspirin, clopidogrel, dipyridamole, tissue plasminogen activator (tPA), and anticoagulants (e.g., alteplase, warfarin, dabigatran).

In methods of treating, preventing, and/or slowing the onset or progression of ALS or related symptoms associated with ALS, the aminosterol composition can be co-administered or combined with drugs commonly prescribed to treat Amyotrophic lateral sclerosis or related symptoms, such as riluzole (Rilutek®), KNS-760704 (an enantiomer of pramipexole), olesoxime (TRO19622), talampanel, arimoclomol, medications to help reduce fatigue, ease muscle cramps, control spasticity, reduce excess saliva and phlegm, control pain, depression, sleep disturbances, dysphagia, and constipation.

In methods of treating, preventing, and/or slowing the onset or progression of MS or related symptoms associated with multiple sclerosis, the aminosterol composition can be co-administered or combined with drugs commonly prescribed to treat multiple sclerosis or related symptoms, such as corticosteroids (e.g., methylprednisolone), plasmapheresis, fingolimod (Gilenya®), interferon beta-la (Avonex®, CinnoVex®, ReciGen® and Rebif®), interferon beta-1b (Betaseron® and Betaferon®), glatiramer acetate (Copaxone), mitoxantrone, natalizumab (Tysabri), alemtuzumab (Campath), daclizumab (Zenapax®), rituximab, dirucotide, BHT-3009, cladribine, dimethyl fumarate, estriol, fingolimod, laquinimod, minocycline, statins, temsirolimus teriflunomide, naltrexone, and vitamin D analogs.

In methods of treating, preventing, and/or slowing the onset or progression of cerebral palsy or related symptoms associated with cerebral palsy, the aminosterol composition can be co-administered or combined with drugs commonly prescribed to treat cerebral palsy or related symptoms, such as botulinum toxin A injections.

In methods of treating, preventing, and/or slowing the onset or progression of epilepsy or related symptoms associated with epilepsy, the aminosterol composition can be co-administered or combined with drugs commonly prescribed to treat epilepsy or related symptoms, such as anticonvulsants (e.g., carbamazepine (Tegretol®), clorazepate (Tranxene®), clonazepam (Klonopin®), ethosuximide (Zarontin®), felbamate (Felbatol®), fosphenytoin (Cerebyx®), gabapentin (Neurontin®), lacosamide (Vimpat®), lamotrigine (Lamictal®), levetiracetam (Keppra®), oxcarbazepine (Trileptal®), phenobarbital (Luminal®), phenytoin (Dilantin®), pregabalin (Lyrica®), primidone (Mysoline®), tiagabine (Gabitril®), topiramate (Topamax®), valproate semisodium (Depakote®), valproic acid (Depakene®), and zonisamide (Zonegran®), clobazam (Frisium®), vigabatrin (Sabre), retigabine, brivaracetam, seletracetam, diazepam (Valium® and Diastat®), lorazepam (Ativan®), paraldehyde (Paral®), midazolam (Versed), pentobarbital (Nembutal®), acetazolamide (Diamox®), progesterone, adrenocorticotropic hormone (ACTH and Acthar®), various corticotropic steroid hormones (prednisone), and bromide.

In methods of treating, preventing, and/or slowing the onset or progression of cognitive impairment or related symptoms associated with cognitive impairment, the aminosterol composition can be co-administered or combined with drugs commonly prescribed to treat cognitive impairment, such as donepezil (Aricept®) galantamine (Razadyne®), rivastigmine (Exelon®); and stimulants such as caffeine, amphetamine (Adderall®), lisdexamfetamine (Vyvanse®), and methylphenidate (Ritalin®); NMDA antagonists such as memantine (Nameda supplements such as *Ginko biloba*, L-theanine, piracetam, oxiracitam, aniracetam, tolcapone, atomoxetine, ginseng, and *Salvia officinalis.*

In the methods of treating, preventing, and/or slowing the onset or progression of malignancy or related symptoms associated with malignancies, the aminosterol composition can be co-administered or combined with drugs commonly used to treat malignancies. These include all known cancer drugs, such as but not limited to those listed at http://www.cancer.gov/cancertopics/druginfo/alphalist as of May 5, 2014, which is specifically incorporated by reference. In one embodiment, the drug commonly used to treat malignancies may be selected from the group consisting of actinomycin-D, alkeran, ara-C, anastrozole, BiCNU, bicalutamide, bleomycin, busulfan, capecitabine, carboplatin, carboplatinum, carmustine, CCNU, chlorambucil, cisplatin, cladribine, CPT-11, cyclophosphamide, cytarabine, cytosine arabinoside, cytoxan, dacarbazine, dactinomycin, daunorubicin, dexrazoxane, docetaxel, doxorubicin, DTIC, epirubicin, ethyleneimine, etoposide, floxuridine, fludarabine, fluorouracil, flutamide, fotemustine, gemcitabine, hexamethylamine, hydroxyurea, idarubicin, ifosfamide, irinotecan, lomustine, mechlorethamine, melphalan, mercaptopurine, methotrexate, mitomycin, mitotane, mitoxantrone, oxaliplatin, paclitaxel, pamidronate, pentostatin, plicamycin, procarbazine, steroids, streptozocin, STI-571, tamoxifen, temozolomide, teniposide, tetrazine, thioguanine, thiotepa, tomudex, topotecan, treosulphan, trimetrexate, vinblastine, vincristine, vindesine, vinorelbine, VP-16, xeloda, asparaginase, AIN-457, bapineuzumab, belimumab, brentuximab, briakinumab, canakinumab, cetuximab, dalotuzumab, denosumab, epratuzumab, estafenatox, farletuzumab, figitumumab, galiximab, gemtuzumab, girentuximab (WX-G250), herceptin, ibritumomab, inotuzumab, ipilimumab, mepolizumab, muromonab-CD3, naptumomab, necitumumab, nimotuzumab, ocrelizumab, ofatumumab, otelixizumab, ozogamicin, pagibaximab, panitumumab, pertuzumab, ramucirumab, reslizumab, rituximab, REGN88, solanezumab, tanezumab, teplizumab, tiuxetan, tositumomab, trastuzumab, tremelimumab, vedolizumab, zalutumumab, zanolimumab, SFC, accutane hoffmann-la roche, AEE788 novartis, AMG-102, anti neoplaston, AQ4N (Banoxantrone), AVANDIA (Rosiglitazone Maleate), avastin (Bevacizumab) genetech, BCNU, biCNU carmustine, CCI-779, CCNU, CCNU lomustine, celecoxib (Systemic), chloroquine, cilengitide (EMD 121974), CPT-11 (CAMPTOSAR, Irinotecan), dasatinib (BMS-354825, Sprycel), dendritic cell therapy, etoposide (Eposin, Etopophos, Vepesid), GDC-0449, gleevec (imatinib mesylate), gliadel wafer, hydroxychloroquine, IL-13, IMC-3G3, immune therapy, iressa (ZD-1839), lapatinib (GW572016), methotrexate for cancer (Systemic), novocure, OSI-774, PCV, RAD001 novartis (mTOR inhibitor), rapamycin (Rapamune, Sirolimus), RMP-7, RTA 744, simvastatin, sirolimus, sorafenib, SU-101, SU5416 sugen, sulfasalazine (Azulfidine), sutent (Pfizer), TARCEVA (erlotinib HCl), taxol, TEMODAR schering-plough, TGF-B anti-sense, thalomid (thalidomide), topotecan (Systemic), VEGF trap, VEGF-trap, vorinostat (SAHA), XL 765, XL184, XL765, zarnestra (tipifarnib), ZOCOR (simvastatin), cyclophosphamide (Cytoxan), (Alkeran), chlorambucil (Leukeran), thiopeta (Thioplex), busulfan (Myleran), procarbazine (Matulane), dacarbazine (DTIC), altretamine (Hexalen), clorambucil, cisplatin (Platinol), ifosafamide, methotrexate (MTX), 6-thiopurines (Mercaptopurine [6-MP], Thioguanine [6-TG]), mercaptopurine (Purinethol), fludarabine phosphate, (Leustatin), flurouracil (5-FU), cytarabine (ara-C), azacitidine, vinblastine (Velban), vincristine (Oncovin), podophyllotoxins (etoposide {VP-16} and teniposide {VM-26}), camptothecins (topotecan and irinotecan), taxanes such as paclitaxel (Taxol) and docetaxel (Taxotere), (Adriamycin, Rubex, Doxil), dactinomycin (Cosmegen), plicamycin (Mithramycin), mitomycin: (Mutamycin), bleomycin (Blenoxane), estrogen and androgen inhibitors (Tamoxifen), gonadotropin-releasing hormone agonists (Leuprolide and Goserelin (Zoladex)), aromatase inhibitors (Aminoglutethimide and Anastrozole (Arimidex)), amsacrine, asparaginase (El-spar), mitoxantrone (Novantrone), mitotane (Lysodren), retinoic acid derivatives, bone marrow growth factors (sargramostim and filgrastim), amifostine, pemetrexed, decitabine, iniparib, olaparib, veliparib, everolimus, vorinostat, entinostat (SNDX-275), mocetinostat (MGCD0103), panobinostat (LBH589), romidepsin, valproic acid, flavopiridol, olomoucine, roscovitine, kenpaullone, AG-024322 (Pfizer), fascaplysin, ryuvidine, purvalanol A, NU2058, BML-259, SU 9516, PD-0332991, P276-00, geldanamycin, tanespimycin, alvespimycin, radicicol, deguelin, BIIB021, cis-imidazoline, benzodiazepinedione, spiro-oxindoles, isoquinolinone, thiophene, 5-deazaflavin, tryptamine, aminopyridine, diaminopyrimidine, pyridoisoquinoline, pyrrolopyrazole, indolocarbazole, pyrrolopyrimidine, dianilinopyrimidine, benzamide, phthalazinone, tricyclic indole, benzimidazole, indazole, pyrrolocarbazole, isoindolinone, morpholinyl anthracycline, a maytansinoid, ducarmycin, auristatins, calicheamicins (DNA damaging agents), α-amanitin (RNA polymerase II inhibitor), centanamycin, pyrrolobenzodiazepine, streptonigtin, nitrogen mustards, nitrosorueas, alkane sulfonates, pyrimidine analogs, purine analogs, antimetabolites, folate analogs, anthracyclines, taxanes, vinca alkaloids, topoisomerase inhibitors, hormonal agents, and any combination thereof.

In the methods of treating, preventing, and/or slowing the onset or progression of depression or related symptoms associated with depression, the aminosterol composition can be co-administered or combined with drugs commonly used to treat depression. These include selective serotonin reuptake inhibitors (SSRIs) such as citalopram (Celexa®, Cipramil®), escitalopram (Lexapro®, Cipralex®), paroxetine (Paxil®, Seroxat®), fluoxetine (Prozac®), fluvoxamine (Luvox®, Faverin®), sertraline (Zoloft®, Lustral®), indalpine (Upstene®), zimelidine (Normud®, Zelmid®); serotonin-norepinephrine reuptake inhibitors (SNRIs) such as desvenlafaxine (Pristiq®), duloxetine (Cymbalta®), levomilnacipran (Fetzima®), milnacipran (Ixel®, Savella®), venlafaxine (Effexor®); serotonin modulators and stimulators (SMSs) such as vilazodone (Viibryd®), vortioxetine (Trintellix®); serotonin antagonists and reuptake inhibitors such as nefazodone (Dutonin®, Nefadar®, Serzone®), trazodone (Desyrel®), etoperidone; norepinephrine reuptake inhibitors (NRIs) such as reboxetine (Edronax®), teniloxazine (Lucelan®, Metatone®), viloxazine (Vivalan®), atomoxetine (Strattera®); norepinephrine-dopamine reuptake inhibitors such as bupropion (Wellbutrin®), amineptine (Survector®, Maneon®), nomifensine (Merital®, Alival®), methylphenidate (Ritalin®, Concerta®), lisdexamfetamine (Vyvanse®); tricyclic antidepressants such asamitriptyline (Elavil®, Endep®), amitriptylinoxide (Amioxid®, Ambivalon®, Equilibrin®), clomipramine (Anafranil®), desipramine (Norpramin®, Pertofrane®), dibenzepin (Noveril®, Victoril®), dimetacrine (Istonil®), dosulepin (Prothiaden®), doxepin (Adapin®, Sinequan®), imipramine (Tofranil®), lofepramine (Lomont®, Gamanil®), melitracen (Dixeran®, Melixeran®, Trausabun®), nitroxazepine (Sintamil®), nortriptyline (Pamelor®, Aventyl®), noxiptiline (Agedal®, Elronon®, Nogedal®), opipramol (Insidon®), pipofezine (Azafen®/Azaphen®), protriptyline (Vivactil®), trimipramine (Surmontil®), butriptyline (Evadyne®), demexiptiline (Deparon®, Tinoran®), fluacizine (Phtorazisin®), imipraminoxide (Imiprex®, Elepsin®), iprindole (Prondol®, Galatur®, Tertran®), metapramine (Timaxel®), propizepine (Depressing, Vagran®), quinupramine (Kinupril®, Kevopril®), tiazesim (Altinil®), tofenacin (Elamol®, Tofacine®), amineptine (Survector®, Maneon®), tianeptine (Stablon®, Coaxil®); tetracyclic antidepressants such as amoxapine (Asendin®), maprotiline (Ludiomil®), mianserin (Bolvidon®, Norval®, Tolvon®), mirtazapine (Remeron®), setiptiline (Tecipul®), mianserin, mirtazapine, setiptiline; monoamine oxidase inhibitors (MAOIs) such as isocarboxazid (Marplan®), phenelzine (Nardil®), tranylcypromine (Parnate®), benmoxin (Neuralex®), iproclozide (Sursum®), iproniazid (Marsilid®), mebanazine (Actomol®), nialamide (Niamid®), octamoxin (Ximaol®), phenisprazine (Catron®), phenoxypropazine (Drazine®), pivhydrazine (Tersavid®), safrazine (Safra®), selegiline (Eldepryl®, Zelapar®, Emsam®), caroxazone (Surodil®, Timostenil®), metralindole (Inkazan®), moclobemide (Aurorix®, Manerix®), pirlindole (Pirazidol®), toloxatone (Humoryl®), eprobemide (Befol®), minaprine (Brantur®, Cantor®), bifemelane (Alnert®, Celeport®); atypical antipsychotics such as amisulpride (Solian®), lurasidone (Latuda®), quetiapine (Seroquel®); and N-methyl D-aspartate (NMDA) antagonists such ketamine (Ketalar®).

In methods of treating and/or preventing obesity, the aminosterol composition can be co-administered or combined with drugs commonly prescribed to treat obesity, including but not limited to Orlistat (Xenical), Lorcaserin (Belviq), Phentermine-topiramate (Qsymia), Naltrexone-bupropion (Contrave), Liraglutide (Saxenda), phentermine, benzphetamine, diethylpropion, and phendimetrazine.

Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents administered first, followed by the second. The regimen selected can be administered concurrently since activation of the aminosterol induced response does not require the systemic absorption of the aminosterol into the bloodstream and thus eliminates concern over the likelihood systemic of drug-drug interactions between the aminosterol and the administered drug.

IX. Definitions

The following definitions are provided to facilitate understanding of certain terms used throughout this specification.

Technical and scientific terms used herein have the meanings commonly understood by one of ordinary skill in the art, unless otherwise defined. Any suitable materials and/or methodologies known to those of ordinary skill in the art can be utilized in carrying out the methods described herein.

The terms "pharmacologically effective amount" or "therapeutically effective amount" of a composition, aminosterol or agent, as provided herein, refer to a nontoxic but sufficient amount of the composition, aminosterol or agent to provide the desired response. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein. For convenience only, exemplary dosages are provided herein. Those skilled in the art can adjust such amounts in accordance with the methods disclosed herein to treat a specific subject suffering from a specified symptom or disorder. The therapeutically effective amount may vary based on the route of administration and dosage form.

As used herein, the term "comprising" is intended to mean that the compounds, compositions and methods include the recited elements, but not exclude others. "Consisting essentially of" when used to define compounds, compositions and methods, shall mean excluding other elements of any essential significance to the combination. Thus, a composition consisting essentially of the elements as defined herein would not exclude trace contaminants, e.g., from the isolation and purification method and pharmaceutically acceptable carriers, preservatives, and the like. "Consisting of" shall mean excluding more than trace elements of other ingredients. Embodiments defined by each of these transition terms are within the scope of this technology.

All numerical designations, e.g., mass, temperature, time, and concentration, including ranges, are approximations which are varied (+) or (−) by increments of 1, 5, or 10%. It is to be understood, although not always explicitly stated that all numerical designations are preceded by the term "about."

The term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term. For example, in some embodiments, it will mean plus or minus 5% of the particular term. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number.

"Optional" or "optionally" means that the subsequently described circumstance may or may not occur, so that the description includes instances where the circumstance occurs and instances where it does not.

"Pharmaceutically acceptable excipient or carrier" refers to an excipient that may optionally be included in the compositions of the disclosure and that causes no significant adverse toxicological effects to the patient.

"Substantially" or "essentially" means nearly totally or completely, for instance, 95% or greater of some given quantity. In some embodiments, "substantially" or "essentially" means 95%, 96%, 97%, 98%, 99%, 99.5%, or 99.9%.

As used in the description of the disclosure and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

As used herein the term "aminosterol" refers to an amino derivative of a sterol. A non-limiting example of a suitable aminosterol for use in the composition and methods disclosed herein included ENT-03 (Compound III).

The term "administering" as used herein includes prescribing for administration as well as actually administering and includes physically administering by the subject being treated or by another.

As used herein "regulatory phosphatase" or "phosphatase" refers to an enzyme known to thos of ordinary skill in the art that that removes a phosphate group from the phosphorylated amino acid residue of its substrate protein. Non-limiting examples include protein Ser/Thr phosphatases including type 1 (PP1) and type 2 (PP2, i.e., PP2A, PP2C and PP2B) such as PPP1CA, PPP1CB, PPP1CC, PPP2CA, PPP2CB, PPP3CA, PPP3CB, PPP3CC, PPP4C PPP5C, and PPP6C; Class I Cys-based protein tyrosine phosphatases (PTPs); Class II Cys-based PTPs; Class III Cys-based PTPs; Class IV Cys-based DSPs (dual-specificity phosphatases); PTPs such as PTP1B, CDC14s (CDC14A, CDC14B, CDC14C, CDKN3); phosphatase and tensin homologs such as PTEN; slingshots such as SSH1, SSH2, and SSH3; dual specifity phosphatases such as DUSP1, DUSP2, DUSP3, DUSP4, DUSP5, DUSP6, DUSP7, DUSP8, DUSP9, DUSP10, DUSP11, DUSP12, DUSP13, DUSP14, DUSP15, DUSP16, DUSP18, DUSP19, DUSP21, DUSP22, DUSP23, DUSP26, DUSP27, and DUSP28; and other phosphatases such as CTDP1, CTDSP1, CTDSP2, CTDSPL, DULLARD, EPM2A, ILKAP, MDSP, PGAM5, PHLPP1, PHPLPP2, PPEF1, PPEF2, PPM1A, PPM1B, PPM1D, PPM1E, PPM1F, PPM1G, PPM1H, PPM1J, PPM1K, PPM1L, PPM1M, PPM1N, PPTC7, PTPMT1, SSU72, UBLCP1, PP1B, PP1A, PP2Aalpha/PP2R1A complex, PTPN6/SHP1, PTPRC/CD45, DUSP22/MKPX, PTPN2/TC-PTP, PTPN7/LC-PTP, PTPN12/PTP-PEST, PTPN1/PTP1B-CD, PTPN11/SHP2, PTPN11/SHP2-FL, and PTPN11/SHP2-FL(E76K).

As used herein "subject," "patient," or "individual" refers to any subject, patient, or individual, and the terms are used interchangeably herein. In this regard, the terms "subject," "patient," and "individual" includes mammals, and, in particular humans. When used in conjunction with "in need thereof," the term "subject," "patient," or "individual" intends any subject, patient, or individual having or at risk for a specified symptom or disorder.

The terms "treatment," "treating," or any variation thereof includes reducing, ameliorating, or eliminating (i) one or more specified symptoms and/or (ii) one or more symptoms or effects of a specified disorder. The terms "prevention," "preventing," or any variation thereof includes reducing, ameliorating, or eliminating the risk of developing (i) one or more specified symptoms and/or (ii) one or more symptoms or effects of a specified disorder.

"Prodrug" a prodrug is a medication or compound that, after administration, is metabolized (i.e., converted within the body) into a pharmacologically active drug, for example, ENT-03 (Compound III). In some embodiments, a prodrug comprises a derivative of ENT-03 (Compound III), wherein the alcohol and/or the carboxylate has been esterified.

"Optionally substituted" refers to a group selected from that group and a substituted form of that group. A "substituted" group, refers to that group substituted with a chemical substituent, for example be replacement of a C—H bond with a bond between that C and the substituent. In one embodiment, substituents are selected from, for example, $CF_3$, $OCF_3$, halo, haloaryl, $C_1$-$C_6$ alkoxy, acyl, propionyl, butyrl, acylamino, acyloxy, amino, substituted amino, aminocarbonyl, aminothiocarbonyl, aminocarbonylamino, aminothiocarbonylamino, carboxyl ester, carboxyl ester amino, (carboxyl ester)oxy, haloalkyl, aryloxy, haloalkoxy, hydroxyl, thiol, dihydroxy, aminohydroxy, carboxy, amido, sulfoxy, sulfonyl, haloaryloxy, aryl, benzyl, benzyloxy, heteroaryl, nitrile, $C_1$-$C_6$ alkyl, $C_1$-$C_6$ alkenyl, $C_1$-$C_6$ alkynyl, $C_3$-$C_6$ cycloalkyl, $C_1$-$C_6$ haloalkyl, $C_1$-$C_6$ haloalkenyl, $C_1$-$C_6$ haloalkynyl, $C_3$-$C_6$ halocycloalkyl, $C_6$-$C_{10}$ aryl, $C_3$-$C_8$ cycloalkyl, $C_2$-$C_{10}$ heterocyclyl, $C_1$-$C_{10}$ heteroaryl, —$N_3$, nitro, —$CO_2H$ or a $C_1$-$C_6$ alkyl ester thereof, or combinations thereof.

"Derivatives" as used herein, refers to, for example, Compounds III, III-P, IV, and IV-P, or salts or solvates thereof. "Derivatives" of ENT-03 (Compound III) may also refer to deuterated deriviatives of ENT-03 (Compound III), for example, ENT-03-d4 and ENT-03-d3 disclosed herein.

X. Examples

Example 1: ENT-03 (Compound III) Activity as an Inhibitor of Protein Tyrosine Phosphatase 1B (PTP1B)

This example tested the PTP1B inhibitory activity of ENT-03 (Compound III) and ENT-02 (MSI-1436). Also included is comparative data of the inhibitory activity of D7-1436 (D-1436), an aminosterol derivative having the structure:

$D_7$-1436

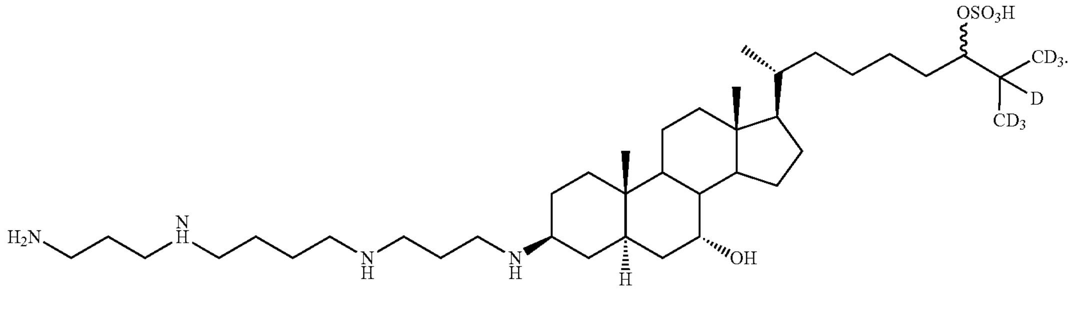

ENT-02 (MSI-1436), ENT-03 (Compound III), and D-1436 were dissolved in dimethyl sulfoxide (DMSO) to a stock concentration of 10 mM. A known PTP1B inhibitor, 3-(3,5-Dibromo-4-hydroxy-benzoyl)-2-ethyl-benzofuran-6-sulfonicacid-(4-(thiazol-2-ylsulfamyl)-phenyl)-amide (Wiesmann et al., 2004), served as a control. The compounds were tested in a 10-dose $IC_{50}$ mode with 3-fold serial dilution, in singlet, starting at 100 μM. The enzyme was the human truncated form (1-321), recombinantly produced in *Escherichia coli*. Fluorescence was measured to monitor enzyme activity. The phosphatase activities were monitored as a time-course measurement of the increase in fluorescence signal from fluorescent substrate, and initial linear portion of slope (signal/min) was analyzed. No compounds exhibited fluorescent background that could interfere with the assay.

Figure 4A:
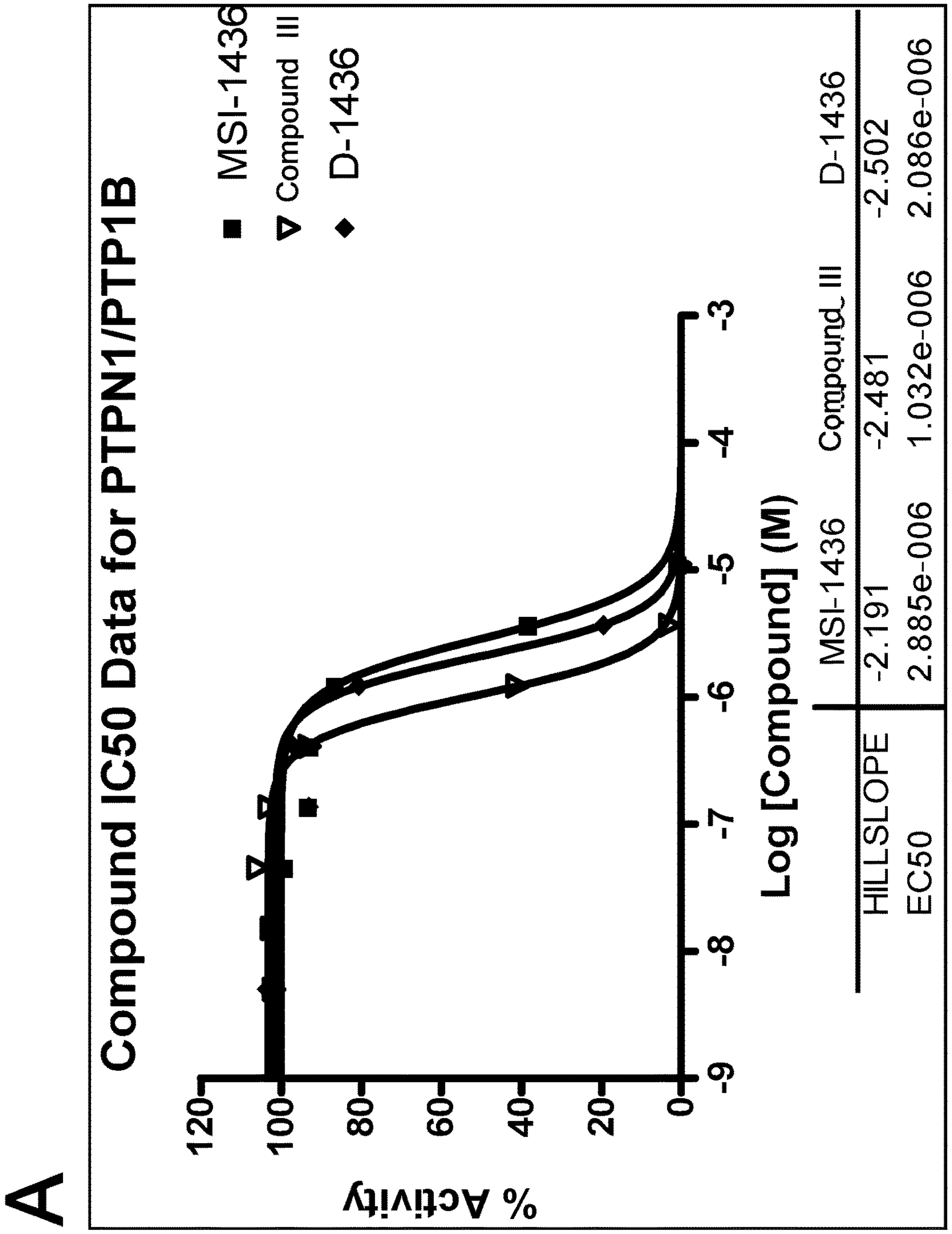
FIG. 4A) and a control PTP1B inhibitor (FIG. 4B) according to Example 1.
Figure 4B:
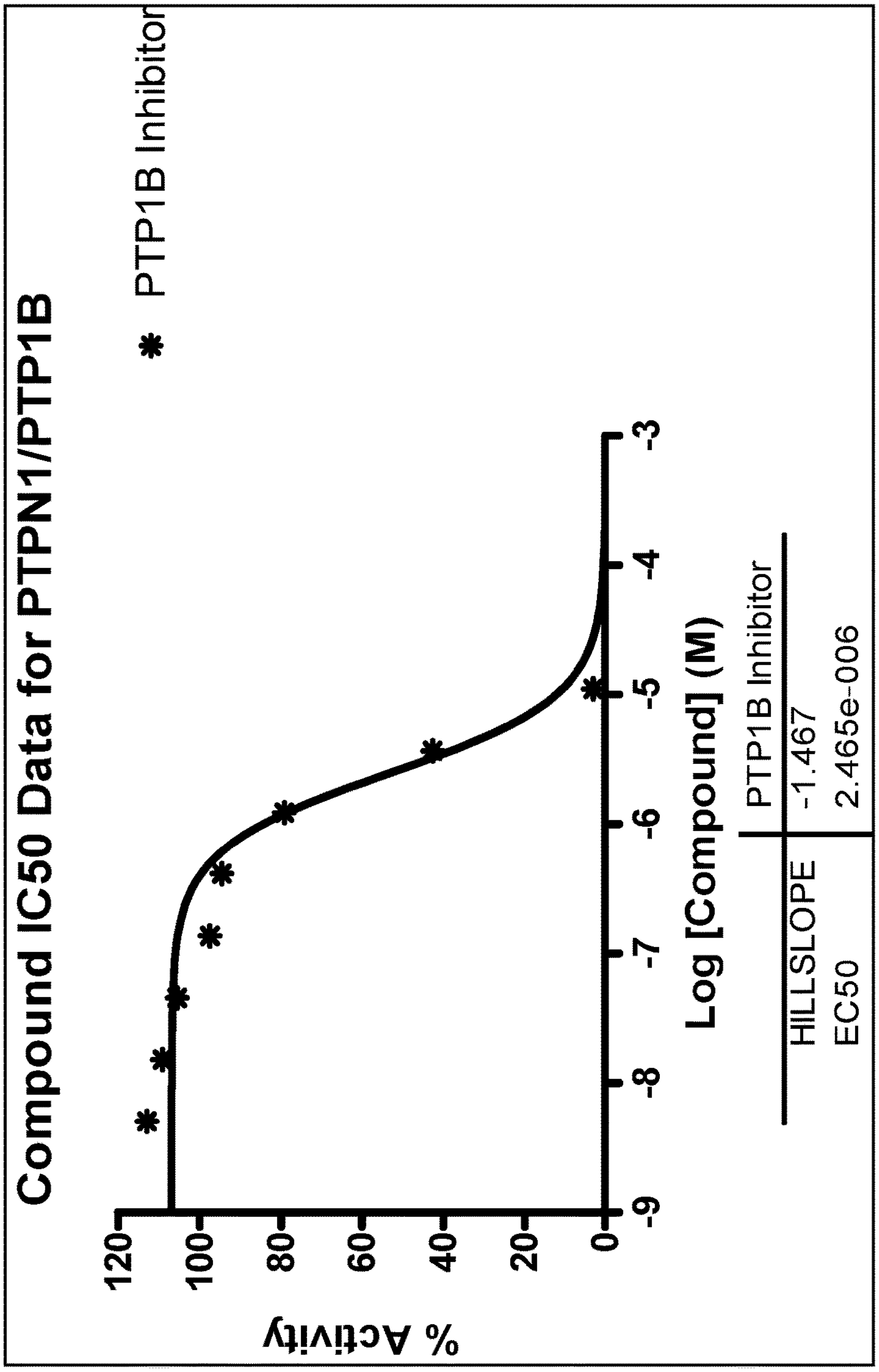
FIG. 4 shows $IC_{50}$ curves for PTP1B inhibition by three aminosterols tested ENT-02 (MSI-1436), ENT-03 (Compound III), and D-1436.

$IC_{50}$ curves were generated for the three aminosterols tested (FIG. 4A) and the control compound (FIG. 4B). Curve fits were performed when the activities at the highest concentration of compounds were less than 65%.

As seen in Table 2, ENT-02 (MSI-1436), already known to inhibit PTP1B, exhibited an $IC_{50}$ of 2.89 μM; ENT-03 (Compound III) exhibited an $IC_{50}$ of 1.03 μM; D-1436 exhibited an $IC_{50}$ of 2.09 μM; and the control PTP1B compound exhibited an $IC_{50}$ of 2.47 μM.

TABLE 2A

| Phosphatase profiling report for: PTPN1/PTP1B | | | | |
|---|---|---|---|---|
| Conc (M) | ENT-02 (MSI-1436) | ENT-03 (Compound III) | PTP1B Inhibitor | $D_7$-1436 |
| Slope (signal/min) | | | | |
| 1.00E−04 | −68 | −334 | −810 | −161 |
| 3.33E−05 | −440 | −201 | −444 | −362 |
| 1.11E−05 | 292 | 109 | 1291 | −319 |
| 3.70E−06 | 16431 | 1266 | 18367 | 8429 |
| 1.23E−06 | 37260 | 17650 | 34136 | 34760 |
| 4.12E−07 | 39959 | 40062 | 40760 | 41755 |
| 1.37E−07 | 40137 | 44343 | 42024 | 40150 |
| 4.57E−08 | 42717 | 45535 | 45466 | 43697 |
| 1.52E−08 | 44021 | 44067 | 47019 | 43819 |
| 5.08E−09 | 43513 | 43877 | 48684 | 44655 |
| DMSO | 47697 | 44496 | 47769 | 47400 |
| % Activity | | | | |
| 1.00E−04 | −0.16 | −0.77 | −1.88 | −0.37 |
| 3.33E−05 | −1.02 | −0.47 | −1.03 | −0.84 |
| 1.11E−05 | 0.68 | 0.25 | 2.99 | −0.74 |
| 3.70E−06 | 38.12 | 2.94 | 42.61 | 19.55 |
| 1.23E−06 | 86.43 | 40.94 | 79.19 | 80.63 |
| 4.12E−07 | 92.69 | 92.93 | 94.55 | 96.86 |
| 1.37E−07 | 93.11 | 102.86 | 97.48 | 93.14 |
| 4.57E−08 | 99.09 | 105.63 | 105.47 | 101.36 |
| 1.52E−08 | 102.11 | 102.22 | 109.07 | 101.65 |
| 5.08E−09 | 100.94 | 101.78 | 112.93 | 103.59 |
| DMSO | 110.64 | 103.22 | 110.81 | 109.95 |
| HILLSLOPE | −2.19 | −2.48 | −1.47 | −2.50 |
| $IC_{50}$ (M) | 2.89E−06 | 1.03E−06 | 2.47E−06 | 2.09E−06 |

The activity of ENT-03 and ENT-06 on a number of other phosphatases was also investigated. Both compounds were assayed in vitro against human phosphatases (Tables 2B and 2C). The two compounds exhibited a very similar phosphatase "fingerprint" with respect to their corresponding $IC_{50}$. These data strongly support the hypothesis that ENT-03 and trodusquemine are phylogenetic chemical orthologs. The compounds were found to be inactive at PP1A, PP1B, PP2A alpha, PTPN6, and PTPN2.

TABLE 2B

| Activity of aminosterols on various phosphatases Compound IC50 (M) | | | | | | |
|---|---|---|---|---|---|---|
| Compound ID | PP1B | PP1A | PP2A Alpha/ PP2R1A Complex | PTPN6/ SHP1 | PTPRC/ CD45 | DUSP22/ MKPX |
| ENT-02 (MSI-1436) | >1.0E−04 | >1.0E−04 | 5.72E−05 | >1.0E−04 | 4.94E−07 | 6.39E−07 |
| ENT-03 (Compound III) | >1.0E−04 | >1.0E−04 | >1.0E−04 | >1.0E−04 | 5.71E−07 | 1.38E−06 |
| PTP1B Inhibitor | 3.46E−05 | 2.15E−05 | ND | 5.75E−06 | 5.70E−05 | 1.45E−05 |
| Canthardic Acid | ND | ND | 1.70E−08 | ND | ND | ND |
| SHP099 | ND | ND | ND | ND | ND | ND |

TABLE 2C

| Activity of aminosterols on various phosphatases Compound IC50 (M) | | | | | | | |
|---|---|---|---|---|---|---|---|
| Compound ID | PTPN2/ TC-PTP | PTPN7/ LC-PTP | PTPN12/ PTP-PEST | PTPN1/ PTP1B-CD | PTPN11/ SHP2 | PTPN11/ SHP2-FL | PTPN11/ SHP2-FL (E76K) |
| ENT-02 (MSI-1436) | >1.0E−04 | 1.65E−06 | 1.72E−06 | 9.44E−07 | 3.75E−07 | 7.52E−07 | 2.92E−07 |
| ENT-03 (Compound III) | >1.0E−04 | 6.34E−07 | 8.61E−07 | 1.17E−07 | 5.00E−06 | 1.42E−06 | 2.94E−07 |

TABLE 2C-continued

| Activity of aminosterols on various phosphatases Compound IC50 (M) | | | | | | | |
|---|---|---|---|---|---|---|---|
| Compound ID | PTPN2/ TC-PTP | PTPN7/ LC-PTP | PTPN12/ PTP-PEST | PTPN1/ PTP1B-CD | PTPN11/ SHP2 | PTPN11/ SHP2-FL | PTPN11/ SHP2-FL (E76K) |
| PTP1B Inhibitor | 1.34E−05 | 1.28E−05 | 2.99E−05 | 4.25E−06 | 1.82E−06 | ND | ND |
| Canthardic Acid | ND | ND | ND | ND | ND | ND | ND |
| SHP099 | ND | ND | ND | ND | ND | 7.11E−08 | 2.64E−06 |

These data demonstrate that ENT-03 (Compound III) is a potent inhibitor of PTP1B, and has potential therapeutic utility known to be associated with PTP1B inhibitors.

Example 2: ENT-03 (Compound III) as a Weight Loss Agent in Mice

This example demonstrated the promotion of weight loss by ENT-03 (Compound III) in mice.

ENT-02 (MSI-1436) is known to induce weight loss through a mechanism that involves certain brain circuits that control appetite. Trodusquemine causes weight loss and a shift to lipid oxidation when administered systemically to mice. The pharmacological target appears to lie within the hypothalamus, including the arcuate nucleus, median eminence, and the paraventricular nucleus, based on localization of radioactive Trodusquemine, and cFos activation following intraventricular administration (Ahima et al., 2002).

Studies on the structure activity relationship of ENT-02, with respect to weight loss, have demonstrated the high degree of structural specificity required for this pharmacological effect (Zasloff et al., 2001). For example, altering the chirality of the spermine at C-3, the hydroxyl at C-7, or the methyl at C-21 eliminates weight loss. Activity is lost if the spermine is replaced by a spermidine, or if the terminal amino group of spermine is methylated. In contrast, both stereo-isomers of the sulfate at C-24 are equally active, demonstrating that spatial constraints are loosened around the anionic moiety, consistent with the activity observed for ENT-03.

To determine if ENT-03 (Compound III) exhibited a similar activity, male Swiss Webster mice, previously fed ad lib (about 50 grams, N=3 for each group), were treated i.p. with 5 doses of either ENT-02 (MSI-1436) or ENT-03 (Compound III) every other day at 10 mg/kg, e.g., on days 0, 2, 4, 6, 8 and 10. Food was provided ad lib.

Figure 1B:
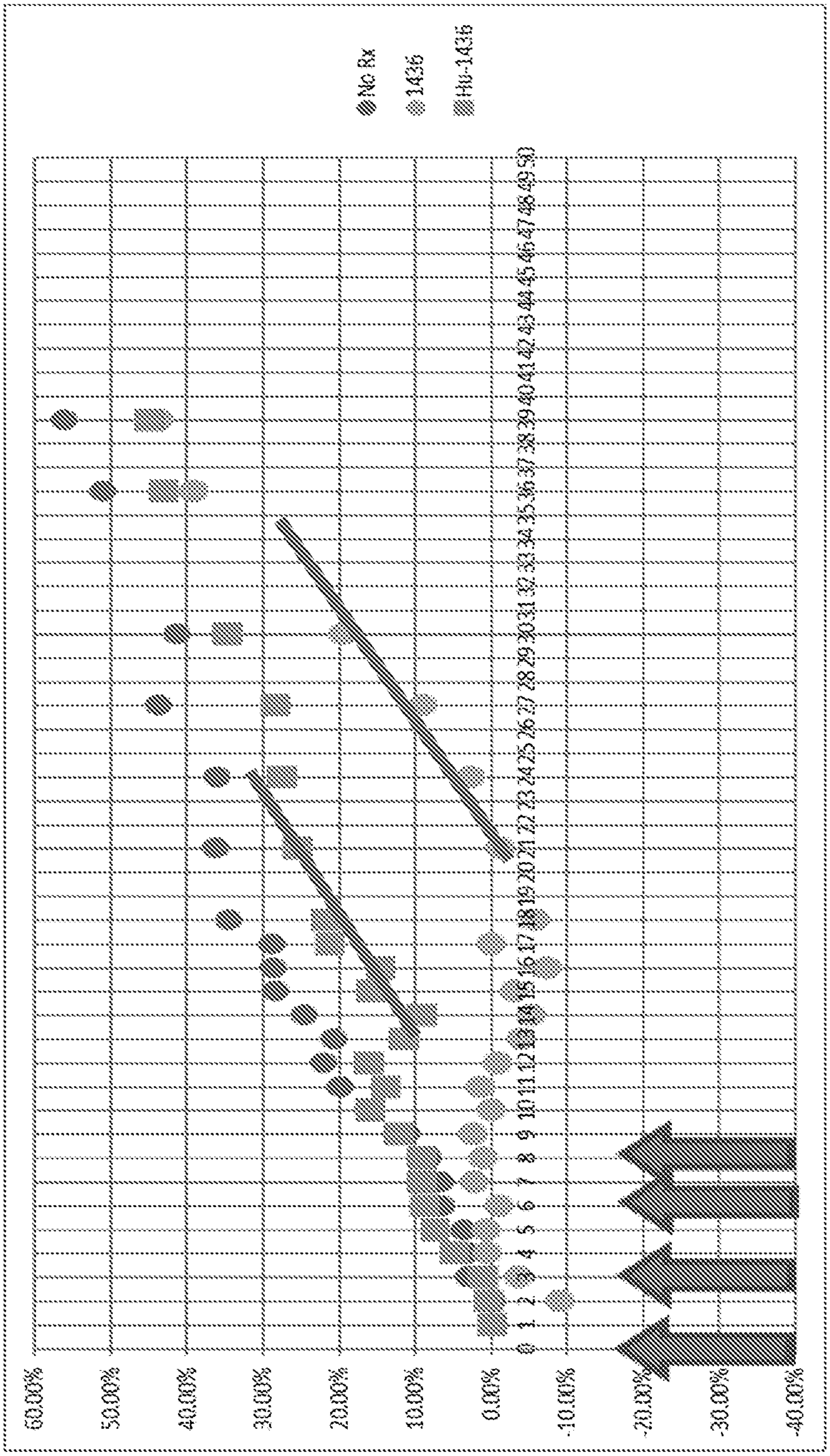

As can be seen in FIGS. 1A, 1B and 2, ENT-03 administration results in weight loss with kinetics similar to that seen following administration of ENT-02. Administration of both compounds resulted in a decrease in weight, with a nadir at about day 16, followed a gradual recovery to the starting weight by about day 45. While the initial decrease in weight was similar for both compounds, by about 10 days the effects diverged, with ENT-02 causing a more severe decline. By 27 days both sets of treated mice had lost about 10% of their starting body weight.

These data demonstrate that ENT-03 (Compound III) exhibits a pharmacological response with respect to weight similar to ENT-02 (MSI-1436) and suggests that ENT-03 (Compound III) can have utility in all therapeutic applications known to be associated with ENT-02 (MSI-1436) as well as other aminosterols.

In a second experiment, growing male mice, about 25 grams, were administered either compound following a similar dosing regimen. As in the previous experiment, both compounds affected weight gain. See FIG. 2. However, in the case of growing mice, ENT-02 had a more profound effect, having suppressed growth as well as having induced consumption of body fat. While the animals treated with ENT-03 continued normal growth, they "slimmed down", suggesting that ENT-03 re-established a new optimal body weight "set point."

Figure 1C:
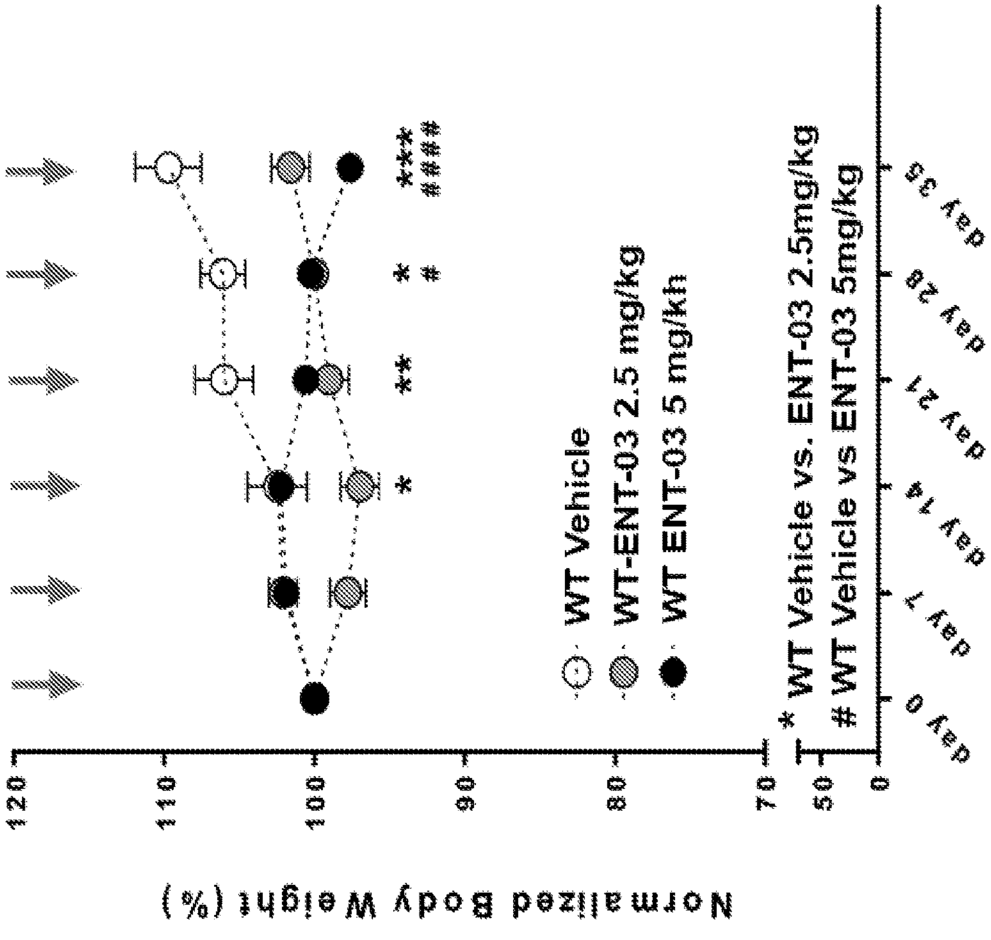
FIG. 1C shows intraperitoneal administration of ENT-03 to C57bl/6 male mice once weekly over 6 weeks caused a dose dependent weight loss.

In a third experiment, as seen in FIG. 1C intraperitoneal administration of ENT-03 to C57bl/6 male mice once weekly over 6 weeks caused a dose dependent weight loss. Other than weight loss the treated animals appeared clinically normal.

Figure 14:
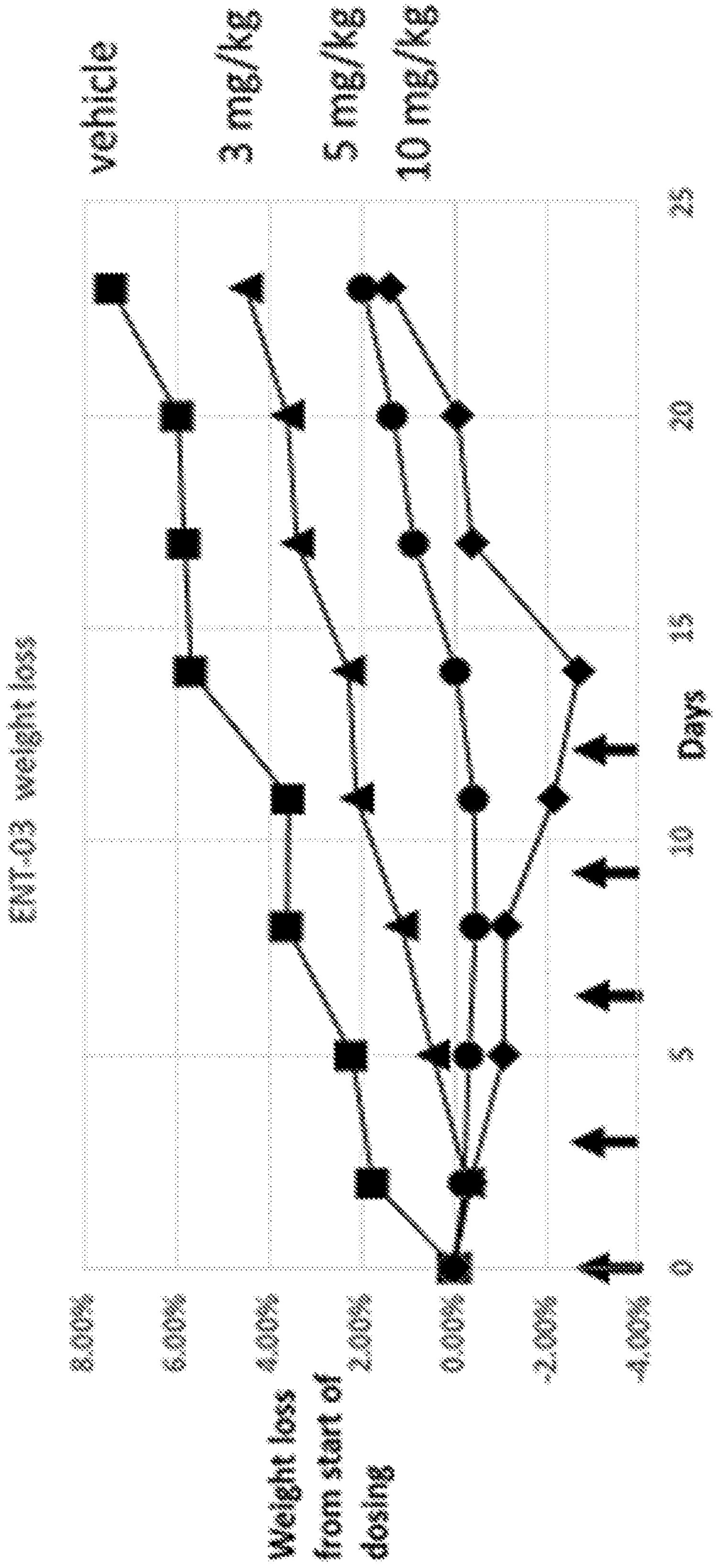
FIG. 14 shows a plot representing the weight loss results of male C57bl6/j (N=5/group) mice administered ENT-03 at varying dosages or vehicle by oral gavage every 3rd day.
Figure 15:
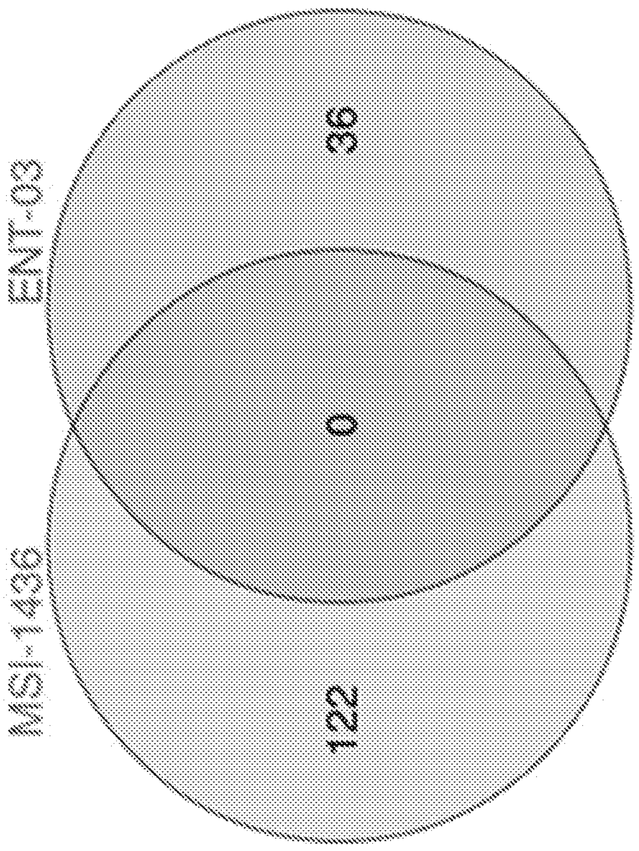
FIG. 15 shows a Venn diagram of transcripts down-regulated in ageing and up-regulated by ENT-03. A plot showing the numbers of overlapping and non-overlapping differentially expressed genes between the two sets of transcripts that were down-regulated in old versus young mice and up-regulated upon treatment compared to control. Numbers of features are shown from treatment with ENT-02 (MSI-1436) and ENT-03.

Finally, in a fourth experiment, as seen in FIG. 14, intraperitoneal administration of ENT-03 (3 mg/kg, 5 mg/kg, 10 mg/kg, or vehicle) to C57bl/6 male mice once weekly over 2 weeks caused a dose dependent weight loss. Other than weight loss the treated animals appeared clinically normal.

These studies demonstrate that ENT-03 (Compound III) exhibits potent pharmacological activity in mice, similar to ENT-02.

Example 3: Rejuvenation of RNA Transcriptome in the Gut

The purpose of this example was to evaluate the impact of oral administration of ENT-02 and ENT-03 (Compound III) on young vs aged gut tissue.

Figure 3:
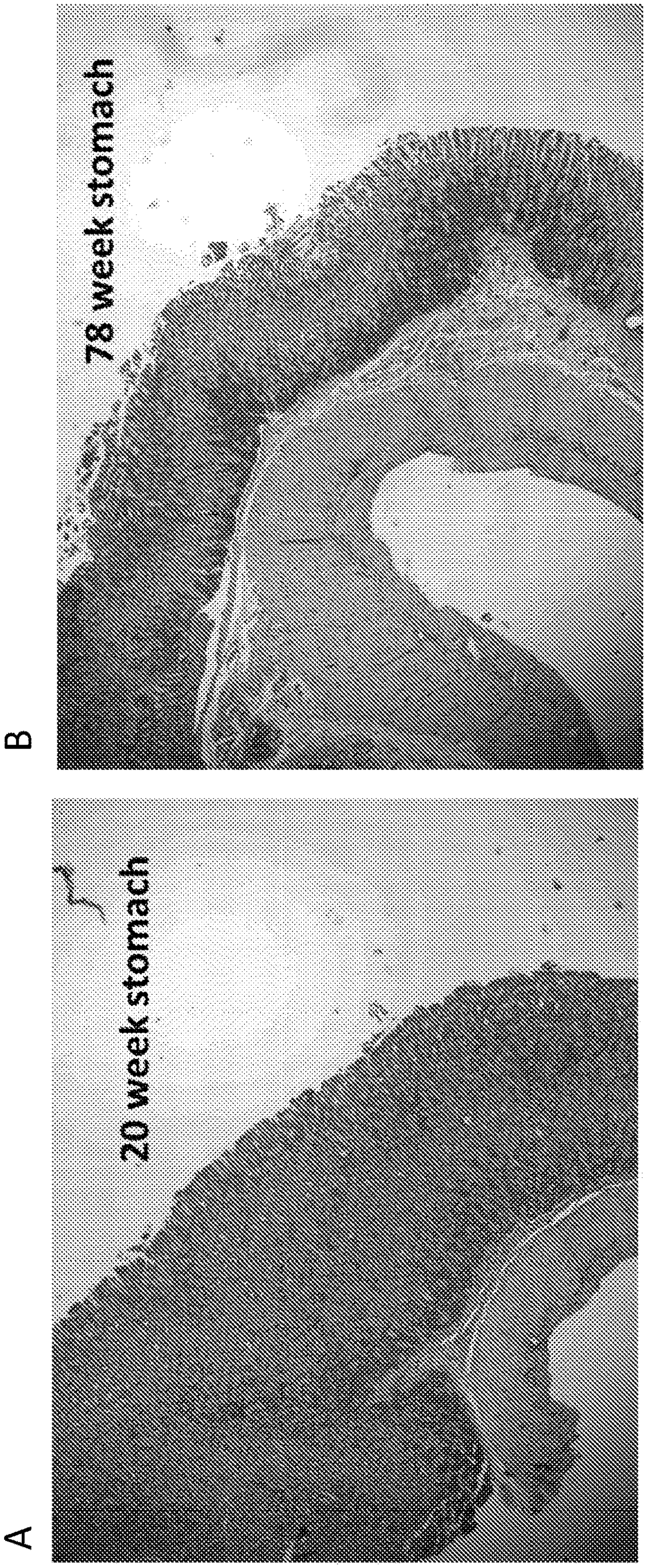
FIG. 3 shows images of a mucosal layer of the stomach showing a reduced mucosal layer in the 78 week old stomach (FIG. 3B) vs. the younger 20 week old stomach (FIG. 3A).

Aging involves a depletion of gene expression in the gut. Comparison of the images showing mucosal tissue in the stomach of a young mouse (20 week, FIG. 3A) versus an old mouse (78 week, FIG. 3B) shows a reduced thickness of the mucosal layer in the older specimen. This reduction in mucosa is associated with a reduced RNA transcriptome in the stomach in aged mice (78 weeks) vs. young mice (20 weeks), see Table 3 below. The present Example evaluated the impact of oral dosing of ENT-01 and ENT-02 and on old mice.

The dosing schedule used to determine the effect of orally administered squalamine and ENT-02 on the GI tracts of young and old mice was as follows. Male C57Bl/6 mice, aged 20 and 78 weeks, were obtained from Jackson labs. Animals were exposed to 12 hr light dark cycles and provided Teklad standard mouse diet and water ad lib. Animals were assigned to the treatment groups shown in Table 3.

TABLE 3

| Group | Dose Level* (mg/kg/day) | Concentration (mg/ml) | Dose Volume (ml/kg) | Age on Day 1 (weeks) | Number of Animals Male |
|---|---|---|---|---|---|
| 1. Control (vehicle) | 0 | 0 | 10.0 | 20 | 5 |
| 2. ENT-01 (Squalamine) | 40 | 4 | 10.0 | 20 | 5 |
| 3. ENT-02 (MSI-1436) | 40 | 4 | 10.0 | 20 | 5 |
| 4. Control (vehicle) | 0 | 0 | 10.0 | 78 | 5 |
| 5. ENT-01 (Squalamine) | 40 | 4 | 10.0 | 78 | 5 |
| 6. ENT-02 (MSI-1436) | 40 | 4 | 10.0 | 78 | 5 |

Animals were dosed once daily by oral gavage in the morning for a total of 14 days. Animals were fasted 3-4 hours prior to dosing and at least 1 hour following dosing, with fasting not to exceed 6 hours. The test article was dissolved in 0.5% hydroxypropylcellulose in water. On day 15 the animals were euthanized by $CO_2$ asphyxiation, necropsied, and tissues prepared for histology and RNAseq analysis.

The GI tracts of the animals were sectioned into stomach, duodenum, jejunum, ileum, caecum, colon, and rectum. The tissues were then sent for histology, and the transcriptomes analyzed by RNAseq. Table 4 shows the respective mRNA amounts in young and old mouse stomach.

As shown in Table 5A below, mRNA levels for all of the genes in the table showed a significant increase after treatment with squalamine (ENT-01). Equally remarkable, while ENT-03 stimulates induction of the transcriptome of these segments of the GI tract of older mice, it has minimal effect in the younger animals, corresponding to a slight repression or induction of certain genes not associated with ageing. Perhaps ENT-03 is complementing a deficiency in the older mice that does not exist in the younger animals. This suggests that squalamine (ENT-01), and by extension structurally related aminosterols, such as ENT-03 (Compound III) and derivatives thereof, have a rejuvenating effect in the gut.

TABLE 4

Respective mRNA amounts in young and old mouse stomach

| Gene | Young | Old | P Value |
|---|---|---|---|
| Epithelial Barrier Functions | | | |
| caspase_14 | 9.228 | 0.835 | 8.45E−10 |
| collagen_type_XVII_alpha_1 | 9.835 | 2.804 | 2.07E−04 |
| Corneodesmosin | 12.75 | 4.295 | 6.74E−04 |
| Cornifelin | 23.74 | 6.442 | 3.01E−05 |
| cystatin_E/M | 9.41 | 1.551 | 5.68E−07 |
| Dermokine | 117.5 | 23.86 | 1.34E−07 |
| desmocollin_1 | 16.09 | 4.175 | 2.6E−05 |
| desmoglein_1_beta | 9.592 | 2.625 | 1.41E−04 |
| Filaggrin | 21.67 | 2.207 | 3.81E−11 |
| gap_junction_protein_beta_4 | 1.882 | 0.239 | 2.52E−04 |
| gap_junction_protein_beta_6 | 2.125 | 0.298 | 2.11E−04 |
| H19_imprinted_maternally_expressed_transcript | 39.95 | 1.909 | 1.59E−17 |
| Hornerin | 13.6 | 3.519 | 3.23E−05 |
| kallikrein_related-peptidase_7_(chymotryptic_stratum_ | 10.14 | 0.656 | 1.33E−11 |
| keratin_1 | 332.6 | 69.79 | 1.72E−07 |
| keratin_10 | 337.7 | 45.93 | 8.03E−11 |
| keratinocyte_differentiation_associated_protein | 184.6 | 37.58 | 1.21E−07 |
| keratinocyte_expressed_proline-rich | 12.93 | 2.267 | 3.87E−07 |
| late_cornified_envelope_1A1 | 17.85 | 2.625 | 1.42E−08 |
| late_cornified_envelope_1A2 | 23.43 | 4.056 | 6.01E−08 |
| late_cornified_envelope_1B | 9.774 | 1.491 | 2.05E−07 |
| late_cornified_envelope_1C | 10.93 | 1.73 | 1.90E−07 |
| late_cornified_envelope_1E | 5.767 | 1.074 | 1.23E−05 |
| late_cornified_envelope_1F | 8.742 | 1.551 | 1.67E−06 |
| late_cornified_envelope_1G | 8.378 | 1.611 | 4.59E−06 |
| late_cornified_envelope_1H | 5.282 | 1.312 | 2.14E−04 |
| late_cornified_envelope_1I | 8.682 | 1.074 | 3.37E−08 |
| late_cornified_envelope_1J | 5.16 | 0.895 | 1.01E−05 |
| late_cornified_envelope_1L | 4.553 | 0.596 | 1.82E−06 |
| late_cornified_envelope_1M | 16.76 | 1.133 | 5.22E−13 |
| late_cornified_envelope_3C | 5.525 | 1.491 | 3.92E−04 |
| late_cornified_envelope_3E | 5.889 | 1.491 | 3.92E−04 |
| late_cornified_envelope_3F | 10.81 | 3.281 | 2.66E−04 |
| lectin_galactose_binding_soluble_7 | 139.3 | 25.77 | 2.70E−08 |
| Loricrin | 275.3 | 45.75 | 3.37E−09 |
| Sciellin | 11.11 | 3.221 | 1.56E−04 |
| Muscle Tissue | | | |
| Myoglobin | 47.9 | 2.923 | 4.10E−16 |
| myosin_binding_protein_C_slow-type | 15.06 | 1.133 | 4.01E−12 |
| myosin_heavy_polypeptide_1_skeletal_muscle | 73.46 | 2.982 | 3.47E−20 |
| myosin_heavy_polypeptide_8_skeletal_muscle | 90.46 | 3.34 | 2.67E−21 |

TABLE 4-continued

| Respective mRNA amounts in young and old mouse stomach | | | |
|---|---|---|---|
| Gene | Young | Old | P Value |
| myosin_light_chain_phosphorylatable_fast_ske | 30.23 | 4.235 | 1.42E−09 |
| myosin_light_polypeptide_3 | 26.77 | 1.312 | 2.72E−16 |
| myozenin_1 | 6.617 | 0.418 | 3.87E−10 |
| myozenin_2 | 4.31 | 0.239 | 7.95E−09 |
| titin-cap | 17.36 | 0.418 | 3.66E−18 |

TABLE 5A

| respective mRNA amounts in old mice versus old mice treated with squalamine (ENT-01) | | | |
|---|---|---|---|
| Gene | Old | Old + Ent-01 | P Value |
| Epithelial Barrier Functions | | | |
| caspase_14 | 0.795 | 6.077 | 2.25E−07 |
| collagen_type_XVII_alpha_1 | 2.668 | 9.509 | 1.43E−04 |
| Corneodesmosin | 4.087 | 7.933 | 4.10E−02 |
| Cornifelin | 6.131 | 22.17 | 4.07E−05 |
| cystatin_E/M | 1.476 | 8.721 | 6.89E−07 |
| Dermokine | 22.71 | 88.45 | 5.65E−06 |
| desmocollin_1 | 3.974 | 8.102 | 2.83E−02 |
| desmoglein_1_beta | 2.498 | 7.089 | 2.14E−03 |
| Filaggrin | 2.1 | 16.32 | 2.05E−09 |
| gap_junction_protein_beta_4 | 0.227 | 1.294 | 3.15E−03 |
| gap_junction_protein_beta_6 | 0.284 | 1.575 | 1.59E−03 |
| H19_imprinted_maternally_expressed_transcript | 1.817 | 13.73 | 5.79E−09 |
| Hornerin | 3.349 | 11.82 | 1.09E−04 |
| kallikrein_related-peptidase_7_(chymotryptic_stratum_ | 0.624 | 5.908 | 3.74E−08 |
| keratin_1 | 66.42 | 348.9 | 3.28E−08 |
| keratin_10 | 43.71 | 310.3 | 1.56E−10 |
| keratinocyte_differentiation_associated_protein | 35.77 | 181.2 | 7.27E−08 |
| keratinocyte_expressed_proline-rich | 2.157 | 7.99 | 1.36E−04 |
| late_cornified_envelope_1A1 | 2.498 | 10.97 | 1.03E−05 |
| late_cornified_envelope_1A2 | 3.86 | 17.78 | 2.08E−06 |
| late_cornified_envelope_1B | 1.419 | 8.102 | 1.33E−06 |
| late_cornified_envelope_1C | 1.646 | 7.202 | 3.26E−05 |
| late_cornified_envelope_1E | 1.022 | 4.501 | 1.17E−04 |
| late_cornified_envelope_1F | 1.476 | 6.47 | 3.92E−05 |
| late_cornified_envelope_1G | 1.533 | 4.557 | 2.78E−03 |
| late_cornified_envelope_1H | 1.249 | 4.164 | 1.38E−03 |
| late_cornified_envelope_1I | 1.022 | 7.708 | 8.29E−08 |
| late_cornified_envelope_1J | 0.852 | 3.376 | 6.62E−04 |
| late_cornified_envelope_1L | 0.568 | 2.644 | 5.13E−04 |
| late_cornified_envelope_1M | 1.079 | 8.158 | 6.04E−08 |
| late_cornified_envelope_3C | 1.419 | 3.263 | 2.79E−02 |
| late_cornified_envelope_3E | 1.419 | 4.332 | 2.50E−03 |
| late_cornified_envelope_3F | 3.122 | 9.115 | 1.15E−03 |
| lectin_galactose_binding_soluble_7 | 24.52 | 142.5 | 7.67E−09 |
| Loricrin | 43.54 | 209.5 | 1.63E−07 |
| Sciellin | 3.066 | 9.79 | 4.25E−04 |
| Muscle Tissue | | | |
| Myoglobin | 2.782 | 17.72 | 2.49E−08 |
| myosin_binding_protein_C_slow-type | 1.079 | 3.173 | 1.42E−03 |
| myosin_heavy_polypeptide_1_skeletal_muscle | 2.838 | 11.03 | 4.18E−05 |
| myosin_heavy_polypeptide_8_skeletal_muscle | 3.179 | 14.97 | 2.20E−06 |
| myosin_light_chain_phosphorylatable_fast_ske | 4.031 | 15.92 | 1.79E−05 |
| myosin_light_polypeptide_3 | 1.249 | 10.58 | 4.49E−09 |
| myozenin_1 | 0.397 | 2.476 | 1.19E−04 |
| myozenin_2 | 0.227 | 1.519 | 8.72E−04 |
| titin-cap | 0.397 | 3.376 | 3.15E−06 |

Applicant also investigated transcriptome changes within each segment of the GI tract. Upon oral administration to aged mice the abundance of gene transcripts that decrease with ageing in the stomach, jejunum, and ileum are increased, in some cases to levels observed in the younger individuals as shown in FIGS. 6A-6C.

Young (20 week) and aged (80 week) C57bl/6 male mice were administered ENT-03 (40 mg/kg) or vehicle (water) by oral gavage daily for 2 weeks. Over this period of time clinical observations were unremarkable as were the gross and microscopic examinations of the GI tract. The transcriptomes of the stomach, jejunum and ileum were analyzed by RNAseq technology. Comparative analyses of the transcripts from untreated animals identified numerous transcripts that differed in abundance between the corresponding tissues from old and young individuals. Differential expression was observed for 86 stomach transcripts (p(adj)<0.05): 70 decreased, and 16 increased with ageing; in the case of the jejunum, over 400 transcripts decreased, 200 increased with ageing; and for the ileum, 700 transcripts decreased, while 400 increased with ageing. Thus, within these three distinct regions of the mouse GI tract, ageing is associated with changes in the transcriptome.

When the effect of oral administration of ENT-03 on the transcriptome of the tissues was examined, in each case it was observed that the transcriptional response in the young was blunted in comparison to that occurring in the aged animals (FIGS. 6A-6C). For example, in the stomach of treated young animals, 13 genes were differentially expressed (p(adj)<0.05), while 63 were in the aged group. Similarly, for the jejunum 42 genes were differentially expressed in the young, and 382 genes on treatment in the aged group. In the ileum, 80 genes were differentially expressed in the young, and 1162 genes in the aged animals treated with ENT-03.

Next, the sets of genes that were differentially expressed (DEGs) with ageing were compared with those that were differentially expressed in the treated aged animals or in the treated young animals. Analysis of the overlapping DEGs between contrasts revealed, for example, in the stomach 37 genes down-regulated in ageing (old versus young) significantly overlapped (P<0.0001, hypergeometric test) with genes up-regulated by treatment with ENT-03 in old mice. In contrast the only significant overlap between the stomach ageing genes and those in the young ENT-03 treated stomach were 12 genes that were further down regulated in the ageing direction.

The "ageing" genes that ENT-03 appears to complement most significantly within the stomach are listed in Table 5B. Notably, in the stomach, the "restored" ageing genes include those involved in tissue renewal (fibroblast growth factor 2; zinc finger protein 383; forkhead box C2); neuronal differentiation (neural cell adhesion molecule 2); immunity (toll-like receptors 9 and 12; interleukin 2 receptor, beta chain), neurotransmitter synthesis and uptake (choline and serotonin transporters), and mitochondrial respiration (cytochrome c oxidase subunit 6B2).

TABLE 5B

| Ageing genes complemented by ENT-03 (30 most significant) Stomach |
|---|
| zinc finger protein 382 |
| nuclear receptor 2C2-associated protein |
| CD300 molecule like family member d |
| fibroblast growth factor 2 |
| transmembrane protein 71 |
| zinc finger protein 449 |
| guanine nucleotide binding protein (G protein), gamma 8 |
| synaptophysin-like 2 |
| interleukin 2 receptor, beta chain |
| nuclear assembly factor 1 ribonucleoprotein |
| predicted gene 20604 |
| toll-like receptor 12 |
| predicted gene 14322 |
| forkhead box C2 |
| solute carrier family 5 (choline transporter), member 7 |
| Ras association and DIL domains |
| cytochrome c oxidase subunit 6B2 |
| neural cell adhesion molecule 2 |
| solute carrier family 6 (neurotransmitter transporter, serotonin), member 4 |
| ELAV like RNA binding protein 3 |
| shadow of prion protein |
| sortilin-related VPS 10 domain containing receptor 1 |
| FXYD domain-containing ion transport regulator 2 |
| toll-like receptor 9 |
| claudin 34C1 |

First, genes that significantly changed in expression between young and aged mice were identified (FDR-adjusted p-value <0.05) (FIG. 6A). With ageing, the expression of 75 genes in the stomach was significantly decreased, and the expression of 11 genes was significantly increased (FIG. 6A). Meanwhile, fewer differences were observed between the gene expression profiles of the jejunum (FIGS. 10A-10D) or ileum (FIGS. 10D-10F) of young and aged mice. In the jejunum, 5 genes decreased in expression and 2 genes increased in expression with ageing. Whereas in the ileum, 19 genes decreased and 9 genes increased in expression. These results are consistent with the recognized reduced regenerative capacity of the ageing rodent stomach (Fukunaga et al., 1998), and the resilience with ageing of the small intestine (Eswaran et al., 2006).

Following oral administration of ENT-03 to young mice (20 weeks), 13 stomach genes responded and all were transcriptionally repressed by ENT-03 treatment (FIG. 6B). The expression of no more than 2 genes changed significantly in response to ENT-03 exposure in the jejunum and ileum for both young and aged mice.

In contrast, a more robust effect on gene expression in the stomach was observed in the older animals (78 weeks) treated with ENT-03. 63 genes were transcriptionally induced (FDR-adjusted p<0.05) (FIG. 6C). Interestingly, 36 of the genes that increased in expression upon ENT-03 treatment of aged mice were the same that decreased in expression with ageing. These genes include those involved in tissue renewal (fibroblast growth factor 2 (Fgf2), zinc finger protein 382 (Zfp382) and forkhead box C2 (Foxc2)); in neuronal differentiation (neural cell adhesion molecule 2 (Ncam2)); in immunity (toll-like receptors 9 and 12 (Tlr9, Tlr12), interleukin 2 receptor, beta chain (Il2rb) and CD300 (Cd300ld)); in neurotransmitter synthesis and uptake (choline and serotonin transporters (Slc5a7, Slc6a4)); and in mitochondrial respiration (cytochrome c oxidase subunit 6B2 (Cox6b2)).

Statistical analysis of RNA-sequencing data was performed using R programming language. Transcripts with less than one read count per million reads in all samples of each tissue were removed. The raw count data for the samples were then normalised using trimmed mean of M-values normalisation and transformed with voom (Law et al., 2014), resulting in log 2-transformed counts per million with associated precision weights. Normalised data provide the input for statistical hypothesis testing, in which genes that are significantly different between sample groups are identified. Statistical comparisons were performed using linear modelling, as implemented in the Bioconductor package limma (Ritchie et al., 2015). Significance values (p-values) were adjusted for multiple testing using Benjamini-Hochberg procedure (Benjamini et al., 1995). For each comparison (e.g. group A versus group B), a positive log 2-transformed fold change indicates up-regulation in group A relative to group B.

To investigate the overlap between contrasts, the number of overlapping differentially expressed genes (defined using adjusted p-value <0.05) between all pairwise combinations of the comparisons performed were counted. For each comparison, the Jaccard index, defined as the intersection over the union, measures the similarity between the two contrasts under consideration. The p-value was calculated using a hypergeometric test taking into account the universe size under the assumption that the contrasts and genes are independent.

Figure 11:
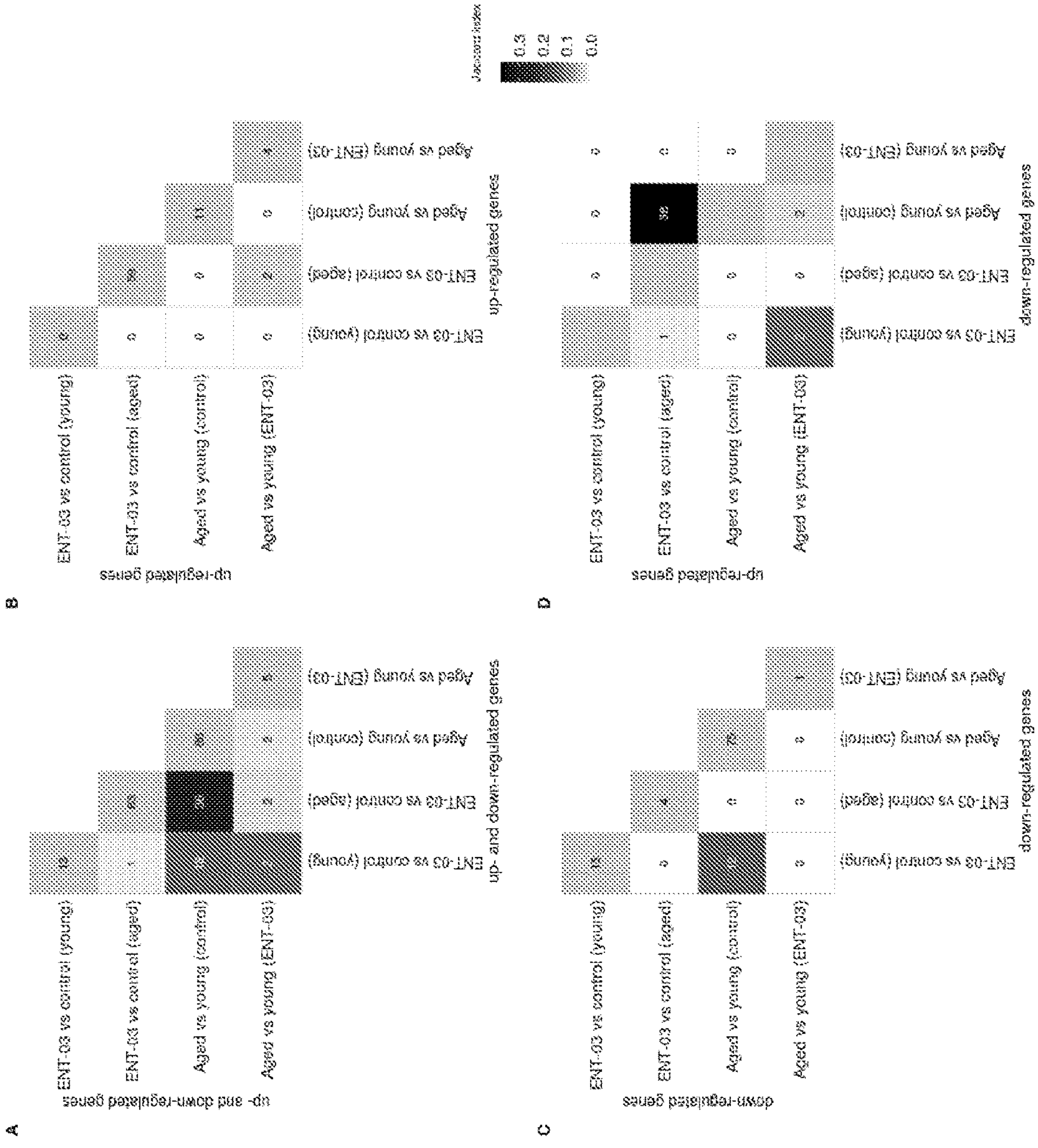
FIG. 11 shows a set of heatmaps investigating the overlap of differentially expressed genes between pairs of contrasts. The values in the plot represent the number of intersecting differentially expressed genes (adjusted p-value$<$0.05) between specific pairs of contrasts. The colours of the squares represent the Jaccard index (a quotient of the intersection and the union of genes) for the contrasts on the x- and y-axis.

FIG. 11 shows a set of heatmaps investigating the overlap of differentially expressed genes between pairs of contrasts.

These data support the hypothesis that oral administration of ENT-03 to old mice can reverse some of the changes in gene expression associated with ageing within the GI tract.

Example 4: Pharmacokinetic Study of ENT-03 (Compound III) Via Intravenous and Oral Administration The objective of this example was to determine the pharmacokinetic profile of ENT-03 (Compound III) via intravenous and oral administration in male SD Rats.

The study groups are shown in Table 6 below.

TABLE 6

Study Groups

| Group | Treatment | Dose Level* (mg/kg) | Dose Volume (mL/kg) | Conc. (mg/mL) | Administration Route | No. of Animals |
|---|---|---|---|---|---|---|
| 1 | ENT-03 | 5 | 5 | 1 | IV | 3 male |
| 2 | (Compound III) | 5 | 10 | 0.5 | PO | 3 male |

*The salt factor of 1.177 is used for the formulation preparation of Compound III.

Animal feeding control: Animals were food fasted overnight prior to dosing and fed 4 hours after administration having free access to water.

Dose formulation processing during dosing: The dose formulation was kept stirring at room temperature and was used within 2 hours.

TABLE 7

PK Time Points

| Group | PK time points |
|---|---|
| 1 | Plasma: 5 min, 15 min, 30 min, 1, 2, 4, 8, 24 hr post dose |
| 2 | Plasma: 15 min, 30 min, 1, 2, 4, 8, 24 hr post dose |

TABLE 8

Acceptable Time Ranges for Blood Collection

| Time Points | Acceptable Time Ranges |
|---|---|
| 5-15 min | Within ± 0.25 minute |
| 0.5-2 hr | Within ± 2 minutes |
| 4-24 hrs | Within ± 10 minutes |

TABLE 9

Blood Sample Collection and Processing

| | |
|---|---|
| Collection Site: | Jugular vein |
| Volume Collected: | ~0.2 mL per time point |
| Anticoagulant: | K2EDTA anti-coagulant tube |
| Plasma Samples Processing and Storage: | 1) Approximately 0.2 mL blood was collected at each time point. Blood of each sample was transferred into plastic micro centrifuge tubes containing anticoagulant of K2EDTA.<br>2) Blood samples were centrifuged at 4,000 g for 5 minutes at 4° C. to obtain plasma.<br>3) The samples were stored in a freezer at −75 ± 15° C. prior to analysis. |

TABLE 10

| Evaluations during the In-life Phase | |
|---|---|
| Procedure | Frequency |
| Cageside Observations: | Twice daily |
| Detailed Clinical Observations: | Once prior to dosing on Day 1 |
| Body Weight: | Once prior to each dosing |

Note:
Unscheduled clinical observations (cageside or detailed) were also performed, as needed.

TABLE 11

| Test System | |
|---|---|
| Species/Strain/Sex: | Rat/SD/Male |
| Source: | Si Bei Fu Laboratory Animal Technology Co. Ltd |
| Age at Day of Dosing: | Approximately 6-8 weeks |
| Weight at Day of Dosing: | Approximately 200-300 ga |

TABLE 12

| Compound Identification | | | |
|---|---|---|---|
| Compound Identification | MW | FW | Salt Factor |
| ENT-03 (Compound III) | 618.98 | 728.36 | 1.177 |

TABLE 13

| Dose Formulation | |
|---|---|
| Formulation Frequency: | Freshly prepared on the day of dosing |

TABLE 13-continued

| Dose Formulation | |
|---|---|
| Vehicle Composition: | IV & PO: Sterile water |
| Storage Condition: | Dose formulation for dosing: Room temperature |
| Preparation Procedures: | Weigh out test articles and dissolve it into vehicle with sonication, vortexing to obtain the targeted concentration of test articles and vehicle component. |
| Dosing Site | For IV dosing, the animals were administered intravenously via tail vein. For PO dosing, the animals were administered via oral gavage. |

PK Sample Analyses: Concentrations of ENT-03 (Compound III) in the plasma and dose samples were analyzed using a LC-MS/MS method. WinNonlin (Phoenix™, version 6.1) or other similar software was used for pharmacokinetic calculations. The following pharmacokinetic parameters were calculated, whenever possible from the plasma concentration versus time data.

IV Bolus administration: $T_{1/2}$, $C_0$, $AUC_{last}$, $AUC_{inf}$, $MRT_{inf}$, Cl, Vss, Number of Points for Regression.

PO administration: F, $T_{1/2}$, $C_{max}$, $T_{max}$, $AUC_{inf}$, $AUC_{last}$, $MRT_{inf}$, Number of Points for Regression.

The pharmacokinetic data was described using descriptive statistics such as mean and standard deviation. All the residual biological samples were retained in the freezer (−75±15° C.) for a period of 6 months after testing. The results are tabulated below in Table 14.

TABLE 14

| Summary of ENT-03 (Compound III) I.V. (group 1) plasma PK parameters | | | | | | | |
|---|---|---|---|---|---|---|---|
| PK parameters | Unit | Rat 1 | Rat 2 | Rat 3 | Mean | SD | CV (%) |
| Cl_obs | mL/min/kg | 0.0903 | 0.0885 | 0.0761 | 0.0850 | 0.0078 | 9.16 |
| $T_{1/2}$ | h | 18.6 | 17.5 | 18.6 | 18.2 | 0.6 | 3.55 |
| $C_0$ | ng/mL | 80402 | 102409 | 76200 | 86337 | 14076 | 16.3 |
| $AUC_{last}$ | h*ng/mL | 557542 | 608321 | 661154 | 609005 | 51810 | 8.51 |
| $AUCl_{Inf}$ | h*ng/mL | 922477 | 941130 | 1095763 | 986457 | 95121 | 9.64 |
| $AUC_{}_{\%Extrap}$_obs | % | 39.6 | 35.4 | 39.7 | 38.2 | 2.5 | 6.42 |
| $MRT_{Inf}$_obs | h | 25.3 | 22.9 | 25.5 | 24.6 | 1.5 | 5.96 |
| $AUC_{last}$/D | h*mg/mL | 111508 | 121664 | 132231 | 121801 | 10362 | 8.51 |
| $V_{ss}$_obs | L/kg | 0.137 | 0.122 | 0.116 | 0.125 | 0.011 | 8.55 |

Example 5: Synthetic Methods for the Preparation of ENT-03

This example describes synthetic methods of making compounds described herein.

Preparation of BDG-5

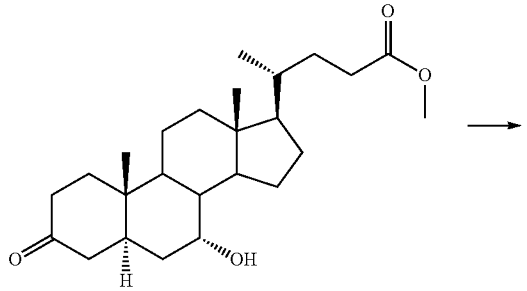

BDG-4

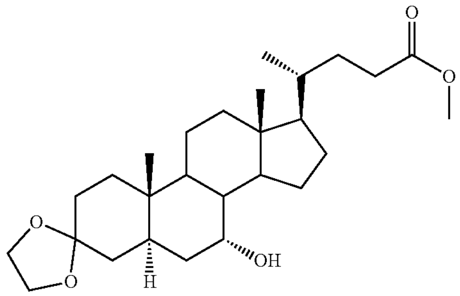

BDG-5

BDG-4 (370.54 g, 916.3 mmol) was dissolved in dichloromethane (DCM, 3,600 mL) and treated with ethylene glycol (210 mL, 3.77 mol, 4.11 eq.) along with p-toluenesulfonic acid-hydrate (36.27 mmol, 0.04 eq.). The mixture was refluxed until the reaction was complete (TLC in 70:30 hexane:acetone showed ca 3-5% residual starting material that did not change). After about 4 h reflux, the mixture was cooled, treated with of 10% potassium carbonate (150 mL), and the layers separated. The DCM was re-extracted with 800 mL of 5% sodium chloride solution and 10 mL of 10% potassium bicarbonate solution. The two aqueous layers were back-extracted with 500 mL of DCM. The combined DCM extracts were dried over magnesium sulfate, filtered, washed with DCM (2×100 mL), and concentrated under vacuum to afford a solid, which was slurried in acetonitrile (4.8 L) containing triethylamine (2 mL) at 55° C. for 1 h, then 35° C. for 1 hour, and finally at 12° C. for 2 h. The product was filtered and washed with cold acetonitrile (2×100 mL) containing triethylamine (0.1 mL). The crystals were dried at 50° C. in the vacuum oven (0.2 mm) overnight to afford BDG-5 (351.0 g, 85%); m.p. was 175.6-177.5° (at 2°/minute from ca 140°); $^1$H NMR (500 MHz, $CDCl_3$) δ 3.93 (m, 4H), 3.82 (br s, 1H), 3.66 (s, 3H), 2.4-2.2 (m, 2H), 1.9-1.2 (m, 24H), 0.92 (d, 3H, J=7 Hz), 0.81 (s, 3H), 0.66 (s, 3H); $^{13}$C NMR ($CDCl_3$) δ 177, 109, 67.9, 64.2, 64.1, 55.8, 51.4, 50.5, 45.6, 42.6, 39.5, 39.4, 37.5, 36.3, 36.1, 35.7, 35.5, 35.4, 31.2, 31.0, 30.9, 28.0, 23.6, 20.9, 18.3, 11.8, 10.4.

Preparation of BDG-6

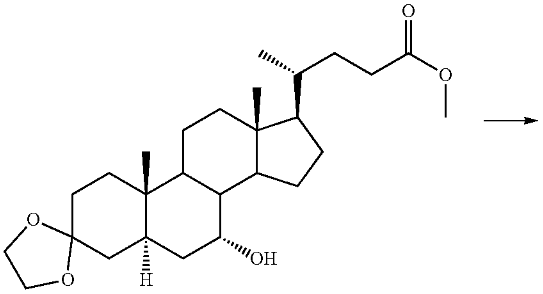

BDG-5

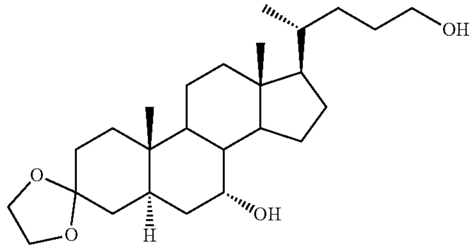

BDG-6

Lithium aluminum hydride (7.44 g, 196.05 mmol, pellets) was added to anhydrous THF (435 mL) under nitrogen and stirred overnight at 20° C. to break up the pellets. The suspension was cooled to 10° C. and a solution of BDG-5 (77.57 g, 172.91 mmol) was added dropwise over 160 min. The mixture was stirred 1 h further, and was quenched by adding 2 mL of ethyl acetate, followed by dropwise addition of 20% aqueous potassium hydroxide solution (7.44 mL) over 10 min. The mixture became very thick, then thinned out and became more granular with additional stirring for 15 h at 20° C. The mixture was filtered through Celite® 545 to remove the aluminum salts. The filter cake was washed with of THF (5×90 mL) to ensure that all the product was obtained in the filtrate, which was concentrated to afford crude BDG-6 (82.01 g, theory=72.7 g). In practice in larger runs, the THF solution was concentrated to dryness, and re-concentrated with DCM to remove traces of water prior to next step; $^1$H NMR (500 MHz, $CDCl_3$) δ 3.93 (m, 4H), 3.82 (br s, 1H), 3.61 (m, 2H), 1.97-1.84 (m, 4H), 1.7-1.0 (m, 22H), 0.93 (d, 3H, J=7 Hz), 0.81 (s, 3H), 0.66 (s, 3H); $^{13}$C NMR ($CDCl_3$) δ 109.3, 67.9, 64.15, 64.13, 63.5, 56.0, 50.6, 45.6, 42.6, 39.51, 39.48, 37.5, 36.3, 36.1, 35.7, 35.6, 35.5, 31.8, 31.2, 29.4, 28.2, 23.6, 20.9, 18.6, 11.8, 10.4.

Preparation of BDG-7

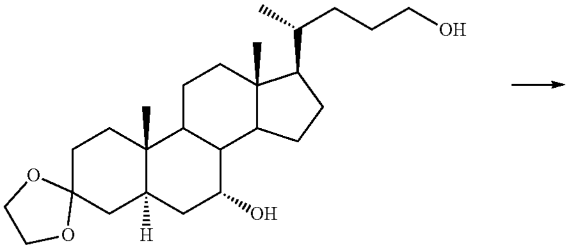

BDG-6

-continued

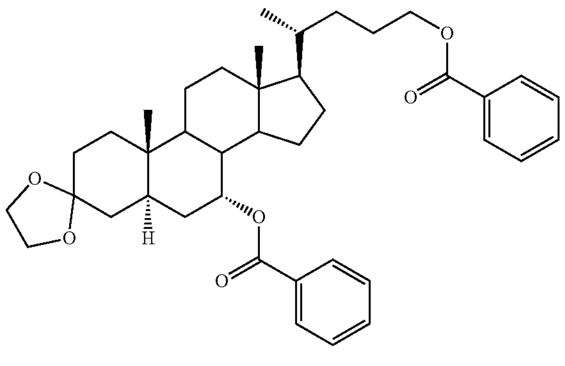

BDG-7

-continued

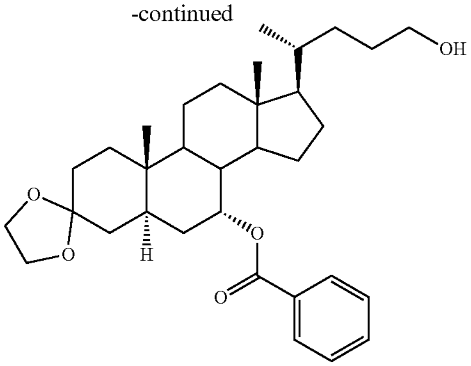

BDG-8

BDG-6 (214.55 g, 510.1 mmol) was dissolved in DCM (3.0 L) and treated with 4-dimethylaminopyridine (250.3 g, 2.048 mol) and then benzoyl chloride (180 mL, 217.98 g, 1.551 mol) dropwise. An exotherm to 31° C. was noted after about 40 mL of benzoyl chloride was added. The temperature was held to 25° C. for the remainder of the addition which took a total of 35 min. The solution was stirred overnight at 25° C., diluted with DCM (200 mL), and treated with 10% aqueous potassium bicarbonate (2 L) generating a small amount of carbon dioxide. The layers were separated and the aqueous layer was re-extracted with DCM (500 mL). The total organic layers were dried over magnesium sulfate and concentrated to afford BDG-7 as a solid (163.6 g, 100%). In practice in larger runs, the dibenzoate solution was concentrated to a suitable volume for the next step. $^{1}H$ NMR (500 MHz, $CDCl_3$) δ 8.07 (d, 2H, J=8 Hz), 8.00 (d, 2H, J=8 Hz), 7.57 (t, 1H, J=8 Hz), 7.53 (t, 1H, J=8 Hz), 7.47 (t, 2H, J=8 Hz), 7.41 (t, 2H, J=8 Hz), 5.16 (br s, 1H), 4.25 (m, 2H), 3.87 (m, 4H), 2.02-1.85 (m, 2H), 1.8-1.1 (m, 22H), 0.95 (d, 3H, J=7 Hz), 0.88 (s, 3H), 0.68 (s, 3H); $^{13}C$ NMR ($CDCl_3$) δ 166.7, 166.0, 132.8, 131.1, 130.5, 129.7, 129.5, 128.4, 128.3, 109.0, 71.9, 65.5, 64.2, 64.1, 55.8, 50.7, 47.2, 42.8, 39.5, 38.6, 37.4, 37.2, 35.7, 35.5, 35.3, 33.3, 32.0, 31.2, 28.0, 25.2, 23.6, 21.1, 18.6, 11.8, 10.5.

Preparation of BDG-8

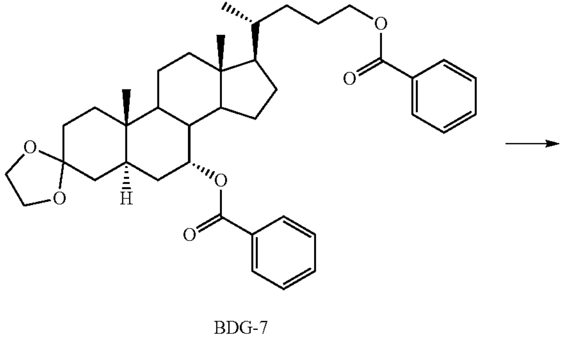

BDG-7

BDG-7 (22.13 kg, 35.2 mol) was dissolved in 1:1 tetrahydrofuran:methanol solution (220 L) at 25° C. and treated with a solution of 50% sodium hydroxide (3.7 L, 70.4 mol, 2.0 eq.) in deionized water (11 L) and stirred for 4 h. An aliquot (0.1 mL) of the reaction mixture was partitioned between ethyl acetate (0.5 mL each) and 1 M potassium bicarbonate solution. The organic layer was analyzed by TLC (70:30 hexane:acetone) and the reaction was judged complete. An aqueous solution of potassium bisulfate was prepared by mixing deionized water (23 L), 96% sulfuric acid (3.7 L, 66.6 moles), and 45% potassium hydroxide (5.7 L, 66.7 moles). The resulting solution of potassium bisulfate was added via sprayball to the reaction mixture to a final pH of 8.39 (pH meter). The mixture was vacuum-distilled to about 60 L volume; and treated with of ethyl acetate (100 L) and water (100 L). The 2-phase mixture was agitated for 10 min, and the layers separated over about 20 min. The aqueous phase was re-extracted with 37 L of ethyl acetate. The total ethyl acetate layer (about 160 L) was vacuum concentrated to a volume of 80 L at 50° C. Another 50 L of ethyl acetate was added, and the solution dried over anhydrous sodium sulfate (15 kg) by stirring overnight. The solution was filtered over Celite® 545 to remove the sodium sulfate. The filter cake and the reactor were rinsed with 2×37 L of ethyl acetate. The dried ethyl acetate solution was vacuum concentrated from about 225 L volume to 40 L. Acetonitrile (50 L) was added and the solution was re-distilled to remove ethyl acetate. A second and third batch of acetonitrile (50 and 100 L) were added and evaporated. Finally, 100 L of acetonitrile was added and this solution was counter-currently extracted with 3×104 L of hexane to remove most of the methyl benzoate. The 3 hexane extracts were re-extracted with a second 104 L of acetonitrile.

The hexane layers were checked by TLC for BDG-8 intermediate and none was present. The acetonitrile (ca. 300 L) was vacuum concentrated to ca. 50 L volume. Isopropanol (57 L) was added and concentrated to ca. 50. L; this operation was repeated 2 more times to remove all the acetonitrile. The volume was adjusted to 100 L with isopropanol and the solution slowly cooled to 0° C. and was seeded with crystalline BDG-8 to initiate crystallization. The mixture was slowly cooled to −20° C. overnight. The crystal slurry was filtered through a jacketed filter at −20° C. and rinsed with 10 L of −20° C. isopropanol. The filter cake was dried by vacuum for several h at −20° C., followed by letting the filter warm slowly to room temperature (about 18° C.) and then drying with warm nitrogen yielding 11.92 kg of BDG-8. The mother liquors were chromatographed to isolate additional product. A column of silica gel (19 kg) was packed in methylene chloride. The filtrate of the product was vacuum concentrated to dryness and ½ was added to the column in methylene chloride. Elution with 100 L of methylene chloride (DCM) gave the product. The column was flushed with 20 L of 85:15 methylene chloride:ethyl acetate, then 20 L of 60:40 methylene chloride:ethyl acetate, and finally back to methylene chloride (40 L).

The second ½ of the mother liquors was similarly chromatographed to give a total of 5.32 kg of pure BDG-8 (Total yield of BDG-8: 17.24 kg, 93.3%). $^{1}H$ NMR (500 MHz, $CDCl_3$) δ 8.07 (d, 2H, J=8 Hz), 7.57 (t, 1H, J=7 Hz), 7.48 (t, 2H, J=7 Hz), 5.15 (br s, 1H), 3.88 (m, 4H), 3.56 (br s, 2H), 2.02-1.84 (m, 2H), 1.75-0.98 (m, 24H), 0.92 (d, 3H, J=6.5 Hz), 0.88 (s, 3H), 0.67 (s, 3H). $^{13}C$ NMR ($CDCl_3$) δ 166.0, 132.7, 131.0, 129.7, 128.4, 109.0, 71.9, 64.2, 64.1, 63.5, 55.8, 50.7, 47.2, 42.7, 39.5, 38.6, 37.3, 37.2 35.7, 35.5, 33.3, 31.7, 31.3, 29.3, 28.0, 23.6, 21.1, 18.6, 11.8, 10.5.

Preparation of Compound 1

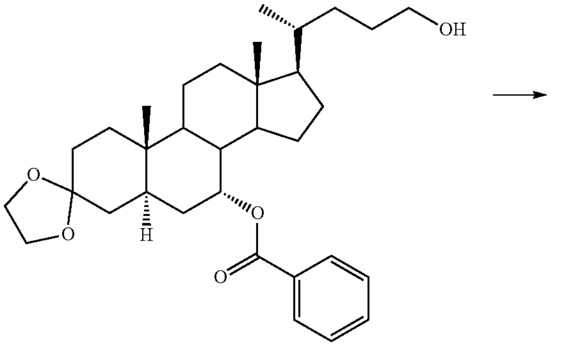

BDG-8

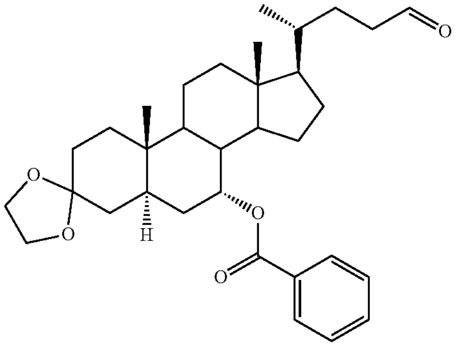

1

A 50 L jacketed reactor under nitrogen was charged with potassium bromide (250 g, 2.23 mol), sodium bicarbonate (265 g, 3.15 mol), and water (5 L); agitated and cooled with a −5° C. jacket. To the reactor was added BDG-8 (5.32 kg, 10.14 mol) dissolved in ~13 L of dichloromethane, followed by rinse from 8 L of dichloromethane. When the reaction mixture attained a temperature <5° C., TEMPO (50 g, 0.286 mole) was added through the manhole. The reactor was then charged via pump with 12.5% bleach (5.5 kg), keeping the mixture <5° C. The reaction was sampled to estimate additional amount of bleach needed. Bleach continued to be added in small portions while sampling periodically until reaction was judged to be complete (<2% BDG-8 remaining; a total of 6.2 kg of bleach was added). A solution of sodium thiosulfate (200 g) in water (1 L) was added with vigorous stirring until a negative starch/iodide test was obtained. Hexane (20 L) was added to the reactor with stirring and the layers settled. The lower aqueous phase was drained, and the organic layer was washed with saturated aqueous potassium bicarbonate (5 L). The organic phase was vacuum filtered through a pad of sodium sulfate/silica gel (1 kg of each) in a sintered glass filter funnel and rinsed with hexane/dichloromethane (1/1), dichloromethane, and finally 5% methyl-t-butyl ether (MTBE) in dichloromethane. The combined filtrates were evaporated in two batches in a Buchi apparatus at 40° C. Hexane was added to each batch and evaporated again until a thick slurry formed. The solids were filtered, washed with hexane, and dried in a vacuum oven to afford 1 (4.58 kg). The filtrates and washings were combined and concentrated to get a second crop, which was filtered and washed with 5% MTBE/hexane, then hexane, and dry to get another 565 g of product for a total yield of 5.145 kg (97% yield) of 1.

The material contained about 1.5% of residual starting material, but no detectable (NMR) carboxylic acid. $^{1}H$ NMR (500 MHz, $CDCl_3$) δ 9.72 (s, 1H), 8.07 (d, 2H, J=7 Hz), 7.59 (t, 1H, J=7 Hz), 7.49 (t, 2H, J=7 Hz), 5.16 (br s, 1H), 3.88 (m, 4H), 2.45-2.27 (m, 2H), 2.00-1.85 (m, 2H), 1.78-1.17 (m, 22H), 0.913 (d, 3H, J=Hz), 0.88 (s, 3H), 0.68 (s, 3H). $^{13}C$ NMR ($CDCl_3$) δ 203, 166, 132.8, 131.0, 129.8, 128.4, 109, 72.0, 64.17, 64.11, 55.7, 50.7, 47.2, 42.8, 40.8, 39.5, 38.6, 37.3, 37.2, 35.7, 35.5, 35.4, 33.3, 31.2, 27.9, 27.8, 23.7, 21.1, 18.3, 11.7, 10.5.

Preparation of Compound 2:

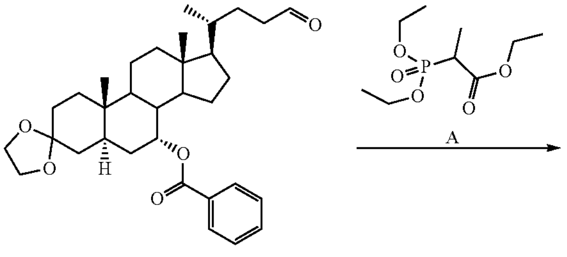

1

Molecular Weight: 522.73

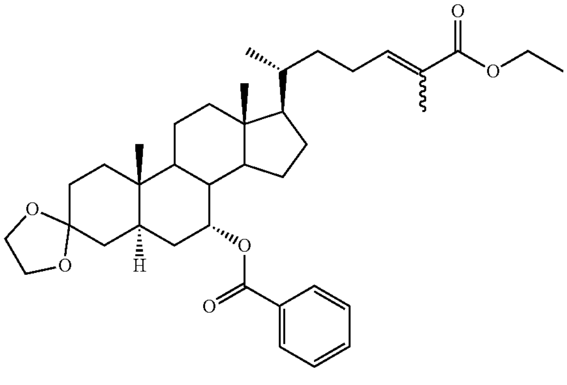

2

Molecular Weight: 606.84

The phosphonate (A, 3.69 g, 15 mmol) was added to anhydrous tetrahydrofuran (100 mL) and chilled in a salt ice bath to ~0° C. Potassium tert-butoxide (1.72 g, 15 mmol) was added with vigorous magnetic stirring under nitrogen and the reaction was allowed to stir for 30 min. Compound 1 (8.0 g, 15 mmol) was added and dissolved in tetrahydrofuran (80 mL), the ice bath was removed and the reaction was allowed to warm to RT overnight. The reaction after approximately 16 h total was worked up by partitioning between hexane/ethyl acetate (50/50, 400 mL) and water (400 mL). The organic layer was washed with an additional portion of water (100 mL) and the organic layer was dried over $Na_2SO_4$, filtered, and the solvent removed in vacuo. The residue was redissolved in a minimal amount of hexane/ethyl acetate 3/1 and passed through a plug of silica gel ~3×9 in.

The eluant was then roto-evaporated to yield Compound 2 (8.3 g, 12.4 mmol, 83%) of satisfactory purity to utilize in the next step without further purification, $^1$H NMR ($CDCl_3$, 300 MHz) δ 8.10-8.07 (m, 2H), 7.60-7.57 (m, 1H), 7.52-7.47 (m, 2H), 6.7, 5.9 (t, 1H), 5.17 (m, 1H), 4.21-4.12 (m, 2H), 3.92-3.88 (m, 4H), 2.06 (s, 3H), 2.2-1.0 (m, 29H), 0.95 (d, 3H, J=7 Hz), 0.90 (s, 3H), 0.69 (s, 3H); MS (ES+) 485.45 ($M-C_7H_7O_2+H$).

Preparation of Compound 3:

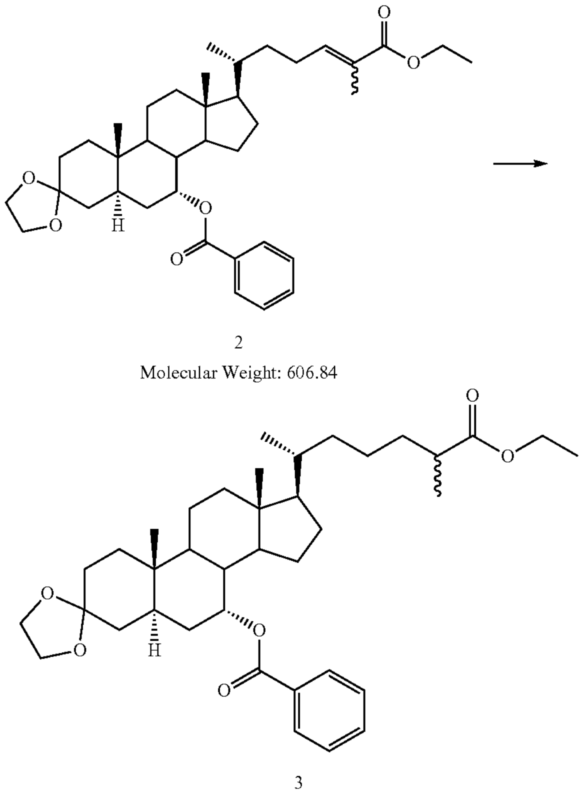

2

Molecular Weight: 606.84

3

Molecular Weight: 608.86

Compound 2 (8.25 g, 13.5 mmol) was dissolved in anhydrous ethanol and 10% Pd on C (400 mg) was added under $N_2$ in a Parr bottle (500 mL). The flask was flushed and filled 2× with vacuum and $N_2$ then hydrogenated at 50 psi for 24 h. The uptake of hydrogen had slowed to a near stop, but TLC showed a possible trace of starting material. An additional portion of catalyst (400 mg) was added, and the reaction was allowed an additional 12 h.

Filtration of catalyst and removal of the solvent in vacuo gave the saturated product in quantitative yield Compound 3 (8.25 g, 13.5 mmol), $^1$H NMR ($CDCl_3$, 300 MHz) δ 8.09-8.06 (m, 2H), 7.58-7.56 (m, 1H), 7.55-7.45 (m, 2H), 5.16 (m, 1H), 4.12-4.05 (m, 2H), 3.90-3.85 (m, 4H), 2.39-2.36 (m, 1H), 2.0-1.0 (m, 35H), 1.11 (d, 3H, J=7 Hz), 0.88 (s, 3H), 0.67 (s, 3H); MS (ES+) 487.46 ($M-C_7H_7O_2+H$).

Preparation of Compound 4:

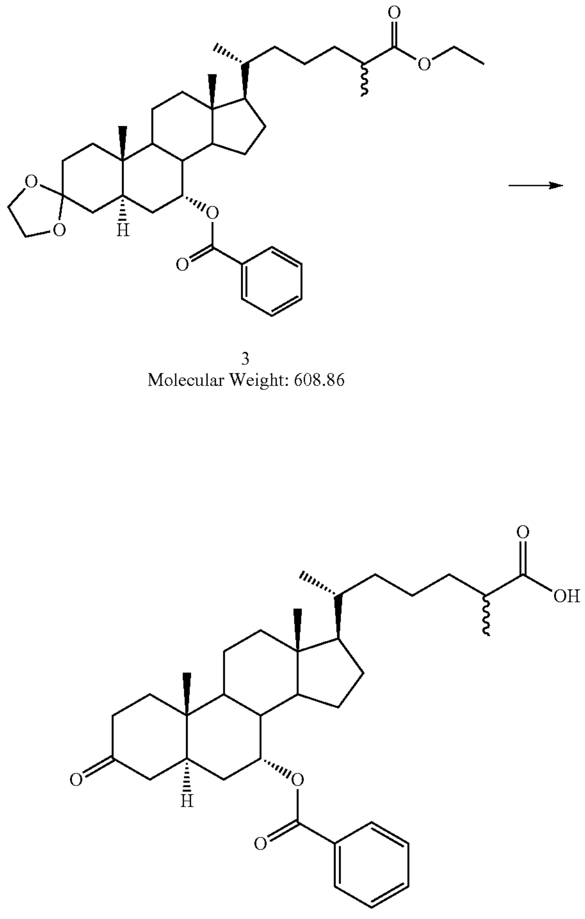

3

Molecular Weight: 608.86

4

Molecular Weight: 536.75

Compound 3 (8.2 g, 13.5 mmol) was dissolved in 3/1/1 tetrahydrofuran/methanol/1M KOH (~100 mL) and stirred until hydrolysis of the ethyl ester appeared to be complete by TLC. There was no evidence of benzoate hydrolysis under these conditions. The solution was neutralized with 1 M hydrochloric acid solution, evaporated to remove the organic solvent, treated with acetone (~100 mL), and evaporated again to ensure removal of any methanol. Acetone (~250 mL) was added to the flask and 3M HCl was added to lower the pH to the point where it registered in the 1-2 range by pH paper. The hydrolysis of the ketal was carried out overnight at RT, water was then added to the flask, and the majority of the acetone was removed in vacuo. The material was partitioned between ethyl acetate and water, and then the organic layer washed with brine. The organic layer was dried in vacuo to give Compound 4 (6.36 g, 11.9 mmol, 87%) of satisfactory purity to be utilized without further purification, $^1$H NMR ($CDCl_3$, 300 MHz) δ 8.05-8.02 (m, 2H), 7.60-7.57 (m, 1H), 7.51-7.45 (m, 2H), 5.21 (m, 1H), 2.4-1.0 (m, 32H), 1.15 (d, 3H, J=7 Hz), 1.09 (s, 3H), 0.91 (d, 3H, J=7 Hz), 0.67 (s, 3H); MS (ES+) 415.52 ($M-C_7H_7O_2+H$).

Preparation of Compound 5:

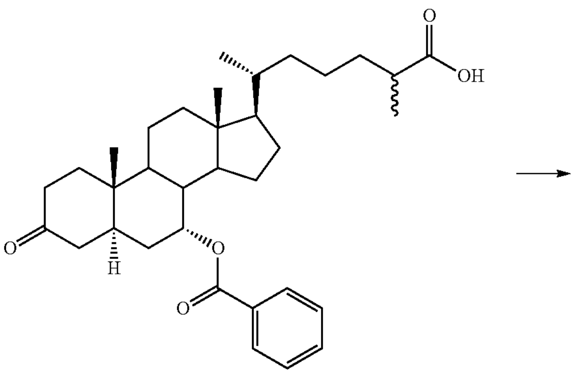

4

Molecular Weight: 536.75

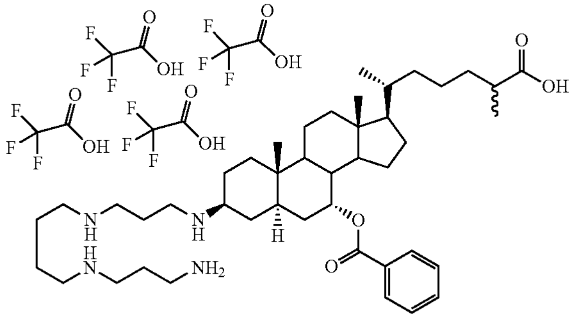

5

Exact Mass: 722.57

Molecular Weight: 723.10

Compound 4 (3.5 g, 6.5 mmol) was dissolved in methanol (100 mL) and treated with spermine (5 g, 24.8 mmol) in methanol (~10 mL). The mixture was stirred for 2 h at RT after which 2-propanol (100 mL) was added, and the majority of the solvent was removed in vacuo. The residue was redissolved in methanol (200 mL) and stirred overnight. Isopropyl alcohol (200 mL) was added and the mixture was evaporated to a thick residue. The residue was dissolved in anhydrous methanol (200 mL), and the solution chilled in a dry ice acetone bath under $N_2$ with vigorous magnetic stirring. When the internal temperature reached ~−74° C., $NaBH_4$ (1.89 g, 50 mmol) was added. The temperature was maintained with the dry ice acetone bath for ~4 h and then allowed to come to RT overnight. The reaction mixture was carefully acidified with 10% trifluoroacetic acid in water until pH paper showed pH 2-3 range. Water was added to the mixture, and the mixture was transferred to an oversized flask (to allow for frothing of the mixture on rotary evaporation) and the majority of the methanol removed in vacuo. The resulting solution was applied directly to amberchrome and eluted with a step gradient of acetonitrile in water with 0.5% TFA (10% increments 500 mL per increment) until aminosterol eluted (~60% acetonitrile). The gradient was held at this point until all of the aminosterol eluted.

The fractions containing aminosterol were analyzed and the relatively clean fractions pooled and lyophilized to afford Compound 5 as the tetra-TFA salt (~4.5 g, 3.8 mmol) of sufficient purity to carry on without further purification, $^1H$ NMR ($CD_3OD$, 300 MHz) δ 8.05-8.02 (m, 2H), 7.66-7.60 (m, 1H), 7.54-7.49 (m, 2H), 5.17 (m, 1H), 3.36-3.04 (m, 13H), 2.37 (m, 1H), 2.1-1.0 (m, 39H), 1.10 (d, 3H, J=7 Hz), 0.95 (m, 6H), 0.74 (s, 3H); MS (ES+) 723.78 (M+H).

Preparation of ENT-03 (Compound III):

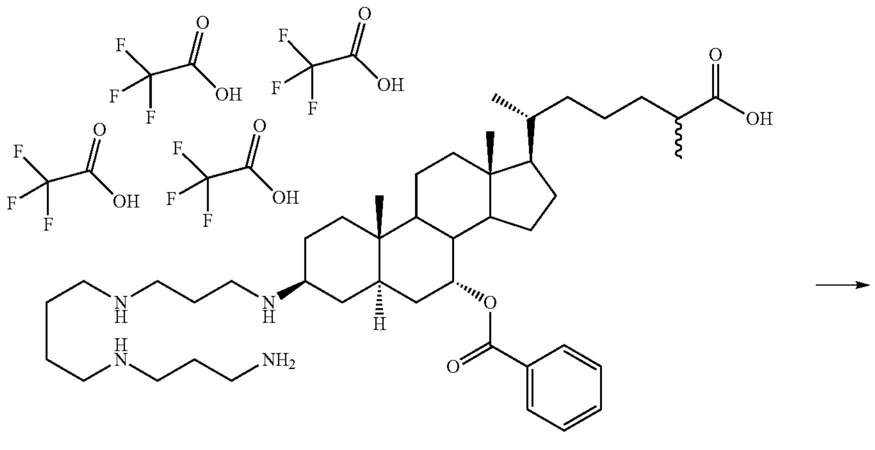

5

Exact Mass: 722.57

Molecular Weight: 1179.19

-continued

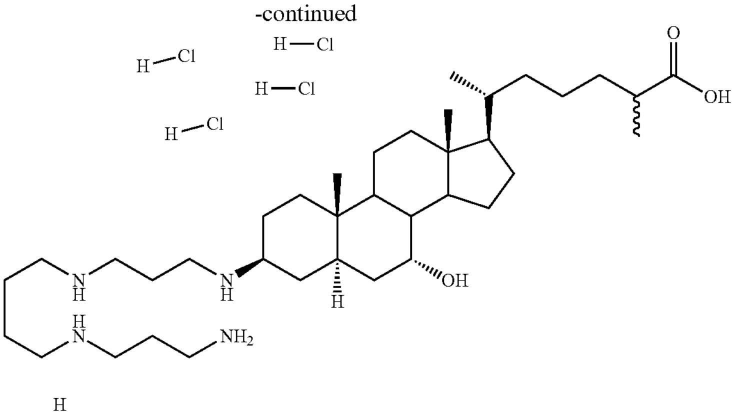

ENT-03

M+1: Exact Mass: 619.55262

Molecular Weight: 1944.01684

Compound 5 (3.0 g, 2.5 mmol) was added to of 5% methanolic potassium hydroxide (40 mL), and the solution was stirred for 2 days under $N_2$ at 110° C., and monitored with TLC (6:3:1 Chloroform, Methanol, conc. $NH_4OH$). After 2 days, the reaction was cooled to room temperature, evaporated under vacuum, and dissolved in $H_2O$ (40 mL). This solution was then acidified with 6M HCl, and the white precipitate was forced back into solution with gentle heat and stirring. The solution was poured onto a large column of Amberchrome, and washed with $H_2O$ (350 mL), increments (500 mL) of 10%, 15%, and 25% acetonitrile/water. Almost as soon as one column volume of 25% solution had passed through, the compound began to elute. The fractions (40 mL) that were collected were analyzed via LC/MS to separate away the 3-α side-product, which came off the column immediately following the desired 3-β product. Although there was some co-elution, a significant portion of the material came off cleanly.

These fractions were combined and lyophilized overnight to give (1.31 g, 1.7 mmol, 68%) of ENT-03 (Compound III) as the tetra-HCl salt, $^1H$ NMR ($CD_3OD$, 300 MHz) δ 3.80 (br s, 1H), 3.20-3.05 (m, 13H), 2.37 (m, 1H), 2.2-1.0 (m, 36H), 1.13 (d, 3H, J=7 Hz), 0.93 (d, 3H, J=7 Hz), 0.87 (s, 3H), 0.69 (s, 3H). ENT-03 was analyzed for purity via HPLC (Waters Acquity ELSD) under the following conditions: Mobile phase A: 0.1% formic acid in water; Mobile phase B: 0.1% formic acid in acetonitrile; Column: Kinetex XB-C18 (2.1×75 mm, 1.7 μm); Gradient: 5-95%/8 min, hold 95% B/1 min; 0.6 mL/min flowrate; ELSD detector; Retention time: 1.96 min and 99.9% peak area. ENT-03 was analyzed by mass spectrometry (Waters Acquity TQD); Mobile phase A: 0.1% formic acid in water; Mobile phase B: 0.1% formic acid acetonitrile; Column: Kinetex XB-C18 (2.1×75 mm, 1.7 μm); Gradient: 5-95%/8 min, hold 95% B/1 min; Flow-rate: 0.6 ml/min; MS (ES+, M+H): Calc'd 619.55; Found: 619.31.

Preparation of ENT-03-d3:

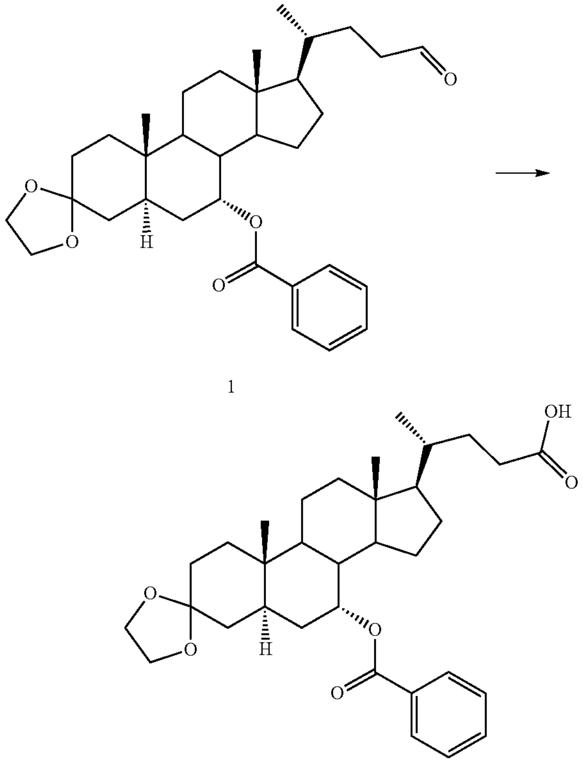

1

11

Compound 1 (2.6 g, 5 mmol) was dissolved in tetrahydrofuran (THF, 50 mL) and stirred over a sodium citrate/citric acid buffer ~0.5 M (100 mL). Sodium chlorite (900 mg, 10 mmol) was dissolved in deionized (DI) water (20 mL) and added to the aldehyde solution with ice bath cooling. A slight yellow color was observed, and TLC ($SiO_2$, 15% EtAc in hexane) shows a rapid conversion to the acid within 20 min. Ethyl acetate/hexane 50/50 (100 mL) was added, the aqueous removed, and the organic layer was washed with water, 10% thiosulfate solution, and brine to give the desired product 11 of satisfactory purity without further purification (2.7 g, 5 mmol, 100%).

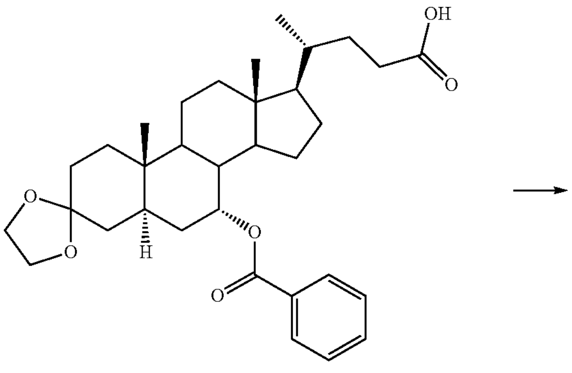

11

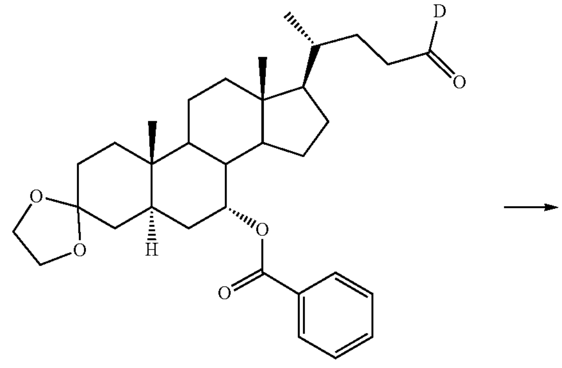

14

Molecular Weight: 523.73210

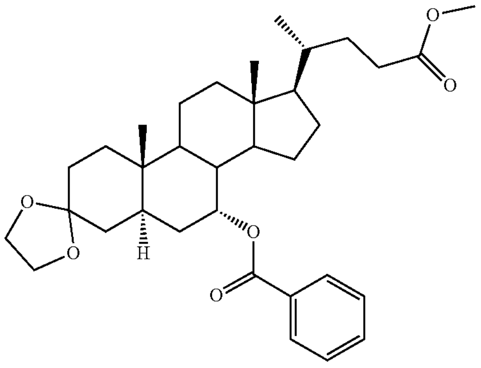

12

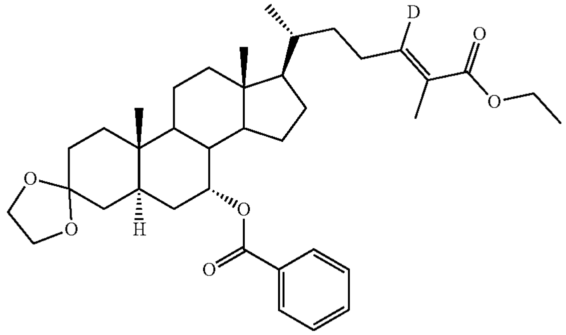

15

Molecular Weight: 607.85010

Compound 11 (2.6 g, 4.9 mmol) was dissolved in N-methylpyrrolidone (NMP, 25 mL) and anhydrous $K_2CO_3$ (~2 g) was added and the reaction mixture was stirred under nitrogen for 20 min. Iodomethane (2.8 g, 20 mmol) was added in one portion and the reaction was stirred overnight under nitrogen. The reaction showed complete conversion to Compound 12 in nearly quantitative yield (2.6 g, 4.9 mmol).

Compound 12 (1.3 g, 2.3 mmol) was dissolved in anhydrous THF (30 mL) and anhydrous lithium chloride (~1 g) was added. This solution was warmed to 40° C. and stirred under nitrogen. A solution of NaBD4 in EtOD was prepared in 500 mg batches (2×3 mL) by dissolving the NaBD4 in EtOD at room temperature and then chilling to prevent decomposition via the alkoxyborohydrides. The NaBD4 solution was added in portions over time (4 h) and then warmed to 50° C. and stirred overnight under nitrogen. The reaction was diluted with water and extracted with 50/50 hexane/ethyl acetate. Organic layers were pooled dried over $Na_2SO_4$ and concentrated in vacuo. The residue was chromatographed on silica gel with 25% ethyl acetate in hexane to give the desired Compound 13 as a white solid (1.1 g, 2.0 mmol, 87%).

Compound 13 (1.0 g, 1.9 mmol) was dissolved in dichloromethane (50 mL), treated with activated 4 Å sieves (~1 g) and 4-methylmorpholine N-oxide (500 mg, 4.3 mmol), and stirred 10 min at rt. Tetrapropylammonium perruthenate (~40 mg) was added to the reaction and stirring was continued at rt overnight under nitrogen. This gave a single product matching the unlabeled Compound 1 by TLC. $^1H$ NMR did not show the aldehydic proton as expected.

Triethyl phosphonopropionate (500 mg 2.0 mmol) was dissolved in EtOD and catalytic sodium ethoxide was added, stirred for 2 h, and the reaction mixture stripped to exchange the majority of the acidic methylene protons for deuterium. The phosphonate was added to anhydrous THF (30 mL) and treated with potassium t-butoxide (225 mg 2.0 mmol) at 0° C. for 30 min under nitrogen. The aldehyde 14 (1.0 g 1.9 mmol) was added in one portion at 0° C. in THF (~5 mL) with rinses. The ice bath was removed, and the reaction mixture was allowed to run overnight at rt. The reaction mixture became slightly cloudy relatively quickly and is likely done in 1-2 h. The reaction mixture was partitioned between hexane/ethyl acetate 50/50 (~100 mL) and water, and then washed with brine. The organic was dried over $Na_2SO_4$ and the solvent removed in vacuo. The relatively clean material was chromatographed on silica gel with a hexane ethyl acetate gradient to afford Compound 15 (860 mg, 1.4 mmol, 74%).

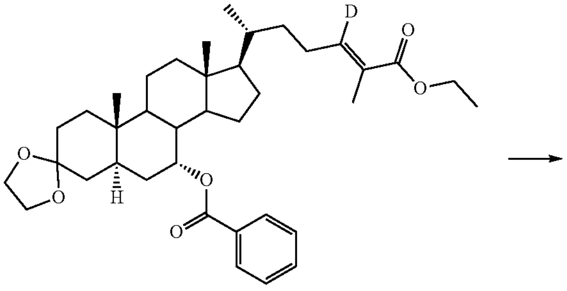

15

Molecular Weight: 607.85010

-continued

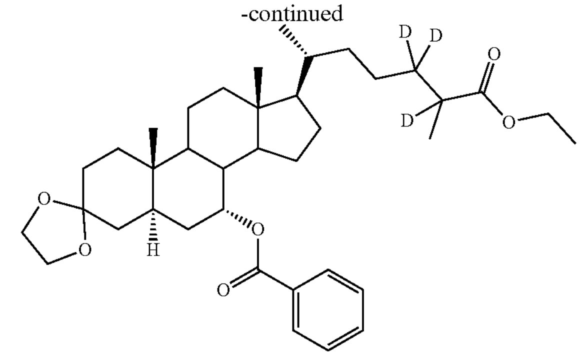

16

Molecular Weight: 611.87831

The unsaturated ester 15 (860 mg, 1.4 mmol) was dissolved in ethyl acetate containing 20% EtOD and treated with the catalyst (10% Pd on Carbon, ~100 mg) under nitrogen. The reaction was purged and backfilled with deuterium gas and then charged to 40 PSI in a 500 mL Parr shaker bottle. Agitation at room temperature overnight yielded a slight decrease in pressure. After an additional 8 h, no additional uptake was observed, so the reaction mixture was purged and backfilled with nitrogen three times and suction filtered through Celite®. The filtrate was evaporated in vacuo to give Compound 16 (850 mg, 1.4 mmol, 100%).

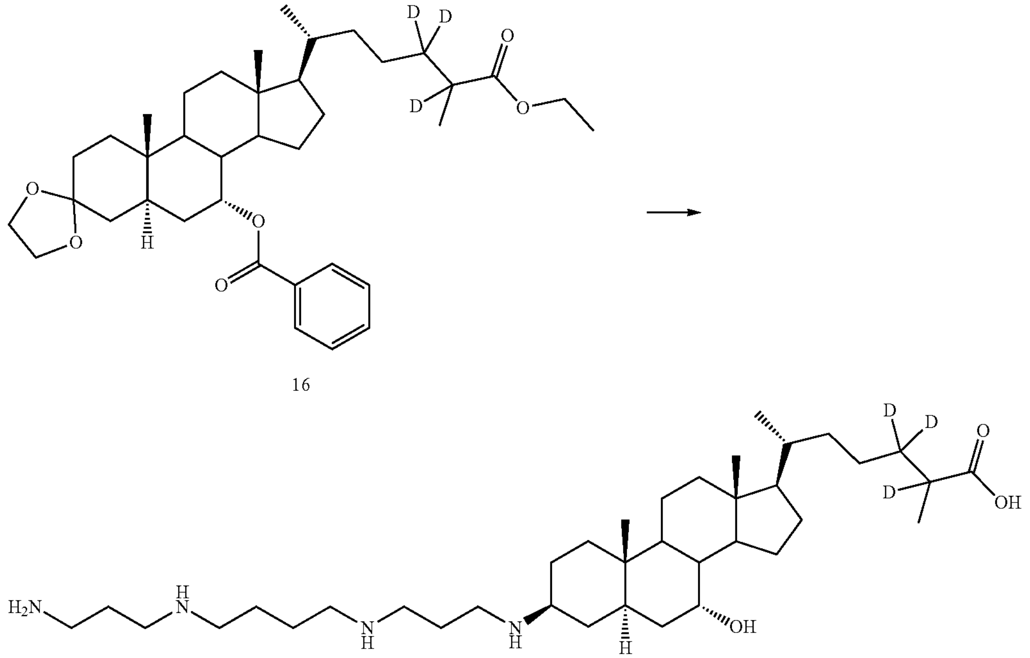

16

ENT-03-d3

Using the same procedures described for conversion of Compound 3 to ENT-03 (Compound III), Compound 16 was converted to ENT-03-d3. $^1H$ NMR (D20, 400 MHz) δ 3.90 (br s, 1H), 3.06-3.01 (m, 13H), 2.0-1.0 (m, 34H), 1.02 (s, 3H), 0.80 (br s, 3H), 0.73 (s, 3H), and 0.57 (s, 3H). ENT-03-d3 was analyzed for purity via HPLC (Agilent) under the following conditions: Mobile phase A: 0.1% formic acid in water; Mobile phase B: 0.1% formic acid in acetonitrile; Column: Kinetex XB-C18 (2.1×75 mm, 1.7 μm); Gradient: 5-95%/8 min, hold 95% B; 0.6 ml/min flowrate; ELSD detector; Retention time: 4.93 and 95.5% peak area. ENT-03-d3 was analyzed by LC/MS (Waters Aquity HPLC-ZQ MS); Mobile phase A: 0.1% formic acid in water; Mobile phase B: acetonitrile; Column: Waters) (Bridge C18 (4.6×50 mm, 3.5 μm). Flowrate: 1.1 mL/min. MS (ES+, M+H): Calc'd: 622.57; Found: 622.60.

Preparation of ENT-03-d4:

Compound 4 (2.14 g, 4.0 mmol) was dissolved in MeOD (50 mL) and 10% $K_2CO_3$ in D20 was added (10 mL). The mixture was stirred under nitrogen at reflux for 16 h. The solvent was removed in vacuo and the residue was resuspended in MeOD (50 mL) and stirred at reflux for 8 h. The only change by TLC was the appearance of a small amount of deprotected C-7 hydroxyl, which was not a concern. The solvent was removed in vacuo and the Compound 21 was resuspended in MeOD (50 mL). Spermine (2.1 g, 10 mmol) was exchanged with MeOD (3×10 mL) by dissolving in the methanol stirring for 5 min. then removing the solvent in vacuo. A final portion of MeOD was added and the spermine solution was added to the exchanged sterol and the mixture was stirred overnight at room temperature. The solvent was removed in vacuo and the residue resuspended in MeOD (50 mL). This solution was stirred at rt for ~9 h before chilling in a dry ice acetone bath for 40 min. Solid $NaBH_4$ (740 mg, 20 mmol) was added as a solid in two portions approximately 15 min apart. The bath was charged with dry ice and allowed to warm to rt overnight. Thin layer chromatography (TLC, $SiO_2$ 6/3/1 $CHCl_3$/MeOH/$NH_4OH$) of the reaction at ~14 h reaction time showed no starting material and very little sign of 3-hydroxyl of Compound 20. The reaction was diluted with deionized (DI) water and acidified slowly with trifluoro acetic acid (TFA) until strongly acidic by pH paper (pH<2). This gave a thick white precipitate, which was filtered, washed with 0.5% TFA in water, and then dissolved in 5% KOH in MeOH (100 mL) and refluxed overnight under nitrogen. After overnight reflux, the C7-benzoate hydrolysis was complete by TLC. The majority of the methanol was removed in vacuo and the material diluted with DI H2O. The material was applied directly to an Amberchrome packed column (5×20 cm) and washed with water until the strongly basic portion had eluted. The column was then washed with 1% TFA and 5% acetonitrile in water until the eluant was acidic. A step gradient was run in 5% steps, and fractions containing the cleanest material by TLC pooled and the majority of the solvent removed in vacuo near the end of the solvent removal.

A solution (1 mL) of 6 N HCl was added and the solvent removed to exchange TFA for HCl. This was repeated three times and 2-propanol (100 mL) was added and quickly stripped off to give a free flowing white solid (700 mg, 0.96 mmol, 24% overall yield) in clean fractions of ENT-03-d4. $^1$H NMR (D20, 400 MHz) δ 3.77 (br s, 1H), 3.06-2.99 (m, 13H), 2.36 (m, 1H), 2.0-1.0 (m, 33H), 1.05 (d, 3H), 0.84 (br s, 3H), 0.73 (s, 3H), and 0.57 (s, 3H). ENT-03-d4 was analyzed for purity via HPLC (Agilent) under the following conditions: Mobile phase A: 0.1% formic acid in water; Mobile phase B: 0.1% formic acid in acetonitrile; Column: Kinetex XB-C18 (2.1×75 mm, 1.7 μm); Gradient: 5-95%/8 min, hold 95% B; 0.6 ml/min flowrate; ELSD detector; Retention time: 4.94 and 100% peak area. ENT-03-d4 was analyzed by LC/MS (Waters Aquity HPLC-ZQ MS); Mobile phase A: 0.1% formic acid in water; Mobile phase B: acetonitrile; Column: Waters)(Bridge C18 (4.6×50 mm, 3.5 μm). Flowrate: 1.1 mL/min. MS (ES+, M+H): Calc'd: 623.58; Found: 623.31.

Example 6: ENT-03 (Compound III) Reverses Alzheimer's in Mice

PTP1B dependent mechanisms have been utilized for reversal of memory impairment and normalization of behavior and reduction in neuronal loss in beta amyloid and tau mouse models of Alzheimer's disease (Ricke, Cruz et al. 2020). Other studies have shown reduction in the toxicity of beta amyloid aggregates by trodusquemine in vitro and in a *C. elegans* model of Alzheimer's disease (Limbocker, Chia et al. 2019).

ENT-02 (MSI-1436) reverses several conditions (in mice) that are associated with ageing, such as metabolic syndrome, Alzheimer's disease, atherosclerosis, cancer and a reduced capacity for regenerative repair. As we have shown in this report, ENT-03 can treat Alzheimer's disease in murine models.

The Morris water maze was used to test the effect of ENT-03 on spatial learning and memory deficits in 2 mouse models of familial Alzheimer's disease, hAPP-J20 mice that express a double mutant of the human amyloid precursor protein (Mucke et al., 2000), and PS19 mice that express the P301S mutant of the human microtubule associated protein tau (Yoshiyama et al., 2007).

hAPP-J20 mice expressing human APP bearing the Swedish and Indiana familial mutations (B6.Cg-Zbtb20Tg (PDGFB-APPSwInd)20Lms/2Mmjax, (Mucke et al., 2000)) and PS19 mice expressing the P301S mutation of human tau protein (B6;C3-Tg(Prnp-MAPT*P301S)PS19Vle/J (Yoshiyama et al., 2007)) were purchased from Jackson laboratories and maintained as colonies in the animal facility of the University of Ottawa. Heterozygous hAPP-J20 and PS19 mice were used. Genotypes were verified by PCR using genomic DNA isolated from tail or ear biopsies.

Clinical grade ENT-03 (provided by Enterin, Inc.) was administered intraperitoneally (i.p.) once per week for 6 weeks at a dose of 2.5 mg/kg bodyweight starting at 4.5 months of age. The behavioral experiments were conducted 10 days after the last injection. Vehicle treated controls received sterile saline (0.9% NaCl in water).

The Morris water maze test to analyze the ability of mice to learn and remember the location of a submerged platform in a pool containing opaque water was conducted in the Faculty of Medicine Behavior Core Laboratory at the University of Ottawa. The 80 $cm^2$ platform surface corresponds to 0.6% of the total pool area. Mice were habituated to the experimental room and consecutive experiments were performed between noon and 4 PM. Mice were trained for 5 days, (four trials per day with an inter-trial interval of 20 minutes and a random start location in one of four positions) to find the invisible, submerged platform at a fixed location. Cues around the pool were provided as spatial references. Trials lasted 1 minute or until the mouse found the platform. Mice were guided to the platform if they did not find the platform. Mice stayed on the platform for 15 seconds of each trial before being removed to their cages. After the training period, the platform was removed from the pool and the probe trial was executed within 1 minute on the following day. On the probe day, crossings of the platform area and target quadrant were counted and swimming speed was measured using Ethovision automated video tracking software (Noldus).

In both disease models, one with amyloidopathy and the other with a tauopathy, learning during the training phase (FIGS. 5A and 5E) and memory on the probe day (FIGS. 5B, 5C, 5F and 5G) were improved with ENT-03 treatment compared to vehicle treated hAPP-J20 or PS19 littermate control mice (FIG. 5). The effect on preventing cognitive decline is similar to what has been observed with the related compound trodusquemine hAPP-J20 and PS19 mice (Ricke et al., 2020).

Figures 5A, 5B:
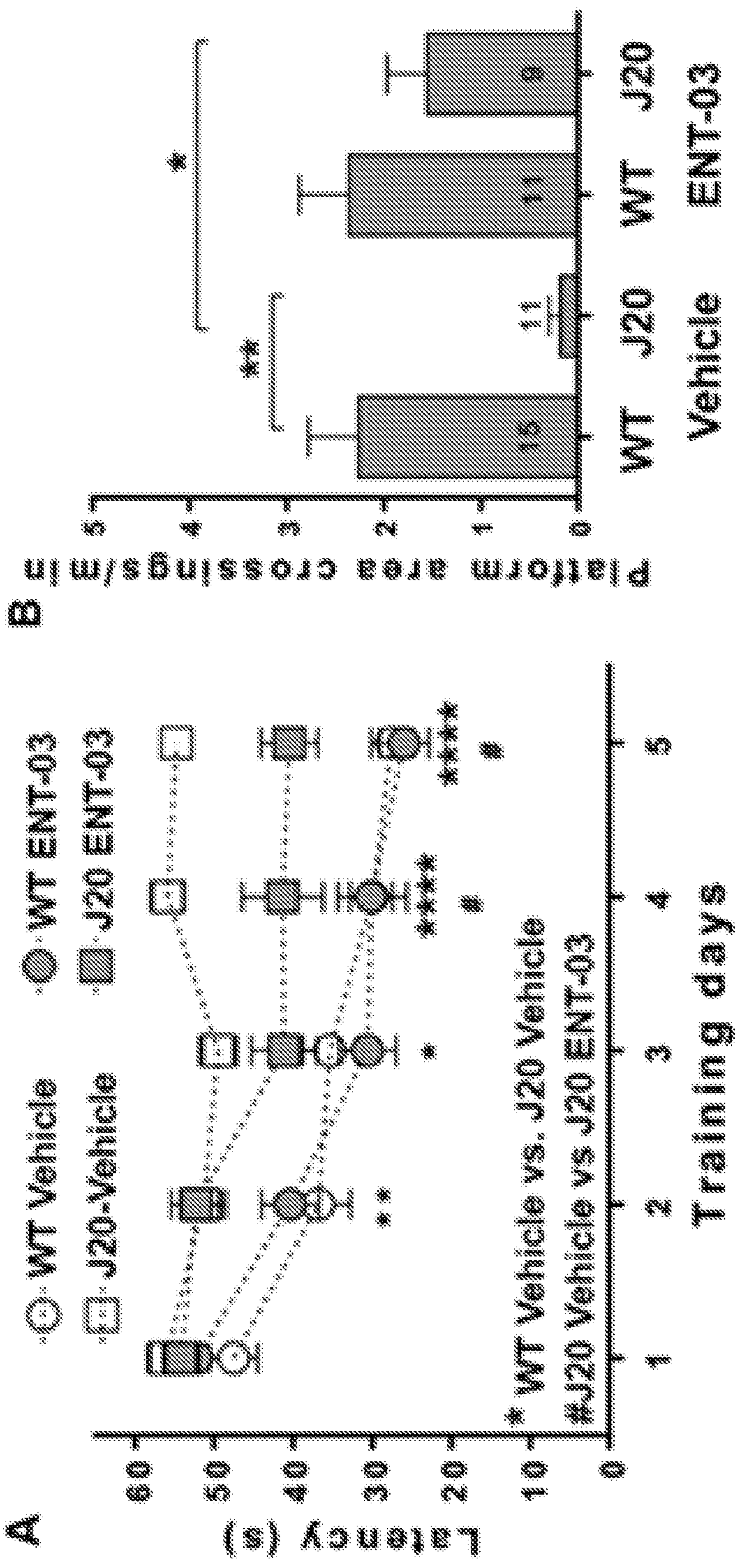
FIGS. 5A-H show that PTP1B inhibition by ENT-03 ameliorates the cognitive impairment of hAPP-J20 (FIGS. 5A-5D) and PS19 (FIGS. 5E-5H) mice.
Figures 5C, 5D:
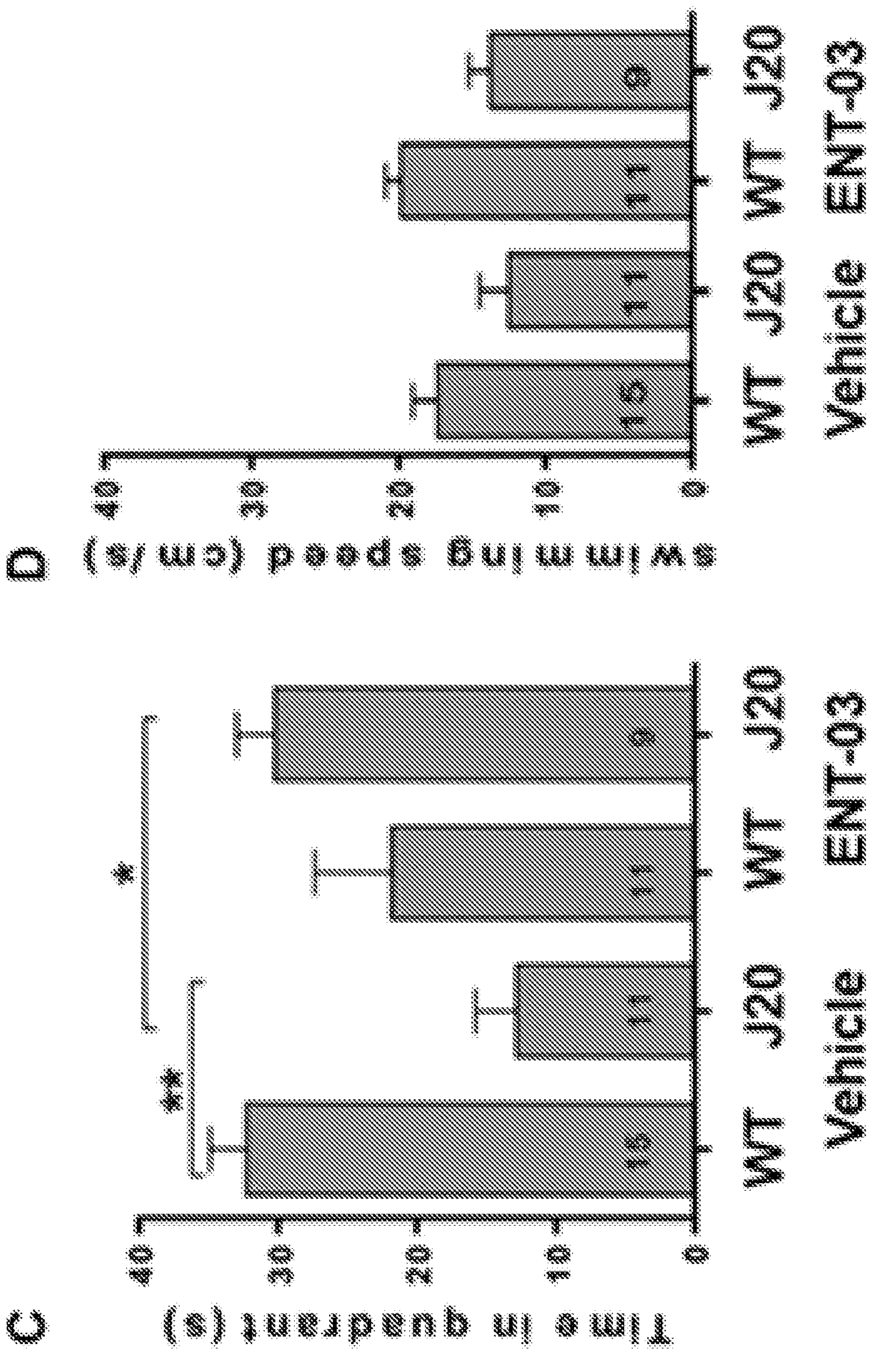
Figures 5E, 5F:
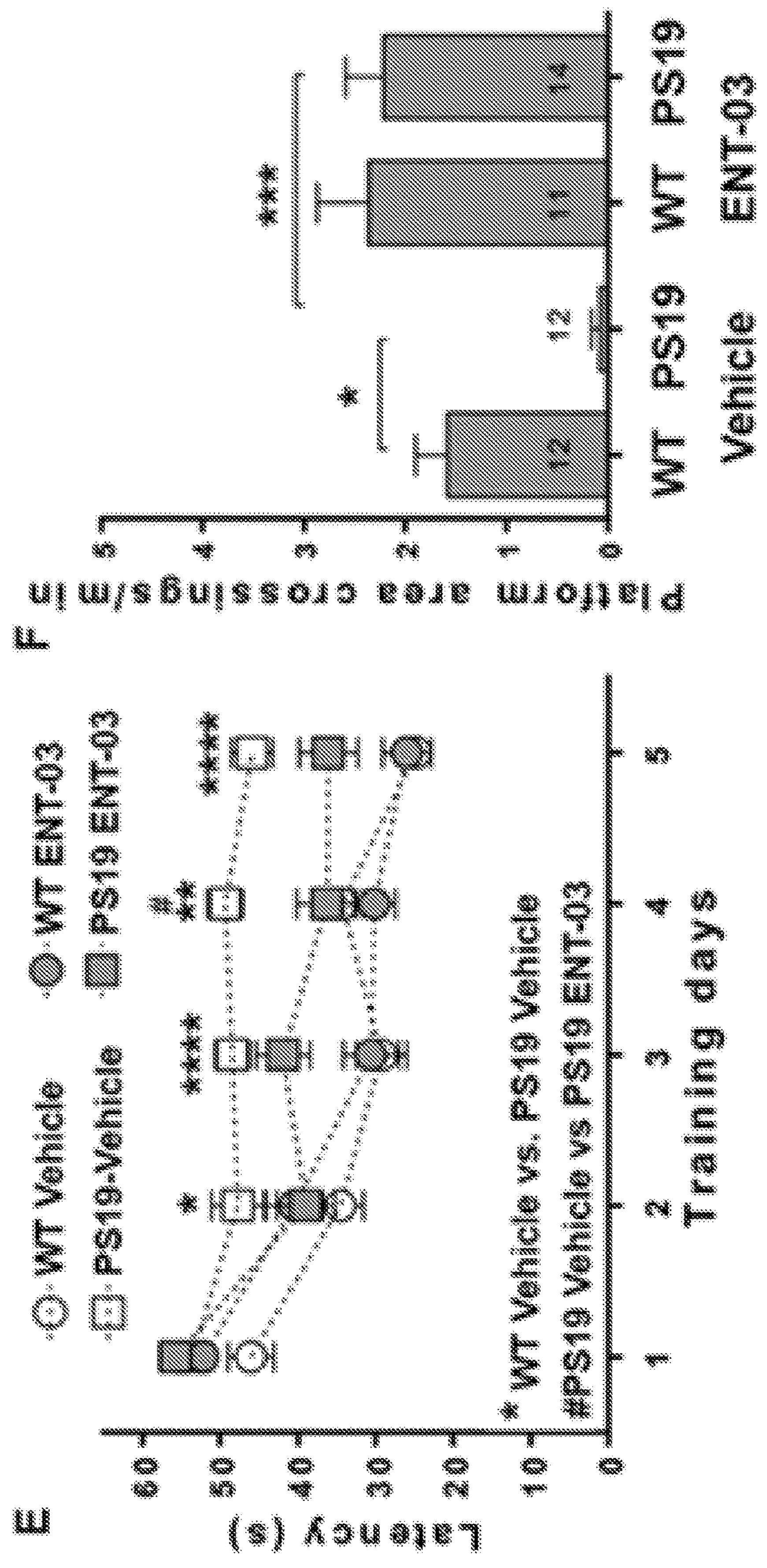
Figures 5G, 5H:
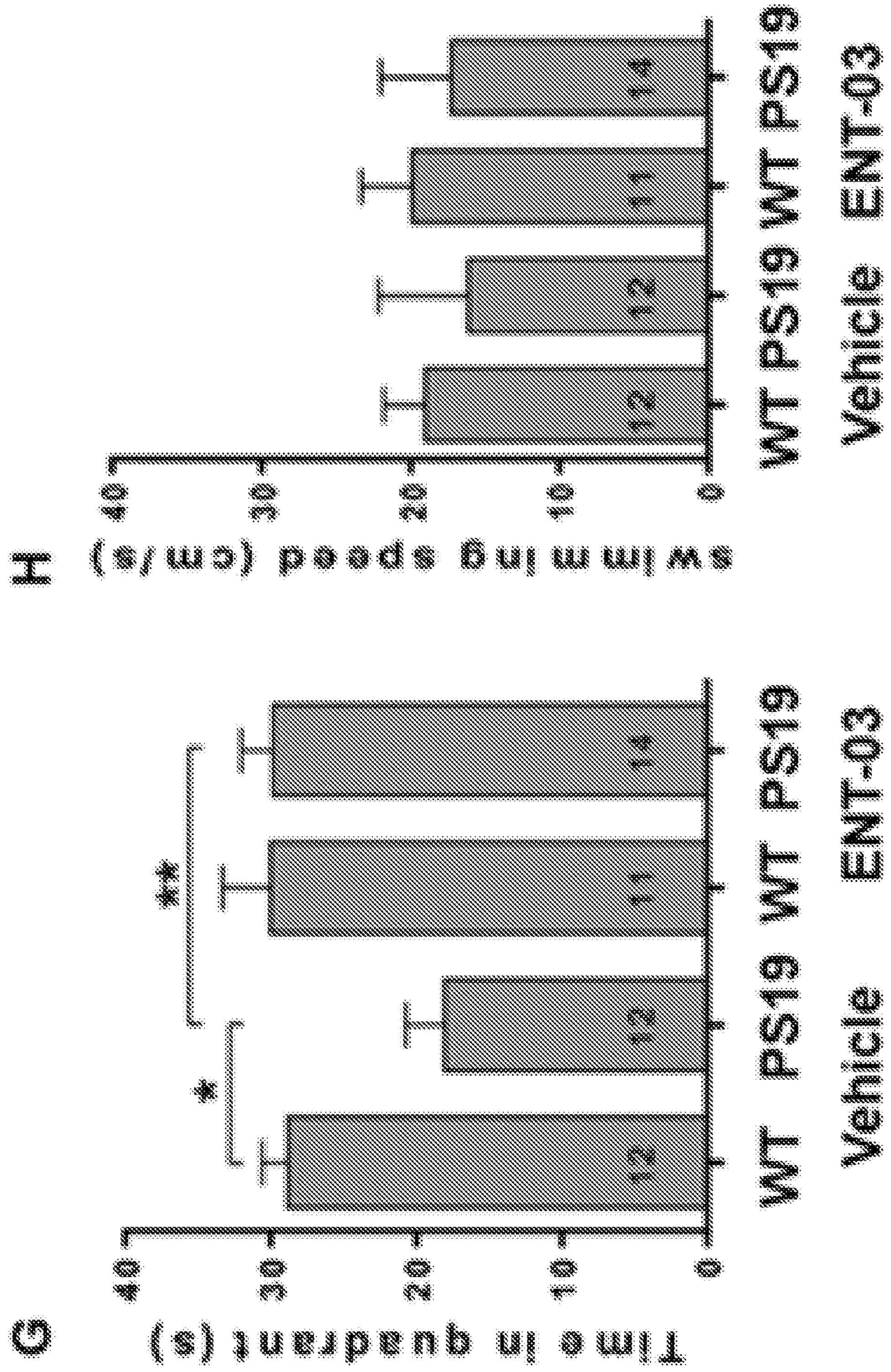

In particular, Morris water maze test reveals ENT-03 treatment over 6 weeks (2.5 mg/kg/wk, i.p.) decreased the latency to find the hidden platform for hAPP-J20 mice during the training phase (FIGS. 5A and 5E) and improved memory (crossings at the area where the platform was located (FIGS. 5B and 5F) and time in the platform area (FIGS. 5C and 5G) on the probe day. (FIGS. 5D and 5H) Swimming speed. FIG. 5A, repeated measures two-way ANOVA: genotype/treatment, F(3,42)=13.47, p<0.0001; time, F(4,168)=23.45, p<0.0001; subjects (matching), F(42, 168)=4.420, p<0.0001; interaction, F(12,168)=3.458, p=0.0001; *, post hoc pairwise comparisons between Veh WT and Veh hAPP-J20, day 2, 3, 4, 5: p=0.0073, 0.0101, <0.0001, <0.0001, respectively; #, post hoc pairwise comparisons between Veh hAPP-J20 and ENT-03 hAPP-J20, day 4, 5: p=0.0260, 0.0298, respectively. FIG. 5B, two-way ANOVA: genotype, F(1,42)=10.44, p=0.0024; treatment, F(1,42)=4.509, p=0.0396; interaction, F(1,42)=3.625, p=0.0638; *, post hoc comparisons between Veh WT and Veh hAPP-J20, p=0.0020 and between Veh and ENT-03 hAPP-J20, p=0.0487. FIG. 5C, two-way ANOVA: genotype, F(1,41)=9.977, p=0.0030; treatment, F(1,41)=4.149, p=0.0482; interaction, F(1,41)=1.570, p=0.2173). *, post hoc comparisons between Veh WT and Veh hAPP-J20, p=0.0080 and between Veh hAPP-J20 and ENT-03 hAPP-J20, p=0.0032. FIG. 5D, two-way ANOVA, genotype, F(1, 42)=10.95, p=0.0019; treatment, F(1, 42)=1.352, p=0.2515; interaction, F(1,42)=0.1378, p=0.7123. FIG. 5E, repeated measures two-way ANOVA: genotype/treatment, F(3,45)=11.90, p<0.0001; time, F(4,180)=29.09, p<0.0001; subjects (matching), F(45,180)=2.780, p<0.0001; interaction, F(12, 180)=2.325, p=0.0087; *, post hoc pairwise comparisons between Veh WT and Veh hAPP-J20, day 2, 3, 4, 5: p=0.0143, <0.0001, 0.0037, <0.0001, respectively; #, post hoc pairwise comparisons between Veh hAPP-J20 and ENT-03 hAPP-J20, day 4: p=0.0111. FIG. 5F, two-way ANOVA: genotype, F(1,45)=5.413, p=0.0245; treatment, F(1,45)=16.87, p=0.0002; interaction, F(1,45)=3.630, p=0.0631; *, post hoc comparisons between Veh WT and Veh hAPP-J20, p=0.0236 and between Veh hAPP-J20 and ENT-03 hAPP-J20, p=0.0004. FIG. 5G, two-way ANOVA: genotype, F(1, 45)=4.829, p=0.0332; treatment, F(1,45)=6,861, p=0.0120; interaction, F(1,45)=4.500, p=0.0394). *, post hoc comparisons between Veh WT and Veh hAPP-J20, p=0.0201 and between Veh hAPP-J20 and ENT-03 hAPP-J20, p=0.0064. FIG. 5H, two-way ANOVA, genotype, F(1,45)=4.572, p=0380; treatment, F(1, 45)=0.6015, p=0.4421; interaction, F(1,45)=0.0090, p=0.9249).

Example 7: Detection of ENT-03 in Humans and Mouse Pup Brain

In 1992 Nagata et al identified high concentrations of the bile acid, 7-alpha hydroxy-3-oxo-4-cholestenoic acid (7-HOCA), in human chronic subdural hematoma fluid, (FIG. 1C) (Nagata et al., 1992) and later in acute subarachnoid hemorrhage (Nagata et al., 1995). In 1997, Zhang et al reported that rat brain cells could metabolize 27-hydroxycholesterol to 7-HOCA (Zhang et al., 1997). Subsequently, Björkhem, Sjövall, Griffiths and their collaborators identified 7-HOCA as the most abundant bile acid in human cerebrospinal fluid (Ogundare et al., 2010; Meaney et al., 2007; Saeed et al., 2014; Saeed et al., 2014). 7-HOCA did not appear to a be a biologically active bile acid, in that it did not activate either the FXR, LXR, or RXR/NURR1 receptors, for which bile acids and oxysterols are known ligands (Ogundare et al., 2010). Bjorkhem has proposed that the brain metabolizes 27-hydroxycholesterol that enters from the periphery into 7-HOCA to facilitate the efflux of the oxysterol back into the circulation (Meaney et al., 2007).

Applicant suggests that the presence of ENT-03 in subdural hematoma fluid reflects its possible role in the development of this structure. Following head injury, generally in older people and rarely in infants, a highly vascularized sac-like "organ" develops, with one side deriving from the dura ("outer membrane"), the other from the subarachnoid ("inner membrane") (Yamashima et al., 2000). High concentrations of numerous growth factors, including VEGF accumulate within the fluid (Edlmann et al., 2017). We suggest that ENT-03 appears within the subdural hematoma in an attempt to repair the intracranial injury. In this context, one might wish to speculate why healthy newborns who (rather commonly) experience intracranial trauma following passage through the birth canal, resulting in subdural and parenchymal hemorrhage, generally recover asymptomatically (Looney et al., 2007).

Human Study

Because of the known high concentrations of Compound Ia (7-HOCA) in the chronic subdural hematoma fluid, Applicant analyzed the fluid evacuated from 3 elderly patients with chronic subdurals via LC/MS/MS for the presence of ENT-03.

Patient #1: 66 yo male with 3 weeks of gait instability, headache, difficulty with fine motor movements. CT with 2.2 cm right sided subacute subdural hematoma (SDH) with significant mass effect/midline shift. Indications for drainage were large, symptomatic SDH. Drainage procedure was right sided craniotomy for evacuation of SDH.

Patient #2: 75 yo male who sustained fall 3 weeks prior. Presented with 2-3 days of worsening headache, gait instability, and left lower extremity weakness. CT with bilateral subacute SDH (1.7 cm on right, 1.6 cm on left). Indications for drainage were large, symptomatic SDH. Drainage procedure was bedside twist drill hole craniostomy.

Patient #3: 94 yo male with progressive confusion/altered mental status/gait instability. Work-up demonstrated bilateral subacute on chronic subdural hematomas, both 2.5-3.0 cm in size and with mass effect/brain compression. Indications for drainage were large, symptomatic SDH. Drainage procedure was a bedside twist drill hole craniostomy.

Brain extracts were analyzed via LC/MS/MS for ENT-03. FIG. 7A shows the presence of ENT-03 in brain extract. FIG. 7B shows a reference sample of synthetic ENT-03.

Mouse Pup Study

Based on these reports Applicant analyzed extracts of brain, liver, and kidneys from newborn mice over the first two postnatal weeks for the presence of ENT-03. 3-oxo-bile acids comprise between 18-40% of the unconjugated bile acids within amniotic fluid during the last trimester of human fetal development (Nakagawa et al. 1990) and are present as a significant percentage of the bile acids in healthy newborn urine, gradually diminishing during the first postnatal month (Wahlen et al., 1989 and Kimura et al., 1999). Since 3-oxo-bile acids are abundant during the newborn period, Applicant focused the search for the putative polyamine-bile acid molecule in neonatal mice. Brain and liver extracts were prepared from mice between day 1 through day 24 of age using a protocol designed to capture ENT-03 based on its physical properties as follows.

Frozen neonatal mice were obtained from Layne Laboratories, and tissues dissected in the frozen state. Tissues were dissected in the frozen state: "pinky" (1 d); "large pinky" (2-5 d); "small fuzzy" (6-9 d); "large fuzzy" (10-14 d); "hopper" (15-18 d); "small frozen" (18-24 d). Tissues (0.5-7 grams) were placed into 4 volumes of methanol containing 0.12N HCl and heated at 80° C. for 5 hours. The tissues were macerated, followed by a brief centrifugation.

The supernatant was collected, the volume reduced under a stream of air, and extracted with 1 volume of chloroform/1 volume of methanol. The upper phase was reduced in volume and the samples further analyzed by LC/MS/MS.

Synthetic ENT-03 was used as internal standard in LC/MS/MS analysis to permit localization and identification of the corresponding molecule within the chromatographic analysis.

ENT-03 (Compound III) could be detected in brain and liver of neonatal mice (FIGS. 8A and 8B, respectively). The identity of the endogenous ENT-03 was established by its retention time, mass ([M+H$^+$] m/z=619.6), and MS/MS MRM of the characteristic fragments of mass 545.57 (FIG. 13A) and 474.39 (FIG. 13B). Approximate concentrations of ENT-03 (Compound III) measured in the brain and liver of neonatal mice over the first 3 weeks of life are presented in FIG. 9. In both brain and liver the highest concentrations appear at birth with a gradual reduction over the following 3 weeks.

Analytical procedures: Tissue extracts were spiked with ENT-03-d4 and analyzed on a Triple Quad 5500 MS/MS system equipped with a ExionLC™ LC (SCIEX, Redwood City, CA) using Analyst® 1.7.1 software for instrumental control.

Separation of ENT-03 (Compound III) from tissue matrix components was achieved using a Kinetex® 5 μm C18 100 Å 50×2.1 mm chromatographic column (Phenomenex, Torrance, CA, USA). The column was maintained at 25° C., the flow rate was 0.3 mL/min, and the injection volume was 10 μL. The mobile phase (MP) consisted of A: 0.1% formic acid in water and B: 0.1% formic acid in acetonitrile (ACN, v/v). The mobile phase gradient was as follows: after injection, initial conditions with MPA at 80% were held for 0.3 min, decreased to 70% in 1.7 min, to 50% in 0.5 min and held constant for 0.5 min, returning to initial conditions for another 3.5 min of reequilibration time.

Retention time of ENT-03 (Compound III) was approximately 2.3 min and total run time was 7 min. A turbo ion spray interface was used as the ion source, operating in positive ion mode. Acquisition was performed in multiple reaction monitoring (MRM) mode using m/z 619.6 ([M+H]$^+$)→545.5 (loss of 74.1 ($C_3H_{10}N_2$) and m/z 619.6 ([M+H]$^+$)→474.4 (loss of 145.2 ($C_7H_{19}N_3$) at unit resolution. The internal standard was ENT-03-d4 using MRM of m/z 623.6 ([M+H]$^+$)→549.5 or m/z 623.6 ([M+H]$^+$)→478.5. Ion spray voltage was 4500 V and collision energy was 55 (619.6/474.5) or 43 (619.5/545.5) V. Declustering potential was 70V. The collision gas was nitrogen and the ion spray temperature was 650° C. The MRM transitions were confirmed with a mass error of 10 ppm or less using high-resolution MRM on a X500 QTOF System (SCIEX).

For ENT-03 (Compound III) tissue level estimation, calibration curves were prepared from ENT-03 chromatographic peak areas ratios to the internal standard and using linear regression with a (1/x$^2$) weighting factor that was chosen based on goodness-of-fit criteria, including coefficient of determination ($r^2$), the back-calculated concentration of individual calibrators, and minimization of the intercept value.

Example 8: ENT-05 and Regulatory Phosphatase Inhibition

The purpose of this example was to evaluate the inhibition of regulatory phosphatases by ENT-05.

ENT-05 was synthesized and assayed against the bank of regulatory phosphatases.

ENT-05

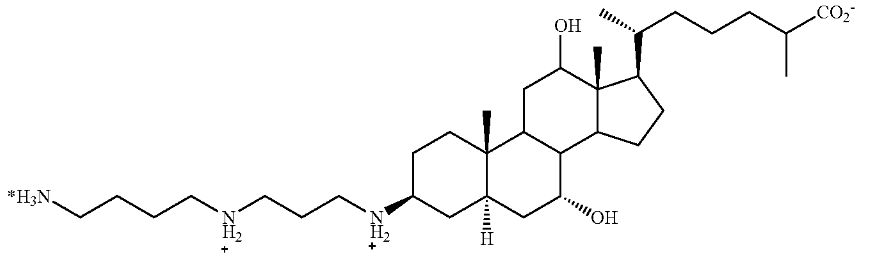

ENT-05, which differs from ENT-03 (Compound III) with respect to the polyamine, and the presence of a hydroxyl group on C12, exhibits inhibitory activity with great specificity against the proto-oncogene PTPN11 (E76K), as shown in Tables 15A and 15B below.

TABLE 15A

| Compound ID | PP1B | PP1A | PP2A Alpha/ PP2R1A Complex | PTPN6/ SHP1 | PTPN11/ SHP | PTPRC/ CD45 | DUSP22/ MKPX |
|---|---|---|---|---|---|---|---|
| ENT-05 | >1.00E−04 | >1.00E−04 | 3.80E−06 | >1.00E−04 | 1.84E−05 | >1.00E−04 | **>1.00E−04 |
| PTP1BInhibitor | 5.99E−06 | 6.91E−06 | ND | 3.47E−06 | 2.31E−06 | 2.80E−05 | 9.63E−06 |
| Canthardic Acid | ND | ND | 2.785E−08 | ND | ND | ND | ND |
| SHP099 | ND | ND | ND | ND | ND | ND | ND |

TABLE 15B

| Compound ID | PTPN2/ TC-PTP | PTPN7/L C-PTP | PTPN12/ PTP-PEST | PTPN1/P TP1B-CD | PN11/ SHP2 | PTPN11/ SHP2-FL (E76K) |
|---|---|---|---|---|---|---|
| ENT-05 | >1.00E−04 | 3.97E−06 | **>1.00E−04 | 2.58E−06 | 9.76E−07 | 4.30E−08 |
| PTP1BInhibitor | 7.53E−06 | 8.65E−06 | 2.16E−06 | 6.23E−06 | ND | ND |
| Canthardic Acid | ND | ND | ND | ND | ND | ND |
| SHP099 | ND | ND | ND | ND | 1.75E−08 | 1.66E−06 |

As another example, ENT-06 was synthesized.

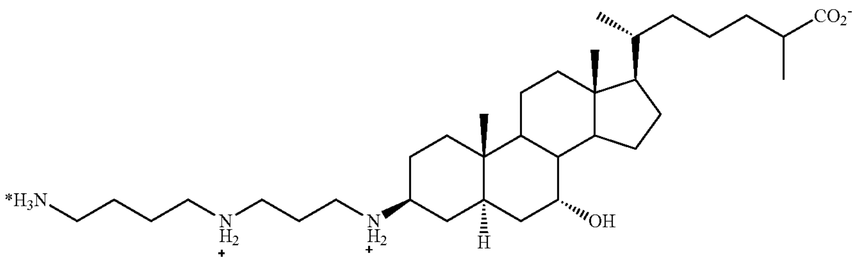

ENT-06

ENT-06 differs from ENT-03 in the substitution of a spermidine for a spermine. ENT-06 exhibits the following inhibitory activity against the human regulatory phosphatases (Tables 16A and 16B):

TABLE 16A

| Compound ID | PP1B | PP1A | PP2A Alpha/ PP2R1A Complex | PTPN6/ SHP1 | PTPN11/ SHP | PTPRC/ CD45 | DUSP22/ MKPXPT |
|---|---|---|---|---|---|---|---|
| ENT-03 | >1.00E−04 | >1.00E−04 | >1.00E−04 | >1.00E−04 | 5.00E−06 | 5.17E−07 | 1.38E−06 |
| ENT-06 | >1.00E−04 | >1.00E−04 | >1.00E−04 | >1.00E−04 | 3.45E−06 | 1.22E−06 | 2.09E−06 |
| PTP1BInhibitor | 4.97E−06 | 6.45E−06 | ND | 3.67E−06 | 2.12E−06 | 2.66E−05 | 7.23E−06 |
| Canthardic Acid | ND | ND | 3.01E−08 | ND | ND | ND | ND |
| SHP099 | ND | ND | ND | ND | ND | ND | ND |

TABLE 16B

| Compound ID | PTPN2/ TC-PTP | PTPN7/ LC-PTP | PTPN12/ PTP-PEST | PTPN1/ PTP1B-CD | PN11/ SHP2 | PTPN11/ SHP2-FL (E76K) |
|---|---|---|---|---|---|---|
| ENT-03 | >1.00E−04 | 6.34E−07 | 8.61E−07 | 1.17E−07 | 1.42E−06 | 2.94E−07 |
| ENT-06 | >1.00E−04 | 1.05E−06 | 8.62E−07 | 1.47E−07 | 3.17E−06 | 3.45E−07 |
| PTP1BInhibitor | 5.86E−06 | 6.89E−06 | 1.21E−06 | 5.10E−06 | ND | ND |
| Canthardic Acid | ND | ND | ND | ND | ND | ND |
| SHP099 | ND | ND | ND | ND | 2.53E−08 | 1.58E−06 |

As can be seen in this example, the substitution of a spermidine for a spermine does not change the inhibitory profile of ENT-03. This example also teaches that the C-12 moiety on ENT-05 (above) drastically alters the specificity of the molecule towards the human regulatory phosphatases.

Phosphatase assays used: The assays used were from Recation Biology Inc. PTPN11/SHP2-FL: Recombinant human PTPN11 full length (Genbank accession #NM_00133043.1; aa 2-597, isoform 1 (canonical)) was expressed in *E Coli* with N-terminal StrepII-TEV, C-terminal His-tag. Mw=71.93 kDa.

PTPN11/SHP2 (E76K)-FL: Recombinant human PTPN11 full length (Genbank accession #NM_00133043.1; aa 2-597, isoform 1 (canonical)) with E76K mutation was expressed in *E. Coli* with N-terminal StrepII-TEV, C-terminal His-tag. Mw=71.93 kDa.

Activation peptide: H2N-LN(pY)IDLDLV(dPEG8)LST(pY)ASINFQK-amide (Fortanet et al., 2016) Substrate: DiFMUP [6,8-difluoro-7-hydroxy-4-methylcoumarin] Final concentration in the assay: For wild type: 0.35 μM Activating peptide; 100 μM DiFMUP; for mutant: No Activating peptide; 100 μM DiFMUP Assay buffer: 60 mM HEPES (pH 7.4), 1 mM EDTA, 75 mM KCl, 75 mM NaCl, 0.01% Brij-35, 5 mM DTT, and 10% DMSO (final).

Other phosphatases assayed: Assay buffer: 25 mM HEPES (pH 7.5), 5 mM $MgCl_2$, 0.01% Brij-35, 1 mM DTT, and 1% DMSO. For PP2A Alpha/PPP2R1A Complex, PP1A, and PP1B 1 mM $MnCl_2$ was added to the assay buffer. The concentration of DiFMUP varied with the phosphatase chosen: 2 μM for PTPN1/PTP1B-CD; 30 μM for PP1B; 10 μM for all other phosphatases. The phosphatase inhibitors were PTP1B CAS 765317-72-4 (Sigma Aldrich cat #539741); Cantharidic acid (Santa Cruz Biotech, cat #sc-201323); SHP009 (ChemieTek, cat #CT-SHP099).

General procedure: Enzyme and substrate are freshly prepared in assay buffer; the enzyme solution is introduced into the reaction well, followed by delivery of the inhibitors in 100% DMSO via acoustic technology (Echo550; nanoliter range); the reaction is incubated for 20 min at room temperature; substrate is then delivered into the reaction well to initiate the reaction; the enzyme activities are monitored (Ex/Em 355/460) by an increase in fluorescence for 120 min at room temperature. The slope (signal/min) of the linear portion of time course is determined and the rates calculated in the presence of inhibitor relative to the DMSO control.

Example 9: Assessment of In Vivo Activity of ENT-05

The purpose of this example was to evaluate the activity of ENT-05 in vivo.

To assess the activity of ENT-05 in vivo, the compound was added to 500 ml of distilled water to a concentration of 10 μg/ml. A *Xenopus leavis* tadpole, premetamorphic, was placed into the solution. Over the course of about 1 hour, the tadpole gradually swelled, stopped moving, and eventually died. A second animal was placed in 500 ml of water, containing 10 μg/ml ENT-05, but also 50 mM NaCl. In this case, the animal survived. The animal was then transferred to spring water without either salt or ENT-05 and remained active over the following days. No similar effect could be observed with ENT-06 or ENT-03.

This example demonstrates that modification of ENT-03 to create ENT-05 yielded a compound with specificity towards PTPN11 (E76K) and likely other as yet undescribed phosphatases. The in vivo pharmacological effect on the tadpole is that of inhibition of sodium reabsorption, most likely in the kidney. The likely target is the sodium-potassium chloride cotransporter type 2 (NKCC2). Very little is currently known about the phosphatases that regulate the activity the NKCC2 of the renal tubule.

The example teaches that ENT-05 has identified a phosphatase that activates the NKCC2 transporter of the channel that can be inhibited by ENT-05. ENT-05 clearly has a potential utility in the treatment of hypertension, similar to the drug furosemide which inhibits renal NKCC2 by a mechanism not involving inhibition of phosphatase activity as well as intracranial hypertension (raised intracranial pressure) and intraocular hypertension (glaucoma).

Example 10: Evaluation of a Deuterated ENT-03 Compound

ENT-03, a polyamine-bile acid conjugate, is expected to be metabolized through the chain of reactions utilized in the synthesis of bile acids. The following molecule was synthesized ENT-03D3 ($C24D_2$, $C25D_1$)

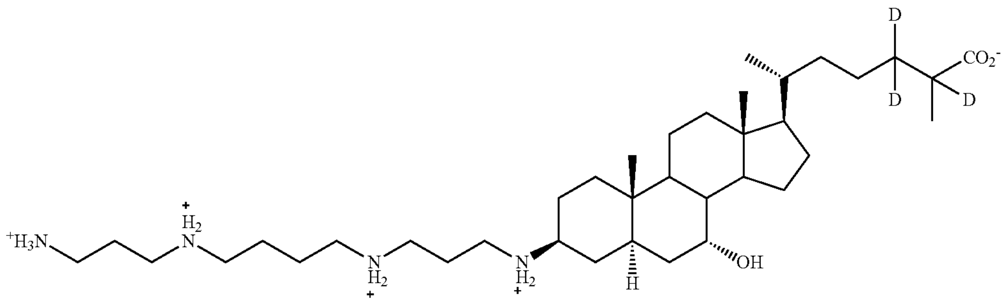

Figure 12:
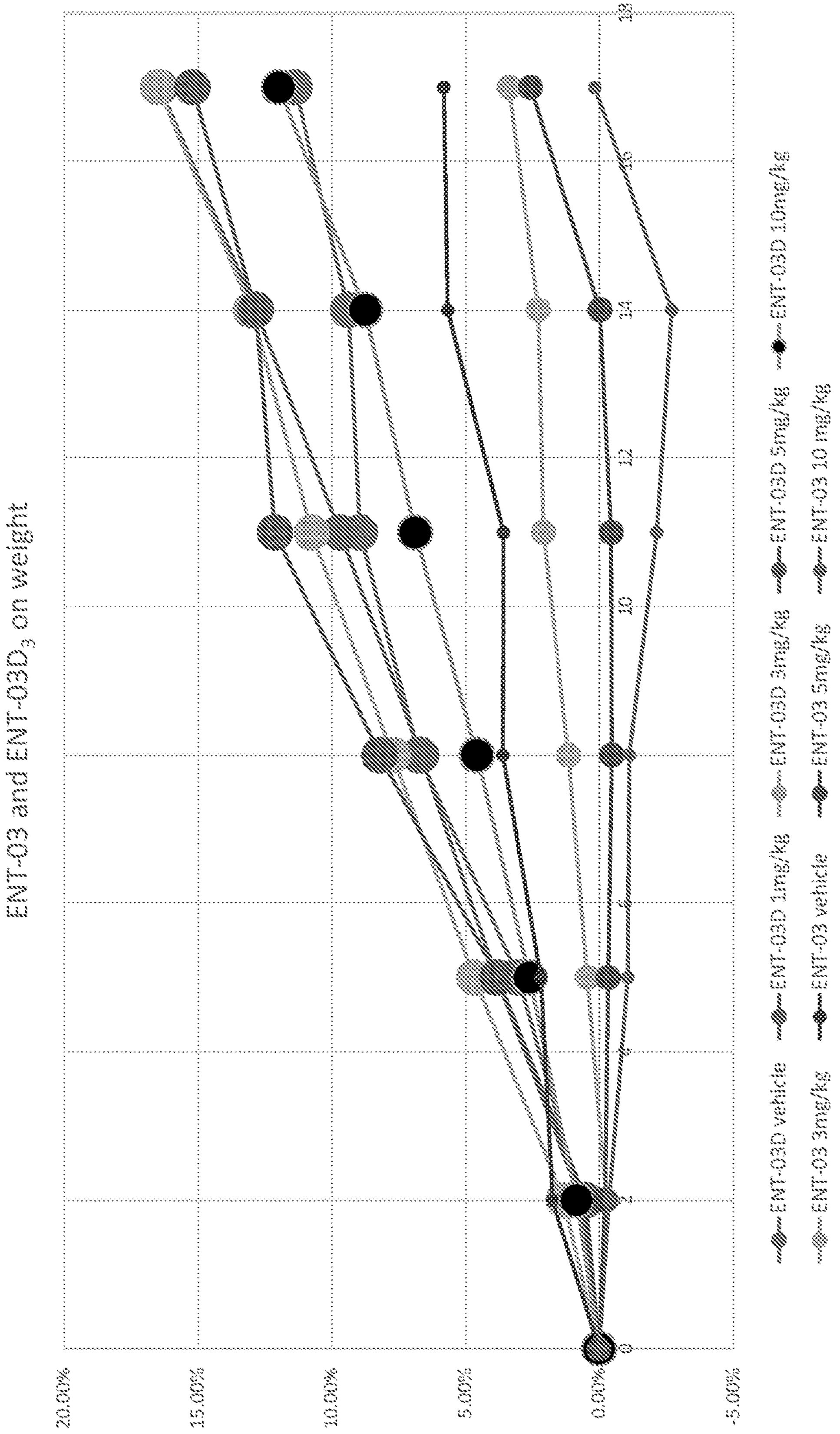
FIG. 12 shows the results on mouse weight gain following administration of ENT-03 as compared to administration of a deuterated form of ENT-03, ENT-03D3.

When administered i.p. to mice the animals gained weight, in contrast to the loss of weight observed when ENT-03 was administered. See FIG. 12. The pharmacological effect is best explained by the presence of the deuterium isotope on the kinetics of the enzymes that successively metabolize the cholesterol side chain, since the deuterated form of ENT-03 should exhibit the same pharmacology as ENT-03. The presence of the deuterium on the side chain likely slows the action of the 2-methylacyl-coenzyme A racemase on C-25, the subsequent action of the dehydrogenase that produces the 24,25-trans-unsaturated derivative by removing the deuterium atoms at C24 and C25, and the subsequent hydration and oxidation at the C24 bond catalyzed by the D-bifunctional protein. Instead, the metabolism of ENT-03D3 will begin with the oxidation at C24 by CYP46A1, yielding the following compound:

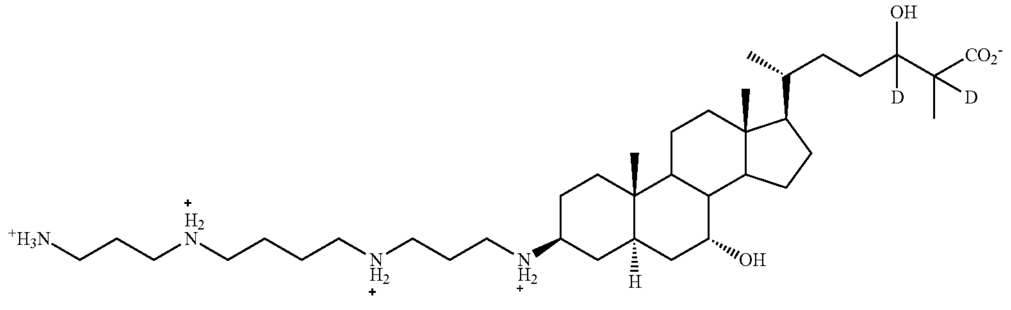

Since the pharmacological effect is weight gain, one can readily predict that the compound inhibits the PTPN11/SHP2 with highest specificity, since SHP2 is known to enhance the central leptin pathway. Inhibition of SHP2 would increase leptin resistance, which would result in an increase in appetite and accumulation of adipose tissue.

Example 11: ENT-03 Stimulates the Transcription of Genes Involved in Red Blood Cell Production and Immune Cell Function in the Spleen of Aged Mice As in humans, the spleen of the mouse plays a primary immune function (Smith et al., 2019). In the adult mouse, however, the spleen can become a red blood cell forming organ in a variety of experimental settings (Morita et al., 2011), although it normally cedes this function to the bone marrow during the first few weeks of postnatal life (Wolber et al., 2002).

To explore the effects of ENT-03 (Compound III) on the hematopoietic and immune systems of the spleens of young and aged mice, the transcriptomes of the spleens of the animals described in the previous rejuvenation of gut transcriptome Example were studied.

The transcriptional response to ENT-03 (Compound III) in the aged spleen (Table 17, below) was more intense than in the spleen of the younger animals (Table 18, below). 109 genes in the aged spleen were significantly upregulated by ≥1.5 fold, compared with 4 genes in the young. The genes most robustly induced in the old spleen are responsible for erythropoiesis (italicized rows in Table 17) and immune functions (bold rows in Table 17). The genes involved in hemoglobin synthesis are at the top of the list (hemoglobin α and β proteins, aminolevulinic acid synthase) along with abundant proteins involved in the structure/function of the red blood cell (the chloride-bicarbonate exchanger, band 4.2 protein, and 2,3 biphosphoglycerate mutase). These data are compatible with the hypothesis that ENT-03 is stimulating a program in the aged mouse normally operational during the first few weeks of postnatal life.

Generally speaking, the immune genes induced by ENT-03 correspond to those of the innate arm. These include IL-21, secreted by T cells and NKT cells, which has broad stimulatory effects across the breadth of the innate immune system (Spolski et al., 2014); and the IL22 binding protein (IL22ra2), secreted by numerous innate immune cells, that helps curb the action of the proinflammatory cytokine IL22 following resolution of an infection (Huber et al., 2012) reducing the probability of post-inflammatory tumorigenesis (Huber et al., 2012). Other highly induced genes encode for receptors that are expressed by dendritic cells and macrophages, such as DC-SIGN (CD209) which plays a key role in the recognition by dendritic cells of viruses and other pathogens (Svajger et al., 2010); the macrophage chemokine receptor CCR2, which plays a critical role in the normal reparative response to tissue injury (Boniakowski et al., 2018); and the Fc alpha/mu receptor (Fcamr) that mediates endocytosis of IgM coated pathogens by the macrophage (Shibuya et al., 2000).

None of the splenic genes highly induced by ENT-03 in the aged spleen appear in the set of responsive genes in the spleen of young animals.

TABLE 17

Transcriptional response in ENT-03 treated vs. untreated aged spleen

| Gene | Chrom | log2FoldΔ (treated vs untreated) | padj | gene description |
|---|---|---|---|---|
| Hbb-bt | chr7 | 3.7347 | 1.0409E−18 | hemoglobin_beta_adult_t_chain |
| Hbb-bs | chr7 | 3.7096 | 3.6524E−17 | hemoglobin_beta_adult_s_chain |
| Hba-a1 | chr11 | 3.3063 | 2.5751E−12 | hemoglobin_alpha_adult_chain_1 |
| Alas2 | chrX | 3.1518 | 5.5197E−10 | aminolevulinic_acid_synthase_2_erythroid |
| Apol11b | chr15 | 2.866 | 1.2774E−06 | apolipoprotein_L_11b |
| Snca | chr6 | 2.7302 | 6.7702E−08 | synuclein_alpha |
| Il21 | chr3 | 2.6995 | 1.4958E−07 | interleukin_21 |
| Trim10 | chr17 | 2.6019 | 1.4584E−06 | tripartite_motif-containing_10 |
| Slc4a1 | chr11 | 2.4837 | 0.000018554 | solute_carrier_family_4_(anion_exchanger)_member_1 |
| Crisp3 | chr17 | 2.4801 | 0.00001087 | cysteine-rich_secretory_protein_3 |
| BC094916 | chr1 | 2.4206 | 1.6453E−12 | cDNA_sequence_BC094916 |
| Klra13-ps | chr6 | 2.2739 | 0.000055312 | killer_cell_lectin-like_receptor_subfamily_A_member_13 |
| Ms4a4c | chr19 | 2.2629 | 1.4648E−06 | membrane-spanning_4-domains_subfamily_A_member_4C |
| Gm15674 | chr1 | 2.2616 | 0.00025227 | predicted_gene_15674 |
| Fcamr | chr1 | 2.26 | 0.00023611 | Fc_receptor_IgA_IgM_high_affinity |
| Cd209a | chr8 | 2.2387 | 9.2759E−08 | CD209a_antigen |
| Il22ra2 | chr10 | 2.1757 | 0.000018994 | interleukin_22_receptor_alpha_2 |
| Klri1 | chr6 | 2.1282 | 0.00021207 | killer_cell_lectin-like_receptor_family_1_member_1 |
| Apol1c | chr15 | 2.1187 | 1.9578E−07 | apolipoprotein_L_7c |
| S100a4 | chr3 | 2.0775 | 1.1352E−06 | S100_calcium_binding_protein_A4 |
| Dscaml1 | chr9 | 2.0299 | 0.0013572 | Down_syndrome_cell_adhesion_molecule_like_1 |
| Angptl1 | chr1 | 2.0064 | 0.0017673 | angiopoietin-like_1 |
| Gm4841 | chr18 | 1.993 | 0.0016464 | predicted_gene_4841 |
| Bex6 | chr16 | 1.9805 | 0.001294 | brain_expressed_gene_6 |
| Epb4.2 | chr2 | 1.9538 | 0.0024314 | erythrocyte_protein_band_4.2 |
| Gml5056 | chr8 | 1.9402 | 0.00074293 | predicted_gene_15056 |
| Gml5848 | chr1 | 1.9395 | 0.0014089 | predicted_gene_15848 |
| RP23-291K4.3 | chr12 | 1.9042 | 0.0034892 | predicted_gene_29361 |
| Slfn4 | chr11 | 1.9041 | 0.0033094 | schlafen_4 |
| Erv3 | chr2 | 1.9021 | 0.00041989 | endogenous_retroviral_sequence_3 |
| Adipoq | chr16 | 1.8937 | 0.0037472 | adiponectin_C1Q_and_collagen_domain_containing |
| Ccr2 | chr9 | 1.8781 | 0.00066331 | chemokine_(C—C_motif)_receptor_2 |
| Gml6170 | chr11 | 1.8443 | 0.0018004 | predicted_gene_16170 |
| Hba-a2 | chr11 | 1.8432 | 0.0050296 | hemoglobin_alpha_adult_chain_2 |
| Chordc1 | chr9 | 1.8282 | 0.000022877 | cysteine_and_histidine-rich_domain_(CHORD)-containing_zinc-binding_protein_1 |
| Ms4a4b | chr19 | 1.8267 | 0.00074293 | membrane-spanning_4-domains_subfamily_A_member_4B |
| Ceacam2 | chr7 | 1.8202 | 0.0019663 | carcinoembryonic_antigen-related_cell_adhesion_molecule_2 |
| Trim59 | chr3 | 1.8191 | 0.00051144 | tripartite_motif-containing_59 |
| A430104N18Rik | chr11 | 1.7777 | 0.0012186 | Mir142_host_gene_(non-protein_coding) |
| H3f3c | chr2 | 1.7761 | 0.006137 | H3_histone_family_3C |
| Gpr174 | chrX | 1.7489 | 0.0013772 | G_protein-coupled_receptor_174 |
| Ccl22 | chr8 | 1.7457 | 0.0017096 | chemokine_(C—C_motif)_ligand_22 |
| Bpgm | chr6 | 1.7452 | 0.0012861 | 23-bisphosphoglycerate_mutase |
| 9130020K20Rik | chr4 | 1.744 | 0.0086611 | RIKEN_cDNA_9130020K20_gene |
| 4632427E13Rik | chr7 | 1.736 | 0.0051337 | RIKEN_cDNA_4632427E13_gene |
| Mndal | chr1 | 1.7343 | 0.00029797 | myeloid_nuclear_differentiation_antigen_like |
| Klra10 | chr6 | 1.7308 | 0.0092544 | killer_cell_lectin-like_receptor_subfamily_A_member_10 |
| Cr2 | chr1 | 1.7172 | 0.000057646 | complement_receptor_2 |
| Chil5 | chr3 | 1.715 | 0.00659 | chitinase-like_5 |
| Art2a-ps | chr7 | 1.714 | 0.000026233 | ADP-ribosyltransferase_2a_pseudogene |
| Gml8853 | chr7 | 1.7076 | 0.010528 | predicted_gene_18853 |
| Samd9l | chr6 | 1.6916 | 0.0025867 | sterile_alpha_motif_domain_containing_9-like |
| Kmo | chr1 | 1.6871 | 3.5618E−07 | kynurenine_3-monooxygenase_(kynurenine_3-hydroxylase) |
| Nudt17 | chr3 | 1.6761 | 0.0062584 | nudix_(nucleoside_diphosphate_linked_moiety_X)-type_motif_17 |
| Pyhin1 | chr1 | 1.6712 | 0.0016474 | pyrin_and_HIN_domain_family_member_1 |
| Gm14446 | chr19 | 1.6636 | 7.5769E−09 | predicted_gene_14446 |
| Gm16754 | chr9 | 1.663 | 0.013156 | predicted_gene_16754 |
| Skint3 | chr4 | 1.6602 | 0.0066421 | selection_and_upkeep_of_intraepithelial_T_cells_3 |
| Gm15382 | chr15 | 1.6598 | 0.013129 | predicted_gene_15382 |
| Gm14539 | chrX | 1.6584 | 0.011189 | predicted_gene_14539 |
| B3galt2 | chr1 | 1.6529 | 0.012914 | UDP-Gal:betaGlcNAc_beta_13-galactosyltransferase_polypeptide_2 |
| Gm20506 | chr17 | 1.6511 | 0.0055872 | predicted_gene_20506 |
| Trbv3 | chr6 | 1.6449 | 0.00075871 | T_cell_receptor_beta_variable_3 |
| Gvin1 | chr7 | 1.6426 | 0.0030561 | GTPase_very_large_interferon_inducible_1 |
| Gapdhs | chr7 | 1.6401 | 0.012163 | glyceraldehyde-3-phosphate_dehydrogenase_spermatogenic |
| Igkv10-95 | chr6 | 1.6339 | 0.004547 | immunoglobulin_kappa_variable_10-95 |
| Tgtp1 | chr11 | 1.6241 | 8.2575E−07 | T_cell_specific_GTPase_1 |
| Tnfrsf4 | chr4 | 1.6208 | 6.0546E−08 | tumor_necrosis_factor_receptor_superfamily_member_4 |
| Gpr171 | chr3 | 1.6192 | 2.4193E−06 | G_protein-coupled_receptor_171 |

TABLE 17-continued

Transcriptional response in ENT-03 treated vs. untreated aged spleen

| Gene | Chrom | log2FoldΔ (treated vs untreated) | padj | gene description |
|---|---|---|---|---|
| Gm12359 | chr11 | 1.612 | 0.017289 | predicted_gene_12359 |
| Tespa1 | chr10 | 1.6091 | 2.5415E−07 | thymocyte_expressed_positive_selection_associated_1 |
| Cxcr6 | chr9 | 1.6084 | 0.00074332 | chemokine_(C—X—C_motif)_receptor_6 |
| Gm9733 | chr3 | 1.6052 | 0.0033127 | predicted_gene_9733 |
| Phf11a | chr14 | 1.5879 | 0.000072239 | PHD_finger_protein_11A |
| Bcl2114 | chr6 | 1.5821 | 0.0054825 | BCL2-like_14_(apoptosis_facilitator) |
| Wfikkn1 | chr17 | 1.5812 | 0.019127 | WAP_FS_Ig_KU_and_NTR-containing_protein_1 |
| Gm12064 | chr11 | 1.5812 | 0.017839 | predicted_gene_12064 |
| Stat4 | chr1 | 1.5777 | 0.00028359 | signal_transducer_and_activator_of_transcription_4 |
| Gimap1os | chr6 | 1.5766 | 0.000022374 | GTPase_IMAP_family_member_1_opposite_strand |
| AI504432 | chr3 | 1.5764 | 0.00043427 | expressed_sequence_AI504432 |
| Ddx43 | chr9 | 1.5727 | 0.014119 | DEAD_(Asp-Glu-Ala-Asp)_box_polypeptide_43 |
| Cyp4b1-ps2 | chr4 | 1.5655 | 0.02129 | cytochrome_P450_family_4_subfamily_b_polypeptide_1_pseudogene_2 |
| Hsph1 | chr5 | 1.5639 | 5.0637E−09 | heat_shock_105 kDa/110 kDa_protein_1 |
| Gm26613 | chr11 | 1.5638 | 0.017312 | predicted_gene_26613 |
| Phf11c | chr14 | 1.562 | 0.00010438 | PHD_finger_protein_11C |
| Mterf1a | chr5 | 1.5619 | 0.0012861 | mitochondrial_transcription_termination_factor_1a |
| Igkv4-74 | chr6 | 1.5563 | 0.022022 | immunoglobulin_kappa_variable_4-74 |
| Ifi203 | chr1 | 1.5516 | 0.00025302 | interferon_activated_gene_203 |
| Hbq1b | chr11 | 1.5454 | 0.020239 | hemoglobin_theta_1B |
| Insm1 | chr2 | 1.5427 | 0.0010054 | insulinoma-associated_1 |
| Placs | chr5 | 1.5426 | 6.9197E−14 | placenta-specific_8 |
| Gad1-ps | chr10 | 1.5374 | 0.019744 | glutamate_decarboxylase_1_pseudogene |
| Cdcp1 | chr9 | 1.5358 | 0.00036257 | CUB_domain_containing_protein_1 |
| Ly6d | chr15 | 1.5352 | 8.0833E−10 | lymphocyte_antigen_6_complex_locus_D |
| Serpina1e | chr12 | 1.5291 | 0.015891 | serine_(or_cysteine)_peptidase_inhibitor_clade_A_member_1E |
| Gpr82 | chrX | 1.5279 | 0.024478 | G_protein-coupled_receptor_82 |
| Gm10521 | chr1 | 1.5248 | 0.0029372 | predicted_gene_10521 |
| Stap1 | chr5 | 1.5241 | 0.00044727 | signal_transducing_adaptor_family_member_1 |
| Ms4a1 | chr19 | 1.5233 | 0.0019425 | membrane-spanning_4-domains_subfamily_A_member_1 |
| Bzrap1 | chr11 | 1.5216 | 0.020864 | benzodiazepine_receptor_associated_protein_1 |
| Il4i1 | chr7 | 1.521 | 0.000013199 | interleukin_4_induced_1 |
| Tgtp2 | chr11 | 1.5203 | 2.163E−08 | T_cell_specific_GTPase_2 |
| Caps1 | chr15 | 1.5194 | 0.02621 | calcyphosine-like |
| 4631405J19Rik | chr2 | 1.5184 | 0.02629 | RIKEN_cDNA_4631405J19_gene |
| A430110L20Rik | chr1 | 1.5155 | 0.025229 | RIKEN_cDNA_A430110L20_gene |
| Malat1 | chr19 | 1.51 | 0.0013738 | metastasis_associated_lung_adenocarcinoma_transcript_1_(non-coding_RNA) |
| Asprv1 | chr6 | 1.508 | 0.0062434 | aspartic_peptidase_retroviral-like_1 |
| Ighj4 | chr12 | 1.507 | 0.000033775 | immunoglobulin_heavy_joining_4 |
| Spo11 | chr2 | 1.5059 | 0.016958 | SPO11_meiotic_protein_covalently_bound_to_DSB_homolog (*S._cerevisiae*) |

TABLE 18

Transcriptional response in ENT-03 treated vs. untreated young spleen

| GeneName | Chrom | log2FoldΔ | padj | Gene description |
|---|---|---|---|---|
| BC147527 | chr13 | 1.5492 | 5.13E−09 | cDNA_sequence_BC147527 |
| Actr | chr10 | 1.5441 | 5.13E−09 | ARP6_actin-related_protein_6 |
| Gt(ROSA)26Sor | chr6 | 1.5188 | 0.0043575 | gene_trap_ROSA_26_Philippe_Soriano |
| Lsm7 | chr10 | 1.5096 | 1.164E−06 | LSM7_homolog_U6_small_nuclear_RNA_associated_(*S._cerevisiae*) |

Example 12: Treatment Induced Gene Expression in Mouse Stomach Tissues, Comparison of ENT-03 and ENT-02 (MSI-1436)

The purpose of this example is to identify transcriptional changes between young and old mice and compare the effects of ENT-02 (MSI-1436) treatments on gene expression with those of ENT-03. Mice were treated with ENT-03, ENT-02 (MSI-1436) or a vehicle control. Samples of stomach tissues from the mice were analysed by RNA-sequencing on an Illumina platform.

The aims of this analysis were to: identify transcriptional changes between young and old mice; determine if ENT-01 or ENT-02 (MSI-1436) treatments could reverse those age-related changes; and compare the effects of ENT-02 (MSI-1436) treatments on gene expression with those of ENT-03.

To achieve these aims, data were subject to a quality control evaluation, differential expression and functional enrichment analyses, as well as a congruence analysis. Data for ENT-ENT-03 treatments were compared to the results generated for ENT-02 (MSI-1436).

To identify those genes that were significantly differentially expressed between groups, an arbitrary threshold was applied based on fold changes in expression. A four-fold change in expression between groups was used as a measure of pseudo-significance in the absence of replicate samples. At this threshold, differentially expressed genes were identified in all contrasts. For gene expression changes associated with ageing, or ENT-02 (MSI-1436) treatments in young mice, the proportions of down-regulated genes (72-80%) were higher than the proportions of upregulated genes (20-28%). The trend was opposite for both treatments in old mice, where 82-89% of gene expression changes were up-regulation and 12-18% were down-regulation.

When comparing differentially expressed genes across contrasts, it was apparent that genes downregulated in aged mice overlapped significantly with genes up-regulated in response to ENT-02 treatment in old mice (hypergeometric P<0.0001). To a lesser extent, there was also significant overlap in genes down-regulated in aged mice and up-regulated in response to treatment in old mice. In young mice, genes that were down-regulated upon ENT-02 treatment significantly overlapped with the down-regulated genes associated with ageing. This result was also true for genes up-regulated in both contrasts.

For each comparison, the number of sample genes significant at various statistical thresholds and fold change 4 were tallied. As mentioned previously, for statistical robustness, only those with an adjusted p-value <0.05 should be considered.

The following statistical significance threshold was chosen to define differentially expressed genes: ● fold change ≥4

To investigate the overlap between significant genes from the contrasts performed, a set of scatter plots was generated comparing the fold change between pairs of contrasts. Functional enrichment analysis was performed upon those genes where expression differences were greater than four-fold in individual contrasts. Reactome and GO term databases were interrogated to identify relevant terms that were significantly enriched in differentially expressed genes (enrichment P<0.05). Pathways related to the immune system such as platelet degranulation, antimicrobial peptides and complement cascade were generally amongst the most enriched pathways across the contrasts. Pathways such as keratinisation and keratinocyte differentiation were enriched in genes changed upon ageing or ENT-02 (MSI-1436) treatments in old mice. Pathways such as muscle contractions and sarcomere organisation were enriched in genes changed upon ageing, but were also enriched in ENT-02 treatment-affected genes in young mice.

Significant genes (at fold change 4) from each contrast were analysed for enrichment of Reactome pathway membership using a hypergeometric test by mapping genes to genes (if appropriate). Enrichment (p-value <0.05) was assessed for the union of selected genes.

Genes that were differentially expressed in response to ENT-02 treatment, as identified in this study, were compared to those that were associated with ENT-03 treatments, respectively. ENT-03 treatment-associated gene expression changes were identified previously.

Across all contrasts at the relevant statistical thresholds used to identify significant features, there were ten or less genes that changed in expression upon both treatments (ENT-02 and ENT-03). Note that this included the gene expression changes associated with ageing. Specifically, the expression of only one gene, Syp12, was changed significantly between the old and young mice of both studies.

Comparisons of the genes which were down-regulated in ageing and up-regulated in treatment revealed that genes affected by ENT-02-treatment did not overlap with those affected by ENT-03.

TABLE 19

Summary of effect size evaluations: The number of significant features in each comparison at a range of effect size thresholds. Each row relates to a single comparison, while each column relates to a fold change threshold

| Contrast | Direction | Any | 1.3× | 2× | 4× | 8× | 16× |
|---|---|---|---|---|---|---|---|
| ENT-01 vs control (young) | Up-regulated | 7460 | 1430 | 232 | 58 | 38 | 28 |
| ENT-01 vs control young) | Down-regulated | 7553 | 2367 | 642 | 144 | 47 | 12 |
| ENT-02 (MSI-1436) vs control (young) | Up-regulated | 7346 | 1860 | 232 | 30 | 7 | 1 |
| ENT-02 (MSI-1436) vs control (young) | Down-regulated | 7667 | 2429 | 531 | 120 | 43 | 16 |
| ENT-01 vs control (old) | Up-regulated | 7553 | 2430 | 766 | 317 | 168 | 116 |
| ENT-01 vs control (old) | Down-regulated | 7460 | 2235 | 431 | 66 | 25 | 11 |
| ENT-02 (MSI-1436) vs control (old) | Up-regulated | 7416 | 2109 | 657 | 298 | 139 | 42 |
| ENT-02(MSI-1436) vs control (old) | Down-regulated | 7597 | 1395 | 203 | 38 | 7 | 1 |
| Old vs young (control) | Up-regulated | 7386 | 1715 | 312 | 76 | 28 | 11 |
| Old vs young (control) | Down-regulated | 7627 | 2486 | 734 | 218 | 85 | 39 |
| Old vs young (ENT-01) | Up-regulated | 7479 | 1647 | 559 | 263 | 178 | 135 |
| Old vs young (ENT-01) | Down-regulated | 7534 | 1606 | 267 | 69 | 36 | 27 |
| Old vs young (ENT-02 (MSI-1436)) | Up-regulated | 7669 | 2644 | 676 | 190 | 78 | 39 |
| Old vs young (ENT-02 (MSI-1436)) | Down-regulated | 7344 | 1986 | 314 | 63 | 8 | 4 |

To investigate the overlap between selected genes from the multiple contrasts performed, the number of overlapping differentially expressed genes were counted (defined using fold change 4) between all pairwise combinations of the comparisons performed. The amount of overlap is represented in FIGS. 28A-28D. For each comparison, the value in the plot represents the number of intersecting selected genes and the colour represents the Jaccard index (the intersection over the union) for the two contrasts under consideration.

Congruence analysis was performed. Specifically, the analysis compared the effects of human- or shark-origin compound analogues on murine stomach tissue gene expression profile as follows:

ENT-02 (MSI-1436) was compared to ENT-03.

Scatter plots, upset plots, venn diagrams, hypergeometric tests and Spearman rank correlation tests were employed to assess the level of overlap as shown in FIGS. 15-27.

Note that significantly differentially expressed genes in ENT-03-specific contrasts were determined using a statistical threshold of FDR-adjusted $P<0.05$. Whereas the ENT-02 (MSI-1436)-specific contrasts in this study defined significant genes using a cutoff of greater than four-fold change in expression.

Genes Down-Regulated in Ageing and Up-Regulated Upon Treatment

Transcripts that were significantly down-regulated in ageing and up-regulated by treatment of old mice were identified for each compound. Congruence between these sets of genes was then assessed by comparing ENT-02 (MSI-1436)-affected genes to those of ENT-03, these results are illustrated in the Venn diagram in FIG. 15.

Figure 16:
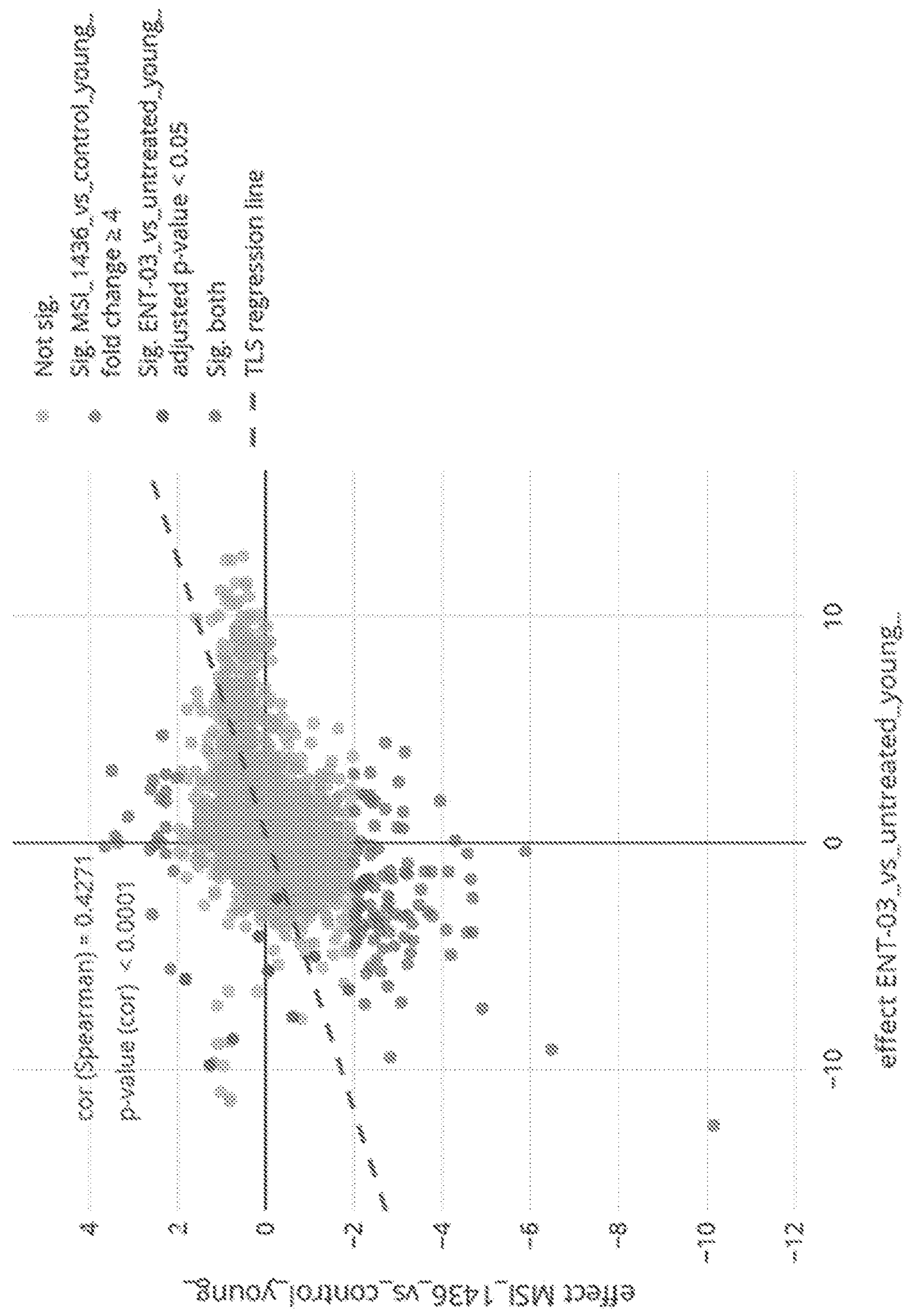
FIG. 16 shows a scatter plot comparing significant genes in ENT-02 (MSI-1436) vs control (young) against ENT-03 vs untreated (young). Genes are represented by points. The color of the point indicates which set the gene is assigned to. For each gene the log 2(fold change) in the ENT-02 (MSI- 1436) vs control (young) contrast (y-axis) and the log 2(fold change) in the ENT-03 vs untreated (young) contrast (x-axis) are shown.
Figure 17:
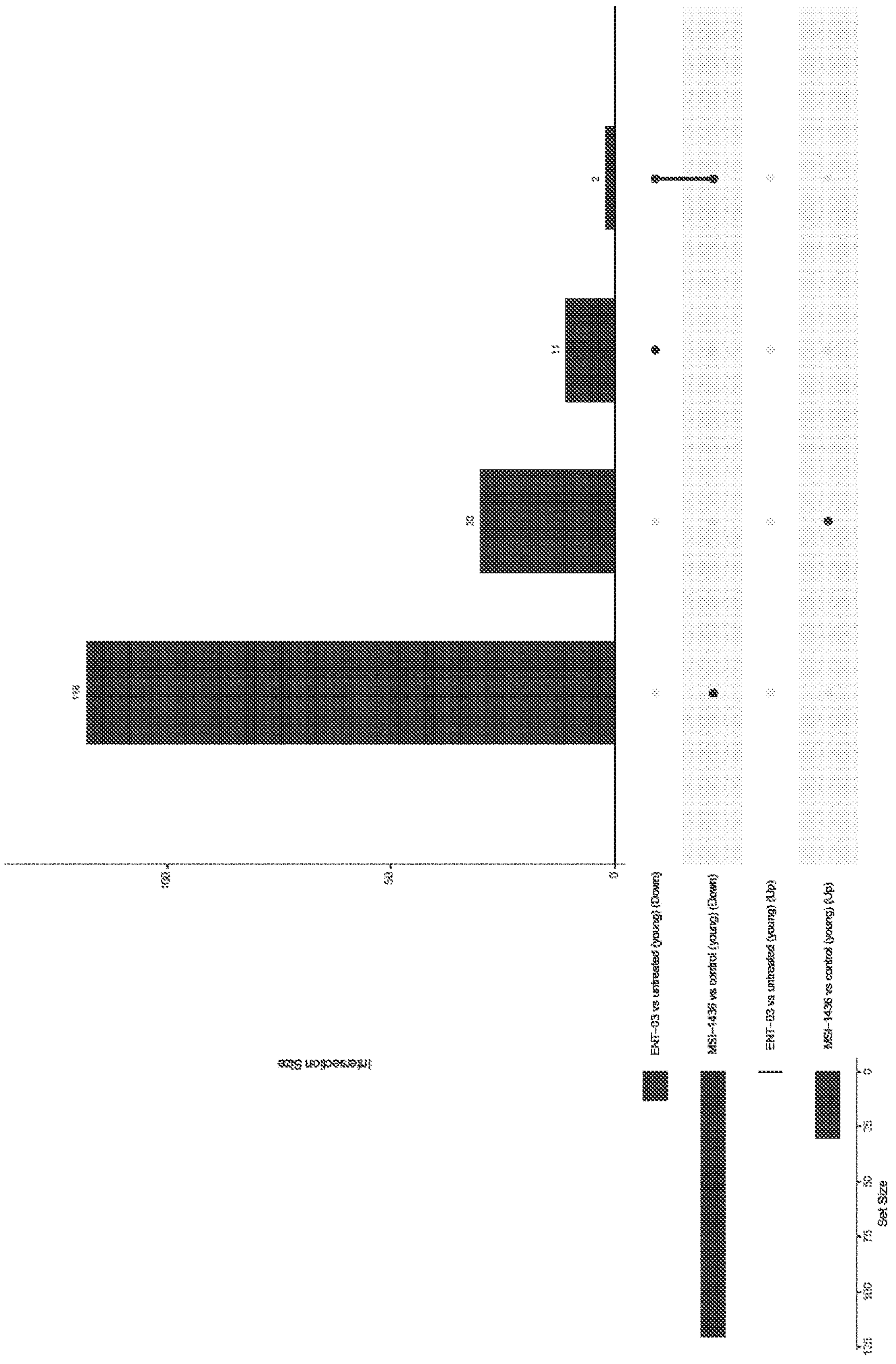
FIG. 17 shows an upset plot of significant genes according to Example 12. A plot showing the interaction between sets of up- and down-regulated genes. The leftmost barchart shows the size of each set used as input. The top barchart shows the exclusive size of each set (i.e., each gene is only counted once in this barchart). The dot-plot in the centre shows the sets interacting in each case.
Figure 22:
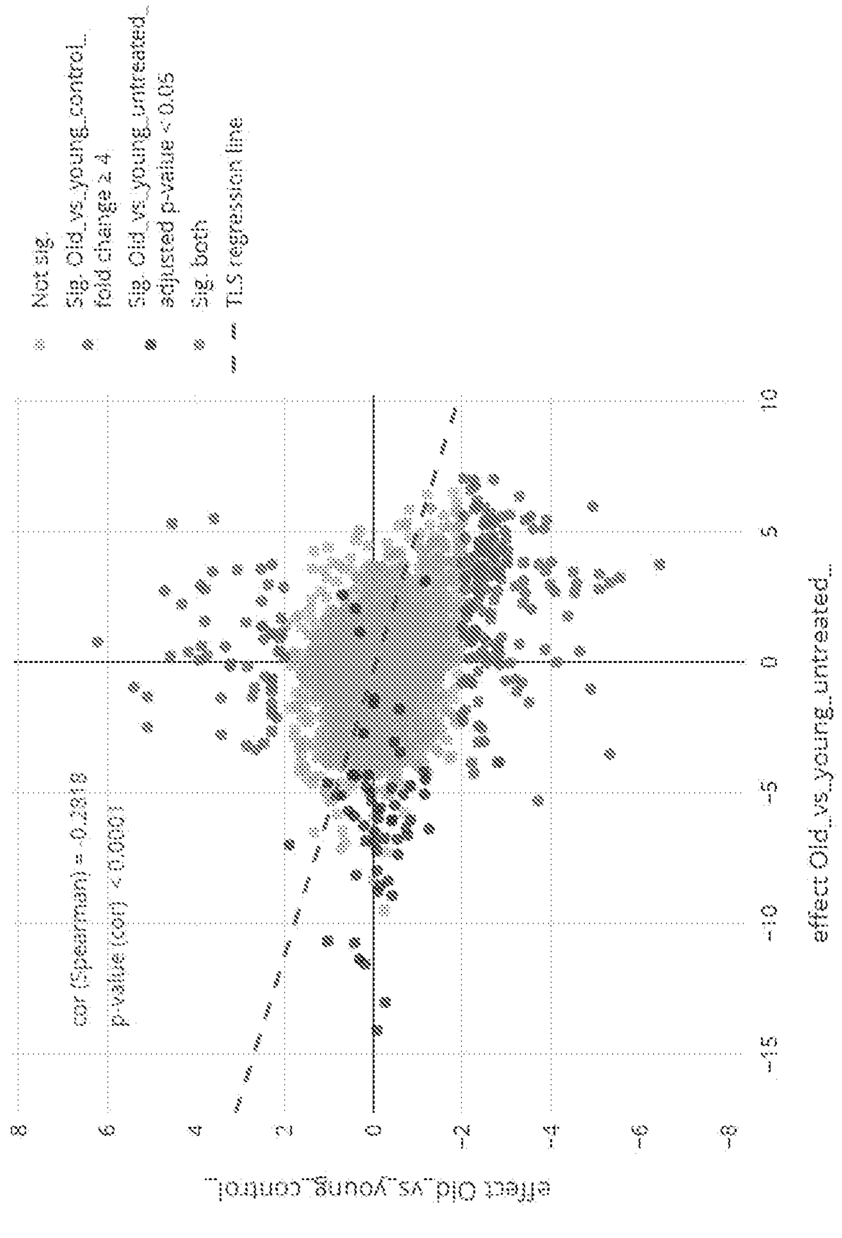
FIG. 22 shows a scatter plot comparing significant genes in Old vs young (control) against Old vs young (untreated). Genes are represented by points. The colour of the point indicates which set the gene is assigned to. For each gene the log 2(fold change) in the Old vs young (control) contrast (y-axis) and the log 2(fold change) in the Old vs young (untreated) contrast (x-axis) are shown.
Figure 23:
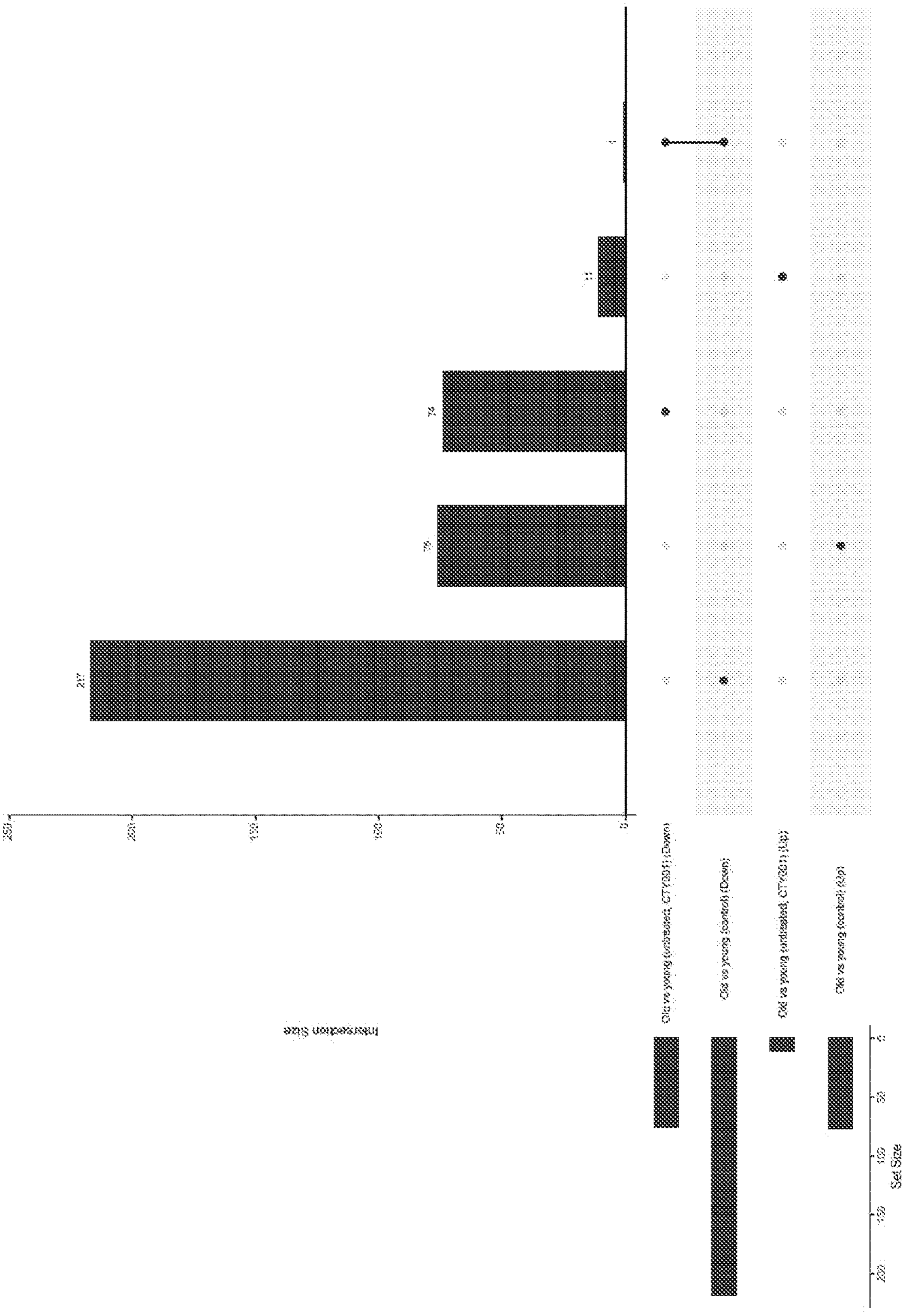
FIG. 23 shows a Upset plot of significant genes according to Example 12. A plot showing the interaction between sets of up- and down-regulated genes. The leftmost barchart shows the size of each set used as input. The top barchart shows the exclusive size of each set (i.e., each gene is only counted once in this barchart). The dot-plot in the centre shows the sets interacting in each case.
Figure 25:
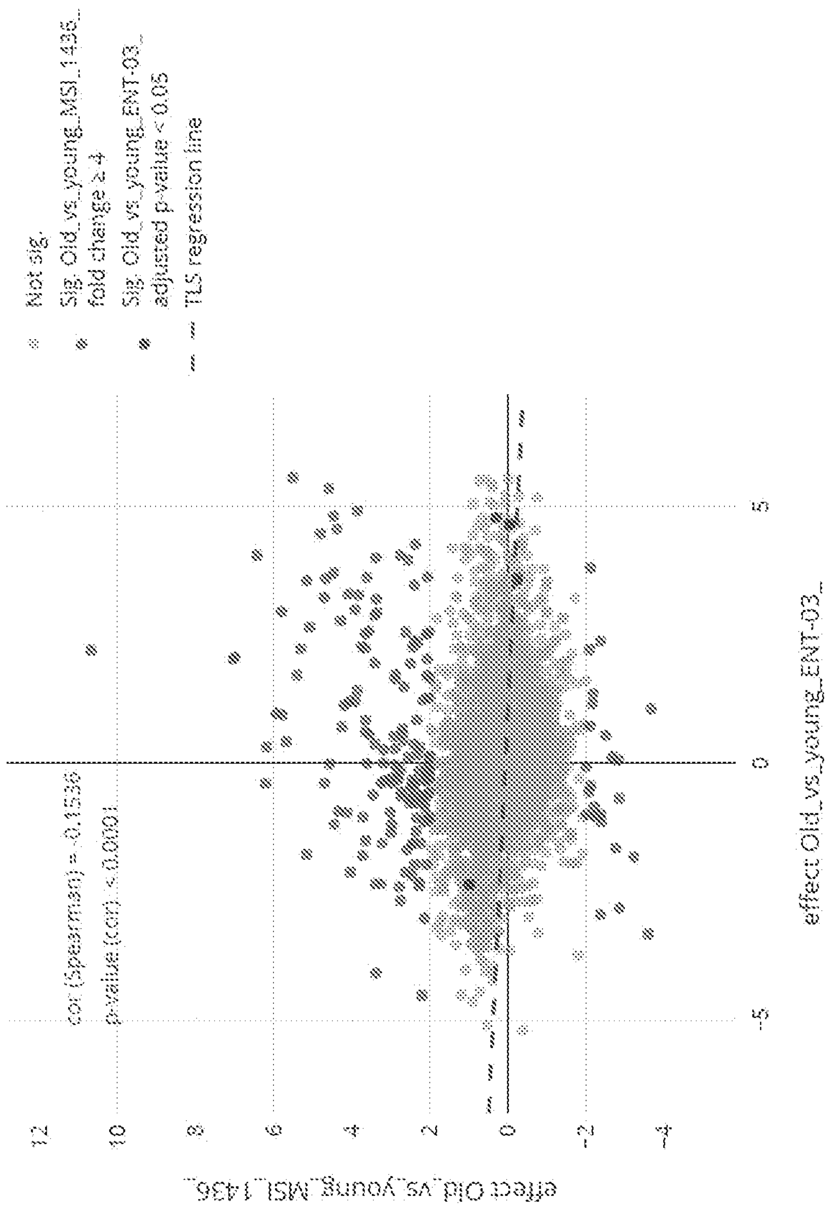
FIG. 25 shows a scatter plot comparing significant genes in Old vs young (ENT-02; MSI-1436) against Old vs young (ENT-03). Genes are represented by points. The colour of the point indicates which set the gene is assigned to. For each gene the log 2(fold change) in the Old vs young (ENT-02; MSI-1436) contrast (y-axis) and the log 2(fold change) in the Old vs young (ENT-03) contrast (x-axis) are shown.
Figure 26:
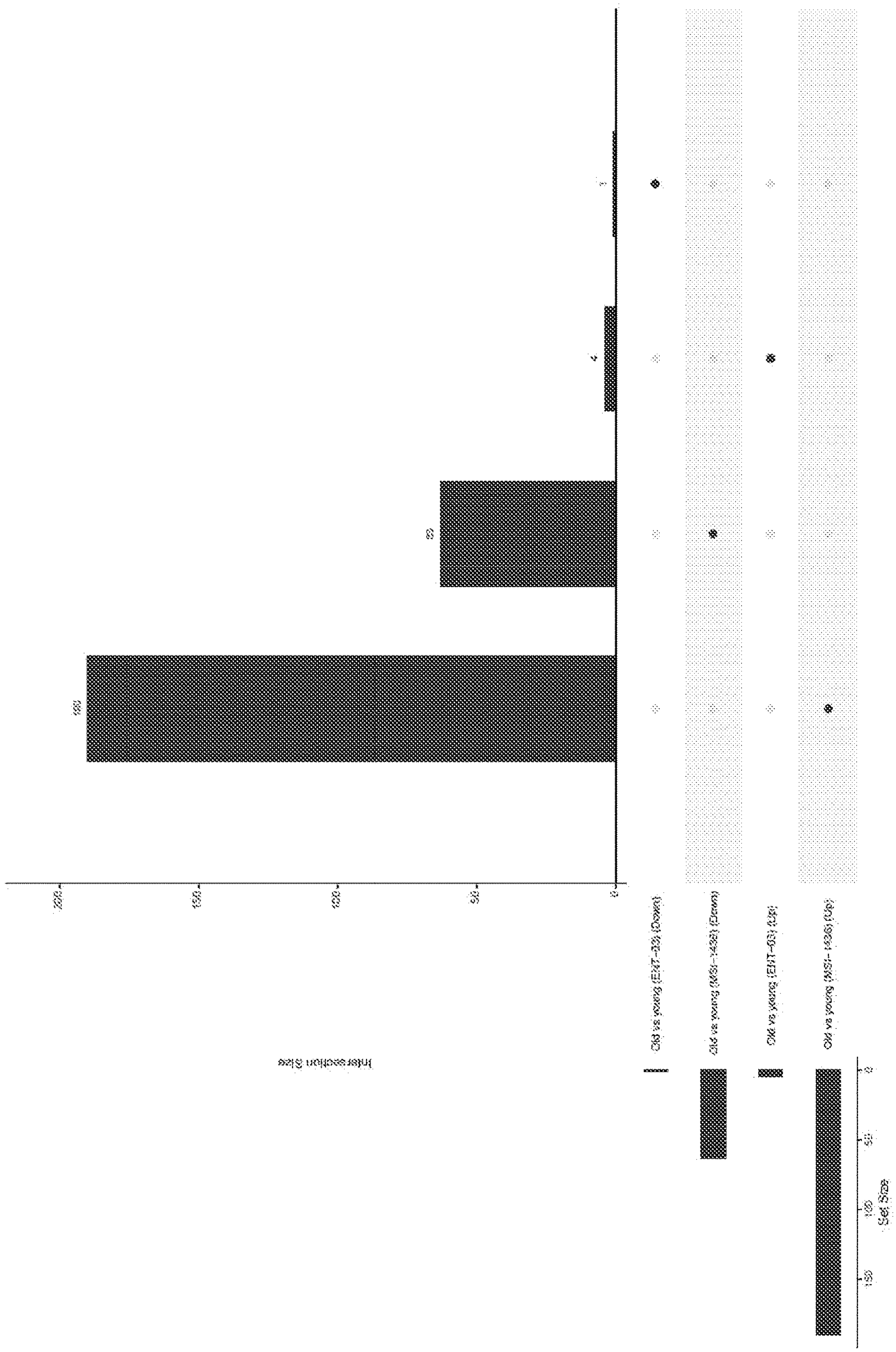
FIG. 26 shows an Upset plot of significant genes according to Example 12. A plot showing the interaction between sets of up- and down-regulated genes. The leftmost barchart shows the size of each set used as input. The top barchart shows the exclusive size of each set (i.e., each gene is only counted once in this barchart). The dot-plot in the centre shows the sets interacting in each case.

Congruence analysis results are shown in FIG. 16 which shows a scatter plot comparing significant genes in ENT-02 (MSI-1436) vs. control (young) against ENT-03 vs untreated (young). FIG. 22 shows a scatter plot comparing significant genes in Old vs young (control) against Old vs young (untreated). FIG. 25 shows a scatter plot comparing significant genes in Old vs young (ENT-02 (MSI-1436)) against Old vs young (ENT-03).

Figure 18:
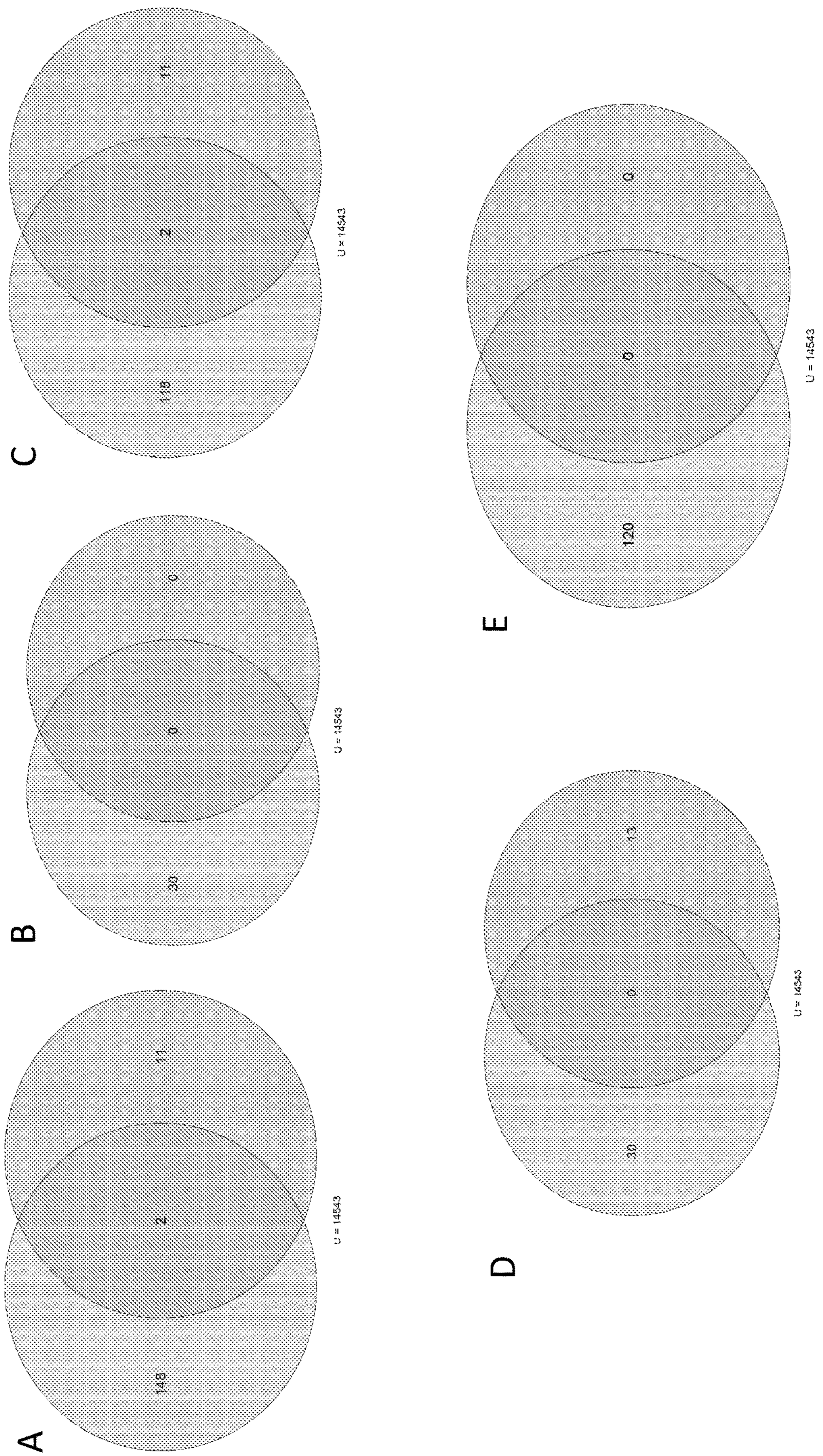
FIGS. 18A-18E.

FIG. 18 shows venn diagrams of significant genes in ENT-02 (MSI-1436) vs control (young) against ENT-03 vs untreated (young). Each plot considers a different interaction of sets; either ignoring direction of perturbation, considering only up-regulated genes, considering only down-regulated genes, or examining the over-lap between those genes up-regulated in one contrast and those genes down-regulated in another. The symbol U denotes the universe.

Figure 19:
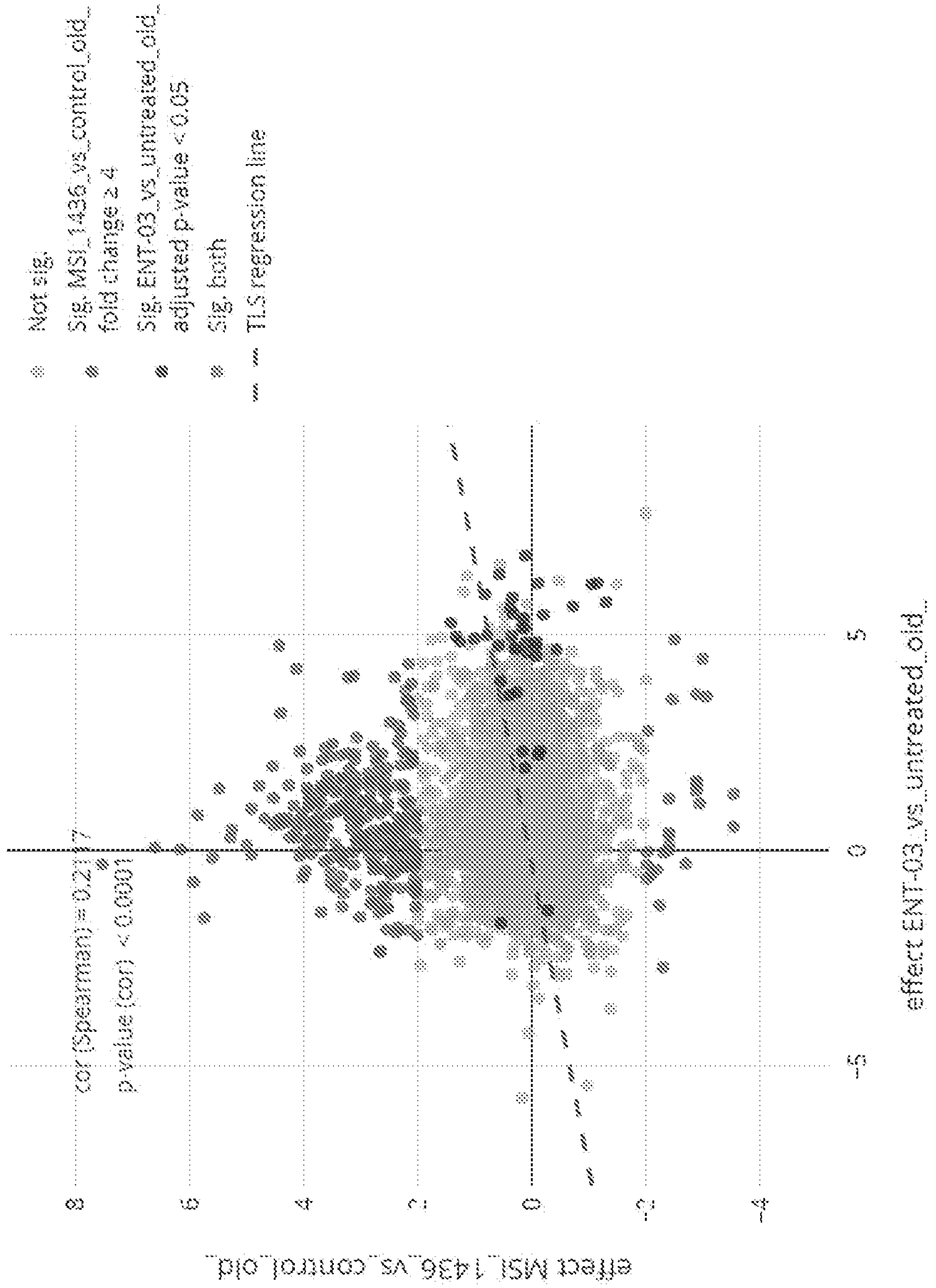
FIG. 19 shows a scatter plot comparing significant genes in MSI-1436 (aminosterol 1436) vs control (old) against ENT-03 vs untreated (old). Genes are represented by points. The colour of the point indicates which set the gene is assigned to. For each gene the log 2(fold change) in the MSI-1436 vs control (old) contrast (y-axis) and the log 2(fold change) in the ENT-03 vs untreated (old) contrast (x-axis) are shown.
Figure 20:
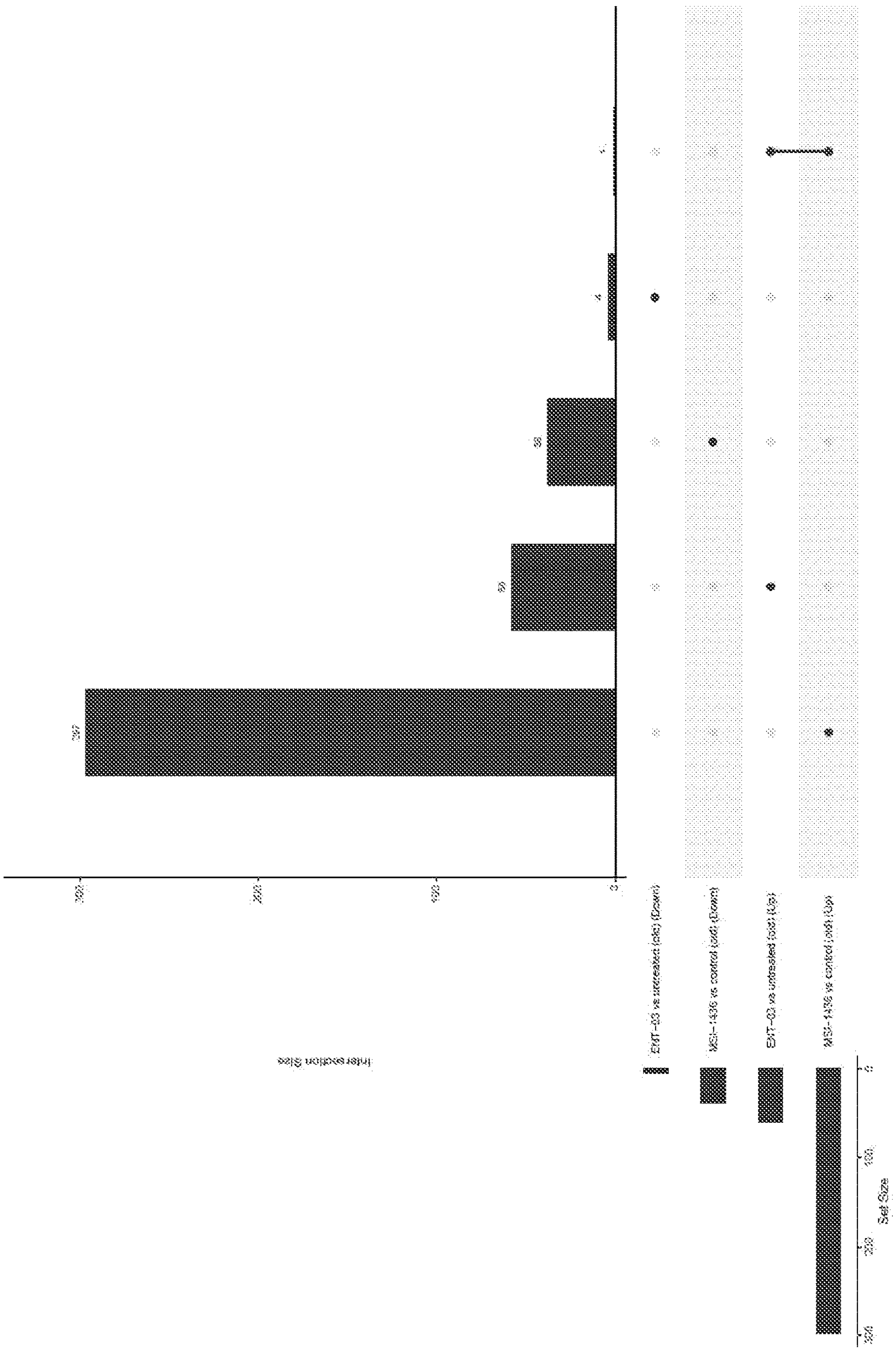
FIG. 20 shows an Upset plot of significant genes according to Example 12. A plot showing the interaction between sets of up- and down-regulated genes. The leftmost barchart shows the size of each set used as input. The top barchart shows the exclusive size of each set (i.e., each gene is only counted once in this barchart). The dot-plot in the centre shows the sets interacting in each case.
Figure 21:
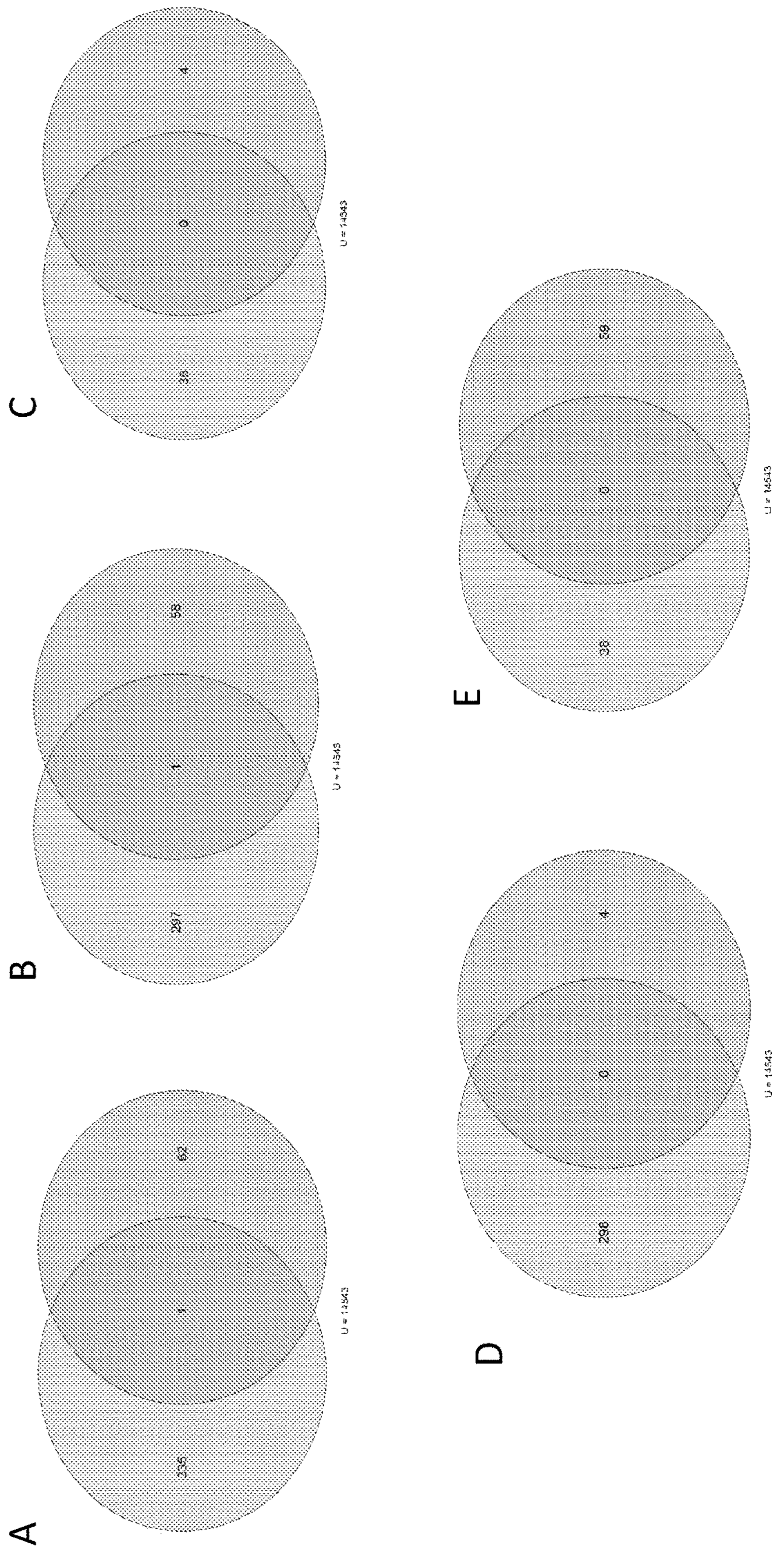
FIGS. 21A-21E.
Figure 24:
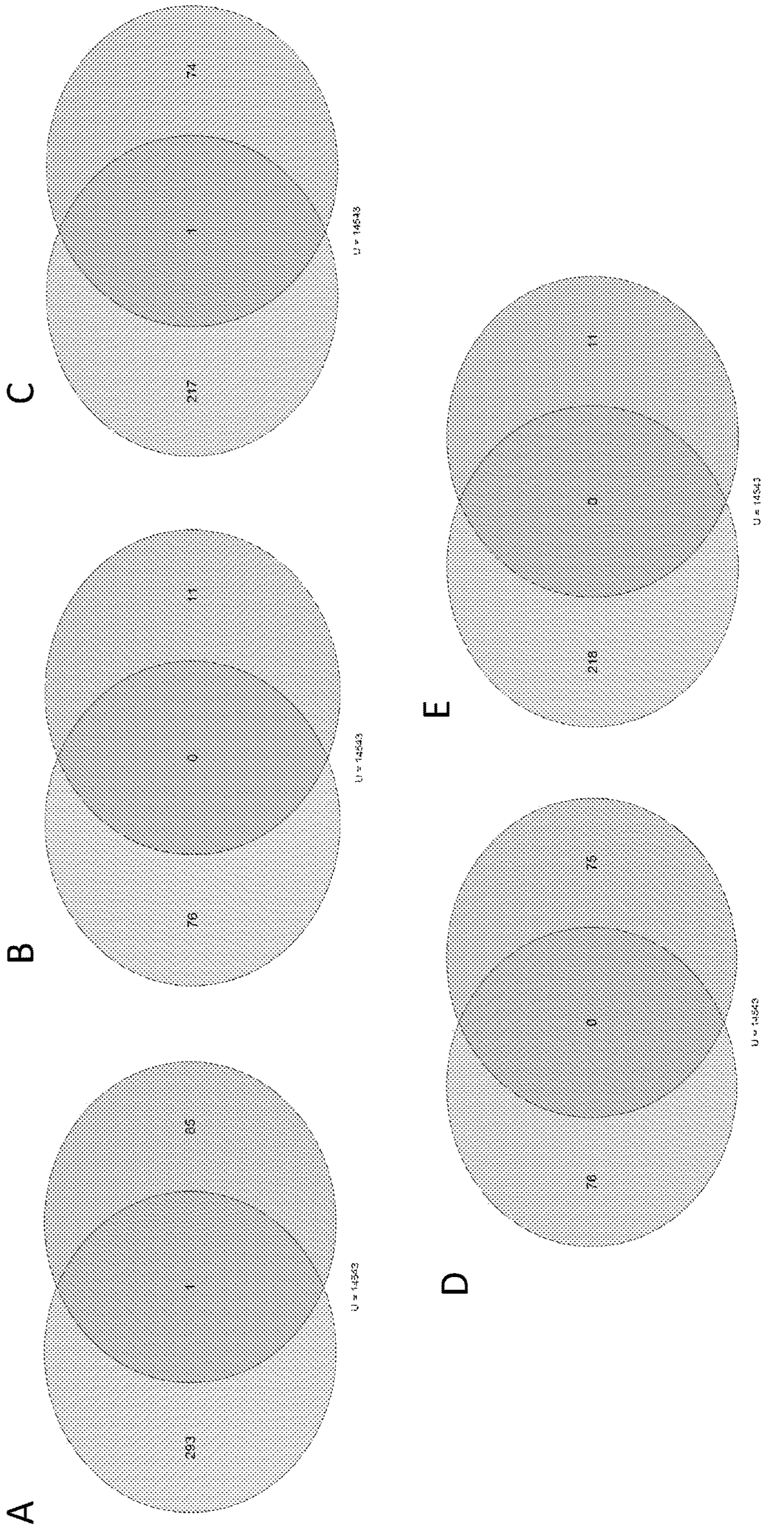
FIGS. 24A-24E.
Figure 27:
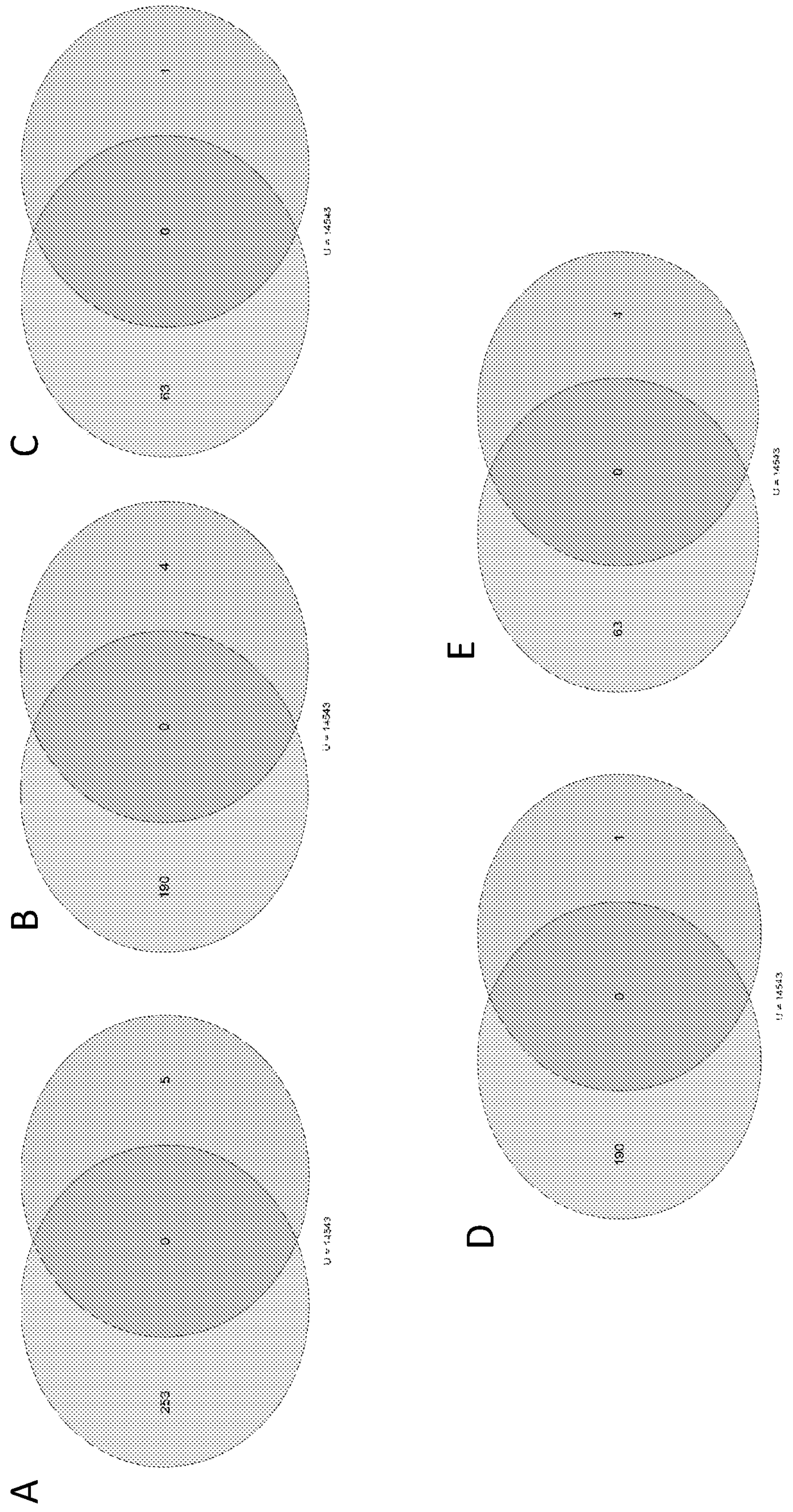
FIGS. 27A-27E.
Figure 28A:
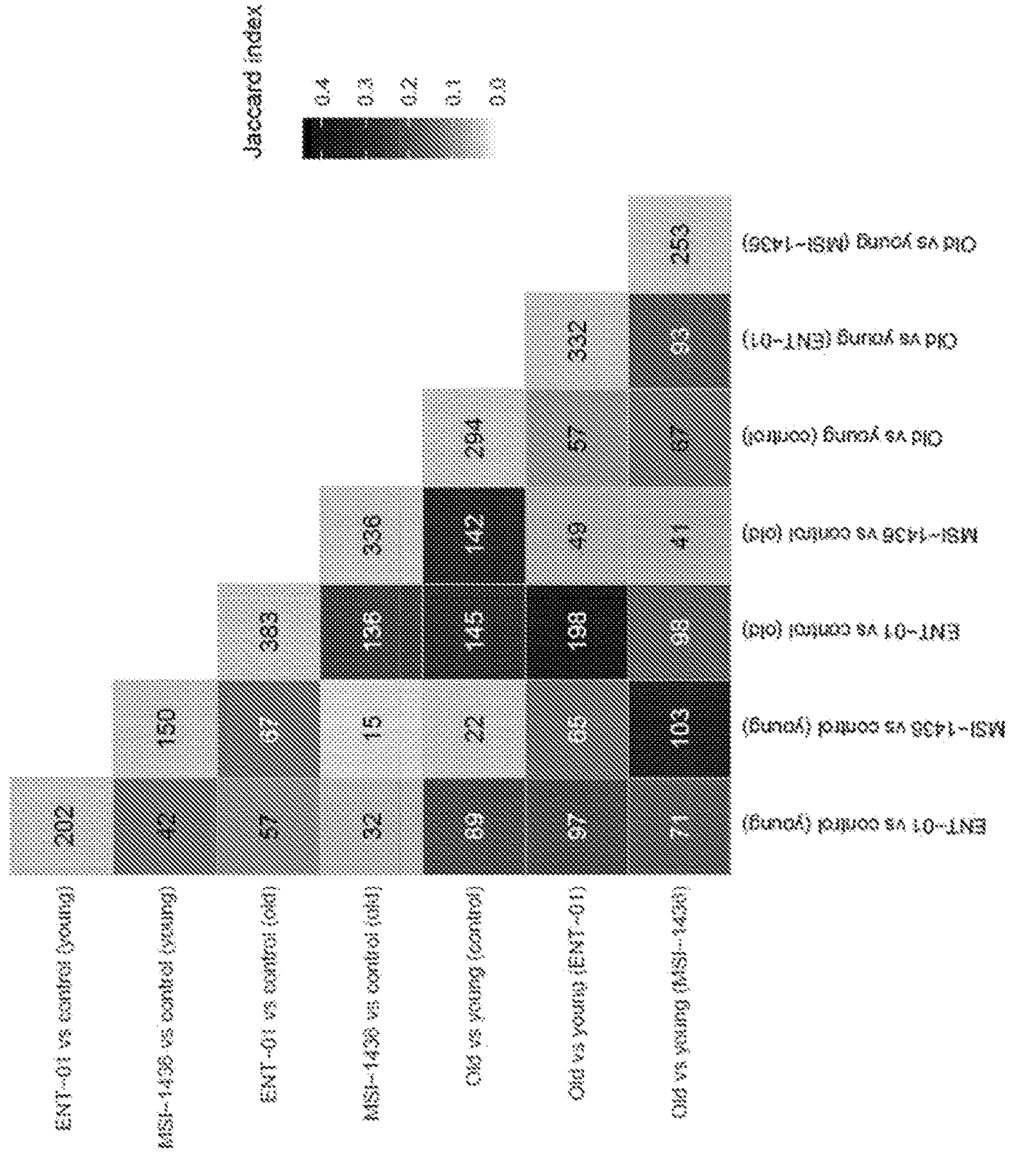
FIG. 28A: Heatmap of overlaps of up- and down-regulated (y-axis) vs. up- and down-regulated (x-axis) selected genes for each contrast.
Figure 28B:
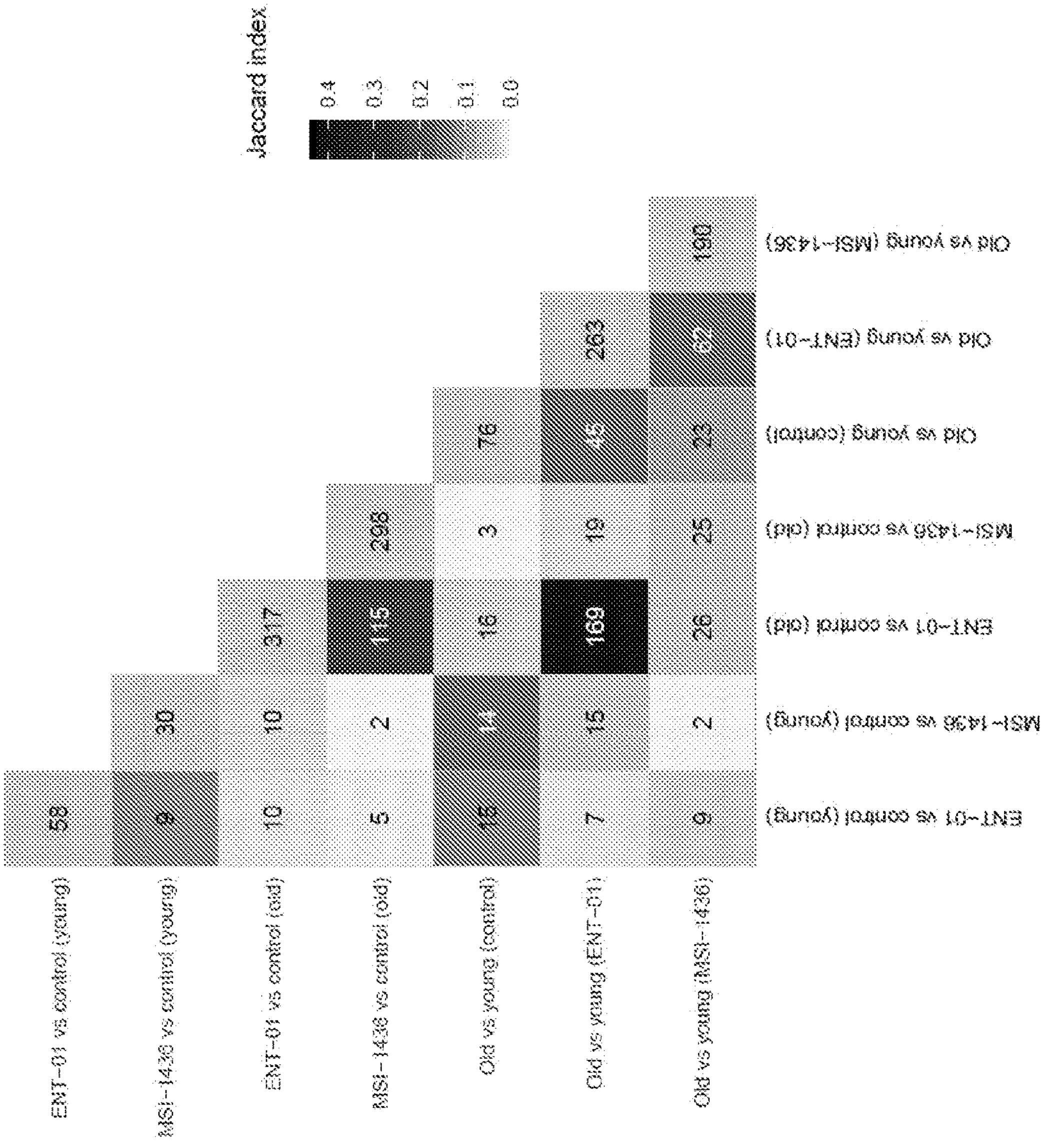
FIG. 28B: Heatmap of overlaps of up-regulated (y-axis) vs. up-regulated (x-axis) selected genes for each contrast.
Figure 28C:
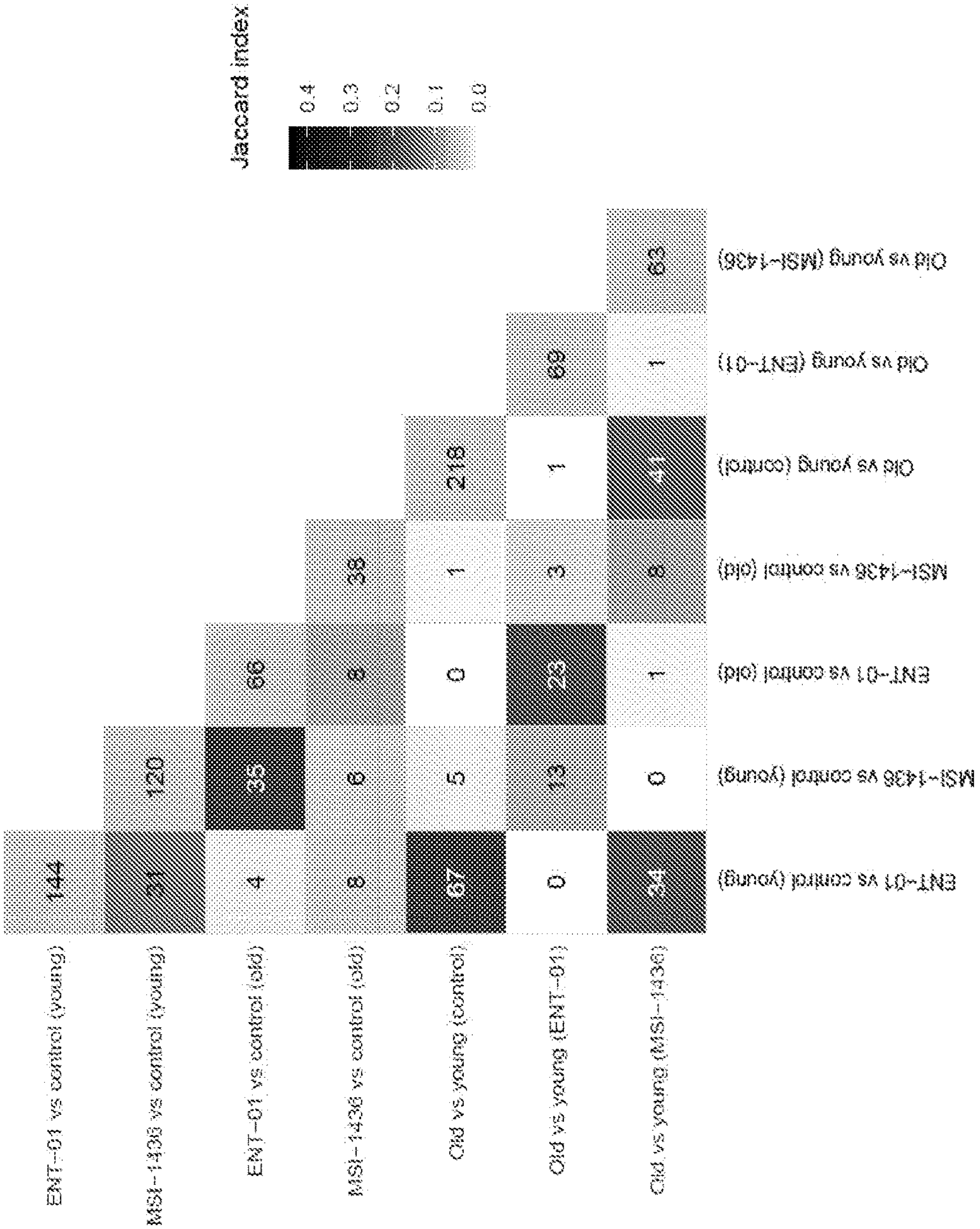
FIG. 28C: Heatmap of overlaps of down-regulated (y-axis) vs. down-regulated (x-axis) selected genes for each contrast.
Figure 28D:
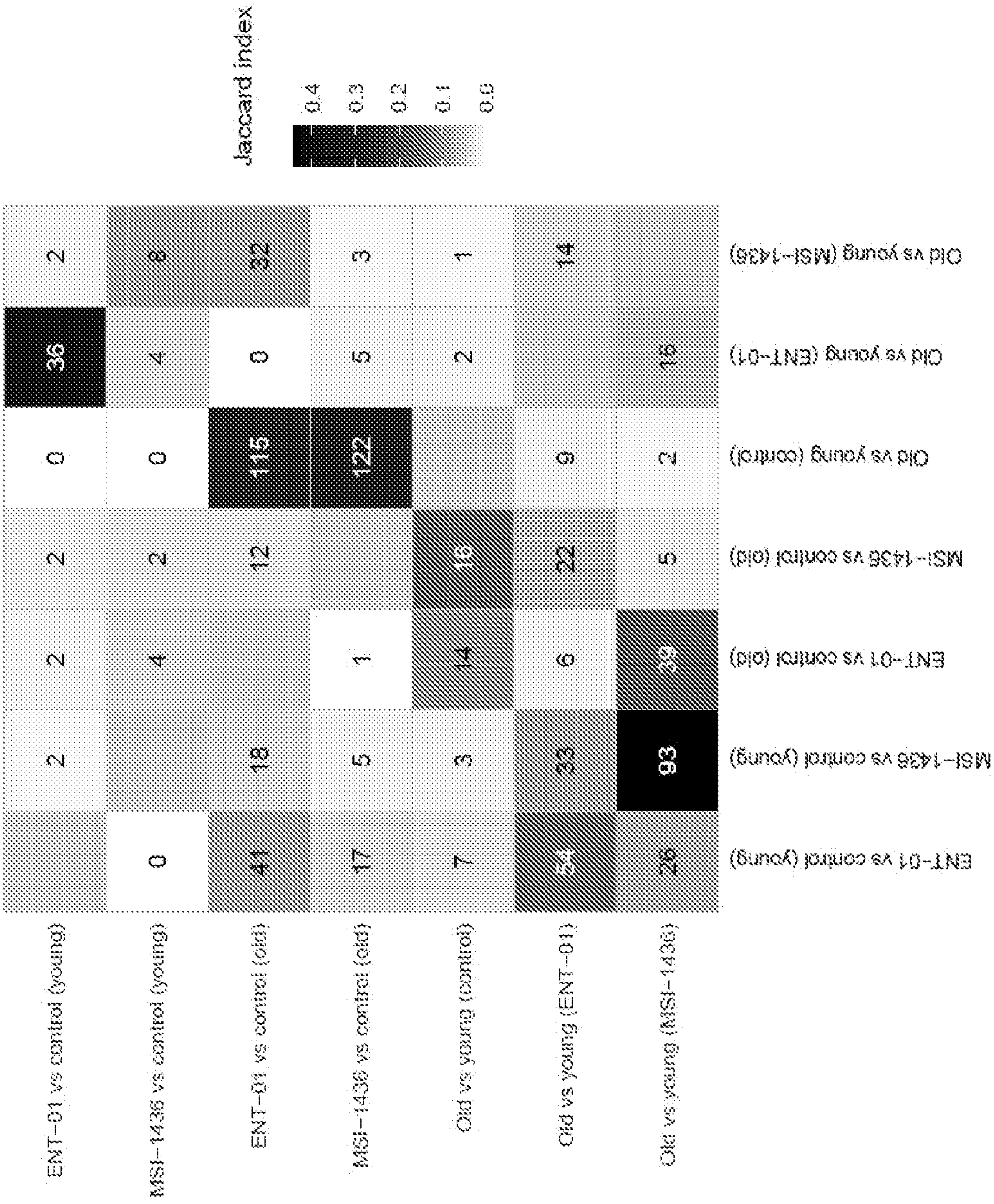
FIG. 28D: Heatmap of overlaps of up-regulated (y-axis) vs. down-regulated (x-axis) selected genes for each contrast.

Congruence analysis results are shown in FIG. 19 which shows a scatter plot comparing significant genes in ENT-02 (MSI-1436) vs. control (old) against ENT-03 vs untreated (old). FIG. 21 shows Venn diagrams of significant genes in ENT-02 (MSI-1436) vs control (old) against ENT-03 vs untreated (old). FIG. 24 shows Venn diagrams of significant genes in Old vs young (control) against Old vs young (untreated). FIG. 27 shows Venn diagrams of significant genes in Old vs young (ENT-02 (MSI-1436)) against Old vs young (ENT-03). Venn diagrams of up- and down-regulated genes. Each plot considers a different interaction of sets; either ignoring direction of perturbation, considering only up-regulated genes, considering only down-regulated genes, or examining the overlap between those genes up-regulated in one contrast and those genes down-regulated in another. The symbol U denotes the universe.

While certain embodiments have been illustrated and described, it should be understood that changes and modifications can be made therein in accordance with ordinary skill in the art without departing from the technology in its broader aspects as defined in the following claims.

The embodiments illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

As will be understood by one skilled in the art, for any and all purposes, particularly in terms of providing a written description, all ranges disclosed herein also encompass any and all possible subranges and combinations of subranges thereof, inclusive of the endpoints. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

REFERENCES

Aarsland et al., "Neuropsychiatric symptoms in patients with Parkinson's disease and dementia: frequency, profile and associated care giver stress," *J. Neurol. Neurosurg. Psychiatry,* 78:36-42 (2007).

Acsadi et al., "Alpha-synuclein loss in spinal muscular atrophy," *J. Mol. Neurosci.,* 43(3):275-83 (2011).

Ahima R S, Flier J S. "Leptin," *Annu Rev Physiol* 62, 413-437 (2000).

Ahima R S, Patel H R, Takahashi N, Qi Y, Hileman S M, Zasloff M A. "Appetite suppression and weight reduction by a centrally active aminosterol," Diabetes, 51(7):2099-104 (2002).

Akhter, S., S. K. Nath, et al. (1999). "Squalamine, a novel cationic steroid, specifically inhibits the brush-border Na+/H+ exchanger isoform NHE3." *Am J Physiol* 276(1 Pt 1): C136-44.

Andresen, et al., "Effect of 5 Days Linaclotide on Transit and Bowel Function in Females With Constipation-Predominant Irritable Bowel Syndrome," *Gastroenterology*, Volume 133, Issue 3, September 2007, Pages 761-768.

Antonelou et al., "Decreased levels of alpha-synuclein in cerebrospinal fluid of patients with clinically isolated syndrome and multiple sclerosis," *J. Neurochem.,* 134(4): 748-55 (2015).

Antonio-Rubio, et al., "Abnormal thermography in Parkinson's disease," *Parkinsonism Relat Disord.,* 2015 August; 21(8):852-7.

Auyeung et al., "Ten year survival and outcomes in a prospective cohort of new onset Chinese Parkinson's disease patients," *J. Neurol. Neurosurg. Psychiatry,* 83:607-11 (2012).

Berg et al., "MDS Research Criteria for Prodromal Parkinson's Disease," *Mov. Disord.,* 30:1600-1611 (2015).

Beach et al. *Neurol Ther.* 2017 July; 6(Suppl 1): 5-13

Bhargava et al., "A phase I and pharmacokinetic study of squalamine, a novel antiangiogenic agent, in patients with advanced cancers," *Clin. Cancer Res.,* 7:3912-9 (2001).

Bjorkhem, "Five decades with oxysterols," *Biochimie* 95, 448-454 (2013).

Boeve et al., "Synucleinopathy pathology and REM sleep behavior disorder plus dementia or parkinsonism," *Neurology* 61(1):40-5 (July 2003).

A. E. Boniakowski et al., Murine macrophage chemokine receptor CCR2 plays a crucial role in macrophage recruitment and regulated inflammation in wound healing. *Eur J Immunol* 48, 1445-1455 (2018).

(a) Braak et al., "Idiopathic Parkinson's disease: possible routes by which vulnerable neuronal types may be subject to neuroinvasion by an unknown pathogen," *J Neural. Transm.* (*Vienna*), 110:517-36 (2003).

(b) Braak et al., "Staging of brain pathology related to sporadic Parkinson's disease," *Neurobiol. Aging,* 24:197-211 (2003).

Breen, et al., "Sleep and circadian rhythm regulation in early Parkinson disease," *JAMA Neurol.,* 2014 May; 71(5):589-595.

Brundin, et al., "Prying into the Prion Hypothesis for Parkinson's Disease," *J Neurosci.,* 2017 Oct. 11; 37(41): 9808-9818.

Brunel et al., "Squalamine: A Polyvalent Drug of the Future?" *Current Cancer Drug Targets,* 5(4):267-272(6) (2005)

Celotti, et al., "The 5 alpha-reductase in the brain: molecular aspects and relation to brain function," *Front Neuroendocrinol* 13, 163-215 (1992).

Chen, et al., "Allosteric inhibition of SHP2 phosphatase inhibits cancers driven by receptor tyrosine kinases," *Nature* 535, 148-152 (2016).

Claassen et al., "REM sleep behavior disorder preceding other aspects of synucleinopathies by up to half a century," *Neurology,* 75(6):494-499 (August 2010).

Combs A P, "Recent advances in the discovery of competitive protein tyrosine phosphatase 1B inhibitors for the treatment of diabetes, obesity, and cancer" *J Med. Chem.,* 53(6):2333-44 (2010)

Connolly, et al., "Squalamine Lactate for Exudative Age-Related Macular Degeneration," *Ophthalmology Clinics of North America,* 19, 381-391 (2006).

Corrochano et al., "α-synuclein levels modulate Huntington's disease in mice," *Hum. Mol. Genet.,* 21(3):485-94 (February 2012).

Courtney, et al., "CD45 functions as a signaling gatekeeper in T cells," *Sci Signal* 12, (2019).

Crick et al., "The oxysterol and cholestenoic acid profile of mouse cerebrospinal fluid," *Steroids,* 99, 172-177 (2015).

Demirel et al., "Decreased Expression of α-Synuclein, Nogo-A and UCH-L1 in Patients with Schizophrenia: A Preliminary Serum Study," *Psychiatry Invest.,* 14(3) (2017).

Diederich et al., "Hallucinations in Parkinson disease," *Nat. Rev. Neurol.,* 5:331-42 (2006).

Edlmann, et al., "Pathophysiology of chronic subdural haematoma: inflammation, angiogenesis and implications for pharmacotherapy," *J Neuroinflammation* 14, 108 (2017).

Elchebly et al., "Increased insulin sensitivity and obesity resistance in mice lacking the protein tyrosine phosphatase-1B gene" *Science.* 1999 Mar. 5; 283(5407):1544-8.

Eswaran et al., "Crystal structures and inhibitor identification for PTPNS, PTPRR and PTPN7: a family of human MAPK-specific protein tyrosine phosphatases," *Biochem J,* 395, 483-491 (2006).

Fahn S E R, Members of the UPDRS Development Committee. UNIFIED PARKINSON'S DISEASE RATING SCALE. Florham Park, NJ: Macmillan Health Care Information (1987).

J. Garcia Fortanet et al., Allosteric Inhibition of SHP2: Identification of a Potent, Selective, and Orally Efficacious Phosphatase Inhibitor. *J. Med Chem* 59, 7773-7782 (2016)

Frank, et al., "Psychometric validation of a constipation symptom assessment questionnaire," *Scand J Gastroenterol.,* 1999 September; 34(9):870-7.

Frisinia, et al., "The neuropathological basis for depression in Parkinson's disease," *Parkinsonism Relat Disord.,* 2009 February; 15(2): 144-148.

Fukunaga, et al., "Role of MAP kinase in neurons," *Mol Neurobiol* 16, 79-95 (1998).

Genaidy, et al., "Effect of Squalamine on Iris Neovascularization in Monkeys," *Retina*, December 2002—Volume 22—Issue 6—p 772-778.

Gjerstad et al., "Excessive daytime sleepiness in Parkinson disease: is it the drugs or the disease?" *Neurology,* 67:853-8 (2006).

Goetz, et al., "Risk factors for nursing home placement in advanced Parkinson's disease," *Neurology,* 43:2227-9 (1993).

Griffiths, et al., "Oxysterol research: a brief review," *Biochem Soc Trans* 47, 517-526 (2019).

Hao et al., "A Phase I and pharmacokinetic study of squalamine, an aminosterol angiogenesis inhibitor," *Clin. Cancer Res.,* 9:2465-71 (2003).

Heaton, et al., "Defecation frequency and timing, and stool form in the general population: a prospective study," *Gut.,* 1992 June; 33(6): 818-824.

Herbst, Roy S. et al., "A Phase I/IIA Trial of Continuous Five-Day Infusion of Squalamine Lactate (MSI-1256F) Plus Carboplatin and Paclitaxel in Patients with Advanced Non-Small Cell Lung Cancer," *Clin. Cancer Res.* 9(11) (2003).

Higgins, et al., "Regression of Retinopathy by Squalamine in a Mouse Model," *Pediatric Research*, volume 56, pages 144-149 (2004).

Higgins, et al., "Squalamine Improves Retinal Neovascularization," *Investigative Ophthalmology & Visual Science*, May 2000, Vol. 41, 1507-1512.

Hofmann, et al., "Bile salts of vertebrates: structural variation and possible evolutionary significance," *J Lipid Res* 51, 226-246 (2010).

Holmqvist, et al., "Direct evidence of Parkinson pathology spread from the gastrointestinal tract to the brain in rats," *Acta neuropathological,* 128. 10.1007/s00401-014-1343-6 (2014).

Hosokawa et al., "Accumulation of multiple neurodegenerative disease-related proteins in familial frontotemporal lobar degeneration associated with granulin mutation," *Scientific Reports,* 7:1513 (2017).

S. Huber et al., IL-22BP is regulated by the inflammasome and modulates tumorigenesis in the intestine. *Nature* 491, 259-263 (2012).

Hughes, et al., "What features improve the accuracy of clinical diagnosis in Parkinson's disease," *Neurology*, Jun. 1, 1992; 42 (6).

Javitt, "25R,26-Hydroxycholesterol revisited: synthesis, metabolism, and biologic roles," *J Lipid Res* 43, 665-670 (2002).

Kim et al., "Poststroke Induction of α-Synuclein Mediates Ischemic Brain Damage," *J. Neurosci.,* 36(26):7055-65 (2016).

Kimura, et al., "Profile of urinary bile acids in infants and children: developmental pattern of excretion of unsaturated ketonic bile acids and 7beta-hydroxylated bile acids," *Pediatr Res* 45, 603-609 (1999).

Krishnan, et al., "Targeting the disordered C terminus of PTP1B with an allosteric inhibitor," *Nat Chem Biol* 10, 558-566 (2014).

Krishnan et al., "A potent, selective, and orally bioavailable inhibitor of the protein-tyrosine phosphatase PTP1B improves insulin and leptin signaling in animal models," *J. Biol. Chem.,* 293(5):1517-1525 (Feb. 2, 2018).

Kuo, et al., "Tyrosine phosphatases Shp1 and Shp2 have unique and opposing roles in oligodendrocyte development," *J Neurochem* 113, 200-212 (2010).

Lantz, et al., "Inhibition of PTP1B by trodusquemine (MSI-1436) causes fat-specific weight loss in diet-induced obese mice," *Obesity* (Silver Spring) 18, 1516-1523 (2010).

Lee, et al., "Protein tyrosine phosphatase-PEST and beta8 integrin regulate spatiotemporal patterns of RhoGDI1 activation in migrating cells," *Mol Cell Biol* 35, 1401-1413 (2015).

Lewis, et al., "Stool form scale as a useful guide to intestinal transit time,". *Scand Gastroenterol.,* 1997; 32:920-924.

S. M. Lewis, A. Williams, S. C. Eisenbarth, Structure and function of the immune system in the spleen. *Sci Immunol* 4, (2019).

Limbocker, et al., "Trodusquemine enhances Abeta42 aggregation but suppresses its toxicity by displacing oligomers from cell membranes," *Nat Commun* 10, 225 (2019).

Lin, et al., "Genetics and genomics of Parkinson's disease," *Genome Medicine,* 2014 6:48.

Liu, et al., "Nuclear hormone receptor regulation of microRNAs controls innate immune responses in *C. elegans,*" *PLoS Pathog* 9, e1003545 (2013).

Looney, et al., "Intracranial hemorrhage in asymptomatic neonates: prevalence on MR images and relationship to obstetric and neonatal risk factors," *Radiology* 242, 535-541 (2007).

MacDonald, D. (1995). "Squalamine for STDs." Abstract no F7 35th ICAAC conference.

Madrid-Navarro, et al., "Multidimensional Circadian Monitoring by Wearable Biosensors in Parkinson's Disease," *Front Neurol.,* 2018; 9: 157.

Magen et al., "Mouse Models of Cognitive Deficits Due to Alpha-Synuclein Pathology," *J. of Parkinson's Dis.,* 1:217-227 (2011).

Marquis, et al., "Development and validation of the Patient Assessment of Constipation Quality of Life questionnaire," *Scand J Gastroenterol.,* 2005 May; 40(5):540-51.

Mahanti, et al., "Comparative metabolomics reveals endogenous ligands of DAF-12, a nuclear hormone receptor, regulating *C. elegans* development and lifespan," *Cell Metab* 19, 73-83 (2014).

McDowell et al., "Sleep dysfunction and EEG alterations in mice overexpressing alpha-synuclein," *J. Parkinsons Dis.,* 4(3):531-539 (2014).

McKhann, et al., "The diagnosis of dementia due to Alzheimer's disease: recommendations from the National Institute on Aging-Alzheimer's Association workgroups on diagnostic guidelines for Alzheimer's disease," *Alzheimers Dement.,* 2011 May; 7(3):263-9.

Meaney, et al., "Novel route for elimination of brain oxysterols across the blood-brain barrier: conversion into 7alpha-hydroxy-3-oxo-4-cholestenoic acid," *J Lipid Res* 48, 944-951 (2007).

Mearin et al., "Bowel Disorders," *Gastroenterology,* 150(6): 1393-1407 (2016).

Moore, et al., "Squalamine: an aminosterol antibiotic from the shark," *Proceedings of the National Academy of Sciences of the United States of America* 90, 1354-1358 (1993).

Morairty, "Detecting Neurodegenerative Diseases Before Damage Is Done," SRI International (Jul. 26, 2013).

Y. Morita et al., Functional characterization of hematopoietic stem cells in the spleen. *Exp Hematol* 39, 351-359 e353 (2011).

Motola, et al., "Identification of ligands for DAF-12 that govern dauer formation and reproduction in *C. elegans,*" *Cell* 124, 1209-1223 (2006).

Moussaud et al., "Alpha-synuclein and tau: teammates in neurodegeneration?" *Mol. Neurodeg.,* 9:43 (2014).

Mucke, et al., "High-level neuronal expression of abeta 1-42 in wild-type human amyloid protein precursor transgenic mice: synaptotoxicity without plaque formation," *J Neurosci* 20, 4050-4058 (2000).

Mucke, et al., "High-Level Neuronal Expression of A?1-42 in Wild-Type Human Amyloid Protein Precursor Transgenic Mice: Synaptotoxicity without Plaque Formation," *The Journal of Neuroscience* 20, 4050-4058 (2000).

Nagata, et al., "Changes in the level of 7 alpha-hydroxy-3-oxo-4-cholestenoic acid in cerebrospinal fluid after subarachnoid hemorrhage," *Neurol Med Chir* (Tokyo) 35, 294-297 (1995).

Nagata, et al., "Identification of 7 alpha-hydroxy-3-oxo-4-cholestenoic acid in chronic subdural hematoma," *Biochim Biophys Acta* 1126, 229-236 (1992).

Nakagawa, et al., "Bile acid metabolism in early life: studies of amniotic fluid," *J Lipid Res* 31, 1089-1098 (1990).

Ogundare, et al., "Cerebrospinal fluid steroidomics: are bioactive bile acids present in brain?" *J Biol Chem* 285, 4666-4679 (2010).

Ondo et al., "Daytime sleepiness and other sleep disorders in Parkinson's disease," *Neurology,* 57:1392-6 (2001).

Ondo, et al., "Placebo-controlled trial of lubiprostone for constipation associated with Parkinson disease," *Neurology,* 2012 May 22; 78(21):1650-4.

Ortiz-Tudela et al., "Ambulatory circadian monitoring (ACM) based on thermometry, motor activity and body position (TAP): a comparison with polysomnography," *Physiol. Behav.,* 126:30-8 (2014).

Palma et al., "Treatment of autonomic dysfunction in Parkinson disease and other synucleinopathies". *Mov. Disord.* (Review), 33(3):372-90 (March 2018).

Palsetia et al., "The Clock Drawing Test versus Mini-mental Status Examination as a Screening Tool for Dementia: A Clinical Comparison," *Indian J. Psychol. Med.,* 40:1-10 (2018).

Pandey, et al., "LMO4 is required to maintain hypothalamic insulin signaling," *Biochem Biophys Res Commun* 450, 666-672 (2014).

Pandey, et al., "The LEVI domain only 4 protein is a metabolic responsive inhibitor of protein tyrosine phosphatase 1B that controls hypothalamic leptin signaling," *J Neurosci* 33, 12647-12655 (2013).

Papapetropoulos et al., "A questionnaire-based (UM-PDHQ) study of hallucinations in Parkinson's disease," *BMC Neurol.,* 8:21 (2008).

Pelkmans, L. and A. Helenius (2003). "Insider information: what viruses tell us about endocytosis." *Curr Opin Cell Biol* 15(4): 414-22.

Perni, et al., "Multistep Inhibition of alpha-Synuclein Aggregation and Toxicity in Vitro and in Vivo by Trodusquemine," *ACS Chem Biol* 13, 2308-2319 (2018).

Phillips, et al., "Alpha-synuclein-immunopositive myenteric neurons and vagal preganglionic terminals: autonomic pathway implicated in Parkinson's disease?," *Neuroscience.* 2008 May 15; 153(3):733-50.

Pulido, et al., "PTPs emerge as PIPs: protein tyrosine phosphatases with lipid-phosphatase activities in human disease," *Hum Mol Genet* 22, R66-76 (2013).

Qin, et al., "Chronic stress induces anxiety via an amygdalar intracellular cascade that impairs endocannabinoid signaling," *Neuron* 85, 1319-1331 (2015).

Rao, et al., "Aminosterols from the dogfish shark Squalus acanthias," *J Nat Prod* 63, 631-635 (2000).

Ricke, et al., "Neuronal Protein Tyrosine Phosphatase 1B Hastens Amyloid beta-Associated Alzheimer's Disease in Mice," *J Neurosci* 40, 1581-1593 (2020).

Rocca et al., "The Role of T1-Weighted Derived Measures of Neurodegeneration for Assessing Disability Progression in Multiple Sclerosis," Front Neurol., 8:433 (Sep. 4, 2017).

Saeed, et al., "7alpha-hydroxy-3-oxo-4-cholestenoic acid in cerebrospinal fluid reflects the integrity of the blood-brain barrier," *J Lipid Res* 55, 313-318 (2014).

Saeed, et al., "Effects of a disrupted blood-brain barrier on cholesterol homeostasis in the brain," *J Biol Chem* 289, 23712-23722 (2014).

Salmi et al., "Squalamine: An Appropriate Strategy against the Emergence of Multidrug Resistant Gram-Negative Bacteria?" *PLoS One.* 3(7):e2765 (2008).

Sarabia et al., "Circadian rhythm of wrist temperature in normal-living subjects A candidate of new index of the circadian system," *Physiol. Behav.,* 95:570-80 (2008).

Schiller, J H and G. Bittner, "Potentiation of platinum antitumor effects in human lung tumor xenografts by the angiogenesis inhibitor squalamine: effects on tumor neovascularization," *Clin Cancer Res.* 5(12):4287-94 (1999).

Shehata et al., "Neuronal stimulation induces autophagy in hippocampal neurons that is involved in AMPA receptor degradation after chemical long-term depression," *J. Neurosci.,* 32:10413-22 (2012).

A. Shibuya et al., Fc alpha/mu receptor mediates endocytosis of IgM-coated microbes. *Nat Immunol* 1, 441-446 (2000).

Sills Jr., Allen K., et al., "Squalamine Inhibits Angiogenesis and Solid Tumor Growth in Vivo and Perturbs Embryonic Vasculature," *Cancer Research* 58:2784-2792 (1998).

Smith, et al., "The protein tyrosine phosphatase 1B inhibitor MSI-1436 stimulates regeneration of heart and multiple other tissues," *NPJ Regen Med* 2, 4 (2017).

Sokoloff, et al., "Adjunctive therapy for men with high risk localized and locally advanced prostate cancer: targeting disseminated tumor cells," *J Urol.,* 2004 December; 172(6 Pt 2):2539-44.

R. Spolski, W. J. Leonard, Interleukin-21: a double-edged sword with therapeutic potential. *Nat Rev Drug Discov* 13, 379-395 (2014).

Sriwimol and Limprasert, "Significant Changes in Plasma Alpha-Synuclein and Beta-Synuclein Levels in Male Children with Autism Spectrum Disorder," *BioMed Research International,* 2018, 7 pages (2018).

Steer et al., "Use of the Beck Depression Inventory-II with depressed geriatric inpatients," *Behav. Res. Ther.,* 38:311-8 (2000).

Stiasny-Kolster et al., "The REM sleep behavior disorder screening questionnaire—a new diagnostic instrument," *Movement disorders: Official J. of the Movement Dis. Soc.,* 22:2386-93 (2007).

Stoessl, "Neuroimaging in the early diagnosis of neurodegenerative disease," *Transl. Neurodegener.,* 1: 5 (2012).

U. Svajger, M. Anderluh, M. Jeras, N. Obermajer, C-type lectin DC-SIGN: an adhesion, signalling and antigen-uptake molecule that guides dendritic cells in immunity. *Cell Signal* 22, 1397-1405 (2010).

Svensson, et al., "Vagotomy and subsequent risk of Parkinson's disease," *Ann. Neurol.,* 2015; 78:522-529.

Takahashi, et al., "A novel aminosterol reverses diabetes and fatty liver disease in obese mice," *J Hepatol* 41, 391-398 (2004).

The US Burden of Disease Collaborators, "The State of US Health, 1990-2016: Burden of Diseases, Injuries, and Risk Factors Among US States," *JAMA,* 319(14):1444-1472 (2018)

Thompson, et al., "Pharmacological inhibition of protein tyrosine phosphatase 1B protects against atherosclerotic plaque formation in the LDLR(−/−) mouse model of atherosclerosis," *Clin Sci* (Lond) 131, 2489-2501 (2017).

Videnovic, et al., "Circadian Dysregulation in Parkinson's Disease," *Neurobiol Sleep Circadian Rhythms,* 2017 January; 2:53-58.

Wahlen, et al., "Ketonic bile acids in urine of infants during the neonatal period," *J Lipid Res* 30, 1847-1857 (1989).

Williams, J I et al., "Squalamine treatment of human tumors in nu/nu mice enhances platinum-based chemotherapies," *Clin Cancer Res*. (2001).

Wiesmann, C et al., 2004. *Nat. Struct. Mol. Biol.* 11, 730.

Wimo, et al., "The worldwide economic impact of dementia 2010*," Alzheimer's Dement.,* 9: 1-11 (2013).

F. M. Wolber et al., Roles of spleen and liver in development of the murine hematopoietic system. *Exp Hematol* 30, 1010-1019 (2002).

Yamashima, "The inner membrane of chronic subdural hematomas: pathology and pathophysiology," *Neurosurg Clin N Am* 11, 413-424 (2000).

Yancopoulou et al., "Tau and alpha-synuclein inclusions in a case of familial frontotemporal dementia and progressive aphasia," *J. Neuropathol. Exp. Neurol.,* 64(3):245-53 (2005).

Yin, M., C. Gentili, et al. (2002). "Antiangiogenic treatment delays chondrocyte maturation and bone formation during limb skeletogenesis," *J. Bone Miner Res* 17(1):56-65.

Yoshiyama, et al., "Synapse loss and microglial activation precede tangles in a P301S tauopathy mouse model," *Neuron* 53, 337-351 (2007).

Zabolotny, et al., "PTP1B regulates leptin signal transduction in vivo," *Dev Cell* 2, 489-495 (2002).

Zahodne, et al., "Components of Depression in Parkinson Disease," *J Geriatr Psychiatry Neurol.,* 2012 September; 25(3): 131-137.

Zasloff, et al., "A spermine-coupled cholesterol metabolite from the shark with potent appetite suppressant and antidiabetic properties," *Int J Obes Relat Metab Disord.,* 2001 May; 25(5):689-97.

Zasloff, et al., "A spermine-coupled cholesterol metabolite from the shark with potent appetite suppressant and antidiabetic properties," *Int J Obes Relat Metab Disord* 25, 689-697 (2001).

Zhang, et al., "Metabolism of 27-, 25- and 24-hydroxycholesterol in rat glial cells and neurons," *Biochem J* 322 (Pt 1), 175-184 (1997).

Zhang, et al., "Neuronal Shp2 tyrosine phosphatase controls energy balance and metabolism," *Proceedings of the National Academy of Sciences of the United States of America* 101, 16064-16069 (2004).

Zheng, et al., "Gain-of-function mutations in the gene encoding the tyrosine phosphatase SHP2 induce hydrocephalus in a catalytically dependent manner," *Sci Signal* 11, (2018).

Zhao et al., "A comparative study of the amount of α-synuclein in ischemic stroke and Parkinson's disease," *Neurol. Sci.* 37(5):749-54 (2016).

Zinsmeister et al., "Pharmacodynamic and clinical endpoints for functional colonic disorders: statistical considerations," *Dig. Dis. Sci.,* 58:509-18 (2013).

What is claimed is:

1. An aminosterol compound having the formula:

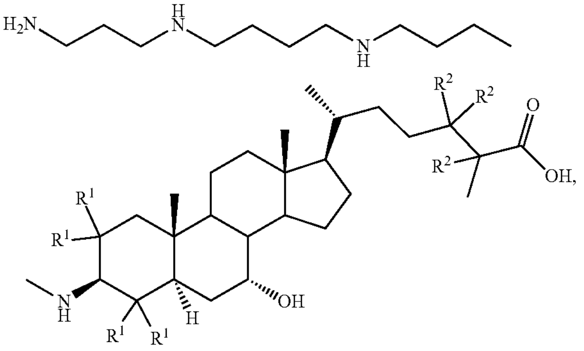

wherein:

$R^1$ is H or D; and $R^2$ is H or D;

provided that all of $R^1$ are H, all of $R^2$ are H, or all of $R^1$ and $R^2$ are H, or a pharmaceutically acceptable salt, solvate, prodrug, or derivative thereof.

2. The aminosterol compound of claim 1 having the formula:

ENT-03 (Compound III)

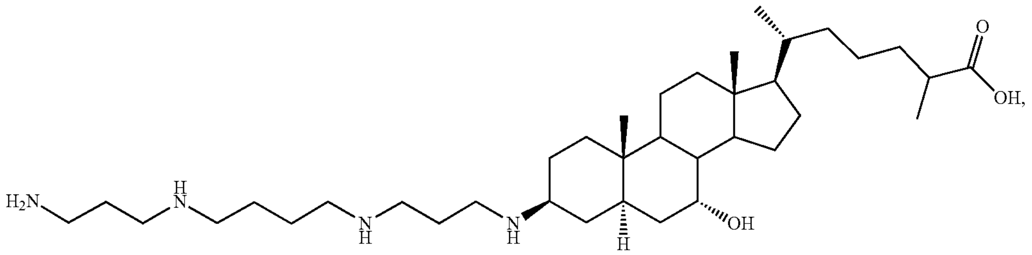

or a pharmaceutically acceptable salt, solvate, prodrug, or derivative thereof.

3. The aminosterol compound of claim 1:

(a) having the formula:

$C_{25}$ (*R*) ENT-03 (Compound III)

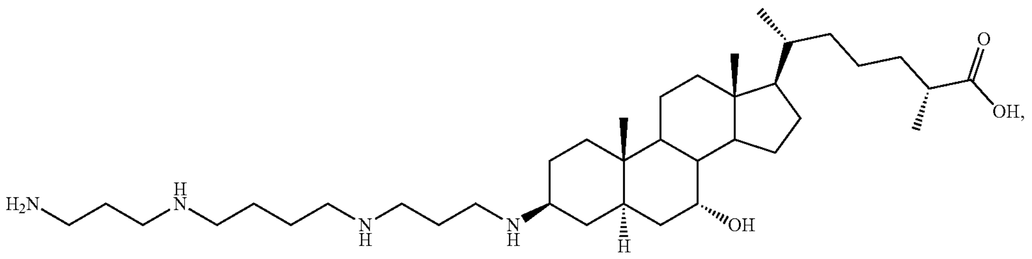

or a pharmaceutically acceptable salt, solvate, prodrug, or derivative thereof; or
(b) having the formula:
ENT-03-d4
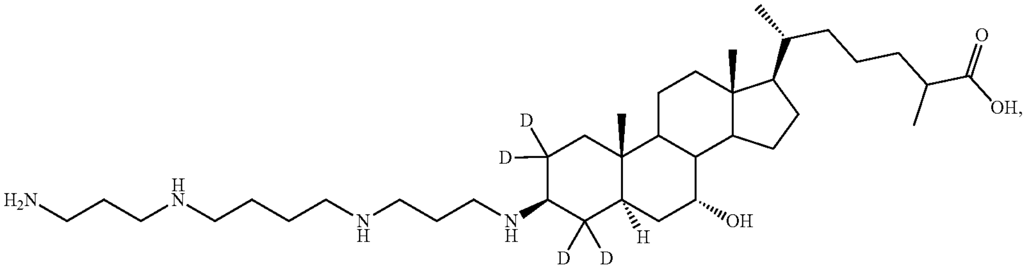
or a pharmaceutically acceptable salt, solvate, prodrug, or derivative thereof; or
(c) having the formula:
ENT-03-d3
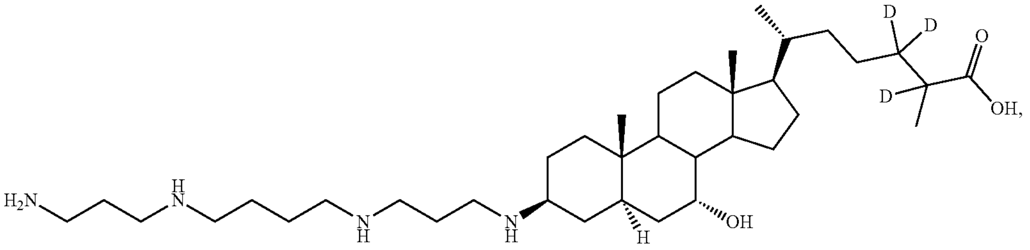
or a pharmaceutically acceptable salt, solvate, prodrug, or derivative thereof.
4. An aminosterol compound:
(a) having the formula:
Compound IV (Δ5 ENT-03)
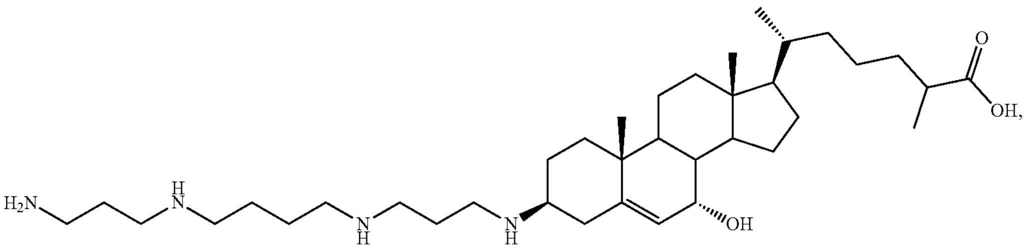

or a pharmaceutically acceptable salt, solvate, prodrug, or derivative thereof; or (b) having the formula:

Compound V (Δ4 ENT-03)

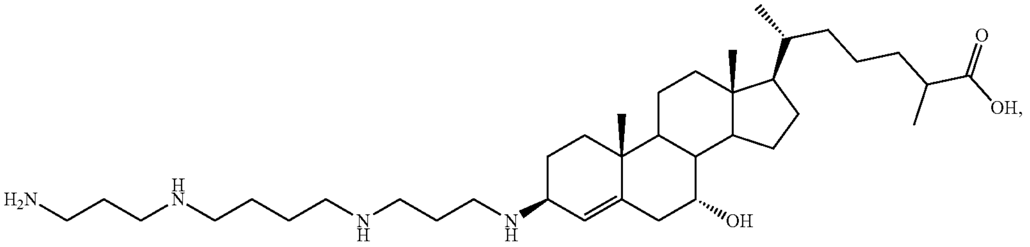

or a pharmaceutically acceptable salt, solvate, prodrug, or derivative thereof; or (c) having the formula:

Compound IV-P

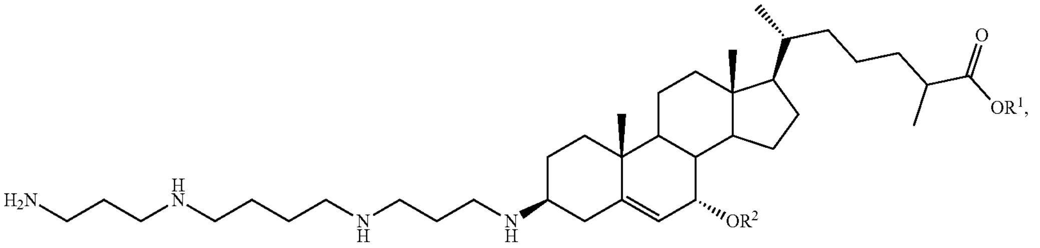

wherein:

$R^1$ is H, an optionally substituted aryl, optionally substituted heteroaryl, optionally substituted $C_1$-$C_6$ alkyl, optionally substituted $C_1$-$C_6$ alkynyl, optionally substituted heterocyclyl, optionally substituted $C_3$-$C_8$ cycloalkyl, and optionally substituted $C_1$-$C_6$ alkenyl; and $R^2$ is H or —C(O)$R^3$, wherein $R^3$ is an optionally substituted aryl, optionally substituted heteroaryl, optionally substituted $C_1$-$C_6$ alkyl, optionally substituted $C_1$-$C_6$ alkynyl, optionally substituted heterocyclyl, optionally substituted $C_3$-$C_8$ cycloalkyl, or optionally substituted $C_1$-$C_6$ alkenyl;

provided that at least one of $R^1$ and $R^2$ is not H, or a pharmaceutically acceptable salt, solvate, prodrug, or derivative thereof; or (d) having the formula:

Compound V-P

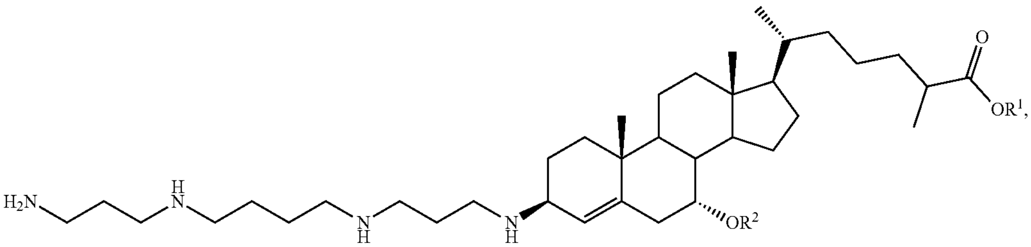

wherein:

$R^1$ is H, an optionally substituted aryl, optionally substituted heteroaryl, optionally substituted $C_1$-$C_6$ alkyl, optionally substituted $C_1$-$C_6$ alkynyl, optionally substituted heterocyclyl, optionally substituted $C_3$-$C_8$ cycloalkyl, and optionally substituted $C_1$-$C_6$ alkenyl; and $R^2$ is H or —C(O)$R^3$, wherein $R^3$ is an optionally substituted aryl, optionally substituted heteroaryl, optionally substituted $C_1$-$C_6$ alkyl, optionally substituted $C_1$-$C_6$ alkynyl, optionally substituted heterocyclyl, optionally substituted $C_3$-$C_8$ cycloalkyl, or optionally substituted $C_1$-$C_6$ alkenyl;

provided that at least one of $R^1$ and $R^2$ is not H, or a pharmaceutically acceptable salt, solvate, prodrug, or derivative thereof; or (e) having the formula:

Compound III-P

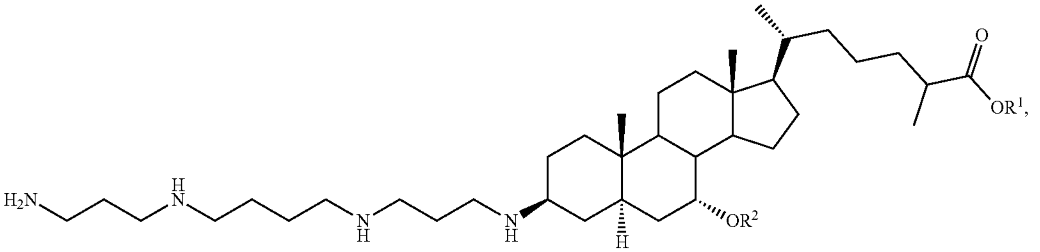

wherein:

$R^1$ is H, optionally substituted aryl, optionally substituted heteroaryl, optionally substituted $C_1$-$C_6$ alkyl, optionally substituted $C_1$-$C_6$ alkynyl, optionally substituted heterocyclyl, optionally substituted $C_3$-$C_8$ cycloalkyl, or optionally substituted $C_1$-$C_6$ alkenyl; and $R^2$ is H or —C(O)$R^3$, wherein $R^3$ is an optionally substituted aryl, optionally substituted heteroaryl, optionally substituted $C_1$-$C_6$ alkyl, optionally substituted $C_1$-$C_6$ alkynyl, optionally substituted heterocyclyl, optionally substituted $C_3$-$C_8$ cycloalkyl, or optionally substituted $C_1$-$C_6$ alkenyl;

provided that at least one of $R^1$ and $R^2$ is not H, or a pharmaceutically acceptable salt, solvate, prodrug, or derivative thereof.

5. The aminosterol compound of claim 4, wherein:

(a) the compound of subsection (a) of claim 4 has the formula:

$C_{25}$ (*R*) Compound IV (Δ5 ENT-03)

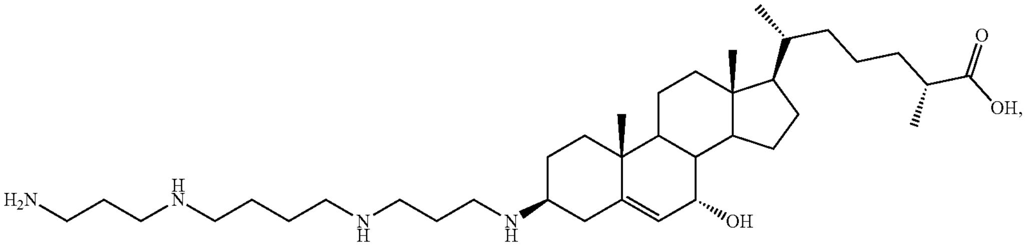

or a pharmaceutically acceptable salt, solvate, prodrug, or derivative thereof; or (b) the compound of subsection (b) of claim 4 has the formula:

$C_{25}$ (*R*) Compound V (Δ4 ENT-03)

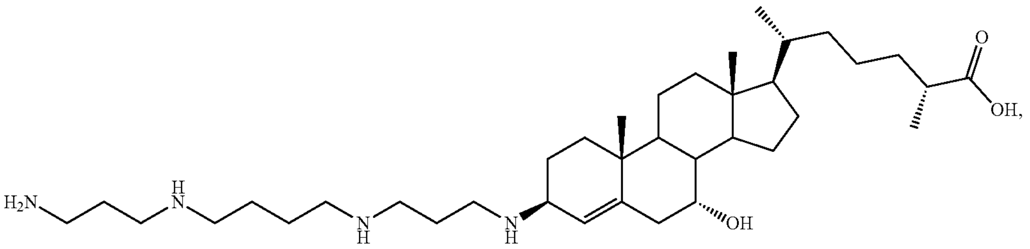

or a pharmaceutically acceptable salt, solvate, prodrug, or derivative thereof; or (c) the compound of subsection (c) of claim 4 has the formula:

$C_{25}$ (*R*) Compound IV-P

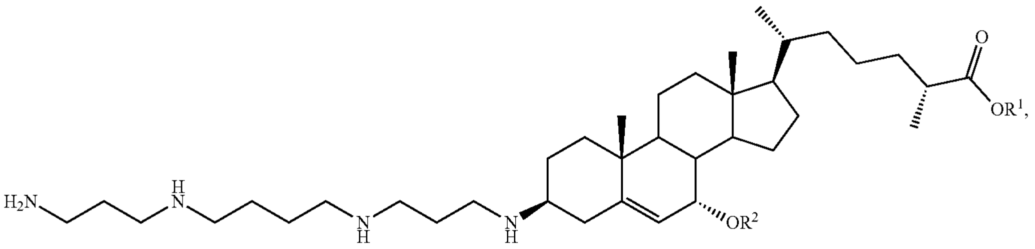

or a pharmaceutically acceptable salt, solvate, prodrug, or derivative thereof; or (d) the compound of subsection (d) of claim 4 has the formula:

$C_{25}$ (*R*) Compound V-P

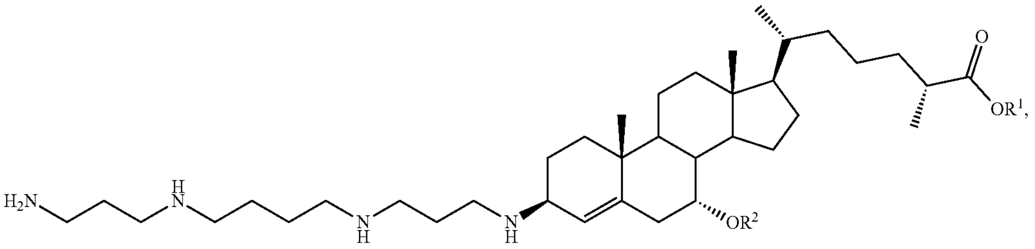

or a pharmaceutically acceptable salt, solvate, prodrug, or derivative thereof; or (e) the compound of subsection (e) of claim 4 has the formula:

$C_{25}$ (*R*) Compound III-P

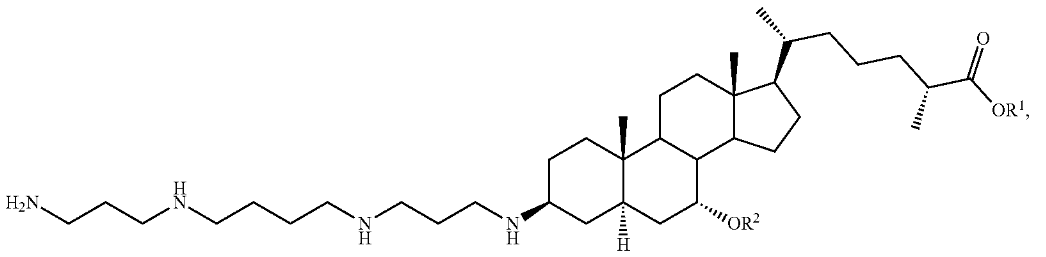

or a pharmaceutically acceptable salt, solvate, prodrug, or derivative thereof.

6. The aminosterol compound of claim 1:

(a) formulated as a pharmaceutically acceptable salt; or (b) formulated as a pharmaceutically acceptable phosphate salt.

7. A composition comprising an aminosterol compound according to claim 1, wherein:

(a) the composition comprises and at least one pharmaceutically acceptable carrier or excipient; and/or (b) the composition further comprises at least one additional active agent; and/or (c) the composition is formulated for administration selected from the group consisting of oral, pulmonary, rectal, colonic, parenteral, intracisternal, intravaginal, intraperitoneal, intravenous, subcutaneous, intramuscular, nebulization, inhalation, ocular, otic, local, buccal, nasal, and topical administration; and/or (d) the composition is formulated into a dosage form selected from the group consisting of liquid dispersions, gels, aerosols, ointments, creams, lyophilized formulations, tablets, capsules; and/or (e) the composition is formulated into a dosage form selected from the group consisting of controlled release formulations, fast melt formulations, delayed release formulations, extended release formulations, pulsatile release formulations, and mixed immediate release and controlled release formulations; and/or (f) the composition is formulated into any combination of (c), (d), and (e);

(g) the composition is formulated for oral administration; and/or (h) the composition is formulated as an oral tablet or capsule; and/or (i) the composition is formulated for intranasal administration; and/or (j) the composition comprises one or more of the following:

(i) an aqueous carrier;

(ii) a buffer;

(iii) a sugar; and/or (iv) a polyol compound.

8. An aminosterol compound having the formula:

ENT-05

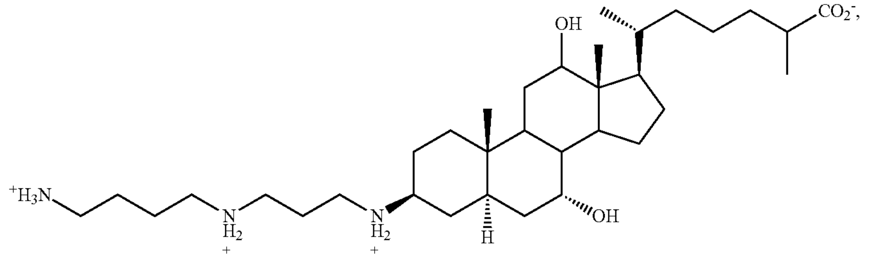

or a pharmaceutically acceptable salt, solvate, prodrug, or derivative thereof; or

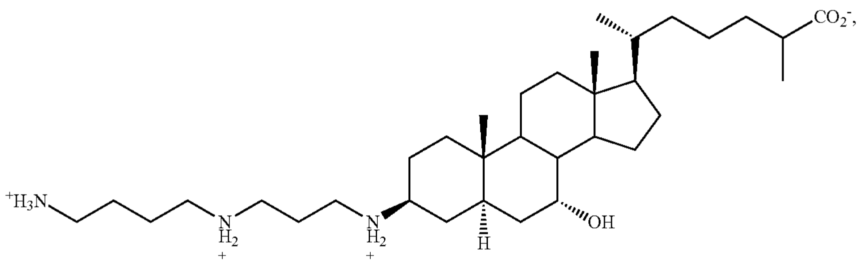

ENT-06 or a pharmaceutically acceptable salt, solvate, prodrug, or derivative thereof.

9. The aminosterol compound of claim 8:

(a) formulated as a pharmaceutically acceptable salt; or (b) formulated as a pharmaceutically acceptable phosphate salt.

10. A composition comprising an aminosterol compound according to claim 8, wherein:

(a) the composition comprises and at least one pharmaceutically acceptable carrier or excipient; and/or (b) the composition further comprises at least one additional active agent; and/or (c) the composition is formulated for administration selected from the group consisting of oral, pulmonary, rectal, colonic, parenteral, intracisternal, intravaginal, intraperitoneal, intravenous, subcutaneous, intramuscular, nebulization, inhalation, ocular, otic, local, buccal, nasal, and topical administration; and/or (d) the composition is formulated into a dosage form selected from the group consisting of liquid dispersions, gels, aerosols, ointments, creams, lyophilized formulations, tablets, capsules; and/or (e) the composition is formulated into a dosage form selected from the group consisting of controlled release formulations, fast melt formulations, delayed release formulations, extended release formulations, pulsatile release formulations, and mixed immediate release and controlled release formulations; and/or (f) the composition is formulated into any combination of (c), (d), and (e);

(g) the composition is formulated for oral administration; and/or (h) the composition is formulated as an oral tablet or capsule; and/or (i) the composition is formulated for intranasal administration; and/or (j) the composition comprises one or more of the following:

(i) an aqueous carrier;

(ii) a buffer;

(iii) a sugar; and/or (iv) a polyol compound.

* * * * *